US009512111B2

(12) United States Patent
Glick et al.

(10) Patent No.: US 9,512,111 B2
(45) Date of Patent: Dec. 6, 2016

(54) N-SULFONYLATED TETRAHYDROQUINOLINES AND RELATED BICYCLIC COMPOUNDS FOR INHIBITION OF RORγ ACTIVITY AND THE TREATMENT OF DISEASE

(75) Inventors: Gary D. Glick, Ann Arbor, MI (US); Peter L. Toogood, Ann Arbor, MI (US); Arthur G. Romero, Chesterfield, MO (US); Chad A. Van Huis, Hartland, MI (US); Thomas D. Aicher, Ann Arbor, MI (US); Carl Kaub, San Mateo, CA (US); Matthew N. Mattson, Santa Clara, CA (US); William D. Thomas, San Jose, CA (US); Karin A. Stein, Mountain View, CA (US); Erik Krogh-Jespersen, Palo Alto, CA (US); Zhan Wang, San Jose, CA (US)

(73) Assignee: Lycera Corporation, Ann Arbor, MI (US)

( * ) Notice: Subject to any disclaimer, the term of this patent is extended or adjusted under 35 U.S.C. 154(b) by 268 days.

(21) Appl. No.: 13/883,419

(22) PCT Filed: Nov. 8, 2011

(86) PCT No.: PCT/US2011/059788
§ 371 (c)(1),
(2), (4) Date: Nov. 19, 2013

(87) PCT Pub. No.: WO2012/064744
PCT Pub. Date: May 18, 2012

(65) Prior Publication Data
US 2014/0088094 A1    Mar. 27, 2014

Related U.S. Application Data

(60) Provisional application No. 61/411,084, filed on Nov. 8, 2010.

(51) Int. Cl.
| C07D 413/06 | (2006.01) |
| C07D 209/08 | (2006.01) |
| C07D 209/34 | (2006.01) |
| C07D 215/58 | (2006.01) |
| C07D 231/56 | (2006.01) |
| C07D 241/50 | (2006.01) |
| C07D 265/36 | (2006.01) |
| C07D 401/04 | (2006.01) |
| C07D 401/12 | (2006.01) |
| C07D 403/12 | (2006.01) |
| C07D 405/12 | (2006.01) |
| C07D 409/12 | (2006.01) |
| C07D 413/04 | (2006.01) |
| C07D 413/12 | (2006.01) |
| C07D 417/12 | (2006.01) |
| C07D 471/04 | (2006.01) |

(52) U.S. Cl.
CPC .......... *C07D 413/06* (2013.01); *C07D 209/08* (2013.01); *C07D 209/34* (2013.01); *C07D 215/58* (2013.01); *C07D 231/56* (2013.01); *C07D 241/50* (2013.01); *C07D 265/36* (2013.01); *C07D 401/04* (2013.01); *C07D 401/12* (2013.01); *C07D 403/12* (2013.01); *C07D 405/12* (2013.01); *C07D 409/12* (2013.01); *C07D 413/04* (2013.01); *C07D 413/12* (2013.01); *C07D 417/12* (2013.01); *C07D 471/04* (2013.01)

(58) Field of Classification Search
CPC  C07D 209/08; C07D 209/34; C07D 215/58; C07D 241/50; C07D 265/36; C07D 401/04; C07D 401/12; C07D 403/12; C07D 405/12; C07D 409/12; C07D 413/04; C07D 413/06; C07D 413/12; C07D 417/12; C07D 471/04
See application file for complete search history.

(56) References Cited

U.S. PATENT DOCUMENTS

| 5,985,903 | A  | 11/1999 | Assmann et al. |
| 6,020,354 | A  | 2/2000  | Assmann et al. |
| 6,037,367 | A  | 3/2000  | Christensen, IV et al. |
| 6,160,001 | A  | 12/2000 | Assmann et al. |
| 6,172,092 | B1 | 1/2001  | Assmann et al. |
| 6,180,643 | B1 | 1/2001  | Zablocki et al. |
| 6,348,032 | B1 | 2/2002  | Sperl et al. |
| 6,352,985 | B1 | 3/2002  | Yamasaki et al. |
| 6,387,939 | B1 | 5/2002  | Assmann et al. |

(Continued)

FOREIGN PATENT DOCUMENTS

| CN | WO 2012037108 A1 * | 3/2012  | ............. A61K 31/47 |
| DE | WO 2009149819 A1 * | 12/2009 | ........... C07D 413/14 |

(Continued)

OTHER PUBLICATIONS

Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem, 1379-90 (1990).
Guimond et al., "Rhodium(III)-Catalyzed Isoquinolone Synthesis: The N—O Bond as a Handle for C—N Bond Formation and Catalyst Turnover," 132(20) J. Am, Chem. Soc. 6908-09 (2010).
Ishikura et al., "An Efficient Synthesis of 3-Heteroarylpyridines via Diethyl-(3-pyridyl)-borane," Synthesis 936-38 (1984).
Jiang et al., "Synthesis and Cytotoxicity Evaluation of Novel Indolylpyrimidines and Indolylpyrazines as Potential Antitumor Agents," 9 Bioorg. Med, Chem. 1149-54 (2001).

(Continued)

*Primary Examiner* — Sarah Pihonak
(74) *Attorney, Agent, or Firm* — Goodwin Procter LLP

(57) ABSTRACT

The invention provides tetrahydroquinoline and related compounds, pharmaceutical compositions, methods of inhibiting RORγ activity, reducing the amount of IL-17 in a subject, and treating immune disorders and inflammatory disorders using such tetrahydroquinoline and related compounds are provided.

15 Claims, No Drawings

(56) References Cited

U.S. PATENT DOCUMENTS

| | | |
|---|---|---|
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |
| 7,084,176 B2 | 8/2006 | Morie et al. |
| 7,138,401 B2 | 11/2006 | Kasibhatla et al. |
| 7,329,675 B2 | 2/2008 | Cox et al. |
| 7,420,059 B2 | 9/2008 | O'Connor et al. |
| 7,482,342 B2 | 1/2009 | D'Orchymont et al. |
| 7,569,571 B2 | 8/2009 | Dong et al. |
| 7,696,200 B2 | 4/2010 | Ackermann et al. |
| 7,713,996 B2 | 5/2010 | Ackermann et al. |
| 7,741,495 B2 | 6/2010 | Liou et al. |
| 7,799,933 B2 | 9/2010 | Ceccarelli et al. |
| 2006/0004000 A1 | 1/2006 | D'Orchymont et al. |
| 2006/0100230 A1 | 5/2006 | Bischoff et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0191603 A1 | 8/2007 | Ackermann et al. |
| 2007/0281922 A1 | 12/2007 | Liu et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0305169 A1 | 12/2008 | Miki et al. |
| 2009/0075973 A1 | 3/2009 | Newcom et al. |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0130484 A1 | 5/2010 | Ackermann et al. |
| 2010/0234340 A1 | 9/2010 | Schunk et al. |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0178063 A1 | 7/2011 | Baldwin et al. |
| 2014/0088094 A1 | 3/2014 | Glick et al. |

FOREIGN PATENT DOCUMENTS

| | | | | |
|---|---|---|---|---|
| DE | WO 2009149820 A1 * | 12/2009 | ........... | C07D 413/10 |
| EP | 0 882 718 A1 | 12/1998 | | |
| EP | 1820515 A1 | 8/2007 | | |
| EP | 2 181 710 A1 | 5/2010 | | |
| JP | H06250441 A | 9/1994 | | |
| JP | 2004-307487 A | 11/2004 | | |
| WO | WO-92/13856 A1 | 8/1992 | | |
| WO | WO-97/01561 A1 | 1/1997 | | |
| WO | WO-97/48697 A1 | 12/1997 | | |
| WO | WO-98/22457 A1 | 5/1998 | | |
| WO | WO-00/17202 A1 | 3/2000 | | |
| WO | WO-01/12600 A1 | 2/2001 | | |
| WO | WO-02/100819 A1 | 12/2002 | | |
| WO | WO-03/014075 A2 | 2/2003 | | |
| WO | WO-2004/056830 A1 | 7/2004 | | |
| WO | WO-2005/028434 A2 | 3/2005 | | |
| WO | WO-2005/037834 A1 | 4/2005 | | |
| WO | WO-2006/007486 A2 | 1/2006 | | |
| WO | WO-2006/057460 A1 | 6/2006 | | |
| WO | WO-2007/024944 A1 | 3/2007 | | |
| WO | WO-2007/031429 A1 | 3/2007 | | |
| WO | WO-2007/093507 A1 | 8/2007 | | |
| WO | WO-2007/125405 A2 | 11/2007 | | |
| WO | WO-2007/138998 A1 | 12/2007 | | |
| WO | WO-2008/003703 A1 | 1/2008 | | |
| WO | WO-2008/045664 A2 | 4/2008 | | |
| WO | WO-2008/062740 A1 | 5/2008 | | |
| WO | WO-2008/074692 A1 | 6/2008 | | |
| WO | WO-2008/097428 A2 | 8/2008 | | |
| WO | WO-2009/032667 A1 | 3/2009 | | |
| WO | WO-2009/035997 A2 | 3/2009 | | |
| WO | WO-2009/077956 A2 | 6/2009 | | |
| WO | WO-2009/147187 A1 | 12/2009 | | |
| WO | WO-2009/157196 A1 | 12/2009 | | |
| WO | WO-2010/017827 A1 | 2/2010 | | |
| WO | WO-2010/038901 A1 | 4/2010 | | |
| WO | WO-2010/057101 A2 | 5/2010 | | |
| WO | WO-2010/059602 A2 | 5/2010 | | |
| WO | WO-2010/102958 A | 9/2010 | | |
| WO | WO-2010/117425 A1 | 10/2010 | | |
| WO | WO-2010/123139 A1 | 10/2010 | | |
| WO | WO-2010/125082 A1 | 11/2010 | | |
| WO | WO-2011/019634 A2 | 2/2011 | | |
| WO | WO-2011/067364 A1 | 6/2011 | | |
| WO | WO-2011/067365 A1 | 6/2011 | | |
| WO | WO-2011/067366 A1 | 6/2011 | | |
| WO | WO-2011/109059 A1 | 9/2011 | | |
| WO | WO-2012/032065 A1 | 3/2012 | | |
| WO | WO-2012/032067 A1 | 3/2012 | | |
| WO | WO-2012/037108 A1 | 3/2012 | | |
| WO | WO-2013169704 A2 | 11/2013 | | |

OTHER PUBLICATIONS

Murase et al., "A New Concise Synthesis of Arcyriacyanin A and Its Unique Inhibitory Activity against a Panel of Human Cancer Cell Line," 48(1) Chem. Pharm. Bull. 81-84 (2000).

Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).

Yeh et al., "Practical Cu-catalyzed amination of functionalized heteroaryl halides," 47(34) Tetrahedron Lett. 6011-16 (2006).

André et al., "Disruption of retinoid-related orphan receptor β changes circadian behavior, causes retinal degeneration and leads to *vacillans* phenotype in mice," 17(14) The EMBO J. 3867-77 (1998).

Becker-André et al., "Identification of nuclear receptor mRNAs by RT-PCR amplification of conserved zinc-finger motif sequences," 194(3) Biochem. Biophys. Res. Comm. 1371-79 (1993).

Berge et al., "Pharmaceutical salts," 66(1) J. Pharm. Sci. 1-19 (1977).

Carlberg et al., "RZRs, a new family of retinoid-related orphan receptors that function as both monomers and homodimers," 8 Mol. Endocrinol. 757-70 (1994).

Dussault et al., "Orphan nuclear receptor RORα-deficient mice display the cerebellar defects of *staggerer*," 70 Mech. Develop. 147-53 (1998).

Giguère et al., "Isoform-specific amino-terminal domains dictate Dna-binding properties of RORα, a novel family of orphan hormone nuclear receptors," 8 Genes & Develop. 538-53 (1994).

Gould, "Salt selection for basic drugs," 33 Int'l J. Pharmaceutics 201-217 (1986).

He et al., "RORγt, a Novel Isoform of an Orphan Receptor, Negatively Regulates Fas Ligand Expression and IL-2 Production in T Cells," 9 Immunity 797-806 (1998).

Hirose et al., "RORγ: the third member of ROR/RZR orphan receptor subfamily that is highly expressed in skeletal muscle," 205 Biochem. Biophys. Res. Comm. 1976-83 (1994).

Jayashree et al., "Design and synthesis of 2-quinolones as antioxidants and antimicrobials: a rational approach," 19 Med. Chem. Res. 193-209 (2010).

Medvedev et al., "Cloning of a cDNA encoding the murine orphan receptor RZR/RORg and characterization of its response element," 181 Gene 199-206 (1996).

Ortiz et al., "TOR: a new orphan receptor expressed in the thymus that can modulate retinoid and thyroid hormone signals," 9 Mol. Endocrinol. 1679-91 (1995).

Villey et al., "RORgT, a thymus-specific isoform of the orphan nuclear receptor RORg/TOR, is up-regulated by signaling through the pre-T cell receptor and binds to the TEA promoter," 29 Eur. J. Immunol. 4072-80 (1999).

Wiesenberg et al., "Transcriptional activation of the nuclear receptor RZRa by the pineal gland hormone melatonin and identification of CGP 52608 as a synthetic ligand," 23(3) Nucl. Acids Res. 327-33 (1995).

(56) References Cited

OTHER PUBLICATIONS

Chang et al., "7-Aroyl-aminoindoline-1-sulfonamides as a Novel Class of Potent Antitubulin Agents," 49 J. Med. Chem. 6656-59 (2006).
International Search Report and Written Opinion for PCT/US2011/059788 dated May 23, 2012 (23 pages).
International Search Report and Written Opinion for PCT/US2013/040085 dated Oct. 23, 2013 (9 pages).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
Li et al., "Chemical Libraries via Sequential C—H Functionalization of Phenols," 10 J. Comb. Chem 170-74 (2008).
Liu et al., "1-Sulfonylindazoles as potent and selective 5-HT6 ligands," 19 Bioorg. Med. Chem. Lett. 2413-15 (2009).
STN Columbus, pp. 1-40 (2011).

* cited by examiner

N-SULFONYLATED TETRAHYDROQUINOLINES AND RELATED BICYCLIC COMPOUNDS FOR INHIBITION OF RORγ ACTIVITY AND THE TREATMENT OF DISEASE

CROSS REFERENCE TO RELATED APPLICATIONS

This application is the national stage of International (PCT) Patent Application Serial No. PCT/US2011/059788, filed Nov. 8, 2011 which claims the benefit of and priority to U.S. Provisional Patent Application Ser. No. 61/411,084, filed Nov. 8, 2010, the contents of which provisional patent application are hereby incorporated by reference.

FIELD OF THE INVENTION

The invention provides tetrahydroquinoline and related compounds, methods of inhibiting RORγ activity and/or reducing the amount of IL-17 in a subject, and therapeutic uses of the tetrahydroquinoline and related compounds. In particular, the present invention provides 1-arylsulfonamide-tetrahydroquinoline and related compounds, methods of using such compounds to inhibit RORγ activity and/or reduce the amount of IL-17 in a subject, and treat immune disorders and inflammatory disorders.

BACKGROUND OF THE INVENTION

Retinoid-related orphan receptors (ROR) are reported to have an important role in numerous biological processes. See, for example, Dussault et al. in *Mech. Dev.* (1998) vol. 70, 147-153; and Andre et. al. in *EMBO J.* (1998) vol. 17, 3867-3877. Scientific investigations relating to each of retinoid-related orphan receptors RORα, RORβ, and RORγ have been described in the literature. See, for example, Hirose et al. in *Biochem. Biophys. Res. Commun.* (1994) vol. 205, 1976-1983; Giguere et al. in *Genes. Dev.* (1994) vol. 8, 538-553; Medvedev et al. in *Gene* (1996) vol. 181, 199-206; Ortiz et al. in *Mol. Endocrinol.* (1995) vol. 9, 1679-1691; Wiesenberg et al. in *Nucleic Acids Res.* (1995) vol. 23, 327-333; Carlberg et al. in *Mol. Endocrinol.* (1994) vol. 8, 757-770; and Becker-Andre et al. in *Biochem. Biophys. Res. Commun.* (1993) vol. 194, 1371-1379. Continuing research in this field is spurred by the promise of developing new therapeutic agents to treat medical disorders associated with retinoid-related orphan receptor activity.

RORγ has been reported to be expressed in high concentration in various tissues, such as thymus, kidney, liver, muscle, and certain fat tissue. See, for example, Hirose et al. in *Biochem. Biophys. Res. Commun.* (1994) vol. 205, 1976-1983; Medvedev et al. in *Gene* (1996) vol. 181, 199-206; Ortiz et al. in *Mol. Endocrinol.* (1995) vol. 9, 1679-1691; and He et al. in *Immunity* (1998) vol. 9, 797-806. Two isoforms of RORγ have been identified and are referred to as γ1 and γ2 (also referred to as RORγt). See, for example, He et al. in *Immunity* (1998) vol. 9, 797-806. Expression of the γ2 isoform has been reported to appear in, for example, double-positive thymocytes. See, for example, He et al. in *Immunity* (1998) vol. 9, 797-806; and Villey et al. in *Eur. J. Immunol.* (1999) vol. 29, 4072-4080. Compounds capable of modulating RORγt activity are contemplated to provide a therapeutic benefit in the treatment of multiple medical disorders, including immune and inflammatory disorders.

Numerous immune and inflammatory disorders continue to afflict millions of patients worldwide. Significant advances have been made in treating these disorders. However, current therapies do not provide satisfactory results for all patients due to, for example, detrimental side effects or insufficient efficacy. Treatments for immune and inflammatory disorders vary depending on the particular medical disorder, and often involve use of immunosuppressive drugs. Surgery (e.g., splenectomy), plasmapheresis, or radiation can be used in certain instances.

One exemplary immune disorder in need of better therapy is psoriasis. Psoriasis is a T cell-mediated inflammatory disease that affects approximately 2% to 3% of adults and has a substantial adverse impact on the quality of life for patients suffering from this disorder. Plaques resulting from psoriasis can be painful and are visually unappealing. Various therapeutics have been developed in an attempt to treat psoriasis. However, the traditional therapies for psoriasis often have toxic adverse effects.

An exemplary inflammatory disorder in need of better treatment is rheumatoid arthritis. This form of arthritis is characterized by inflammation in the synovial membrane and results in destruction of bone. Numerous therapeutics have been developed in an attempt to treat this disorder. Exemplary therapeutics for treating rheumatoid arthritis include corticosteroids, methotrexate, hydroxychloroquine, sulfasalazine, and leflunomide. However, current therapies are not effective for all patients. Moreover, some patients develop resistance to current therapies.

Accordingly, a need exists for improved treatments for immune disorders and inflammatory disorders. The present invention addresses this need and provides other related advantages.

SUMMARY

The present invention provides tetrahydroquinoline and related compounds, pharmaceutical compositions, methods of inhibiting RORγ activity and/or reducing the amount of IL-17 in a subject, and methods of treating various medical disorders using such compounds. In particular, one aspect of the invention provides a collection of tetrahydroquinoline and related compounds, such as a compound represented by Formula I:

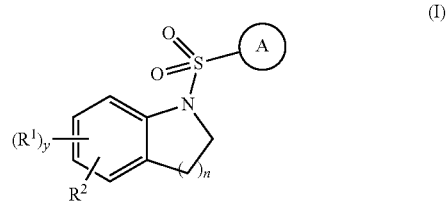

or a pharmaceutically acceptable salt or solvate thereof; wherein the variables are as defined in the detailed description. Other illustrative aspects of the invention provide a collection of tetrahydroquinoline and related compounds, such as a compound represented by Formula III:

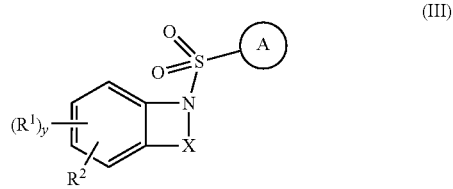

or a pharmaceutically acceptable salt or solvate thereof; wherein the variables are as defined in the detailed description. Further description of additional collections of tetrahydroquinoline and related compounds are described in the detailed description.

Another aspect of the invention provides a method of treating a subject suffering from a medical disorder. The method comprises administering to the subject a therapeutically effective amount of one or more tetrahydroquinoline or related compounds described herein, e.g., a compound of Formula I, II, III, IV, V, VI, VII, VIII, or IX, wherein Formulae I-IX are as described in the detailed description. A large number of disorders can be treated using the tetrahydroquinoline and related compounds described herein. For example, the compounds described herein can be used to treat an immune disorder or inflammatory disorder, such as rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, epidermal hyperplasia, and other medical disorders described herein. In certain other embodiments, the disorder is rheumatoid arthritis.

Another aspect of the invention provides a method of inhibiting the activity of RORγ. The method comprises exposing a RORγ to an effective amount of one or more tetrahydroquinoline or related compounds described herein, e.g., a compound of Formula I, II, III, IV, V, VI, VII, VIII, or IX, or a pharmaceutical composition described herein.

Another aspect of the invention provides a method of reducing the amount of IL-17 in a subject. The method comprises administering to a subject an effective amount of one or more tetrahydroquinoline or related compounds described herein, e.g., a compound of Formula I, II, III, IV, V, VI, VII, VIII, or IX, or a pharmaceutical composition described herein, to reduce the amount of IL-17 in the subject.

DETAILED DESCRIPTION OF THE INVENTION

The invention provides tetrahydroquinoline and related compounds, pharmaceutical compositions, methods of inhibiting RORγ activity and/or reducing the amount of IL-17 in a subject, and therapeutic uses of the tetrahydroquinoline and related compounds. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. Exemplary alkyl groups include methyl, ethyl, n-propyl, isopropyl, n-butyl, sec-butyl, isobutyl, tert-butyl, cyclopropyl, and cyclobutyl.

The term "alkylene" refers to a diradical of an alkyl group. Exemplary alkylene groups include —CH$_2$CH$_2$—,

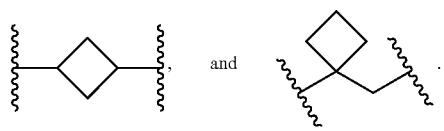

The term "cycloalkylene" refers to a diradical of a cycloalkyl group. Exemplary cycloalkylene groups include

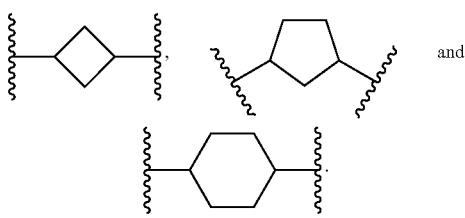

The term "haloalkyl" refers to an alkyl group that is substituted with at least one halogen. Exemplary haloalkyl groups include —CH$_2$F, —CHF$_2$, —CF$_3$, —CH$_2$CF$_3$, —CF$_2$CF$_3$, and the like.

The term "hydroxyalkyl" refers to an alkyl group that is substituted with at least one hydroxyl group. Exemplary hydroxyl alkyl groups include —CH$_2$OH, —CH$_2$CH$_2$OH, —C(H)(OH)C(OH)H$_2$, and the like.

The term "aralkyl" refers to an alkyl group substituted with an aryl group. Exemplary aralkyl groups include

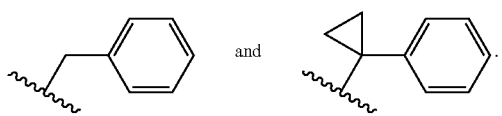

The term "aralkylene" refers to a diradical of an aralkyl group. An exemplary aralkylene group is

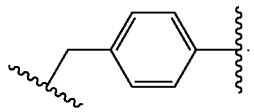

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, amino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group.

The term "arylene" as used herein refers to a divalent radical of a carbocyclic aromatic group. Arylene may be optionally substituted as described for aryl, or as otherwise indicated. An exemplary arylene group is

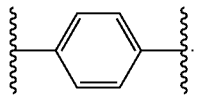

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, amino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more carbons are common to two adjoining rings (the rings are "fused rings") wherein all of the fused rings are heteroaromatic, e.g., in a naphthyridinyl group.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The term "heteroarylene" as used herein refers to a divalent radical of aromatic groups that include at least one ring heteroatom, for example, one to four heteroatoms, such as nitrogen, oxygen, and sulfur. Heteroarylene may be optionally substituted as described for heteroaryl, or as otherwise indicated. An exemplary heteroarylene group is

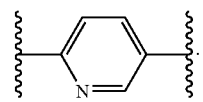

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include, but not limited to, pyridine, pyrimidine, indole, purine, quinoline and isoquinoline. Nonlimiting examples of nonaromatic heterocyclic compounds include, but not limited to, piperidine, piperazine, morpholine, pyrrolidine and pyrazolidine. Examples of oxygen containing heterocyclic rings include, but not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, amino, amido, carboxylic acid, —C(O) alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-7 membered ring that, unless specified otherwise, is substituted or unsubstituted.

The term "heterocycloalkyl" refers to a saturated heterocyclyl group having, for example, 3-7 ring atoms.

The term "heterocycloalkylene" refers to a diradical of a heterocycloalkyl group. Exemplary heterocycloalkylene groups include

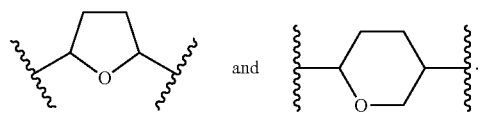

The terms "amine" and "amino" are art-recognized and refer to both unsubstituted and substituted amines, e.g., a moiety that may be represented by the general formulas:

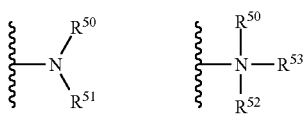

wherein $R^{50}$, $R^{51}$, $R^{52}$ and $R^{53}$ each independently represent a hydrogen, an alkyl, an alkenyl, —$(CH_2)_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —$(CH_2)_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and —O—$(CH_2)_m$—$R^{61}$, where m and $R^{61}$ are described above.

The symbol "～" indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound' or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

The location of a substituent on the tetrahydroquinoline or benzoxazine core can be characterized according to positional numbering in accordance with the rules of chemical nomenclature. Positional numbering for the tetrahydroquinoline and benzoxazine cores is illustrated below.

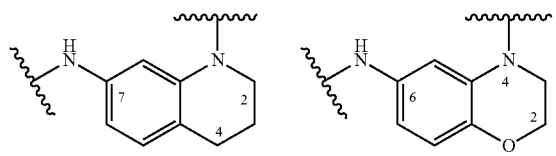 [SMILES: *Nc1ccc2c(c1)N(*)CCC2 ; *Nc1ccc2c(c1)N(*)CCO2]

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Nonlimiting examples of suitable solvates include ethanolates, methanolates, and the like. "Hydrate" is a solvate wherein the solvent molecule is $H_2O$.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$IC_{50}$" is art-recognized and refers to the concentration of a compound that is required for 50% inhibition of its target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NWL_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention include compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

The term "SEA Syndrome" refers to Seronegativity, Enthesopathy, Arthropathy Syndrome.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate As a general matter, compositions specifying a percentage are by weight unless otherwise specified.

I. Tetrahydroquinoline and Related Compounds

One aspect of the invention provides a compound represented by Formula I:

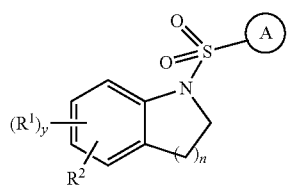

(I)

or a pharmaceutically acceptable salt or solvate thereof; wherein:

A is aryl or aralkyl; each of which is substituted with 1, 2, or 3 substituents independently selected from the group consisting of $C_{1-6}$haloalkyl, $C_{1-6}$hydroxyalkyl, —$N(R^3)(R^4)$, hydroxyl, —$CO_2R^6$, —$C_{1-6}$alkylene-$N(R^3)(R^4)$, —$C_{1-6}$alkylene-$C_{1-6}$alkoxy, —$C_{1-6}$alkylene-$CO_2R^6$, —O-aryl, —O—$C_{1-6}$alkylene-$N(R^3)(R^4)$, —O—$C_{1-6}$alkylene-$CO_2R^6$, —$N(R^5)C(O)$—$C_{1-6}$alkylene-$N(R^3)(R^4)$, —CN, —$S(O)_pC_{1-6}$alkyl, —$SO_2N(R^3)(R^4)$, —$N(R^3)SO_2(C_{1-6}$alkyl), heterocyclyl, —$C(O)$—$C_{1-6}$alkyl, —$C(O)N(R^3)(R^4)$, and —$N(R^3)C(O)N(R^3)(R^4)$;

$R^1$ represents independently for each occurrence hydrogen, halogen, or $C_{1-6}$alkyl;

$R^2$ is —$N(R^7)C(O)R^8$, —$(C_{1-2}$alkylene$)$-$N(R^7)C(O)R^8$, —$N(R^7)C(O)N(R^7)(R^8)$, or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —$N(R^3)(R^4)$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —$C(R^6)_2$-cycloalkyl, —$C(R^6)_2$-cycloalkenyl, —$C(R^6)_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^3)(R^4)$, —CN, —$CO_2$—$C_{1-6}$alkyl, —$C(O)$—$C_{1-6}$alkyl, —$C(O)N(R^3)(R^4)$, —$S(O)_pC_{1-6}$alkyl, —$SO_2N(R^3)(R^4)$, and —$N(R^3)SO_2(C_{1-6}$alkyl);

n is 1 or 2;

p represents independently for each occurrence 0, 1, or 2;

y is 1 or 2; and wherein the stereochemical configuration at a stereocenter in a compound represented by Formula I is R, S, or a mixture thereof.

In certain embodiments, A is phenyl substituted with 1, 2, or 3 substituents independently selected from the group consisting of $C_{1-6}$haloalkyl, —$N(R^3)(R^4)$, —$CO_2R^6$, —$C_{1-6}$alkylene-$N(R^3)(R^4)$, —$C_{1-6}$alkylene-$C_{1-6}$alkoxy, —$C_{1-6}$alkylene-$CO_2R^6$, —O—$C_{1-6}$alkylene-$N(R^3)(R^4)$, and —$N(R^5)C(O)$—$C_{1-6}$alkylene-$N(R^3)(R^4)$. In certain embodiments, $R^2$ is —$N(R^7)C(O)R^8$. In certain embodiments, $R^8$ is aryl substituted with 1, 2, or 3 substituents independently selected from the group consisting of halogen, $C_{1-6}$alkyl, and $C_{1-6}$haloalkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group. In certain embodiments, y is 1.

Another aspect of the invention provides a compound represented by Formula I-A:

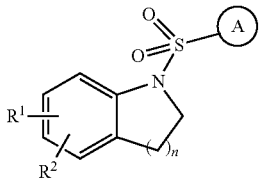

(I-A)

or a pharmaceutically acceptable salt or solvate thereof; wherein:

A is aryl or aralkyl; each of which is substituted with 1, 2, or 3 substituents independently selected from the group consisting of $C_{1-6}$haloalkyl, —$N(R^3)(R^4)$, hydroxyl, —$CO_2R^6$, —$C_{1-6}$alkylene-$N(R^3)(R^4)$, —$C_{1-6}$alkylene-$C_{1-6}$alkoxy, —$C_{1-6}$alkylene-$CO_2R^6$, —O—$C_{1-6}$alkylene-$N(R^3)(R^4)$, —$C_{1-6}$alkylene-$CO_2R^6$, —$N(R^5)C(O)$—$C_{1-6}$alkylene-$N(R^3)(R^4)$, —CN, —$S(O)_pC_{1-6}$alkyl, —$SO_2N(R^3)(R^4)$, and —$N(R^3)SO_2(C_{1-6}$alkyl);

$R^1$ represents independently for each occurrence hydrogen, halogen, or $C_{1-6}$alkyl;

$R^2$ is —$N(R^7)C(O)R^8$, —$(C_{1-2}$alkylene$)$-$N(R^7)C(O)R^8$, or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —$N(R^3)(R^4)$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —$C(R^6)_2$-cycloalkyl, —$C(R^6)_2$-cycloalkenyl, —$C(R^6)_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —$N(R^3)(R^4)$, —CN, —$CO_2$—$C_{1-6}$alkyl, —$C(O)$—$C_{1-6}$alkyl, —$S(O)_pC_{1-6}$alkyl, —$SO_2N(R^3)(R^4)$, and —$N(R^3)SO_2(C_{1-6}$alkyl);

n is 1 or 2;

p represents independently for each occurrence 0, 1, or 2; and wherein the stereochemical configuration at a stereocenter in a compound represented by Formula I-A is R, S, or a mixture thereof.

In certain embodiments, A is phenyl substituted with 1, 2, or 3 substituents independently selected from the group consisting of $C_{1-6}$haloalkyl, —$N(R^3)(R^4)$, hydroxyl, —$CO_2R^6$, —$C_{1-6}$alkylene-$N(R^3)(R^4)$, —$C_{1-6}$alkylene-$C_{1-6}$ alkoxy, —$C_{1-6}$alkylene-$CO_2R^6$, —O—$C_{1-6}$alkylene-$N(R^3)(R^4)$, and —$N(R^5)C(O)$—$C_{1-6}$alkylene-$N(R^3)(R^4)$. In certain embodiments, n is 2. In certain embodiments, n is 2, and $R^2$ is attached to the 7-position of the tetrahydroquinoline ring. In certain embodiments, $R^2$ is —$N(R^7)C(O)R^8$. In certain embodiments, $R^8$ is aryl optionally substituted with 1, 2, or 3 substituents independently selected from the group consisting of halogen, hydroxyl, $C_{1-6}$alkoxy, $C_{1-6}$alkyl, $C_{1-6}$haloalkyl, —$N(R^3)(R^4)$, —CN, —$CO_2$—$C_{1-6}$alkyl, —$C(O)$—$C_{1-6}$alkyl, and —S—$C_{1-6}$alkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group.

Another aspect of the invention provides a compound represented by Formula I-B:

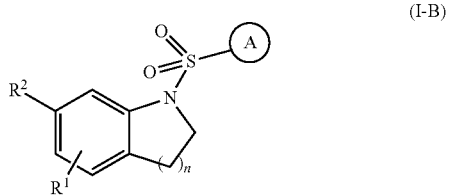

(I-B)

or a pharmaceutically acceptable salt or solvate thereof; wherein:

A is aryl or aralkyl; each of which is substituted with 1, 2, or 3 substituents independently selected from the group consisting of $C_{1-6}$haloalkyl, —$N(R^3)(R^4)$, hydroxyl, —$CO_2R^6$, —$C_{1-6}$alkylene-$N(R^3)(R^4)$, —$C_{1-6}$alkylene-$C_{1-6}$ alkoxy, —$C_{1-6}$alkylene-$CO_2R^6$, —O—$C_{1-6}$alkylene-$N(R^3)(R^4)$, —O—$C_{1-6}$alkylene-$CO_2R^6$, —$N(R^5)C(O)$—$C_{1-6}$alkylene-$N(R^3)(R^4)$, —CN, —$S(O)_pC_{1-6}$alkyl, —$SO_2N(R^3)(R^4)$, and —$N(R^3)SO_2(C_{1-6}$alkyl);

$R^1$ represents independently for each occurrence hydrogen, halogen, or $C_{1-6}$alkyl;

$R^2$ is —$N(R^7)C(O)R^8$, —$(C_{1-2}$alkylene)-$N(R^7)C(O)R^8$, or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —$N(R^3)(R^4)$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —$C(R^6)_2$-cycloalkyl, —$C(R^6)_2$-cycloalkenyl, —$C(R^6)_2$- heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —$N(R^3)(R^4)$, —CN, —$CO_2$—$C_{1-6}$alkyl, —$C(O)$—$C_{1-6}$alkyl, —$S(O)_pC_{1-6}$alkyl, —$SO_2N(R^3)(R^4)$, and —$N(R^3)SO_2(C_{1-6}$alkyl);

n is 1 or 2;

p represents independently for each occurrence 0, 1, or 2; and wherein the stereochemical configuration at a stereocenter in a compound represented by Formula I-B is R, S, or a mixture thereof.

In certain embodiments, variables A, $R^1$ through $R^8$, n, and p for Formula I-B are as defined by one of the further embodiments specified above in connection with Formula I-A.

Another aspect of the invention provides a compound of Formula II:

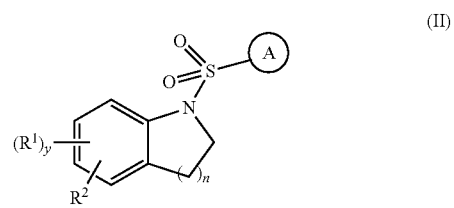

(II)

or a pharmaceutically acceptable salt or solvate thereof; wherein:

A is cycloalkyl, heterocycloalkyl, or heteroaryl containing at least one ring nitrogen or ring oxygen atom; each of which is optionally substituted with 1, 2, or 3 substituents independently selected from the group consisting of halogen, $C_{1-6}$alkyl, $C_{1-6}$haloalkyl, $C_{1-6}$hydroxyalkyl, —$N(R^3)(R^4)$, —$CO_2R^6$, —$C_{1-6}$alkylene-$N(R^3)(R^4)$, —$C_{1-6}$alkylene-$C_{1-6}$ alkoxy, —$C_{1-6}$alkylene-$CO_2R^6$, —O-aryl, —O—$C_{1-6}$alkylene-$N(R^3)(R^4)$, —$N(R^5)C(O)$—$C_{1-6}$alkylene-$N(R^3)(R^4)$, —CN, —$S(O)_pC_{1-6}$alkyl, —$SO_2N(R^3)(R^4)$, —$N(R^3)SO_2$ ($C_{1-6}$alkyl), heterocyclyl, —$C(O)$—$C_{1-6}$alkyl, —$C(O)N(R^3)(R^4)$, and —$N(R^3)C(O)N(R^3)(R^4)$;

$R^1$ represents independently for each occurrence hydrogen or $C_{1-6}$alkyl;

$R^2$ is —$N(R^7)C(O)R^8$, —$(C_{1-2}$alkylene)-$N(R^7)C(O)R^8$, —$N(R^7)C(O)N(R^7)(R^8)$, or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —$N(R^3)(R^4)$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —$C(R^6)_2$-cycloalkyl, —$C(R^6)_2$-cycloalkenyl, —$C(R^6)_2$- heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^3)(R^4)$, —CN, —$CO_2$—$C_{1-6}$alkyl, —$C(O)$—$C_{1-6}$ alkyl, —$C(O)N(R^3)(R^4)$, —$S(O)_pC_{1-6}$alkyl, —$SO_2N(R^3)(R^4)$, and —$N(R^3)SO_2(C_{1-6}$alkyl);

n is 1 or 2;

p represents independently for each occurrence 0, 1, or 2;

y is 1 or 2; and wherein the stereochemical configuration at a stereocenter in a compound represented by Formula II is R, S, or a mixture thereof.

In certain embodiments, n is 2, and $R^2$ is attached at the 7-position of the tetrahydroquinoline ring.

In certain embodiments, A is phenyl substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), and —N($R^6$)C(O)—$C_{1-6}$alkylene-N($R^3$)($R^4$).

In certain embodiments, $R^2$ is —N($R^7$)C(O)$R^8$.

In certain embodiments, $R^8$ is aryl substituted with 1, 2, or 3 substituents independently selected from the group consisting of halogen, $C_{1-6}$alkyl, and $C_{1-6}$haloalkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group. In certain embodiments, y is 1.

Another aspect of the invention provides a compound of Formula II-A:

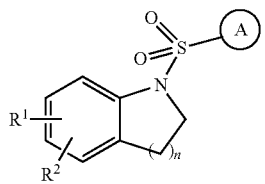

(II-A)

or a pharmaceutically acceptable salt or solvate thereof; wherein:

A is cycloalkyl, heterocycloalkyl, or heteroaryl containing at least one ring nitrogen or ring oxygen atom; each of which is optionally substituted with 1, 2, or 3 substituents independently selected from the group consisting of halogen, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), —N($R^5$)C(O)—$C_{1-6}$alkylene-N($R^3$)($R^4$), —CN, —S(O)$_p$$C_{1-6}$alkyl, —$SO_2$N($R^3$)($R^4$), and —N($R^3$)$SO_2$($C_{1-6}$alkyl);

$R^1$ represents independently for each occurrence hydrogen, halogen, or $C_{1-6}$alkyl;

$R^2$ is —N($R^7$)C(O)$R^8$, —($C_{1-2}$alkylene)-N($R^7$)C(O)$R^8$, or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —N($R^3$)($R^4$);

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —C($R^6$)$_2$-cycloalkyl, —C($R^6$)$_2$-cycloalkenyl, —C($R^6$)$_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, —S(O)$_p$$C_{1-6}$alkyl, —$SO_2$N($R^3$)($R^4$), and —N($R^3$)$SO_2$($C_{1-6}$alkyl);

n is 1 or 2;

p represents independently for each occurrence 0, 1, or 2; and wherein the stereochemical configuration at a stereocenter in a compound represented by Formula II-A is R, S, or a mixture thereof.

In certain embodiments, A is heteroaryl containing at least one ring nitrogen or ring oxygen atom; wherein said heteroaryl is optionally substituted with 1, 2, or 3 substituents independently selected from the group consisting of halogen, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), and —N($R^5$)C(O)—$C_{1-6}$alkylene-N($R^3$)($R^4$). In certain embodiments, $R^1$ is hydrogen. In certain embodiments, $R^2$ is —N($R^7$)C(O)$R^8$. In certain embodiments, n is 2. In certain embodiments, n is 2, and $R^2$ is attached to the 7-position of the tetrahydroquinoline ring. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group.

Another aspect of the invention provides a compound of Formula II-B:

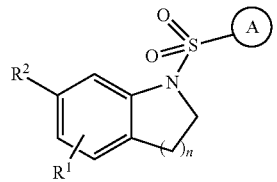

(II-B)

or a pharmaceutically acceptable salt or solvate thereof; wherein:

A is cycloalkyl, heterocycloalkyl, or heteroaryl containing at least one ring nitrogen or ring oxygen atom; each of which is optionally substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), —N($R^5$)C(O)—$C_{1-6}$alkylene-N($R^3$)($R^4$), —CN, —S(O)$_p$$C_{1-6}$alkyl, —$SO_2$N($R^3$)($R^4$), and —N($R^3$)$SO_2$($C_{1-6}$alkyl);

$R^1$ represents independently for each occurrence hydrogen, halogen, or $C_{1-6}$alkyl;

$R^2$ is —N($R^7$)C(O)$R^8$, —($C_{1-2}$alkylene)-N($R^7$)C(O)$R^8$, or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —N($R^3$)($R^4$);

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —C($R^6$)$_2$-cycloalkyl, —C($R^6$)$_2$-cycloalkenyl, —C($R^6$)$_2$-heterocyclyl, or C$_{1-6}$alkyl; each of which is optionally substituted with 1, 2, or 3 substituents independently selected from the group consisting of halogen, hydroxyl, C$_{1-6}$alkoxy, C$_{1-6}$alkyl, C$_{1-6}$haloalkyl, —N($R^3$)($R^4$), —CN, —CO$_2$—C$_{1-6}$alkyl, —C(O)—C$_{1-6}$alkyl, —S(O)$_p$C$_{1-6}$alkyl, —SO$_2$N($R^3$)($R^4$), and —N($R^3$)SO$_2$(C$_{1-6}$alkyl);

n is 1 or 2;

p represents independently for each occurrence 0, 1, or 2; and wherein the stereochemical configuration at a stereocenter in a compound represented by Formula II-B is R, S, or a mixture thereof.

In certain embodiments, variables A, $R^1$ through $R^8$, n, and p for Formula II-B are as defined by one of the further embodiments specified above in connection with Formula II-A.

Another aspect of the invention provides a compound of Formula III:

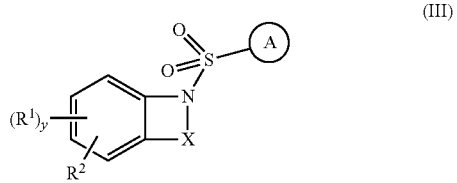

(III)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, C$_{1-6}$alkyl, C$_{1-6}$haloalkyl, C$_{1-6}$hydroxyalkyl, —N($R^3$)($R^4$), —CO$_2$$R^6$, —C$_{1-6}$alkylene-N($R^3$)($R^4$), —C$_{1-6}$alkylene-C$_{1-6}$alkoxy, —C$_{1-6}$alkylene-CO$_2$$R^6$, —O-aryl, —O—C$_{1-6}$alkylene-N($R^3$)($R^4$), —C$_{1-6}$alkylene-CO$_2$$R^6$, —N($R^6$)C(O)—C$_{1-6}$alkylene-N($R^3$)($R^4$), —CN, —S(O)$_p$C$_{1-6}$alkyl, —SO$_2$N($R^3$)($R^4$), —N($R^3$)SO$_2$(C$_{1-6}$alkyl), heterocyclyl, C(O)$R^{11}$, —C($R^{11}$)($R^{12}$)OH, —C(O)N($R^3$)($R^4$), and —N($R^3$)C(O)N($R^3$)($R^4$);

X is —O—[C($R^6$)$_2$]$_m$-ψ, —O—[C($R^6$)($R^9$)C($R^6$)$_2$]-ψ, —O—[C($R^6$)($R^9$)]-ψ, —O—[C($R^6$)$_2$—C(hydroxyC$_{1-6}$alkyl)($R^6$)]-ψ, —C($R^5$)(C$_{1-6}$alkyl)[C($R^5$)$_2$]$_m$-ψ, —[C($R^5$)$_2$]$_m$—C($R^5$)(C$_{1-6}$alkyl)-ψ, —C($R^5$)$_2$—C($R^5$)(C$_{1-6}$alkyl)-C($R^5$)$_2$-ψ, —C($R^5$)$_2$C($R^6$)=C($R^6$)-ψ, —C($R^6$)=C($R^6$)C($R^5$)$_2$-ψ, —C($R^6$)=C($R^6$)-ψ, —N($R^6$)—[C($R^6$)$_2$]$_m$-ψ, —N=C($R^6$)-ψ, —N=C($R^6$)C($R^6$)$_2$-ψ, —N=N-ψ, —C($R^6$)=N- ψ, —C($R^{10}$)=N-ψ, —C($R^6$)$_2$C(O)C($R^6$)$_2$-ψ, —[C($R^6$)$_2$]$_m$—C(O)-ψ, —C($R^6$)=C($R^6$)C(O)-ψ, —C(O)C($R^6$)=C($R^6$)-ψ, —N($R^6$)—C(O)-ψ, or —C(H)(O$R^6$)—[C($R^6$)$_2$]$_m$-ψ; wherein ψ is a bond to the sulfonamide ring nitrogen atom in Formula III;

$R^1$ represents independently for each occurrence hydrogen, halogen, or C$_{1-6}$alkyl;

$R^2$ is —N($R^7$)C(O)$R^8$, —(C$_{1-2}$alkylene)-N($R^7$)C(O)$R^8$, —N($R^7$)C(O)N($R^7$)($R^8$), or heteroaryl, wherein said heteroaryl group is optionally substituted with 1 or 2 substituents independently selected from the group consisting of halogen, hydroxyl, C$_{1-6}$alkoxy, C$_{1-6}$alkyl, C$_{1-6}$haloalkyl, aryl, heteroaryl, and —N($R^3$)($R^4$);

$R^3$ and $R^4$ each represent independently hydrogen or C$_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or C$_{1-6}$alkyl;

$R^6$ and $R^7$ each represent independently for each occurrence hydrogen or C$_{1-6}$alkyl;

$R^8$ is aryl, aralkyl, cycloalkyl, cycloalkenyl, heterocyclyl, —C($R^6$)$_2$-cycloalkyl, —C($R^6$)$_2$-cycloalkenyl, —C($R^6$)$_2$-heterocyclyl, or C$_{1-6}$alkyl; each of which is optionally substituted with 1, 2, or 3 substituents independently selected from the group consisting of halogen, hydroxyl, C$_{1-6}$alkoxy, C$_{1-6}$haloalkoxy, C$_{1-6}$alkyl, C$_{1-6}$haloalkyl, —N($R^3$)($R^4$), —CN, —CO$_2$—C$_{1-6}$alkyl, —C(O)—C$_{1-6}$alkyl, —C(O)N($R^3$)($R^4$), —S(O)$_p$C$_{1-6}$alkyl, —SO$_2$N($R^3$)($R^4$), and —N($R^3$)SO$_2$(C$_{1-6}$alkyl);

$R^9$ and $R^{10}$ each represent independently C$_{1-6}$haloalkyl, C$_{1-6}$hydroxyalkyl, —C$_{1-6}$alkylene-N($R^3$)($R^4$), —C$_{1-6}$alkylene-N($R^3$)C(O)—C$_{1-6}$alkyl, —C$_{1-6}$alkylene-CO$_2$$R^3$, —C$_{1-6}$ alkylene-CN, —C$_{1-6}$alkylene-C$_{1-6}$alkoxy, —C$_{1-6}$alkylene-C(O)N($R^3$)($R^4$), —C(O)N($R^3$)($R^4$), —C$_{1-6}$alkylene-N($R^3$)C(O)N($R^3$)($R^4$), —C$_{1-6}$alkylene-N($R^3$)C(O)—[C(OH)($R^3$)($R^4$)], —C$_{1-6}$alkylene-O—C(O)N($R^3$)($R^4$), —C$_{1-6}$alkylene-SO$_2$N($R^3$)($R^4$), —C$_{1-6}$alkylene-N($R^3$)SO$_2$N($R^3$)($R^4$), C$_{2-4}$alkenyl, -arylene-CO$_2$$R^6$, or —CN;

$R^{11}$ is C$_{1-6}$alkyl, C$_{1-6}$haloalkyl, aryl, aralkyl, heteroaryl, or heterocycloalkyl; each of which is optionally substituted with 1 or 2 substituents independently selected from the group consisting of halogen, C$_{1-6}$alkyl, C$_{1-6}$haloalkyl, hydroxyl, C$_{1-6}$alkoxy, C$_{1-6}$haloalkoxy, —CO$_2$$R^3$, and, —N($R^3$)($R^4$);

$R^{12}$ is hydrogen, C$_{1-6}$alkyl, C$_{1-6}$haloalkyl, aryl, aralkyl, heteroaryl, or heterocycloalkyl; each of which is optionally substituted with 1 or 2 substituents independently selected from the group consisting of halogen, C$_{1-6}$alkyl, C$_{1-6}$haloalkyl, hydroxyl, C$_{1-6}$alkoxy, C$_{1-6}$haloalkoxy, —CO$_2$$R^3$, and, —N($R^3$)($R^4$);

m is 1 or 2;

p represents independently for each occurrence 0, 1, or 2;

y is 1 or 2; and wherein the stereochemical configuration at a stereocenter in a compound represented by Formula III is R, S, or a mixture thereof.

In certain embodiments, A is aryl substituted with 1, 2, or 3 substituents independently selected from the group consisting of halogen, hydroxyl, C$_{1-6}$alkyl, C$_{1-6}$haloalkyl, —N($R^3$)($R^4$), —CN, —CO$_2$$R^6$, —C(O)—C$_{1-6}$alkyl, —C$_{1-6}$alkylene-N($R^3$)($R^4$), —C$_{1-6}$alkylene-C$_{1-6}$alkoxy, —C$_{1-6}$alkylene-CO$_2$$R^6$, —O—C$_{1-6}$alkylene-N($R^3$)($R^4$), and —N($R^6$)C(O)—C$_{1-6}$alkylene-N($R^3$)($R^4$). In certain other embodiments, A is phenyl substituted with 1, 2, or 3 substituents independently selected from the group consisting of halogen, hydroxyl, C$_{1-6}$alkyl, C$_{1-6}$haloalkyl, —N($R^3$)($R^4$), —CN, —CO$_2$$R^6$, —C(O)—C$_{1-6}$alkyl, —C$_{1-6}$alkylene-N($R^3$)($R^4$), —C$_{1-6}$alkylene-C$_{1-6}$alkoxy, —C$_{1-6}$alkylene-CO$_2$$R^6$, —O—C$_{1-6}$alkylene-N($R^3$)($R^4$), and —N($R^6$)C(O)—C$_{1-6}$alkylene-N($R^3$)($R^4$). In yet other embodiments, A is phenyl substituted with 1, 2, or 3 substituents independently selected from the group consisting of halogen, C$_{1-6}$alkyl, C$_{1-6}$haloalkyl, and —CN.

In certain embodiments, X is —O—[C($R^6$)$_2$]$_m$-ψ or —O—[C($R^6$)($R^9$)C($R^6$)$_2$]-ψ. In certain other embodiments, X is —C($R^6$)=N-ψ or —C($R^{10}$)=N-ψ. In yet other embodiments, X is —C($R^5$)(C$_{1-6}$alkyl)[C($R^5$)$_2$]$_m$-ψ, —[C($R^5$)$_2$]$_m$—C($R^5$)(C$_{1-6}$alkyl)-ψ, —C($R^5$)$_2$—C($R^5$)(C$_{1-6}$alkyl)-C($R^5$)$_2$-ψ, —C($R^5$)$_2$C($R^6$)=C($R^6$)-ψ, —C($R^6$)=C($R^6$)C($R^5$)$_2$-ψ, or —C($R^6$)=C($R^6$)-ψ.

In certain embodiments, $R^2$ is —N($R^7$)C(O)$R^8$.

In certain embodiments, $R^8$ is aryl or aralkyl, each of which is substituted with 1, 2, or 3 substituents independently selected from the group consisting of halogen, $C_{1-6}$alkyl, and $C_{1-6}$haloalkyl. In certain other embodiments, $R^8$ is aryl substituted with 1, 2, or 3 substituents independently selected from the group consisting of halogen, $C_{1-6}$alkyl, and $C_{1-6}$haloalkyl. In certain other embodiments, $R^8$ is phenyl substituted with 1, 2, or 3 substituents independently selected from the group consisting of halogen, $C_{1-6}$alkyl, and $C_{1-6}$haloalkyl. In certain other embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group.

In certain embodiments, y is 1.

Another aspect of the invention provides a compound of Formula III-A:

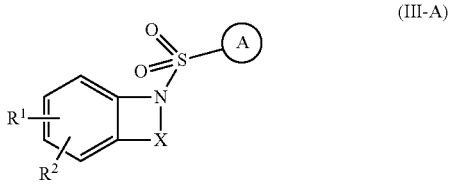

(III-A)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), —$C_{1-6}$alkylene-$CO_2R^6$, —N($R^6$)C(O)—$C_{1-6}$alkylene-N($R^3$)($R^4$), —CN, —S(O)$_p$$C_{1-6}$alkyl, —$SO_2$N($R^3$)($R^4$), and —N($R^3$)$SO_2$($C_{1-6}$alkyl);

X is —C($R^5$)($C_{1-6}$alkyl)[C($R^5$)$_2$]$_m$-ψ, —[C($R^5$)$_2$]$_m$—C($R^5$)($C_{1-6}$alkyl)-ψ, —C($R^5$)$_2$—C($R^5$)($C_{1-6}$alkyl)-C($R^5$)$_2$-ψ, —C($R^5$)$_2$C($R^6$)=C($R^8$)-ψ, —C($R^6$)=C($R^6$)C($R^5$)$_2$-ψ, —C($R^6$)=C($R^6$)-ψ, —O—[C($R^6$)$_2$]$_m$-ψ, —N($R^6$)—[C($R^6$)$_2$]$_m$-ψ, —N=C($R^6$)-ψ, —N=C($R^6$)C($R^6$)$_2$-ψ, —N=N-ψ, —C($R^6$)=N- ψ, —C(O)—[C($R^6$)$_2$]$_m$-ψ, —C($R^6$)$_2$C(O)C($R^6$)$_2$-ψ, —[C($R^6$)$_2$]$_m$—C(O)-ψ, —C($R^6$)=C($R^6$)C(O)-ψ, —C(O)C($R^6$)=C($R^6$)-ψ, —N($R^6$)—C(O)-ψ, or —C(H)(O$R^6$)—[C($R^6$)$_2$]$_m$-ψ; wherein ψ is a bond to the sulfonamide ring nitrogen atom in Formula III-A;

$R^1$ represents independently for each occurrence hydrogen, halogen, or $C_{1-6}$alkyl;

$R^2$ is —N($R^7$)C(O)$R^8$, —($C_{1-2}$alkylene)-N($R^7$)C(O)$R^8$, or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —N($R^3$)($R^4$);

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —(R^6)$_2$-cycloalkyl, —($R^6$)$_2$-cycloalkenyl, —($R^6$)$_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, —S(O)$_p$$C_{1-6}$alkyl, —$SO_2$N($R^3$)($R^4$), and —N($R^3$)$SO_2$($C_{1-6}$alkyl);

m is 1 or 2;

p represents independently for each occurrence 0, 1, or 2; and wherein the stereochemical configuration at a stereocenter in a compound represented by Formula III-A is R, S, or a mixture thereof.

In certain embodiments, A is phenyl optionally substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), and —N($R^6$)C(O)—$C_{1-6}$alkylene-N($R^3$)($R^4$). In certain embodiments, X is —C($R^5$)($C_{1-6}$alkyl)[C($R^5$)$_2$]$_m$-ψ, —[C($R^5$)$_2$]$_m$—C($R^5$)($C_{1-6}$alkyl)-ψ, —C($R^5$)$_2$—C($R^5$)($C_{1-6}$alkyl)-C($R^5$)$_2$-ψ, —C($R^5$)$_2$C($R^6$)=C($R^8$)-ψ, —C($R^6$)=C($R^6$)C($R^5$)$_2$-ψ, or —C($R^6$)=C($R^6$)-ψ. In certain embodiments, X is —C(O)—[C($R^6$)$_2$]$_m$-ψ. In certain embodiments, $R^2$ is —N($R^7$)C(O)$R^8$. In certain embodiments, $R^5$ is hydrogen. In certain embodiments, $R^8$ is aryl optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, and —S—$C_{1-6}$alkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group.

Another aspect of the invention provides a compound of Formula III-B:

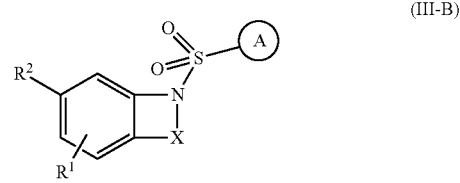

(III-B)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), —$C_{1-6}$alkylene-$CO_2R^6$, —N($R^6$)C(O)—$C_{1-6}$alkylene-N($R^3$)($R^4$), —CN, —S(O)$_p$$C_{1-6}$alkyl, —$SO_2$N($R^3$)($R^4$), and —N($R^3$)$SO_2$($C_{1-6}$alkyl);

X is —C($R^5$)($C_{1-6}$alkyl)[C($R^5$)$_2$]$_m$-ψ, —[C($R^5$)$_2$]$_m$—C($R^5$)($C_{1-6}$alkyl)-ψ, —C($R^5$)$_2$—C($R^5$)($C_{1-6}$alkyl)-C($R^5$)$_2$-ψ, —C($R^5$)$_2$C($R^6$)=C($R^8$)-ψ, —C($R^6$)=C($R^6$)C($R^5$)$_2$-ψ, —C($R^6$)=C($R^6$)-ψ, —O—[C($R^6$)$_2$]$_m$-ψ, —N($R^6$)—[C($R^6$)$_2$]$_m$-ψ, —N=C($R^6$)-ψ, —N=C($R^6$)C($R^6$)$_2$-ψ, —N=N-ψ, —C($R^6$)=N-ψ, —C(O)—[C($R^6$)$_2$]$_m$-ψ, —C($R^6$)$_2$C(O)C($R^6$)$_2$-ψ, —[C($R^6$)$_2$]$_m$—C(O)-ψ, —C($R^6$)=C($R^6$)C(O)-ψ, —C(O)C($R^6$)=C($R^6$)-ψ, —N($R^6$)—C(O)-ψ, or —C(H)(O$R^6$)—[C($R^6$)$_2$]$_m$-ψ; wherein ψ is a bond to the sulfonamide ring nitrogen atom in Formula III-B;

$R^1$ represents independently for each occurrence hydrogen, halogen, or $C_{1-6}$alkyl;

$R^2$ is $—N(R^7)C(O)R^8$, $—(C_{1-2}$alkylene$)-N(R^7)C(O)R^8$, or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and $—N(R^3)(R^4)$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, $—C(R^6)_2$-cycloalkyl, $—C(R^6)_2$-cycloalkenyl, $—C(R^6)_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, $—N(R^3)(R^4)$, $—CN$, $—CO_2—C_{1-6}$alkyl, $—C(O)—C_{1-6}$alkyl, $—S(O)_pC_{1-6}$alkyl, $—SO_2N(R^3)(R^4)$, and $—N(R^3)SO_2(C_{1-6}$alkyl);

m is 1 or 2;

p represents independently for each occurrence 0, 1, or 2; and wherein the stereochemical configuration at a stereocenter in a compound represented by Formula III-B is R, S, or a mixture thereof.

In certain embodiments, variables A, $R^1$ through $R^8$, n, and p for Formula III-B are as defined by one of the further embodiments specified above in connection with Formula M-A.

Another aspect of the invention provides a compound of Formula III-C:

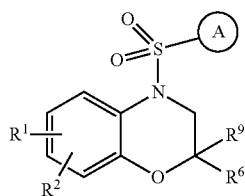

(III-C)

or a pharmaceutically acceptable salt or solvate thereof; wherein:

A is aryl or heteroaryl; each of which is substituted with 1, 2, or 3 substituents independently selected from the group consisting of halogen, hydroxyl, $C_{1-6}$alkyl, $C_{1-6}$haloalkyl, $—CN$, and $—C(O)—C_{1-6}$alkyl;

$R^1$ represents independently for each occurrence hydrogen, halogen, or $C_{1-6}$alkyl;

$R^2$ is $—N(R^7)C(O)R^8$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^6$ and $R^7$ each represent independently for each occurrence hydrogen or $C_{1-6}$alkyl;

$R^8$ is aryl substituted with 1, 2, or 3 substituents independently selected from the group consisting of halogen, $C_{1-6}$alkyl, and $C_{1-6}$haloalkyl;

$R^9$ is $C_{1-6}$haloalkyl, $C_{1-6}$hydroxyalkyl, $—C_{1-6}$alkylene-N$(R^3)(R^4)$, $—C_{1-6}$alkylene-N$(R^3)C(O)—C_{1-6}$alkyl, $—C_{1-6}$alkylene-CN, or $—C_{1-6}$alkylene-$C_{1-6}$alkoxy; and wherein the stereochemical configuration at a stereocenter in a compound represented by Formula III-C is R, S, or a mixture thereof.

In certain embodiments, A is phenyl substituted with 1, 2, or 3 substituents independently selected from the group consisting of halogen, hydroxyl, $C_{1-6}$alkyl, $C_{1-6}$haloalkyl, and $—CN$. In certain embodiments, $R^8$ is phenyl substituted with 1, 2, or 3 substituents independently selected from the group consisting of halogen, $C_{1-6}$alkyl, and $C_{1-6}$haloalkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group. In certain embodiments, $R^9$ is $C_{1-6}$haloalkyl, $C_{1-6}$hydroxyalkyl, $—C_{1-6}$alkylene-N$(R^3)C(O)—C_{1-6}$alkyl, or $—C_{1-6}$alkylene-$C_{1-6}$alkoxy. In certain embodiments, $R^2$ is attached to the 6-position of the benzoxazine ring.

Another aspect of the invention provides a compound of Formula III-D:

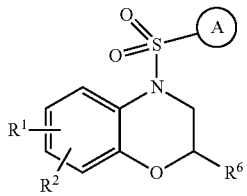

(III-D)

or a pharmaceutically acceptable salt or solvate thereof; wherein:

A is aryl or heteroaryl; each of which is substituted with 1, 2, or 3 substituents independently selected from the group consisting of halogen, hydroxyl, $C_{1-6}$alkyl, $C_{1-6}$haloalkyl, $—CN$, and $—C(O)—C_{1-6}$alkyl;

$R^1$ represents independently for each occurrence hydrogen, halogen, or $C_{1-6}$alkyl;

$R^2$ is $—N(R^7)C(O)R^8$;

$R^6$ is $C_{1-6}$alkyl;

$R^7$ is hydrogen or $C_{1-6}$alkyl;

$R^8$ is aryl substituted with 1, 2, or 3 substituents independently selected from the group consisting of halogen, $C_{1-6}$alkyl, and $C_{1-6}$haloalkyl; and wherein the stereochemical configuration at a stereocenter in a compound represented by Formula III-D is R, S, or a mixture thereof.

In certain embodiments, A is phenyl substituted with 1, 2, or 3 substituents independently selected from the group consisting of halogen, hydroxyl, $C_{1-6}$alkyl, $C_{1-6}$haloalkyl, and $—CN$. In certain embodiments, $R^8$ is phenyl substituted with 1, 2, or 3 substituents independently selected from the group consisting of halogen, $C_{1-6}$alkyl, and $C_{1-6}$haloalkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group. In certain embodiments, $R^6$ is methyl. In certain embodiments, $R^1$ and $R^7$ are hydrogen. In certain embodiments, $R^2$ is attached at the 6-position of the benzoxazine ring.

Another aspect of the invention provides a compound of Formula III-E:

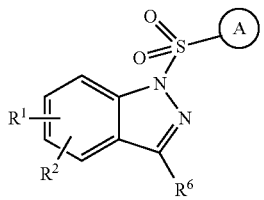

(III-E)

or a pharmaceutically acceptable salt or solvate thereof; wherein:

A is aryl or heteroaryl; each of which is substituted with 1, 2, or 3 substituents independently selected from the group consisting of halogen, hydroxyl, $C_{1-6}$alkyl, $C_{1-6}$haloalkyl, —CN, and —C(O)—$C_{1-6}$alkyl;

$R^1$ represents independently for each occurrence hydrogen, halogen, or $C_{1-6}$alkyl;

$R^2$ is —N($R^7$)C(O)$R^8$;

$R^6$ is $C_{1-6}$alkyl;

$R^7$ is hydrogen or $C_{1-6}$alkyl;

$R^8$ is aryl substituted with 1, 2, or 3 substituents independently selected from the group consisting of halogen, $C_{1-6}$alkyl, and $C_{1-6}$haloalkyl; and wherein the stereochemical configuration at a stereocenter in a compound represented by Formula III-E is R, S, or a mixture thereof.

In certain embodiments, A is phenyl substituted with 1, 2, or 3 substituents independently selected from the group consisting of halogen, hydroxyl, $C_{1-6}$alkyl, $C_{1-6}$haloalkyl, and —CN. In certain embodiments, $R^8$ is phenyl substituted with 1, 2, or 3 substituents independently selected from the group consisting of halogen, $C_{1-6}$alkyl, and $C_{1-6}$haloalkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group. In certain embodiments, $R^1$, $R^6$, and $R^7$ are hydrogen. In certain embodiments, $R^2$ is attached at the 6-position of the indazole ring.

Another aspect of the invention provides a compound of Formula III-F:

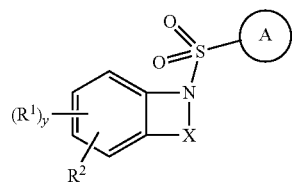

(III-F)

or a pharmaceutically acceptable salt or solvate thereof; wherein:

A is aryl or heteroaryl; each of which is substituted with 1, 2, or 3 substituents independently selected from the group consisting of halogen, hydroxyl, $C_{1-6}$alkyl, $C_{1-6}$haloalkyl, $C_{1-6}$hydroxyalkyl, —N($R^3$)($R^4$), —CO$_2R^6$, —$C_{1-6}$alkylene-N($R^3$)($R^4$), —$C_{1-6}$alkylene-$C_{1-6}$alkoxy, —$C_{1-6}$alkylene-CO$_2R^6$, —O-aryl, —O—$C_{1-6}$alkylene-N($R^3$)($R^4$), —$C_{1-6}$alkylene-CO$_2R^6$, —N($R^6$)C(O)—$C_{1-6}$alkylene-N($R^3$)($R^4$), —CN, —S(O)$_pC_{1-6}$alkyl, —SO$_2$N($R^3$)($R^4$), —N($R^3$)SO$_2$($C_{1-6}$alkyl), heterocyclyl, C(O)$R^{11}$, —C($R^{11}$)($R^{12}$)OH, —C(O)N($R^3$)($R^4$), and —N($R^3$)C(O)N($R^3$)($R^4$);

X is —C($R^6$)=N-ψ or —C($R^{10}$)=N-ψ; wherein ψ is a bond to the sulfonamide ring nitrogen atom in Formula III-F;

$R^1$ represents independently for each occurrence hydrogen, halogen, or $C_{1-6}$alkyl;

$R^2$ is —N($R^7$)C(O)$R^8$ or —($C_{1-2}$alkylene)-N($R^7$)C(O)$R^8$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl or aralkyl; each of which is substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^3$)($R^4$), —CN, —CO$_2$—$C_{1-6}$alkyl, —C(O)—$C_{1-6}$alkyl, —C(O)N($R^3$)($R^4$), —S(O)$_pC_{1-6}$alkyl, —SO$_2$N($R^3$)($R^4$), and —N($R^3$)SO$_2$($C_{1-6}$alkyl);

$R^9$ and $R^{10}$ each represent independently $C_{1-6}$haloalkyl, $C_{1-6}$hydroxyalkyl, —$C_{1-6}$alkylene-N($R^3$)($R^4$), —$C_{1-6}$alkylene-N($R^3$)C(O)—$C_{1-6}$alkyl, —$C_{1-6}$alkylene-CO$_2R^3$, —$C_{1-6}$alkylene-CN, —$C_{1-6}$alkylene-$C_{1-6}$alkoxy, —$C_{1-6}$alkylene-C(O)N($R^3$)($R^4$), —C(O)N($R^3$)($R^4$), —$C_{1-6}$alkylene-N($R^3$)C(O)N($R^3$)($R^4$), —$C_{1-6}$alkylene-N($R^3$)C(O)—[C(OH)($R^3$)($R^4$)], —$C_{1-6}$alkylene-O—C(O)N($R^3$)($R^4$), —$C_{1-6}$alkylene-SO$_2$N($R^3$)($R^4$), —$C_{1-6}$alkylene-N($R^3$)SO$_2$N($R^3$)($R^4$), $C_{2-4}$alkenyl, -arylene-CO$_2R^6$, or —CN;

$R^{11}$ is $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —CO$_2R^3$, and, —N($R^3$)($R^4$);

$R^{12}$ is hydrogen, $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —CO$_2R^3$, and, —N($R^3$)($R^4$);

m is 1 or 2;

p represents independently for each occurrence 0, 1, or 2;

y is 1 or 2; and wherein the stereochemical configuration at a stereocenter in a compound represented by Formula III-F is R, S, or a mixture thereof.

Another aspect of the invention provides a compound of Formula IV:

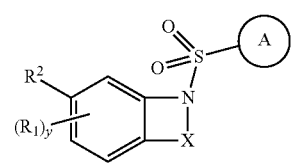

(IV)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), —N($R^6$)C(O)—$C_{1-6}$ alkylene-N($R^3$)($R^4$), —CN, —S(O)$_p C_{1-6}$alkyl, —$SO_2$N($R^3$)($R^4$), —N($R^3$)$SO_2$($C_{1-6}$alkyl), heterocyclyl, —C(O)$R^{11}$, —C($R^{11}$)($R^{12}$)OH, —C(O)N($R^3$)($R^4$), and —N($R^3$)C(O)N($R^3$)($R^4$);

X is —C($R^5$)$_2$C($R^6$)=C($R^6$)-ψ, —C($R^6$)=C($R^6$)C($R^5$)$_2$-ψ, —C(O)—[C($R^6$)$_2$]$_m$ψ, —C($R^6$)$_2$C(O)C($R^6$)$_2$-ψ, —[C($R^6$)$_2$]$_m$—C(O)-ψ, —C($R^6$)=C($R^6$)C(O)-ψ, —C(O)C($R^6$)=C($R^6$)-ψ, —O—[C($R^6$)$_2$]$_m$-ψ, —O—[C($R^6$)($R^9$)C($R^6$)]$_2$-ψ, —O—[C($R^6$)($R^9$)]-ψ, —O—[C($R^6$)$_2$—C(hydroxy$C_{1-6}$alkyl)($R^6$)]-ψ, —C($R^6$)=N-ψ, —C($R^{10}$)=N-ψ, or —C(H)(O$R^6$)—[C($R^6$)$_2$]$_m$-ψ; wherein ψ is a bond to the sulfonamide ring nitrogen atom in Formula IV;

$R^1$ represents independently for each occurrence hydrogen, halogen, or $C_{1-6}$alkyl;

$R^2$ is —C(O)N($R^7$)($R^8$) or —N($R^7$)C(O)N($R^7$)($R^8$);

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —C($R^6$)$_2$-cycloalkyl, —C($R^6$)$_2$-cycloalkenyl, —C($R^6$)$_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, —C(O)N($R^3$)($R^4$), —S(O)$_p C_{1-6}$alkyl, —$SO_2$N($R^3$)($R^4$), and —N($R^3$)$SO_2$($C_{1-6}$alkyl);

$R^9$ and $R^{10}$ each represent independently $C_{1-6}$haloalkyl, $C_{1-6}$hydroxyalkyl, —$C_{1-6}$alkylene-N($R^3$)($R^4$), —$C_{1-6}$alkylene-N($R^3$)C(O)—$C_{1-6}$alkyl, —$C_{1-6}$alkylene-$CO_2R^3$, —$C_{1-6}$ alkylene-CN, —$C_{1-6}$alkylene-$C_{1-6}$alkoxy, —$C_{1-6}$alkylene-C(O)N($R^3$)($R^4$), —C(O)N($R^3$)($R^4$), —$C_{1-6}$alkylene-N($R^3$)C(O)N($R^3$)($R^4$), —$C_{1-6}$alkylene-N($R^3$)C(O)—[C(OH)($R^3$)($R^4$)], —$C_{1-6}$alkylene-O—C(O)N($R^3$)($R^4$), —$C_{1-6}$alkylene-$SO_2$N($R^3$)($R^4$), —$C_{1-6}$alkylene-N($R^3$)$SO_2$N($R^3$)($R^4$), $C_{2-4}$alkenyl, -arylene-$CO_2R^6$, or —CN;

$R^{11}$ is $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —$CO_2R^3$, and, —N($R^3$)($R^4$);

$R^{12}$ is hydrogen, $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —$CO_2R^3$, and, —N($R^3$)($R^4$);

m is 1 or 2;
p represents independently for each occurrence 0, 1, or 2;
y is 1 or 2; and
wherein the stereochemical configuration at a stereocenter in a compound represented by Formula IV is R, S, or a mixture thereof.

In certain embodiments, A is phenyl substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), and —N($R^6$)C(O)—$C_{1-6}$alkylene-N($R^3$)($R^4$). In certain embodiments, $R^8$ is aryl substituted with 1, 2, or 3 substituents independently selected from the group consisting of halogen, $C_{1-6}$alkyl, and $C_{1-6}$haloalkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group. In certain embodiments, y is 1.

Another aspect of the invention provides a compound of Formula IV-A:

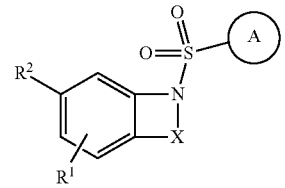

(IV-A)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), —N($R^6$)C(O)—$C_{1-6}$alkylene-N($R^3$)($R^4$), —CN, —S(O)$_p C_{1-6}$alkyl, —$SO_2$N($R^3$)($R^4$), and —N($R^3$)$SO_2$($C_{1-6}$alkyl);

X is —C($R^5$)$_2$C($R^6$)=C($R^8$)-ψ, —C($R^6$)=C($R^6$)C($R^5$)$_2$-ψ, —C(O)—[C($R^6$)$_2$]$_m$-ψ, —C($R^6$)$_2$C(O)C($R^6$)$_2$-ψ, —[C($R^6$)$_2$]$_m$—C(O)-ψ, —C($R^6$)=C($R^6$)C(O)-ψ, —C(O)C($R^6$)=C($R^6$)-ψ, or —C(H)(O$R^6$)—[C($R^6$)$_2$]$_m$-ψ; wherein ψ is a bond to the sulfonamide ring nitrogen atom in Formula IV-A;

$R^1$ represents independently for each occurrence hydrogen, halogen, or $C_{1-6}$alkyl;

$R^2$ is —C(O)N($R^7$)($R^8$);

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —C($R^6$)$_2$-cycloalkyl, —C($R^6$)$_2$-cycloalkenyl, —C($R^6$)$_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, —S(O)$_p C_{1-6}$alkyl, —$SO_2$N($R^3$)($R^4$), and —N($R^3$)$SO_2$($C_{1-6}$alkyl);

m is 1 or 2;

p represents independently for each occurrence 0, 1, or 2; and wherein the stereochemical configuration at a stereocenter in a compound represented by Formula IV-A is R, S, or a mixture thereof.

In certain embodiments, A is phenyl optionally substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), and —N($R^6$)C(O)—$C_{1-6}$alkylene-N($R^3$)($R^4$). In certain embodiments, $R^8$ is aryl optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, and —S—$C_{1-6}$alkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group. In certain embodiments, X is —C(O)—[C($R^6$)$_2$]$_m$-ψ, —C($R^6$)$_2$C(O)C($R^6$)$_2$-ψ, —[C($R^6$)$_2$]$_m$—C(O)-ψ, —C($R^6$)=C($R^6$)C(O)-ψ, or —C(O)C($R^6$)=C($R^6$)-ψ.

Another aspect of the invention provides a compound represented by Formula V:

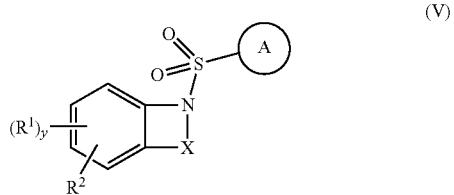

(V)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, $C_{1-6}$alkyl, $C_{1-6}$haloalkyl, $C_{1-6}$hydroxyalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O-aryl, —O—$C_{1-6}$alkylene-N($R^3$)($R^4$), —N($R^6$)C(O)—$C_{1-6}$alkylene-N($R^3$)($R^4$), —CN, —S(O)$_p$$C_{1-6}$alkyl, —$SO_2$N($R^3$)($R^4$), —N($R^3$)$SO_2$($C_{1-6}$alkyl), heterocyclyl, —C(O)$R^{11}$, —C($R^{11}$)($R^{12}$)OH, —C(O)N($R^3$)($R^4$), and —N($R^3$)C(O)N($R^3$)($R^4$);

X is —[C($R^5$)$_2$]$_n$-ψ, —C($R^5$)$_2$C($R^6$)=C($R^6$)-ψ, —C($R^6$)=C($R^6$)C($R^5$)$_2$-ψ, —C($R^6$)=C($R^6$)-ψ, —O—[C($R^6$)$_2$]$_m$-ψ, —O—[C($R^6$)($R^9$)C($R^6$)$_2$]-ψ, —O—[C($R^6$)($R^9$)]-ψ, —O—[C($R^6$)$_2$—C(hydroxy$C_{1-6}$alkyl)($R^6$)]-ψ, —N($R^6$)—[C($R^6$)$_2$]$_m$-ψ, —N=C($R^6$)-ψ, —N=C($R^6$)C($R^6$)$_2$-ψ, —N=N-ψ, —C($R^6$)=N-ψ, —C($R^{10}$)=N-ψ, —C($R^6$)$_2$C(O)C($R^6$)$_2$-ψ, —[C($R^6$)$_2$]$_m$—C(O)-ψ, —C($R^6$)=C($R^6$)C(O)-ψ, —C(O)C($R^6$)=C($R^6$)-ψ, —N($R^6$)—C(O)-ψ, or —C(H)(O$R^6$)—[C($R^6$)$_2$]$_m$-ψ; wherein ψ is a bond to the sulfonamide ring nitrogen atom in Formula V;

$R^1$ represents independently for each occurrence hydrogen, halogen, or $C_{1-6}$alkyl;

$R^2$ is —N($R^7$)C(O)$R^8$, —($C_{1-2}$alkylene)-N($R^7$)C(O)$R^8$, —N($R^7$)C(O)N($R^7$)($R^8$), or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —N($R^3$)($R^4$);

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —C($R^6$)$_2$-cycloalkyl, —C($R^6$)$_2$-cycloalkenyl, —C($R^6$)$_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, —C(O)N($R^3$)($R^4$), —S(O)$_p$$C_{1-6}$alkyl, —$SO_2$N($R^3$)($R^4$), and —N($R^3$)$SO_2$($C_{1-6}$alkyl);

$R^9$ and $R^{10}$ each represent independently $C_{1-6}$haloalkyl, $C_{1-6}$hydroxyalkyl, —$C_{1-6}$alkylene-N($R^3$)($R^4$), —$C_{1-6}$alkylene-N($R^3$)C(O)—$C_{1-6}$alkyl, —$C_{1-6}$alkylene-$CO_2R^3$, —$C_{1-6}$alkylene-CN, —$C_{1-6}$alkylene-$C_{1-6}$alkoxy, —$C_{1-6}$alkylene-C(O)N($R^3$)($R^4$), —C(O)N($R^3$)($R^4$), —$C_{1-6}$alkylene-N($R^3$)C(O)N($R^3$)($R^4$), —$C_{1-6}$alkylene-N($R^3$)C(O)—[C(OH)($R^3$)($R^4$)], —$C_{1-6}$alkylene-O—C(O)N($R^3$)($R^4$), —$C_{1-6}$alkylene-$SO_2$N($R^3$)($R^4$), —$C_{1-6}$alkylene-N($R^3$)$SO_2$N($R^3$)($R^4$), $C_{2-4}$alkenyl, -arylene-$CO_2R^6$, or —CN;

$R^{11}$ is $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —$CO_2R^3$, and —N($R^3$)($R^4$);

$R^{12}$ is hydrogen, $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —$CO_2R^3$, and, —N($R^3$)($R^4$);

n is 1, 2, or 3;

m is 1 or 2;

p represents independently for each occurrence 0, 1, or 2;

y is 1 or 2; and wherein the stereochemical configuration at a stereocenter in a compound represented by Formula V is R, S, or a mixture thereof.

In certain embodiments, A is aryl substituted with 1, 2, or 3 substituents independently selected from the group consisting of halogen, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$CO_2R^6$, —O—$C_{1-6}$alkylene-N($R^3$)($R^4$), and —N($R^6$)C(O)—$C_{1-6}$alkylene-N($R^3$)($R^4$). In certain other embodiments, A is phenyl substituted with 1, 2, or 3 substituents independently selected from the group consisting of halogen, hydroxyl, $C_{1-6}$alkyl, $C_{1-6}$haloalkyl, —N($R^3$)($R^4$), —CN, —$CO_2R^6$, —C(O)—$C_{1-6}$alkyl, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), and —N($R^6$)C(O)—$C_{1-6}$alkylene-N($R^3$)($R^4$). In yet other embodiments, A is phenyl substituted with 1, 2, or 3 substituents independently selected from the group consisting of halogen and $C_{1-6}$haloalkyl. In still other embodiments, A is phenyl substituted at the 4-position with fluorine or chlorine.

In certain other embodiments, X is —[C($R^5$)$_2$]$_n$-ψ, —C($R^5$)$_2$C($R^6$)=C($R^6$)-ψ, —C($R^6$)=C($R^6$)C($R^5$)$_2$-ψ, or —C(R⁶)=C(R⁶)-ψ. In certain other embodiments, X is —O—[C(R⁶)₂]ₘ-ψ or —O—[C(R⁶)(R⁹)C(R⁶)₂]-ψ. In certain other embodiments, X is —C(R⁶)=N-ψ or —C(R¹⁰)=N-ψ.

In certain other embodiments, X is (CH₂)₃-ψ. In certain embodiments, R² is attached to the 7-position of the tetrahydroquinoline ring.

In certain embodiments, R² is —N(R⁷)C(O)R⁸.

In certain embodiments, R⁸ is aryl or aralkyl; each of which is optionally substituted with 1, 2, or 3 substituents independently selected from the group consisting of halogen, hydroxyl, C₁₋₆alkoxy, C₁₋₆alkyl, C₁₋₆haloalkyl, —N(R³)(R⁴), —CN, —CO₂—C₁₋₆alkyl, —C(O)—C₁₋₆alkyl, and —S—C₁₋₆alkyl. In certain other embodiments, R⁸ is aryl substituted with 1, 2, or 3 substituents independently selected from the group consisting of halogen, C₁₋₆alkyl, and C₁₋₆haloalkyl. In certain other embodiments, R⁸ is phenyl substituted with 1, 2, or 3 substituents independently selected from the group consisting of halogen, C₁₋₆alkyl, and C₁₋₆haloalkyl. In certain embodiments, R⁸ is phenyl substituted with 2 substituents independently selected from the group consisting of halogen, C₁₋₆alkyl, and C₁₋₆haloalkyl, where the first substituent is located at the 2-position of the phenyl group, and the second substituent is located at the 6-position of the phenyl group.

In certain embodiments, y is 1.

Another aspect of the invention provides a compound represented by Formula V-A:

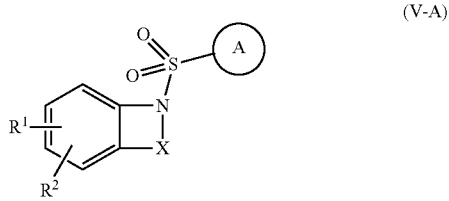

(V-A)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, C₁₋₆alkyl, C₁₋₆haloalkyl, —N(R³)(R⁴), —CO₂R⁶, —C₁₋₆alkylene-N(R³)(R⁴), —C₁₋₆alkylene-C₁₋₆alkoxy, —C₁₋₆alkylene-CO₂R⁶, —O—C₁₋₆alkylene-N(R³)(R⁴), —N(R⁶)C(O)—C₁₋₆alkylene-N(R³)(R⁴), —CN, —S(O)ₚC₁₋₆alkyl, —SO₂N(R³)(R⁴), and —N(R³)SO₂(C₁₋₆alkyl);

X is —[C(R⁵)₂]ₙ-ψ, —C(R⁵)₂C(R⁶)=C(R⁸)-ψ, —C(R⁶)=C(R⁶)C(R⁵)₂-ψ, —C(R⁶)=C(R⁶)-ψ, —O—[C(R⁶)₂]ₘ-ψ, —N(R⁶)—[C(R⁶)₂]ₘ-ψ, —N=C(R⁶)-ψ, —N=C(R⁶)C(R⁶)₂-ψ, —N=N-ψ, —C(R⁶)=N-ψ, —C(O)—[C(R⁶)₂]ₘ-ψ, —C(R⁶)₂C(O)C(R⁶)₂-ψ, —[C(R⁶)₂]ₘ—C(O)-ψ, —C(R⁶)=C(R⁶)C(O)-ψ, —C(O)C(R⁶)=C(R⁶)-ψ, —N(R⁶)—C(O)-ψ, or —C(H)(OR⁶)—[C(R⁶)₂]ₘ-ψ; wherein ψ is a bond to the sulfonamide ring nitrogen atom in Formula V-A;

R¹ represents independently for each occurrence hydrogen, halogen, or C₁₋₆alkyl;

R² is —N(R⁷)C(O)R⁸, —(C₁₋₂alkylene)-N(R⁷)C(O)R⁸, or heteroaryl, wherein said heteroaryl group is optionally substituted with 1 or 2 substituents independently selected from the group consisting of halogen, hydroxyl, C₁₋₆alkoxy, C₁₋₆alkyl, C₁₋₆haloalkyl, aryl, heteroaryl, and —N(R³)(R⁴);

R³ and R⁴ each represent independently hydrogen or C₁₋₆alkyl; or R³ and R⁴ taken together with the nitrogen atom to which they are attached form a 3-7 membered heterocyclic ring;

R⁵ represents independently for each occurrence hydrogen, halogen, or C₁₋₆alkyl;

R⁶ and R⁷ each represent independently for each occurrence hydrogen or C₁₋₆alkyl;

R⁸ is aryl, aralkyl, cycloalkyl, cycloalkenyl, heterocyclyl, —C(R⁶)₂-cycloalkyl, —C(R⁶)₂-cycloalkenyl, —C(R⁶)₂-heterocyclyl, or C₁₋₆alkyl; each of which is optionally substituted with 1, 2, or 3 substituents independently selected from the group consisting of halogen, hydroxyl, C₁₋₆alkoxy, C₁₋₆alkyl, C₁₋₆haloalkyl, —N(R³)(R⁴), —CN, —CO₂—C₁₋₆alkyl, —C(O)—C₁₋₆alkyl, —S(O)ₚC₁₋₆alkyl, —SO₂N(R³)(R⁴), and —N(R³)SO₂(C₁₋₆alkyl);

n is 1, 2, or 3;

m is 1 or 2;

p represents independently for each occurrence 0, 1, or 2; and wherein the stereochemical configuration at a stereocenter in a compound represented by Formula V-A is R, S, or a mixture thereof.

In certain embodiments, A is aryl optionally substituted with 1, 2, or 3 substituents independently selected from the group consisting of halogen, C₁₋₆alkyl, C₁₋₆haloalkyl, —N(R³)(R⁴), —CO₂R⁶, —C₁₋₆alkylene-N(R³)(R⁴), —C₁₋₆alkylene-CO₂R⁶, —O—C₁₋₆alkylene-N(R³)(R⁴), and —N(R⁶)C(O)—C₁₋₆alkylene-N(R³)(R⁴). In certain embodiments, A is phenyl substituted with 1, 2, or 3 substituents independently selected from the group consisting of halogen and C₁₋₆haloalkyl. In certain embodiments, A is phenyl substituted with 1, 2, or 3 substituents independently selected from the group consisting of halogen, hydroxyl, C₁₋₆alkoxy, C₁₋₆alkyl, C₁₋₆haloalkyl, and —N(R³)(R⁴). In certain embodiments, A is phenyl substituted at the 4-position with fluorine or chlorine.

In certain embodiments, X is —[C(R⁵)₂]ₙ-ψ, —C(R⁵)₂C(R⁶)=C(R⁸)-ψ, —C(R⁶)=C(R⁶)C(R⁵)₂-ψ, or —C(R⁶)=C(R⁶)-ψ. In certain embodiments, X is —(CH₂)₃-ψ. In certain embodiments, X is —(CH₂)₃-ψ, and R² is attached to the 7-position of the tetrahydroquinoline ring. In certain embodiments, X is —O—[C(R⁶)₂]ₘ-ψ, —N(R⁶)—[C(R⁶)₂]ₘ-ψ, —N=C(R⁶)-ψ, or —N=C(R⁶)C(R⁶)₂-ψ. In certain embodiments, X is —C(O)—[C(R⁶)₂]ₘ-ψ, —C(R⁶)₂C(O)C(R⁶)₂-ψ, —[C(R⁶)₂]ₘ—C(O)-ψ, —C(R⁶)=C(R⁶)C(O)-ψ, —C(O)C(R⁶)=C(R⁶)-ψ, or —N(R⁶)—C(O)-ψ. In certain embodiments, X is —C(O)—[C(R⁶)₂]ₘ-ψ.

In certain embodiments, R² is —N(R⁷)C(O)R⁸. In certain embodiments, R² is —(C₁₋₂alkylene)-N(R⁷)C(O)R⁸ or —C(O)N(R⁷)(R⁸). In certain embodiments, R² is a heteroaryl group optionally substituted with 1 or 2 substituents independently selected from the group consisting of halogen, hydroxyl, C₁₋₆alkoxy, C₁₋₆alkyl, C₁₋₆haloalkyl, and —N(R³)(R⁴).

In certain embodiments, R⁸ is aryl or aralkyl; each of which is optionally substituted with 1, 2, or 3 substituents independently selected from the group consisting of halogen, hydroxyl, C₁₋₆alkoxy, C₁₋₆alkyl, C₁₋₆haloalkyl, —N(R³)(R⁴), —CN, —CO₂—C₁₋₆alkyl, —C(O)—C₁₋₆alkyl, and —S—C₁₋₆alkyl.

In certain embodiments, R⁸ is aryl or aralkyl; each of which is optionally substituted with 1, 2, or 3 substituents independently selected from the group consisting of halogen, hydroxyl, C₁₋₆alkoxy, C₁₋₆alkyl, C₁₋₆haloalkyl, —N(R³)(R⁴), —CN, and —CO₂—C₁₋₆alkyl. In certain embodiments, R⁸ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group. In certain embodiments, $R^8$ is an aromatic heterocyclyl or —$C(R^6)_2$-(aromatic heterocyclyl); each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —$N(R^3)(R^4)$, —CN, —$CO_2$—$C_{1-6}$alkyl, —$C(O)$—$C_{1-6}$alkyl, and —S—$C_{1-6}$alkyl. In certain embodiments, $R^8$ is cycloalkyl, cycloalkenyl, heterocyclyl, —$C(R^6)_2$-cycloalkyl, —$C(R^6)_2$—cycloalkenyl, —$C(R^6)_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —$N(R^3)(R^4)$, —CN, —$CO_2$—$C_{1-6}$alkyl, —$C(O)$—$C_{1-6}$alkyl, and —S—$C_{1-6}$alkyl. In certain embodiments, $R^8$ is $C_{1-6}$alkyl optionally substituted with 1, 2, or 3 substituents independently selected from the group consisting of halogen, hydroxyl, $C_{1-6}$alkoxy, $C_{1-6}$haloalkyl, —$N(R^3)(R^4)$, —CN, —$CO_2$—$C_{1-6}$alkyl, and —$C(O)$—$C_{1-6}$alkyl.

Another aspect of the invention provides a compound represented by Formula V-B:

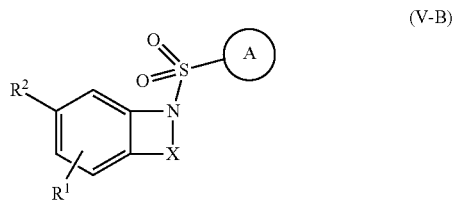

(V-B)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, —$N(R^3)(R^4)$, —$CO_2R^6$, —$C_{1-6}$alkylene-$N(R^3)(R^4)$, —$C_{1-6}$alkylene-$C_{1-6}$alkoxy, —$C_{1-6}$alkylene-$CO_2R^6$, —O—$C_{1-6}$alkylene-$N(R^3)(R^4)$, —$N(R^6)C(O)$—$C_{1-6}$alkylene-$N(R^3)(R^4)$, —CN, —$S(O)_pC_{1-6}$alkyl, —$SO_2N(R^3)(R^4)$, and —$N(R^3)SO_2(C_{1-6}$alkyl);

X is —$[C(R^5)_2]_n$-ψ, —$C(R^5)_2C(R^6)$=$C(R^8)$-ψ, —$C(R^6)$=$C(R^6)C(R^5)_2$-ψ, —$C(R^6)$=$C(R^6)$-ψ, —O—$[C(R^6)_2]_m$-ψ, —$N(R^6)$—$[C(R^6)_2]_m$-ψ, —N=$C(R^6)$-ψ, —N=$C(R^6)C(R^6)_2$-ψ, —N=N-ψ, —$C(R^6)$=N-ψ, —$C(O)$—$[C(R^6)_2]_m$-ψ, —$C(R^6)_2C(O)C(R^6)_2$-ψ, —$[C(R^6)_2]_m$—$C(O)$-ψ, —$C(R^6)$=$C(R^6)C(O)$-ψ, —$C(O)C(R^6)$=$C(R^6)$-ψ, —$N(R^6)$—$C(O)$-ψ, or —$C(H)(OR^6)$—$[C(R^6)_2]_m$-ψ; wherein ψ is a bond to the sulfonamide ring nitrogen atom in Formula V-B;

$R^1$ represents independently for each occurrence hydrogen, halogen, or $C_{1-6}$alkyl;

$R^2$ is —$N(R^7)C(O)R^8$, —$(C_{1-2}$alkylene)-$N(R^7)C(O)R^8$, or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —$N(R^3)(R^4)$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —$C(R^6)_2$-cycloalkyl, —$C(R^6)_2$-cycloalkenyl, —$C(R^6)_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —$N(R^3)(R^4)$, —CN, —$CO_2$—$C_{1-6}$alkyl, —$C(O)$—$C_{1-6}$alkyl, —$S(O)_pC_{1-6}$alkyl, —$SO_2N(R^3)(R^4)$, and —$N(R^3)SO_2(C_{1-6}$alkyl);

n is 1, 2, or 3;

m is 1 or 2;

p represents independently for each occurrence 0, 1, or 2; and wherein the stereochemical configuration at a stereocenter in a compound represented by Formula V-B is R, S, or a mixture thereof.

In certain embodiments, variables A, $R^1$ through $R^8$, n, and p for Formula V-B are as defined by one of the further embodiments specified above in connection with Formula V-A.

Another aspect of the invention provides a compound represented by Formula VI:

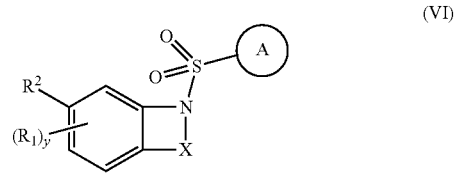

(VI)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, —$N(R^3)(R^4)$, —$CO_2R^6$, —$C_{1-6}$alkylene-$N(R^3)(R^4)$, —$C_{1-6}$alkylene-$C_{1-6}$alkoxy, —$C_{1-6}$alkylene-$CO_2R^6$, —O-aryl, —O—$C_{1-6}$alkylene-$N(R^3)(R^4)$, —$N(R^6)C(O)$—$C_{1-6}$alkylene-$N(R^3)(R^4)$, —CN, —$S(O)_pC_{1-6}$alkyl, —$SO_2N(R^3)(R^4)$, —$N(R^3)SO_2(C_{1-6}$alkyl), heterocyclyl, —$C(O)R^{11}$, —$C(R^{11})(R^{12})OH$, —$C(O)N(R^3)(R^4)$, and —$N(R^3)C(O)N(R^3)(R^4)$;

X is —$[C(R^5)_2]_3$-ψ, —$C(R^5)_2C(R^6)$=$C(R^6)$-ψ, —$C(R^6)$=$C(R^6)C(R^5)_2$-ψ, —$C(R^6)$=$C(R^6)$-ψ, —$C(O)$—$[C(R^6)_2]_m$-ψ, —$C(R^6)_2C(O)C(R^6)_2$-ψ, —$[C(R^6)_2]_m$—$C(O)$-ψ, —$C(R^6)$=$C(R^6)C(O)$-ψ, —$C(O)C(R^6)$=$C(R^6)$-ψ, —$C(R^6)$=N-ψ, —$C(R^{10})$=N-ψ, —O—$[C(R^6)_2]_m$-ψ, —O—$[C(R^6)(R^9)C(R^6)_2]$-ψ, —O—$[C(R^6)(R^9)]$-ψ, —O—$[C(R^6)_2$—C(hydroxy$C_{1-6}$alkyl)$(R^6)]$-ψ, or —$C(H)(OR^6)$—$[C(R^6)_2]_m$-ψ; wherein ψ is a bond to the sulfonamide ring nitrogen atom in Formula VI;

$R^1$ represents independently for each occurrence hydrogen, halogen, or $C_{1-6}$alkyl;

$R^2$ is —$C(O)N(R^7)(R^8)$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl or aralkyl; each of which is optionally substituted with 1, 2, or 3 substituents independently selected from the group consisting of halogen, $C_{1-6}$alkyl, $C_{1-6}$haloalkyl, and —CN;

$R^9$ and $R^{10}$ each represent independently $C_{1-6}$haloalkyl, $C_{1-6}$hydroxyalkyl, —$C_{1-6}$alkylene-$N(R^3)(R^4)$, —$C_{1-6}$alkylene-$N(R^3)C(O)$—$C_{1-6}$alkyl, —$C_{1-6}$alkylene-$CO_2R^3$, —$C_{1-6}$alkylene-CN, —$C_{1-6}$alkylene-$C_{1-6}$alkoxy, —$C_{1-6}$alkylene-$C(O)N(R^3)(R^4)$, —$C(O)N(R^3)(R^4)$, —$C_{1-6}$alkylene-$N(R^3)C(O)N(R^3)(R^4)$, —$C_{1-6}$alkylene-$N(R^3)C(O)$—$[C(OH)(R^3)(R^4)]$, —$C_{1-6}$alkylene-O—$C(O)N(R^3)(R^4)$, —$C_{1-6}$alkylene-$SO_2N(R^3)(R^4)$, —$C_{1-6}$alkylene-$N(R^3)SO_2N(R^3)(R^4)$, $C_{2-4}$alkenyl, -arylene-$CO_2R^6$, or —CN;

$R^{11}$ is $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —$CO_2R^3$, and, —$N(R^3)(R^4)$;

$R^{12}$ is hydrogen, $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —$CO_2R^3$, and, —$N(R^3)(R^4)$;

m is 1 or 2;

p is 0, 1, or 2;

y is 1 or 2; and wherein the stereochemical configuration at a stereocenter in a compound represented by Formula VI is R, S, or a mixture thereof.

In certain embodiments, A is aryl substituted with 1, 2, or 3 substituents independently selected from the group consisting of halogen, hydroxyl, $C_{1-6}$alkyl, $C_{1-6}$haloalkyl, —$N(R^3)(R^4)$, —$CO_2R^6$, —$C_{1-6}$alkylene-$N(R^3)(R^4)$, —$C_{1-6}$alkylene-$CO_2R^6$, —O—$C_{1-6}$alkylene-$N(R^3)(R^4)$, and —$N(R^6)C(O)$—$C_{1-6}$alkylene-$N(R^3)(R^4)$. In certain other embodiments, A is phenyl substituted at the 4-position with fluorine or chlorine. In certain embodiments, $R^8$ is phenyl substituted with 2 or 3 substituents independently selected from the group consisting of halogen, $C_{1-6}$alkyl, and $C_{1-6}$haloalkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group. In certain embodiments, y is 1.

Another aspect of the invention provides a compound represented by Formula VI-A:

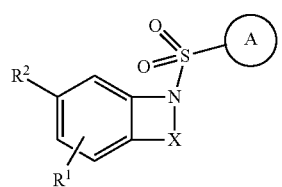

(VI-A)

or a pharmaceutically acceptable salt or solvate thereof;
wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, —$N(R^3)(R^4)$, —$CO_2R^6$, —$C_{1-6}$alkylene-$N(R^3)(R^4)$, —$C_{1-6}$alkylene-$C_{1-6}$alkoxy, —$C_{1-6}$alkylene-$CO_2R^6$, —O—$C_{1-6}$alkylene-$N(R^3)(R^4)$, —$N(R^6)C(O)$—$C_{1-6}$alkylene-$N(R^3)(R^4)$, —CN, —$S(O)_pC_{1-6}$alkyl, —$SO_2N(R^3)(R^4)$, and —$N(R^3)SO_2(C_{1-6}$alkyl);

X is —$[C(R^5)_2]_3$-ψ, —$C(R^5)_2C(R^6)=C(R^8)$-ψ, —$C(R^6)=C(R^6)C(R^5)_2$-ψ, —$C(R^6)=C(R^6)$-ψ, —C(O)—$[C(R^6)_2]_m$-ψ, —$C(R^6)_2C(O)C(R^6)_2$-ψ, —$[C(R^6)_2]_m$—C(O)-ψ, —$C(R^6)=C(R^6)C(O)$-ψ, —$C(O)C(R^6)=C(R^6)$-ψ, or —$C(H)(OR^6)$—$[C(R^6)_2]_m$-ψ; wherein ψ is a bond to the sulfonamide ring nitrogen atom in Formula VI-A;

$R^1$ represents independently for each occurrence hydrogen, halogen, or $C_{1-6}$alkyl;

$R^2$ is —$C(O)N(R^7)(R^8)$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl or aralkyl; each of which is optionally substituted with 1, 2, or 3 substituents independently selected from the group consisting of halogen, $C_{1-6}$alkyl, $C_{1-6}$haloalkyl, and —CN;

m is 1 or 2;

p is 0, 1, or 2; and wherein the stereochemical configuration at a stereocenter in a compound represented by Formula VI-A is R, S, or a mixture thereof.

In certain embodiments, A is aryl optionally substituted with 1, 2, or 3 substituents independently selected from the group consisting of halogen, hydroxyl, $C_{1-6}$alkyl, $C_{1-6}$haloalkyl, —$N(R^3)(R^4)$, —$CO_2R^6$, —$C_{1-6}$alkylene-$N(R^3)(R^4)$, —$C_{1-6}$alkylene-$CO_2R^6$, —O—$C_{1-6}$alkylene-$N(R^3)(R^4)$, and —$N(R^6)C(O)$—$C_{1-6}$alkylene-$N(R^3)(R^4)$. In certain embodiments, A is phenyl substituted at the 4-position with fluorine or chlorine. In certain embodiments, $R^8$ is phenyl substituted with 2 or 3 substituents independently selected from the group consisting of halogen, $C_{1-6}$alkyl, $C_{1-6}$haloalkyl, and —CN. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group.

Another aspect of the invention provides a compound of Formula VII:

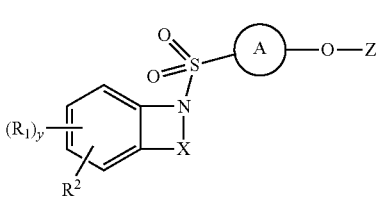

(VII)

or a pharmaceutically acceptable salt or solvate thereof;
wherein:

A is arylene, aralkylene, heteroarylene, cycloalkylene, or heterocycloalkylene; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, —N($R^3$)($R^4$), —CO$_2$$R^6$, —$C_{1-6}$alkylene-N($R^3$)($R^4$), —$C_{1-6}$alkylene-$C_{1-6}$alkoxy, —$C_{1-6}$alkylene-CO$_2$$R^6$, —O-aryl, —O—$C_{1-6}$alkylene-N($R^3$)($R^4$), —$C_{1-6}$alkylene-CO$_2$$R^6$, —N($R^6$)C(O)—$C_{1-6}$alkylene-N($R^3$)($R^4$), —CN, —S(O)$_p$$C_{1-6}$alkyl, —SO$_2$N($R^3$)($R^4$), —N($R^3$)SO$_2$($C_{1-6}$alkyl), heterocyclyl, —C(O)$R^{11}$, —C($R^{11}$)($R^{12}$)OH, —C(O)N($R^3$)($R^4$), and —N($R^3$)C(O)N($R^3$)($R^4$);

X is —C($R^5$)($C_{1-6}$alkyl)[C($R^5$)$_2$]$_m$-ψ, —[C($R^5$)$_2$]$_m$—C($R^5$)($C_{1-6}$alkyl)-ψ, —C($R^5$)$_2$—C($R^5$)($C_{1-6}$alkyl)-C($R^5$)$_2$-ψ, —C($R^5$)$_2$C($R^6$)=C($R^6$)-ψ, —C($R^6$)=C($R^6$)C($R^5$)$_2$-ψ, —C($R^6$)=C($R^6$)-ψ, —O—[C($R^6$)$_2$]$_m$-ψ, —O—[C($R^6$)($R^9$)C($R^6$)$_2$]-ψ, —O—[C($R^6$)($R^9$)]-ψ, —[C($R^6$)$_2$—C(hydroxy$C_{1-6}$alkyl)($R^6$)]-ψ, —N($R^6$)—[C($R^6$)$_2$]$_{m-ψ}$, —N=C($R^6$)-ψ, —N=C($R^6$)C($R^6$)$_2$-ψ, —N=N-ψ, —C($R^6$)=N-ψ, —C($R^{10}$)=N-ψ, —C(O)—[C($R^6$)$_2$]$_m$-ψ, —C($R^6$)$_2$C(O)C($R^6$)$_2$-ψ, —[C($R^6$)$_2$]$_m$—C(O)-ψ, —C($R^6$)=C($R^6$)C(O)-ψ, —C(O)C($R^6$)=C($R^6$)-ψ, —N($R^6$)—C(O)-ψ, or —C(H)(O$R^6$)—[C($R^6$)$_2$]$_m$-ψ; wherein ψ is a bond to the sulfonamide ring nitrogen atom in Formula VII;

Z is $C_{1-6}$alkyl or $C_{1-6}$haloalkyl;

$R^1$ represents independently for each occurrence hydrogen, halogen, or $C_{1-6}$alkyl;

$R^2$ is —N($R^7$)C(O)$R^8$, —($C_{1-2}$alkylene)-N($R^7$)C(O)$R^8$, —N($R^7$)C(O)N($R^7$)($R^8$), or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —N($R^3$)($R^4$);

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —C($R^6$)$_2$-cycloalkyl, —C($R^6$)$_2$-cycloalkenyl, —C($R^6$)$_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^3$)($R^4$), —CN, —CO$_2$—$C_{1-6}$alkyl, —C(O)—$C_{1-6}$alkyl, —C(O)N($R^3$)($R^4$), —S(O)$_p$$C_{1-6}$alkyl, —SO$_2$N($R^3$)($R^4$), and —N($R^3$)SO$_2$($C_{1-6}$alkyl);

$R^9$ and $R^{10}$ each represent independently $C_{1-6}$haloalkyl, $C_{1-6}$hydroxyalkyl, —$C_{1-6}$alkylene-N($R^3$)($R^4$), —$C_{1-6}$alkylene-N($R^3$)C(O)—$C_{1-6}$alkyl, —$C_{1-6}$alkylene-CO$_2$$R^3$, —$C_{1-6}$ alkylene-CN, —$C_{1-6}$alkylene-$C_{1-6}$alkoxy, —$C_{1-6}$alkylene-C(O)N($R^3$)($R^4$), —C(O)N($R^3$)($R^4$), —$C_{1-6}$alkylene-N($R^3$)C(O)N($R^3$)($R^4$), —$C_{1-6}$alkylene-N($R^3$)C(O)—[C(OH)($R^3$)($R^4$)], —$C_{1-6}$alkylene-O—C(O)N($R^3$)($R^4$), —$C_{1-6}$alkylene-SO$_2$N($R^3$)($R^4$), —$C_{1-6}$alkylene-N($R^3$)SO$_2$N($R^3$)($R^4$), $C_{2-4}$alkenyl, -arylene-CO$_2$$R^6$, or —CN;

$R^{11}$ is $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —CO$_2$$R^3$, and, —N($R^3$)($R^4$);

$R^{12}$ is hydrogen, $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —CO$_2$$R^3$, and, —N($R^3$)($R^4$);

m is 1 or 2;
p represents independently for each occurrence 0, 1, or 2;
y is 1 or 2; and
wherein the stereochemical configuration at a stereocenter in a compound represented by Formula VII is R, S, or a mixture thereof.

In certain embodiments, A is aryl substituted with 1, 2, or 3 substituents independently selected from the group consisting of halogen, hydroxyl, $C_{1-6}$alkyl, $C_{1-6}$haloalkyl, —N($R^3$)($R^4$), —CN, —CO$_2$$R^6$, —C(O)—$C_{1-6}$alkyl, —$C_{1-6}$alkylene-N($R^3$)($R^4$), —$C_{1-6}$alkylene-$C_{1-6}$alkoxy, —$C_{1-6}$alkylene-CO$_2$$R^6$, —O—$C_{1-6}$alkylene-N($R^3$)($R^4$), and —N($R^6$)C(O)—$C_{1-6}$alkylene-N($R^3$)($R^4$). In certain other embodiments, A is phenyl substituted with 1, 2, or 3 substituents independently selected from the group consisting of halogen, hydroxyl, $C_{1-6}$alkyl, $C_{1-6}$haloalkyl, —N($R^3$)($R^4$), —CN, —CO$_2$$R^6$, —C(O)—$C_{1-6}$alkyl, —$C_{1-6}$alkylene-N($R^3$)($R^4$), —$C_{1-6}$alkylene-$C_{1-6}$alkoxy, —$C_{1-6}$alkylene-CO$_2$$R^6$, —O—$C_{1-6}$alkylene-N($R^3$)($R^4$), and —N($R^6$)C(O)—$C_{1-6}$alkylene-N($R^3$)($R^4$).

In certain embodiments, X is —O—[C($R^6$)$_2$]$_m$-ψ or —O—[C($R^6$)($R^9$)C($R^6$)$_2$]-ψ. In certain other embodiments, X is —C($R^6$)=N-ψ or —C($R^{10}$)=N-ψ.

In certain embodiments, $R^2$ is —N($R^7$)C(O)$R^8$. In certain embodiments, $R^8$ is aryl substituted with 1, 2, or 3 substituents independently selected from the group consisting of halogen, $C_{1-6}$alkyl, and $C_{1-6}$haloalkyl. In certain other embodiments, $R^8$ is phenyl substituted with 1, 2, or 3 substituents independently selected from the group consisting of halogen, $C_{1-6}$alkyl, and $C_{1-6}$haloalkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group.

In certain embodiments, y is 1.

Another aspect of the invention provides a compound of Formula VIII:

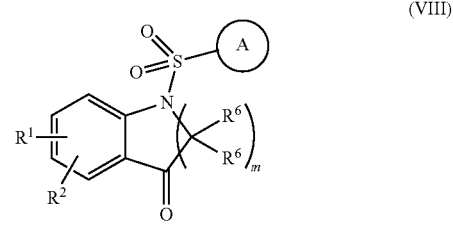

(VIII)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, —N($R^3$)($R^4$), —CO$_2$$R^6$, —$C_{1-6}$alkylene-N($R^3$)($R^4$), —$C_{1-6}$alkylene-$C_{1-6}$alkoxy, —$C_{1-6}$alkylene-CO$_2$$R^6$, —O—$C_{1-6}$alkylene-N($R^3$)($R^4$), —$C_{1-6}$alkylene-CO$_2$$R^6$, —N($R^5$)C(O)—$C_{1-6}$alkylene-N($R^3$)($R^4$), —CN, —S(O)$_p$$C_{1-6}$alkyl, —SO$_2$N($R^3$)($R^4$), and —N($R^3$)SO$_2$($C_{1-6}$alkyl);

$R^1$ represents independently for each occurrence hydrogen, halogen, or $C_{1-6}$alkyl;

$R^2$ is —N($R^7$)C(O)$R^8$, —($C_{1-2}$alkylene)-N($R^7$)C(O)$R^8$, or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —N($R^3$)($R^4$);

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$, $R^6$, and $R^7$ each represent independently for each occurrence hydrogen or $C_{1-6}$alkyl;

$R^8$ is aryl, aralkyl, cycloalkyl, cycloalkenyl, heterocyclyl, —C($R^6$)$_2$-cycloalkyl, —C($R^6$)$_2$-cycloalkenyl, —C($R^6$)$_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —CO$_2$—C$_{1-6}$alkyl, —C(O)—C$_{1-6}$alkyl, —S(O)$_p$C$_{1-6}$alkyl, —SO$_2$N($R^3$)($R^4$), and —N($R^3$)SO$_2$(C$_{1-6}$alkyl);

m is 1 or 2;

p represents independently for each occurrence 0, 1, or 2; and wherein the stereochemical configuration at a stereocenter in a compound represented by Formula VIII is R, S, or a mixture thereof.

In certain embodiments, A is aryl substituted with 1, 2, or 3 substituents independently selected from the group consisting of halogen, hydroxyl, $C_{1-6}$alkyl, $C_{1-6}$haloalkyl, —N($R^3$)($R^4$), —CN, —CO$_2$$R^6$, —C(O)—C$_{1-6}$alkyl, —C$_{1-6}$alkylene-N($R^3$)($R^4$), —C$_{1-6}$alkylene-C$_{1-6}$alkoxy, —C$_{1-6}$alkylene-CO$_2$$R^6$, —O—C$_{1-6}$alkylene-N($R^3$)($R^4$), and —N($R^5$)C(O)—C$_{1-6}$alkylene-N($R^3$)($R^4$). In certain other embodiments, A is phenyl substituted with 1, 2, or 3 substituents independently selected from the group consisting of halogen, hydroxyl, $C_{1-6}$alkyl, $C_{1-6}$haloalkyl, —N($R^3$)($R^4$), —CN, —CO$_2$$R^6$, —C(O)—C$_{1-6}$alkyl, —C$_{1-6}$alkylene-N($R^3$)($R^4$), —C$_{1-6}$alkylene-C$_{1-6}$alkoxy, —C$_{1-6}$alkylene-CO$_2$$R^6$, —O—C$_{1-6}$alkylene-N($R^3$)($R^4$), and —N($R^5$)C(O)—C$_{1-6}$alkylene-N($R^3$)($R^4$).

In certain embodiments, $R^2$ is —N($R^7$)C(O)$R^8$.

In certain embodiments, $R^8$ is aryl substituted with 1, 2, or 3 substituents independently selected from the group consisting of halogen, $C_{1-6}$alkyl, and $C_{1-6}$haloalkyl. In certain embodiments, $R^8$ is phenyl substituted with 1, 2, or 3 substituents independently selected from the group consisting of halogen, $C_{1-6}$alkyl, and $C_{1-6}$haloalkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group.

Another aspect of the invention provides a compound of Formula IX:

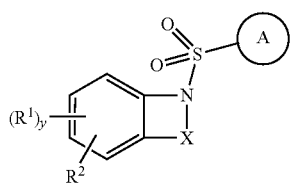

(IX)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, $C_{1-6}$hydroxyalkyl, —N($R^3$)($R^4$), —CO$_2$$R^6$, —C$_{1-6}$alkylene-N($R^3$)($R^4$), —C$_{1-6}$alkylene-C$_{1-6}$alkoxy, —C$_{1-6}$alkylene-CO$_2$$R^6$, —O—C$_{1-6}$alkylene-CO$_2$$R^6$, —N($R^6$)C(O)—C$_{1-6}$alkylene-N($R^3$)($R^4$), —O-aryl, —CN, —S(O)$_p$$C_{1-6}$alkyl, —SO$_2$N($R^3$)($R^4$), —N($R^3$)SO$_2$(C$_{1-6}$alkyl), heterocyclyl, —C(O)$R^{11}$, —C($R^{11}$)($R^{12}$)OH, —C(O)N($R^3$)($R^4$), and —N($R^3$)C(O)N($R^3$)($R^4$);

X is —[C($R^5$)$_2$]$_n$-ψ, —C($R^5$)$_2$C($R^6$)=C($R^6$)-ψ, —C($R^6$)=C($R^6$)C($R^5$)$_2$-ψ, —C($R^6$)=C($R^6$)-ψ, —O—[C($R^6$)$_2$]$_m$-ψ, —O—[C($R^6$)($R^9$)C($R^6$)$_2$]-ψ, —O—[C($R^6$)($R^9$)]-ψ, —O—[C($R^6$)$_2$—C(hydroxyC$_{1-6}$alkyl)($R^6$)]-ψ, —N($R^6$)—[C($R^6$)$_2$]$_m$-ψ, —N=C($R^6$)-ψ, —N=C($R^6$)C($R^6$)$_2$-ψ, —N=N-ψ, —C($R^6$)=N-ψ, —C($R^{10}$)=N-ψ, —C(O)—[C($R^6$)$_2$]$_m$-ψ, —C($R^6$)$_2$C(O)C($R^6$)$_2$-ψ, —[C($R^6$)$_2$]$_m$—C(O)-ψ, —C($R^6$)=C($R^6$)C(O)-ψ, —C(O)C($R^6$)=C($R^6$)-ψ, —N($R^6$)—C(O)-ψ, or —C(H)(OR$^6$)—[C($R^6$)$_2$]$_m$-ψ;

wherein ψ is a bond to the sulfonamide ring nitrogen atom in Formula IX;

$R^1$ represents independently for each occurrence hydrogen, halogen, or $C_{1-6}$alkyl;

$R^2$ is —N($R^7$)C(O)$R^8$, —(C$_{1-2}$alkylene)-N($R^7$)C(O)$R^8$, —C(O)N($R^7$)($R^8$), —N($R^7$)C(O)N($R^7$)($R^8$), or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —N($R^3$)($R^4$);

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^5$ represents independently for each occurrence hydrogen, halogen, or $C_{1-6}$alkyl;

$R^6$ and $R^7$ each represent independently for each occurrence hydrogen or $C_{1-6}$alkyl;

$R^8$ is aryl, aralkyl, cycloalkyl, cycloalkenyl, heterocyclyl, —C($R^6$)$_2$-cycloalkyl, —C($R^6$)$_2$-cycloalkenyl, —C($R^6$)$_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^3$)($R^4$), —CN, —CO$_2$—C$_{1-6}$alkyl, —C(O)—C$_{1-6}$alkyl, —C(O)N($R^3$)($R^4$), —S(O)$_p$$C_{1-6}$alkyl, —SO$_2$N($R^3$)($R^4$), and —N($R^3$)SO$_2$(C$_{1-6}$alkyl);

$R^9$ and $R^{10}$ each represent independently $C_{1-6}$haloalkyl, $C_{1-6}$hydroxyalkyl, —C$_{1-6}$alkylene-N($R^3$)($R^4$), —C$_{1-6}$alkylene-N($R^3$)C(O)—C$_{1-6}$alkyl, —C$_{1-6}$alkylene-CO$_2$$R^3$, —C$_{1-6}$ alkylene-CN, —C$_{1-6}$alkylene-C$_{1-6}$alkoxy, —C$_{1-6}$alkylene-C(O)N($R^3$)($R^4$), —C(O)N($R^3$)($R^4$), —C$_{1-6}$alkylene-N($R^3$)C(O)N($R^3$)($R^4$), —C$_{1-6}$alkylene-N($R^3$)C(O)—[C(OH)($R^3$)($R^4$)], —C$_{1-6}$alkylene-O—C(O)N($R^3$)($R^4$), —C$_{1-6}$alkylene-SO$_2$N($R^3$)($R^4$), —C$_{1-6}$alkylene-N($R^3$)SO$_2$N($R^3$)($R^4$), $C_{2-4}$alkenyl, -arylene-CO$_2$$R^6$, or —CN;

$R^{11}$ is $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —CO$_2$$R^3$, and, —N($R^3$)($R^4$);

$R^{12}$ is hydrogen, $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —CO$_2$$R^3$, and, —N($R^3$)($R^4$);

n is 1, 2, or 3;

m is 1 or 2;

p represents independently for each occurrence 0, 1, or 2;

y is 1 or 2; and wherein the stereochemical configuration at a stereocenter in a compound represented by Formula IX is R, S, or a mixture thereof.

In certain embodiments, A is aryl substituted with 1, 2, or 3 substituents independently selected from the group consisting of halogen, hydroxyl, $C_{1-6}$alkyl, $C_{1-6}$haloalkyl, —N(R$^3$)(R$^4$), —CN, —CO$_2$R$^6$, —C(O)—C$_{1-6}$alkyl, —C$_{1-6}$alkylene-N(R$^3$)(R$^4$), —C$_{1-6}$alkylene-C$_{1-6}$alkoxy, —C$_{1-6}$alkylene-CO$_2$R$^6$, —O—C$_{1-6}$alkylene-N(R$^3$)(R$^4$), and —N(R$^6$)C(O)—C$_{1-6}$alkylene-N(R$^3$)(R$^4$). In certain other embodiments, A is phenyl substituted with 1, 2, or 3 substituents independently selected from the group consisting of halogen, hydroxyl, $C_{1-6}$alkyl, $C_{1-6}$haloalkyl, —N(R$^3$)(R$^4$), —CN, —CO$_2$R$^6$, —C(O)—C$_{1-6}$alkyl, —C$_{1-6}$alkylene-N(R$^3$)(R$^4$), —C$_{1-6}$alkylene-C$_{1-6}$alkoxy, —C$_{1-6}$alkylene-CO$_2$R$^6$, —O—C$_{1-6}$alkylene-N(R$^3$)(R$^4$), and —N(R$^6$)C(O)—C$_{1-6}$alkylene-N(R$^3$)(R$^4$). In yet other embodiments, A is phenyl substituted with 1, 2, or 3 substituents independently selected from the group consisting of halogen, hydroxyl, $C_{1-6}$alkoxy, $C_{1-6}$alkyl, $C_{1-6}$haloalkyl, and —N(R$^3$)(R$^4$). In yet other embodiments, A is phenyl substituted with 1, 2, or 3 substituents independently selected from the group consisting of halogen, hydroxyl, $C_{1-6}$alkyl, $C_{1-6}$haloalkyl, and —CN. In yet other embodiments, A is phenyl substituted with 1, 2, or 3 substituents independently selected from the group consisting of halogen and $C_{1-6}$haloalkyl.

In certain embodiments, X is —O—[C(R$^6$)$_2$]$_m$-ψ or —O—[C(R$^6$)(R$^9$)C(R$^6$)$_2$]-ψ. In certain other embodiments, X is —C(R$^6$)=N-ψ or —C(R$^{10}$)=N-ψ. In yet other embodiments, X is —C(R$^5$)(C$_{1-6}$alkyl)[C(R$^5$)$_2$]$_m$-ψ, —[C(R$^5$)$_2$]$_m$—C(R$^5$)(C$_{1-6}$alkyl)-ψ, —C(R$^5$)$_2$—C(R$^5$)(C$_{1-6}$alkyl)-C(R$^5$)$_2$-ψ, —C(R$^5$)$_2$C(R$^6$)=C(R$^6$)-ψ, —C(R$^6$)=C(R$^6$)C(R$^5$)$_2$-ψ, or —C(R$^6$)=C(R$^6$)-ψ.

In certain embodiments, X is —(CH$_2$)$_3$-ψ. In certain embodiments, R$^2$ is attached to the 7-position of the tetrahydroquinoline ring.

In certain embodiments, X is —C(O)—[C(R$^6$)$_2$]$_m$-ψ.

In certain embodiments, R$^2$ is —N(R$^7$)C(O)R$^8$.

In certain embodiments, R$^8$ is aryl or aralkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N(R$^3$)(R$^4$), —CN, —CO$_2$—C$_{1-6}$alkyl, —C(O)—C$_{1-6}$alkyl, and —S—C$_{1-6}$alkyl. In certain other embodiments, R$^8$ is aryl substituted with 1, 2, or 3 substituents independently selected from the group consisting of halogen, $C_{1-6}$alkyl, and $C_{1-6}$haloalkyl. In yet other embodiments, R$^8$ is phenyl substituted with 1, 2, or 3 substituents independently selected from the group consisting of halogen, $C_{1-6}$alkyl, and $C_{1-6}$haloalkyl. In certain embodiments, R$^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group.

In certain embodiments, y is 1.

Another aspect of the invention provides a compound of Formula IX-A:

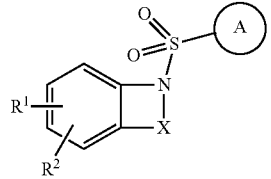

(IX-A)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N(R$^3$)(R$^4$), —CO$_2$R$^6$, —C$_{1-6}$alkylene-N(R$^3$)(R$^4$), —C$_{1-6}$alkylene-C$_{1-6}$alkoxy, —C$_{1-6}$alkylene-CO$_2$R$^6$, —O—C$_{1-6}$alkylene-N(R$^3$)(R$^4$), —O—C$_{1-6}$alkylene-CO$_2$R$^6$, —N(R$^6$)C(O)—C$_{1-6}$alkylene-N(R$^3$)(R$^4$), —O-aryl, —CN, —S(O)$_p$C$_{1-6}$alkyl, —SO$_2$N(R$^3$)(R$^4$), and —N(R$^3$)SO$_2$(C$_{1-6}$alkyl);

X is —[C(R$^5$)$_2$]$_n$-ψ, —C(R$^5$)$_2$C(R$^6$)=C(R$^8$)-ψ, —C(R$^6$)=C(R$^6$)C(R$^5$)$_2$-ψ, —C(R$^6$)=C(R$^6$)-ψ, —O—[C(R$^6$)$_2$]$_m$-ψ, —N(R$^6$)—[C(R$^6$)$_2$]$_m$-ψ, —N=C(R$^6$)-ψ, —N=C(R$^6$)C(R$^6$)$_2$-ψ, —N=N-ψ, —C(R$^6$)=N-ψ, —C(O)—[C(R$^6$)$_2$]$_m$-ψ, —C(R$^6$)$_2$C(O)C(R$^6$)$_2$-ψ, —[C(R$^6$)$_2$]$_m$—C(O)-ψ, —C(R$^6$)=C(R$^6$)C(O)-ψ, —C(O)C(R$^6$)=C(R$^6$)-ψ, —N(R$^6$)—C(O)-ψ, or —C(H)(OR$^6$)—[C(R$^6$)$_2$]$_m$-ψ; wherein ψ is a bond to the sulfonamide ring nitrogen atom in Formula IX-A;

R$^1$ represents independently for each occurrence hydrogen, halogen, or $C_{1-6}$alkyl;

R$^2$ is —N(R$^7$)C(O)R$^8$, —(C$_{1-2}$alkylene)-N(R$^7$)C(O)R$^8$, —C(O)N(R$^7$)(R$^8$), or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, heteroaryl, and —N(R$^3$)(R$^4$);

R$^3$ and R$^4$ each represent independently hydrogen or $C_{1-6}$alkyl; or R$^3$ and R$^4$ taken together with the nitrogen atom to which they are attached form a 3-7 membered heterocyclic ring;

R$^5$ represents independently for each occurrence hydrogen, halogen, or $C_{1-6}$alkyl;

R$^6$ and R$^7$ each represent independently for each occurrence hydrogen or $C_{1-6}$alkyl;

R$^8$ is aryl, aralkyl, cycloalkyl, cycloalkenyl, heterocyclyl, —C(R$^6$)$_2$-cycloalkyl, —C(R$^6$)$_2$-cycloalkenyl, —C(R$^6$)$_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N(R$^3$)(R$^4$), —CN, —CO$_2$—C$_{1-6}$alkyl, —C(O)—C$_{1-6}$alkyl, —S(O)$_p$C$_{1-6}$alkyl, —SO$_2$N(R$^3$)(R$^4$), and —N(R$^3$)SO$_2$(C$_{1-6}$alkyl);

n is 1, 2, or 3;

m is 1 or 2;

p represents independently for each occurrence 0, 1, or 2; and wherein the stereochemical configuration at a stereocenter in a compound represented by Formula IX-A is R, S, or a mixture thereof.

In certain embodiments, A is aryl optionally substituted with 1, 2, or 3 substituents independently selected from the group consisting of halogen, hydroxyl, $C_{1-6}$alkoxy, $C_{1-6}$alkyl, $C_{1-6}$haloalkyl, —N(R$^3$)(R$^4$), —CO$_2$R$^1$, —C$_{1-6}$ alkylene-N(R³)(R⁴), —C₁₋₆alkylene-CO₂R⁶, —O—C₁₋₆alkylene-N(R³)(R⁴), and —N(R⁶)C(O)—C₁₋₆alkylene-N(R³)(R⁴). In certain embodiments, A is phenyl substituted with 1, 2, or 3 substituents independently selected from the group consisting of halogen, hydroxyl, C₁₋₆alkoxy, C₁₋₆alkyl, C₁₋₆haloalkyl, and —N(R³)(R⁴). In certain embodiments, A is phenyl substituted with 1, 2, or 3 substituents independently selected from the group consisting of halogen and C₁₋₆haloalkyl.

In certain embodiments, X—[C(R⁵)₂]ₙ-ψ, —C(R⁵)₂C(R⁶)=C(R⁸)-ψ, —C(R⁶)=C(R⁶)C(R⁵)₂-ψ, or —C(R⁶)=C(R⁶)-ψ. In certain embodiments, X is —(CH₂)₃-ψ. In certain embodiments, X is —(CH₂)₃-ψ, and R² is attached to the 7-position of the tetrahydroquinoline ring. In certain embodiments, X is —O—[C(R⁶)₂]ₘ-ψ, —N(R⁶)—[C(R⁶)₂]ₘ-ψ, —N=C(R⁶)-ψ, or —N=C(R⁶)C(R⁶)₂-ψ. In certain embodiments, X is —C(O)—[C(R⁶)₂]ₘ-ψ, —C(R⁶)₂C(O)C(R⁶)₂-ψ, —[C(R⁶)₂]ₘ—C(O)-ψ, —C(R⁶)=C(R⁶)C(O)-ψ, —C(O)C(R⁶)=C(R⁶)-ψ, or —N(R⁶)—C(O)-ψ. In certain embodiments, X is —C(O)—[C(R⁶)₂]ₘ-ψ.

In certain embodiments, R² is —N(R⁷)C(O)R⁸. In certain embodiments, R² is —(C₁₋₂alkylene)-N(R⁷)C(O)R⁸ or —C(O)N(R⁷)(R⁸). In certain embodiments, R² is a heteroaryl group optionally substituted with 1 or 2 substituents independently selected from the group consisting of halogen, hydroxyl, C₁₋₆alkoxy, C₁₋₆alkyl, C₁₋₆haloalkyl, and —N(R³)(R⁴). In certain embodiments, R⁸ is aryl or aralkyl; each of which is optionally substituted with 1, 2, or 3 substituents independently selected from the group consisting of halogen, hydroxyl, C₁₋₆alkoxy, C₁₋₆alkyl, C₁₋₆haloalkyl, —N(R³)(R⁴), —CN, —CO₂—C₁₋₆alkyl, —C(O)—C₁₋₆alkyl, and —S—C₁₋₆alkyl. In certain embodiments, R⁸ is aryl or aralkyl; each of which is optionally substituted with 1, 2, or 3 substituents independently selected from the group consisting of halogen, hydroxyl, C₁₋₆alkoxy, C₁₋₆alkyl, C₁₋₆haloalkyl, —N(R³)(R⁴), —CN, and —CO₂—C₁₋₆alkyl. In certain embodiments, R⁸ is phenyl substituted with 2 substituents independently selected from the group consisting of halogen, C₁₋₆alkyl, and C₁₋₆haloalkyl, where the first substituent is located at the 2-position of the phenyl group, and the second substituent is located at the 6-position of the phenyl group. In certain embodiments, R⁸ is an aromatic heterocyclyl or —C(R⁶)₂-(aromatic heterocyclyl); each of which is optionally substituted with 1, 2, or 3 substituents independently selected from the group consisting of halogen, hydroxyl, C₁₋₆alkoxy, C₁₋₆alkyl, C₁₋₆haloalkyl, —N(R³)(R⁴), —CN, —CO₂—C₁₋₆alkyl, —C(O)—C₁₋₆alkyl, and —S—C₁₋₆alkyl. In certain embodiments, R⁸ is cycloalkyl, cycloalkenyl, heterocyclyl, —C(R⁶)₂-cycloalkyl, —C(R⁶)₂— cycloalkenyl, —C(R⁶)₂-heterocyclyl, or C₁₋₆alkyl; each of which is optionally substituted with 1, 2, or 3 substituents independently selected from the group consisting of halogen, hydroxyl, C₁₋₆alkoxy, C₁₋₆alkyl, C₁₋₆haloalkyl, —N(R³)(R⁴), —CN, —CO₂—C₁₋₆alkyl, —C(O)—C₁₋₆alkyl, and —S—C₁₋₆alkyl. In certain embodiments, R⁸ is C₁₋₆alkyl optionally substituted with 1, 2, or 3 substituents independently selected from the group consisting of halogen, hydroxyl, C₁₋₆alkoxy, C₁₋₆haloalkyl, —N(R³)(R⁴), —CN, —CO₂—C₁₋₆alkyl, and —C(O)—C₁₋₆alkyl.

In certain embodiments, the compound is a compound of Formula IX-B:

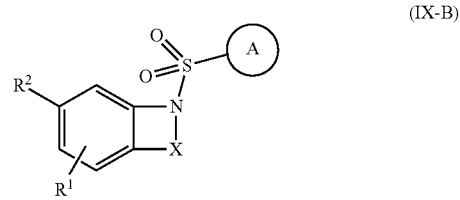

(IX-B)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, C₁₋₆alkoxy, C₁₋₆alkyl, C₁₋₆haloalkyl, —N(R³)(R⁴), —CO₂R⁶, —C₁₋₆alkylene-N(R³)(R⁴), —C₁₋₆alkylene-C₁₋₆alkoxy, —C₁₋₆alkylene-CO₂R⁶, —O—C₁₋₆alkylene-N(R³)(R⁴), —O—C₁₋₆alkylene-CO₂R⁶, —N(R⁶)C(O)—C₁₋₆alkylene-N(R³)(R⁴), —O-aryl, —CN, —S(O)ₚC₁₋₆alkyl, —SO₂N(R³)(R⁴), and —N(R³)SO₂(C₁₋₆alkyl);

X is —[C(R⁵)₂]ₙ-ψ, —C(R⁵)₂C(R⁶)=C(R⁸)-ψ, —C(R⁶)=C(R⁶)C(R⁵)₂-ψ, —C(R⁶)=C(R⁶)-ψ, —O—[C(R⁶)₂]ₘ-ψ, —N(R⁶)—[C(R⁶)₂]ₘ-ψ, —[C(R⁶)₂]ₘ-ψ, —N=C(R⁶)-ψ, —N=C(R⁶)C(R⁶)₂- ψ, —N=N-ψ, —C(R⁶)=N-ψ, —C(O)—[C(R⁶)₂]ₘ-ψ, —C(R⁶)₂C(O)C(R⁶)₂-ψ, —[C(R⁶)₂]ₘ—C(O)-ψ, —C(R⁶)=C(R⁶)C(O)-ψ, —C(O)C(R⁶)=C(R⁶)-ψ, —N(R⁶)—C(O)-ψ, or —C(H)(OR⁶)—[C(R⁶)₂]ₘ-ψ; wherein ψ is a bond to the sulfonamide ring nitrogen atom in Formula IX-B;

R¹ represents independently for each occurrence hydrogen, halogen, or C₁₋₆alkyl;

R² is —N(R⁷)C(O)R⁸, —(C₁₋₂alkylene)-N(R⁷)C(O)R⁸, —C(O)N(R⁷)(R⁸), or heteroaryl, wherein said heteroaryl group is optionally substituted with 1 or 2 substituents independently selected from the group consisting of halogen, hydroxyl, C₁₋₆alkoxy, C₁₋₆alkyl, C₁₋₆haloalkyl, aryl, heteroaryl, and —N(R³)(R⁴);

R³ and R⁴ each represent independently hydrogen or C₁₋₆alkyl; or R³ and R⁴ taken together with the nitrogen atom to which they are attached form a 3-7 membered heterocyclic ring;

R⁵ represents independently for each occurrence hydrogen, halogen, or C₁₋₆alkyl;

R⁶ and R⁷ each represent independently for each occurrence hydrogen or C₁₋₆alkyl;

R⁸ is aryl, aralkyl, cycloalkyl, cycloalkenyl, heterocyclyl, —C(R⁶)₂-cycloalkyl, —C(R⁶)₂-cycloalkenyl, —C(R⁶)₂-heterocyclyl, or C₁₋₆alkyl; each of which is optionally substituted with 1, 2, or 3 substituents independently selected from the group consisting of halogen, hydroxyl, C₁₋₆alkoxy, C₁₋₆alkyl, C₁₋₆haloalkyl, —N(R³)(R⁴), —CN, —CO₂—C₁₋₆alkyl, —C(O)—C₁₋₆alkyl, —S(O)ₚC₁₋₆alkyl, —SO₂N(R³)(R⁴), and —N(R³)SO₂(C₁₋₆alkyl);

n is 1, 2, or 3;

m is 1 or 2;

p represents independently for each occurrence 0, 1, or 2; and wherein the stereochemical configuration at a stereocenter in a compound represented by Formula IX-B is R, S, or a mixture thereof.

In certain embodiments, the compound is a compound of Formula IX-C:

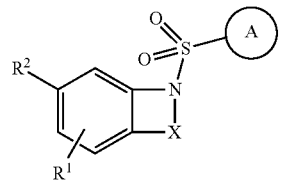

(IX-C)

or a pharmaceutically acceptable salt or solvate thereof; wherein:

A is phenyl, benzyl, or pyridinyl; each of which is substituted with 1, 2, or 3 substituents independently selected from the group consisting of halogen, $C_{1-6}$alkyl, $C_{1-6}$haloalkyl, —N($R^3$)($R^4$), —$C_{1-6}$alkylene-N($R^3$)($R^4$), —$C_{1-6}$alkylene-$C_{1-6}$alkoxy, —$C_{1-6}$alkylene-$CO_2R^6$, —N($R^6$)C(O)—$C_{1-6}$alkylene-N($R^3$)($R^4$), —CN, —S(O)$_2$ $C_{1-6}$alkyl, —SO$_2$N($R^3$)($R^4$), and —N($R^3$)SO$_2$($C_{1-6}$alkyl);

X is —[C($R^5$)$_2$]$_n$-ψ, —C($R^5$)$_2$C($R^6$)=C($R^8$)-ψ, —C($R^6$)=C($R^6$)C($R^5$)$_2$-ψ, —C($R^6$)=C($R^6$)-ψ, or —C(O)—[C($R^6$)$_2$]$_m$-ψ; wherein ψ is a bond to the sulfonamide ring nitrogen atom in Formula IX-C;

$R^1$ represents independently for each occurrence hydrogen, fluoro, or methyl;

$R^2$ is —N($R^7$)C(O)$R^8$ or —(CH$_2$)—N($R^7$)C(O)$R^8$;

$R^3$ and $R^4$ each represent independently hydrogen or methyl;

$R^5$ represents independently for each occurrence hydrogen, fluoro, or methyl;

$R^6$ and $R^7$ each represent independently for each occurrence hydrogen or $C_{1-6}$alkyl;

$R^8$ is phenyl, benzyl, or pyridinyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —CO$_2$—$C_{1-6}$alkyl, —C(O)—$C_{1-6}$alkyl, —S(O)$_2$$C_{1-6}$alkyl, —SO$_2$N($R^3$)($R^4$), and —N($R^3$)SO$_2$($C_{1-6}$alkyl);

n is 1, 2, or 3;

m is 1 or 2;

p represents independently for each occurrence 0, 1, or 2; and wherein the stereochemical configuration at a stereocenter in a compound represented by Formula IX-C is R, S, or a mixture thereof.

The definitions of the variables in Formulae I through IX-C above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

In certain other embodiments, the compound is one of the compounds listed in Tables 1 and 2 herein below, Tables 3-6 in the Examples, or a pharmaceutically acceptable salt of any of the foregoing.

TABLE 1

| No. | Y | Z |
|---|---|---|
| I-1 | 2-Cl, 6-CF$_3$ benzamide | 4-F phenyl |
| I-2 | 2-F, 6-CF$_3$ benzamide | 4-F phenyl |
| I-3 | 2-CF$_3$, 6-CF$_3$ benzamide | 4-F phenyl |
| I-4 | 2-Cl, 6-F benzamide | 4-F phenyl |
| I-5 | 2-F, 6-F benzamide | 3,4-diF phenyl |
| I-6 | 2-Cl, 6-Cl benzamide | 3,4-diF phenyl |

TABLE 1-continued
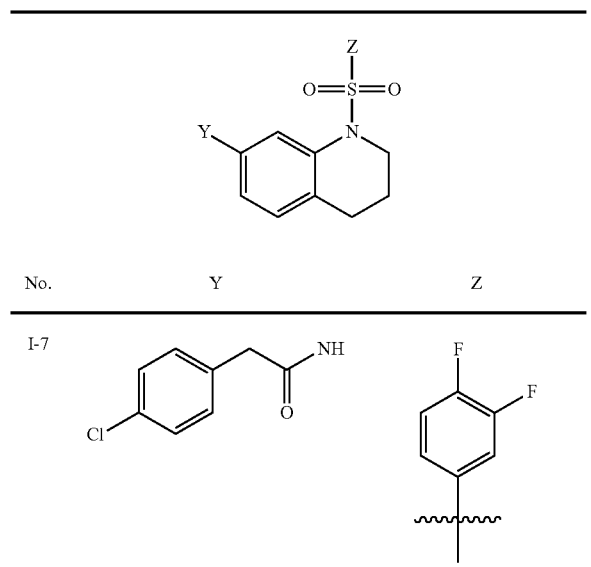
| No. | Y | Z |
|---|---|---|
| I-7 | | |
| I-8 | | |
| I-9 | | |
| I-10 | | |
| I-11 | | |
| I-12 | | |
TABLE 1-continued
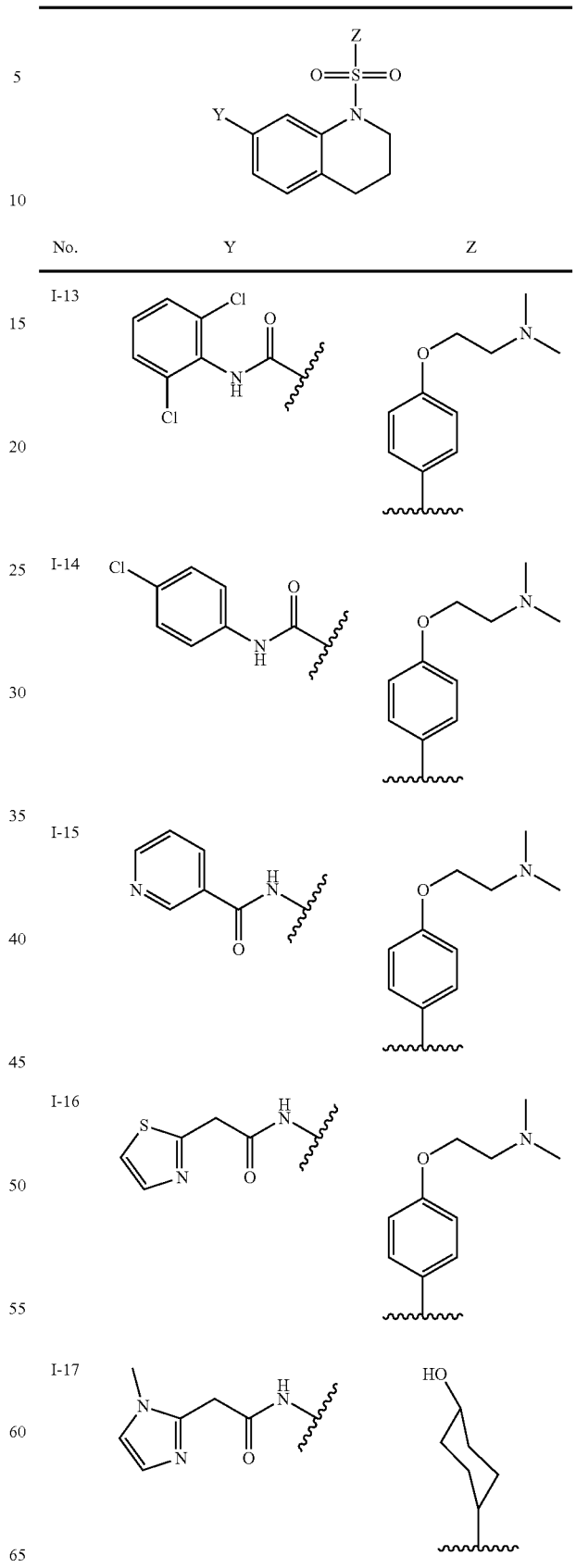
| No. | Y | Z |
|---|---|---|
| I-13 | | |
| I-14 | | |
| I-15 | | |
| I-16 | | |
| I-17 | | |

TABLE 1-continued

| No. | Y | Z |
|---|---|---|
| I-18 | pyrazin-2-yl | 4-hydroxycyclohexyl |
| I-19 | oxazol-2-yl | 4-hydroxycyclohexyl |
| I-20 | 1-methylimidazol-2-yl | 4-hydroxycyclohexyl |
| I-21 | 2-chloro-6-(trifluoromethyl)benzamido | imidazol-1-yl |
| I-22 | 2-fluoro-6-(trifluoromethyl)benzamido | imidazol-1-yl |
| I-23 | 2,6-bis(trifluoromethyl)benzamido | imidazol-1-yl |
| I-24 | 2-chloro-6-fluorobenzamido | imidazol-1-yl |
| I-25 | 2,6-difluorobenzamido | 2-(carboxymethyl)oxazol-5-yl |
| I-26 | 2,6-dichlorobenzamido | 2-(carboxymethyl)oxazol-5-yl |
| I-27 | 2-(4-chlorophenyl)acetamido | 2-(carboxymethyl)oxazol-5-yl |
| I-28 | 2-chloro-6-fluorobenzamido (via CH$_2$) | 2-(carboxymethyl)oxazol-5-yl |
| I-29 | 2-chloro-6-(trifluoromethyl)benzamido | 5-fluoropyridin-2-yl |
| I-30 | 2-fluoro-6-(trifluoromethyl)benzamido | 5-fluoropyridin-2-yl |
| I-31 | 2-chloro-6-fluorobenzamido | 5-fluoropyridin-2-yl |

TABLE 1-continued

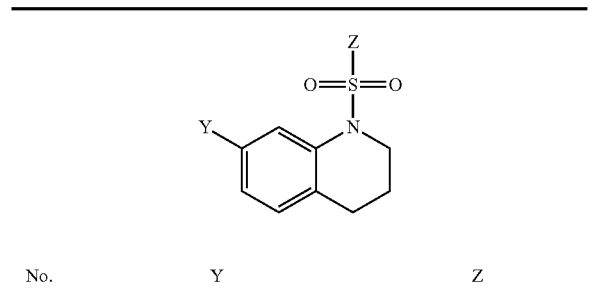

| No. | Y | Z |
|---|---|---|
| I-32 | 2,6-difluorophenyl-C(O)NH- | 5-fluoropyridin-2-yl |
| I-33 | 2,6-dichlorophenyl-C(O)NH- | (methylamino)methyl-cyclopentyl |
| I-34 | 4-chlorophenyl-C(O)NH- | (methylamino)methyl-cyclopentyl |
| I-35 | pyridin-3-yl-C(O)NH- | (methylamino)methyl-cyclopentyl |
| I-36 | thiazol-2-yl-CH2-C(O)NH- | (methylamino)methyl-cyclopentyl |
| I-37 | 2-chloro-6-(trifluoromethyl)phenyl-C(O)NH- | N-(dimethylaminoacetyl)aminocyclopentyl |
| I-38 | 2-fluoro-6-(trifluoromethyl)phenyl-C(O)NH- | N-(dimethylaminoacetyl)aminocyclopentyl |
| I-39 | 2,6-bis(trifluoromethyl)phenyl-C(O)NH- | N-(dimethylaminoacetyl)aminocyclopentyl |
| I-40 | 2-chloro-6-fluorophenyl-C(O)NH- | N-(dimethylaminoacetyl)aminocyclopentyl |

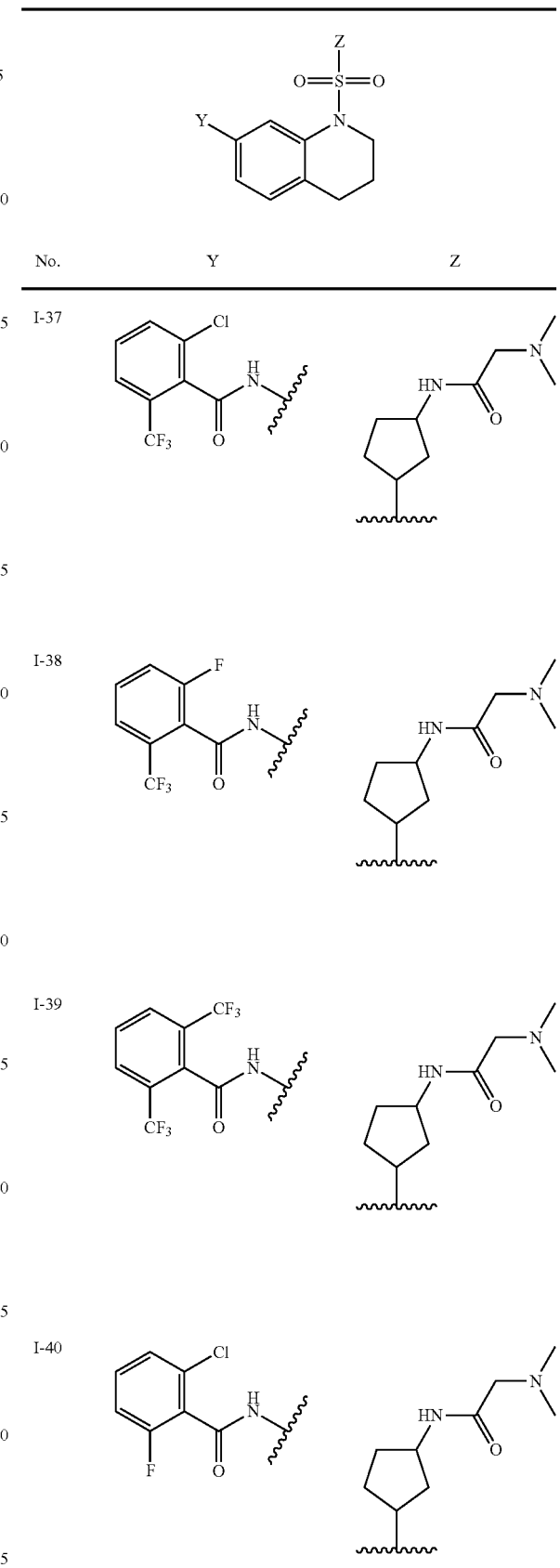

TABLE 1A

| No.   | Y                          | Z                               | X    |
|-------|----------------------------|---------------------------------|------|
| IA-1  | phenyl                     | 4-fluorophenyl                  | —OH  |
| IA-2  | phenyl                     | 5-isopropyl-2-methoxyphenyl     | —OH  |
| IA-3  | phenyl                     | 3-cyanophenyl                   | —OH  |
| IA-4  | 3-methylphenyl             | 4-fluorophenyl                  | —OH  |
| IA-5  | 3-methylphenyl             | 5-isopropyl-2-methoxyphenyl     | —OH  |
| IA-6  | 3-methylphenyl             | 3-cyanophenyl                   | —OH  |
| IA-7  | 3-fluorophenyl             | 4-fluorophenyl                  | —OH  |

TABLE 1A-continued

| No. | Y | Z | X |
|---|---|---|---|
| IA-8 | 3-fluorophenyl (R) | 5-isopropyl-2-methoxyphenyl | —OH |
| IA-9 | 3-fluorophenyl (R) | 3-cyanophenyl | —OH |
| IA-10 | phenyl (R) | 2-methoxypyridin-4-yl | —OH |
| IA-11 | 3-methylphenyl (R) | 2-methoxypyridin-4-yl | —OH |
| IA-12 | 3-fluorophenyl (R) | 2-methoxypyridin-4-yl | —OH |
| IA-13 | phenyl (R) | 4-fluorophenyl | —N(H)C(O)CH$_3$ |
| IA-14 | phenyl (R) | 5-isopropyl-2-methoxyphenyl | —N(H)C(O)CH$_3$ |

TABLE 1A-continued
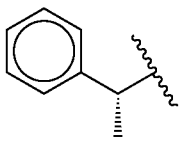
| No. | Y | Z | X |
|---|---|---|---|
| IA-15 | 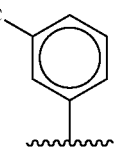 | 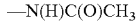 | —N(H)C(O)CH$_3$ |
| IA-16 | 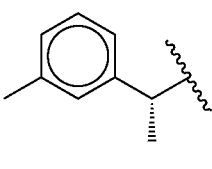 | 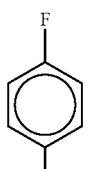 | —N(H)C(O)CH$_3$ |
| IA-17 |  | 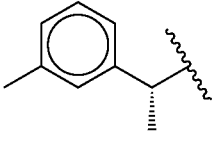 | —N(H)C(O)CH$_3$ |
| IA-18 | 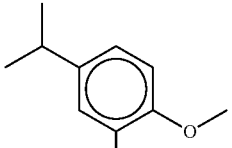 | 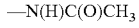 | —N(H)C(O)CH$_3$ |
| IA-19 | 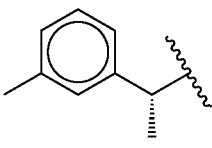 | 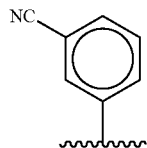 | —N(H)C(O)CH$_3$ |
| IA-20 | 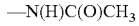 | 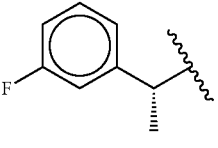 | —N(H)C(O)CH$_3$ |
| IA-21 | 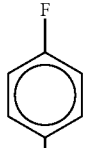 | 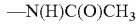 | —N(H)C(O)CH$_3$ |

TABLE 1A-continued

| No. | Y | Z | X |
|---|---|---|---|
| IA-22 | phenyl (S) | 2-methoxypyridin-4-yl | —N(H)C(O)CH₃ |
| IA-23 | 3-methylphenyl (S) | 2-methoxypyridin-4-yl | —N(H)C(O)CH₃ |
| IA-24 | 3-fluorophenyl (S) | 2-methoxypyridin-4-yl | —N(H)C(O)CH₃ |
| IA-25 | phenyl (S) | tetrahydro-2H-pyran-4-yl | —N(H)C(O)CH₃ |
| IA-26 | 3-methylphenyl (S) | tetrahydro-2H-pyran-4-yl | —N(H)C(O)CH₃ |
| IA-27 | 3-fluorophenyl (S) | tetrahydro-2H-pyran-4-yl | —N(H)C(O)CH₃ |
| IA-28 | phenyl (S) | tetrahydro-2H-pyran-4-yl | —OH |
| IA-29 | 3-methylphenyl (S) | tetrahydro-2H-pyran-4-yl | —OH |

TABLE 1A-continued

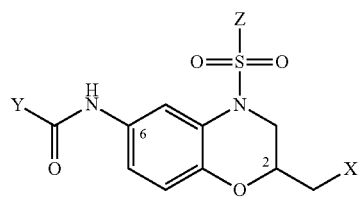

| No. | Y | Z | X |
|---|---|---|---|
| IA-30 | 3-fluorophenyl (with stereochemistry) | tetrahydropyran-4-yl | —OH |

In certain embodiments, the invention provides a compound in Table 1A, where the compound has the R-configuration at the C3-position. In certain other embodiments, the invention provides a compound in Table 1A, where the compound has the S-configuration at the C3-position.

TABLE 2

| No. | Structure |
|---|---|
| II-1 | |
| II-2 | |
| II-3 | |
| II-4 | |
| II-5 | |

TABLE 2-continued

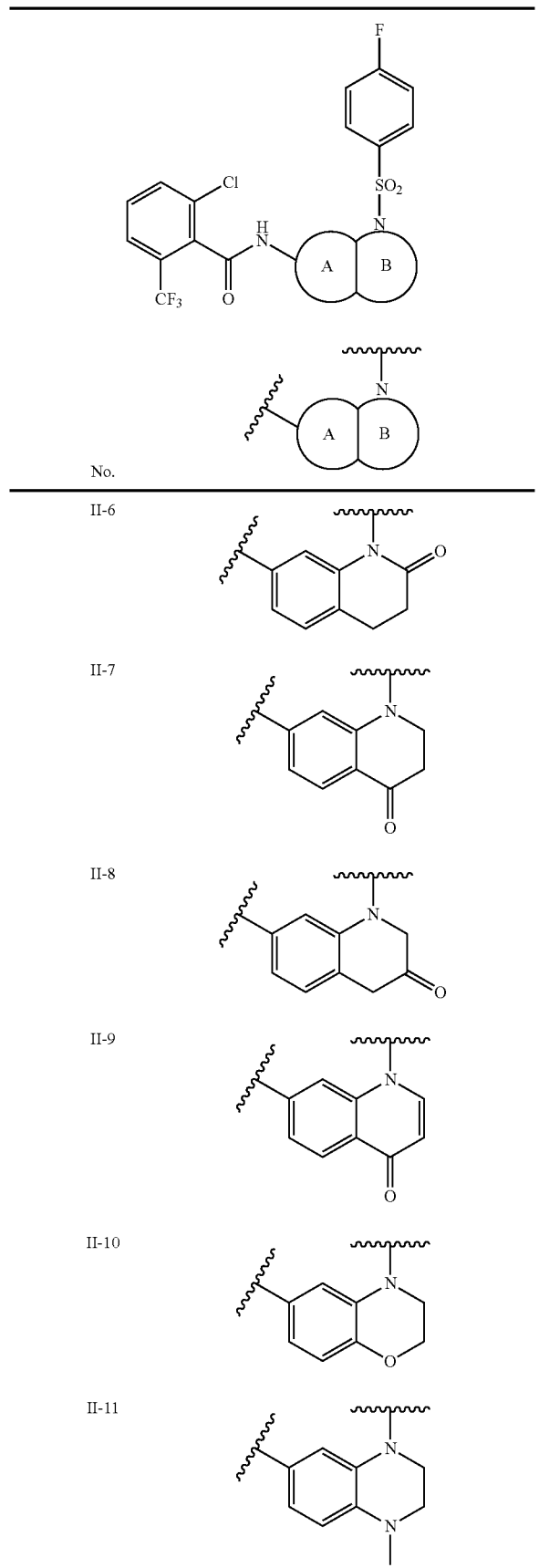

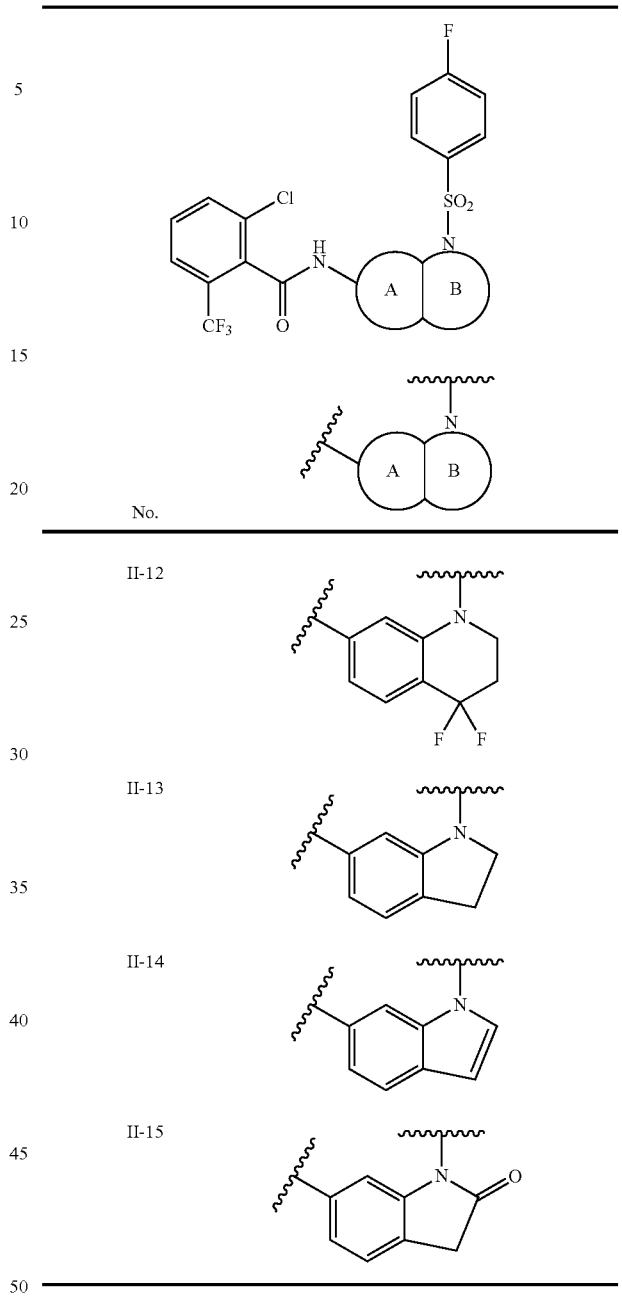

In certain other embodiments, the compound is one of the following: 2-chloro-6-fluoro-N-(1-((3-(1-(methylamino)ethyl)phenyl)sulfonyl)-1,2,3,4-tetrahydroquinolin-7-yl)benzamide; 2-chloro-N-(1-((3-((dimethylamino)methyl)phenyl)sulfonyl)-1,2,3,4-tetrahydroquinolin-7-yl)-6-fluorobenzamide; 2-chloro-6-fluoro-N-(1-((3-(2-(methylamino)ethyl)phenyl)sulfonyl)-1,2,3,4-tetrahydroquinolin-7-yl)benzamide; 2-chloro-N-(1-((4-(2-(dimethylamino)ethoxy)phenyl)sulfonyl)-1,2,3,4-tetrahydroquinolin-7-yl)-6-fluorobenzamide; N-(1-((1H-imidazol-1-yl)sulfonyl)-1,2,3,4-tetrahydroquinolin-7-yl)-2-chloro-6-fluorobenzamide; 2-(2-((7-(2-chloro-6-fluorobenzamido)-3,4-dihydroquinolin-1(2H)-yl)sulfonyl)oxazol-5-yl)acetic acid; 2-chloro-N-(1-((4-((dimethylamino)methyl)phenyl)sulfonyl)-1,2,3,4-tetrahydroquinolin-7-yl)-6-fluorobenzamide; 2-chloro-N-

(1-((4-(2-(dimethylamino)ethoxy)phenyl)sulfonyl)-1,2,3,4-tetrahydroquinolin-7-yl)-6-fluorobenzamide; 2-chloro-N-(1-((5-(2-(dimethylamino)ethoxy)-1,2,4-oxadiazol-3-yl)sulfonyl)-1,2,3,4-tetrahydroquinolin-7-yl)-6-fluorobenzamide; 2-chloro-6-fluoro-N-(1-((4-(methylamino)cyclohexyl)sulfonyl)-1,2,3,4-tetrahydroquinolin-7-yl)benzamide; 2-chloro-6-fluoro-N-(1-((4-hydroxycyclohexyl)sulfonyl)-1,2,3,4-tetrahydroquinolin-7-yl)benzamide; 2-chloro-6-fluoro-N-(1-((3-(methylamino)pyrrolidin-1-yl)sulfonyl)-1,2,3,4-tetrahydroquinolin-7-yl)benzamide; 4-((7-(2-chloro-6-fluorobenzamido)-3,4-dihydroquinolin-1(2H)-yl)sulfonyl)benzoic acid; 2-chloro-6-fluoro-N-(1-((2-((methylamino)methyl)cyclopropyl)sulfonyl)-1,2,3,4-tetrahydroquinolin-7-yl)benzamide; 2-chloro-6-fluoro-N-(1-((3-((methylamino)methyl)cyclopentyl)sulfonyl)-1,2,3,4-tetrahydroquinolin-7-yl)benzamide; 2-chloro-N-(1-((3-(2-(dimethylamino)acetamido)pyrrolidin-1-yl)sulfonyl)-1,2,3,4-tetrahydroquinolin-7-yl)-6-fluorobenzamide; N-(1-((1H-imidazol-1-yl)sulfonyl)-1,2,3,4-tetrahydroquinolin-7-yl)-2-(4-chlorophenyl)acetamide; 2-(2-((7-(2-(4-chlorophenyl)acetamido)-3,4-dihydroquinolin-1(2H)-yl)sulfonyl)oxazol-5-yl)acetic acid; 2-(4-chlorophenyl)-N-(1-((4-((dimethylamino)methyl)phenyl)sulfonyl)-1,2,3,4-tetrahydroquinolin-7-yl)acetamide; 2-(4-chlorophenyl)-N-(1-((4-(2-(dimethylamino)ethoxy)phenyl)sulfonyl)-1,2,3,4-tetrahydroquinolin-7-yl)acetamide; N-(1-((1H-imidazol-1-yl)sulfonyl)-1,2,3,4-tetrahydroquinolin-7-yl)-2-(thiazol-2-yl)acetamide; 2-(2-((7-(2-cyclohexylacetamido)-3,4-dihydroquinolin-1(2H)-yl)sulfonyl)oxazol-5-yl)acetic acid; 2-(4-methoxyphenyl)-N-(1-((4-((dimethylamino)methyl)phenyl)sulfonyl)-1,2,3,4-tetrahydroquinolin-7-yl)acetamide; N-(1-((4-(2-(dimethylamino)ethoxy)phenyl)sulfonyl)-1,2,3,4-tetrahydroquinolin-7-yl)-2-(p-tolyl)acetamide; 2,6-difluoro-N-(6-methyl-1-((3-(1-(methylamino)ethyl)phenyl)sulfonyl)-1,2,3,4-tetrahydroquinolin-7-yl)benzamide; N-(1-((3-((dimethylamino)methyl)phenyl)sulfonyl)-6-methyl-1,2,3,4-tetrahydroquinolin-7-yl)-2,6-difluorobenzamide; 2,6-difluoro-N-(6-methyl-1-((3-(2-(methylamino)ethyl)phenyl)sulfonyl)-1,2,3,4-tetrahydroquinolin-7-yl)benzamide; N-(1-((4-(2-(dimethylamino)ethoxy)phenyl)sulfonyl)-6-methyl-1,2,3,4-tetrahydroquinolin-7-yl)-2,6-difluorobenzamide; 2-chloro-6-fluoro-N-(1-((4-fluorophenyl)sulfonyl)-3-methyl-1,2,3,4-tetrahydroquinolin-7-yl)benzamide; 2-chloro-N-(1-((3,4-difluorophenyl)sulfonyl)-4-methyl-1,2,3,4-tetrahydroquinolin-7-yl)-6-fluorobenzamide; 2,6-difluoro-N-(4-methyl-1-((5-methylisoxazol-4-yl)sulfonyl)-1,2,3,4-tetrahydroquinolin-7-yl)benzamide; N-(1-((4-(2-(dimethylamino)ethoxy)phenyl)sulfonyl)-2-methyl-1,2,3,4-tetrahydroquinolin-7-yl)-2,6-difluorobenzamide; N-(2,6-difluorophenyl)-1-((4-methyl-3-((methylamino)methyl)phenyl)sulfonyl)-1,2,3,4-tetrahydroquinoline-7-carboxamide; N-(2,6-difluorophenyl)-1-((3-((dimethylamino)methyl)phenyl)sulfonyl)-1,2,3,4-tetrahydroquinoline-7-carboxamide; N-(2,6-difluorophenyl)-1-((3-(2-methoxyethyl)phenyl)sulfonyl)-1,2,3,4-tetrahydroquinoline-7-carboxamide; N-(2,6-difluorophenyl)-1-((4-(2-(dimethylamino)ethoxy)phenyl)sulfonyl)-1,2,3,4-tetrahydroquinoline-7-carboxamide; 1-((4-fluorophenyl)sulfonyl)-7-(1H-imidazol-1-yl)-1,2,3,4-tetrahydroquinoline; 2-(2-((6-(1H-pyrazol-5-yl)-3,4-dihydroquinolin-1(2H)-yl)sulfonyl)oxazol-5-yl)acetic acid; 1-(4-((7-(1H-imidazol-1-yl)-3,4-dihydroquinolin-1(2H)-yl)sulfonyl)phenyl)-N,N-dimethylmethanamine; 1-((3,4-difluorophenyl)sulfonyl)-6-(1H-imidazol-1-yl)-1,2,3,4-tetrahydroquinoline; 2-chloro-6-fluoro-N-(1-((4-fluorophenyl)sulfonyl)-2-oxo-1,2,3,4-tetrahydroquinolin-7-yl)benzamide; 2-chloro-N-(1-((3-((dimethylamino)methyl)phenyl)sulfonyl)-2-oxo-1,2,3,4-tetrahydroquinolin-7-yl)-6-fluorobenzamide; 2-chloro-N-(1-((3,4-difluorophenyl)sulfonyl)-2-oxo-1,2,3,4-tetrahydroquinolin-7-yl)-6-fluorobenzamide; N-(1-((4-(2-(dimethylamino)ethoxy)phenyl)sulfonyl)-2-oxo-1,2,3,4-tetrahydroquinolin-7-yl)-2,6-difluorobenzamide; 2-chloro-6-fluoro-N-(1-((4-fluorophenyl)sulfonyl)-4-methyl-1,2-dihydroquinolin-7-yl)benzamide; 2-chloro-N-(1-((3,4-difluorophenyl)sulfonyl)-4-methyl-1,2-dihydroquinolin-7-yl)-6-fluorobenzamide; N-(1-((4-(2-(dimethylamino)ethoxy)phenyl)sulfonyl)-4-methyl-1,2-dihydroquinolin-7-yl)-2,6-difluorobenzamide; 2-chloro-6-fluoro-N-(4-methyl-1-tosyl-1,2-dihydroquinolin-7-yl)benzamide; 2,6-difluoro-N-(1-((4-methyl-3-((methylamino)methyl)phenyl)sulfonyl)-4-oxo-1,2,3,4-tetrahydroquinolin-7-yl)benzamide; N-(1-((3-((dimethylamino)methyl)phenyl)sulfonyl)-4-oxo-1,2,3,4-tetrahydroquinolin-7-yl)-2,6-difluorobenzamide; 2-chloro-6-fluoro-N-(1-((4-fluorophenyl)sulfonyl)-4-oxo-1,2,3,4-tetrahydroquinolin-7-yl)benzamide; 2-chloro-N-(1-((3,4-difluorophenyl)sulfonyl)-4-oxo-1,2,3,4-tetrahydroquinolin-7-yl)-6-fluorobenzamide; 2,6-difluoro-N-(1-((4-methyl-3-((methylamino)methyl)phenyl)sulfonyl)-4-oxo-1,4-dihydroquinolin-7-yl)benzamide; N-(1-((3-((dimethylamino)methyl)phenyl)sulfonyl)-4-oxo-1,4-dihydroquinolin-7-yl)-2,6-difluorobenzamide; 2-chloro-6-fluoro-N-(1-((4-fluorophenyl)sulfonyl)-4-oxo-1,4-dihydroquinolin-7-yl)benzamide; 2-chloro-N-(1-((3,4-difluorophenyl)sulfonyl)-4-oxo-1,4-dihydroquinolin-7-yl)-6-fluorobenzamide; 4-chloro-N-((1-((3,4-difluorophenyl)sulfonyl)-1,2,3,4-tetrahydroquinolin-7-yl)methyl)benzamide; 4-methoxy-N-((1-((4-fluorophenyl)sulfonyl)-1,2,3,4-tetrahydroquinolin-7-yl)methyl)benzamide; 2-chloro-6-fluoro-N-((1-((4-fluorophenyl)sulfonyl)-1,2,3,4-tetrahydroquinolin-7-yl)methyl)benzamide; N-((1-((4-(2-(dimethylamino)ethoxy)phenyl)sulfonyl)-1,2,3,4-tetrahydroquinolin-7-yl)methyl)-4-fluorobenzamide; 4-chloro-N-((1-((3,4-difluorophenyl)sulfonyl)-4-hydroxy-1,2,3,4-tetrahydroquinolin-7-yl)methyl)benzamide; N-((1-((4-fluorophenyl)sulfonyl)-3,3-dimethyl-4-oxo-1,2,3,4-tetrahydroquinolin-7-yl)methyl)-4-methoxybenzamide; 4-fluoro-N-((1-((4-fluorophenyl)sulfonyl)-2-oxo-1,2,3,4-tetrahydroquinolin-7-yl)methyl)benzamide; 4-fluoro-N-((1-((4-hydroxyphenyl)sulfonyl)-1,2,3,4-tetrahydroquinolin-7-yl)methyl)benzamide; 4-chloro-N-((3-((4-fluorophenyl)sulfonyl)-2-oxo-2,3-dihydro-1H-benzo[d]imidazol-5-yl)methyl)benzamide; 4-chloro-N-((3-((3,4-difluorophenyl)sulfonyl)-2-oxo-2,3-dihydro-1H-benzo[d]imidazol-5-yl)methyl)benzamide; 2-chloro-N-(1-((4-(2-(dimethylamino)ethoxy)phenyl)sulfonyl)-2-oxoindolin-6-yl)-6-fluorobenzamide; 2-chloro-6-fluoro-N-(1-((4-fluorophenyl)sulfonyl)-2-oxoindolin-6-yl)benzamide; or a pharmaceutically acceptable salt thereof.

Methods for preparing compounds described herein are illustrated in the following synthetic schemes. The schemes are given for the purpose of illustrating the invention, but not for limiting the scope or spirit of the invention. Starting materials shown in the schemes can be obtained from commercial sources or be prepared based on procedures described in the literature.

The synthetic route illustrated in Scheme 1 is a general method for preparing various amide-substituted tetrahydroquinoline compounds. Nitration of tetrahydroquinoline A by reacting it with a mixture of nitric acid and sulfuric acid provides 7-nitro-tetrahydroquinoline B. A sulfonamide group can be installed by reacting 7-nitro-tetrahydroquinoline B with a mild base and sulfonyl chloride (R—SO₂Cl) to provide sulfonamide C. The nitro group in compound C can be reduced to an amino group providing amino-tetrahydroquinoline D, which can be reacted with an acid chloride to provide the final amide-substituted tetrahydroquinoline E.

The reaction procedures in Scheme 1 are contemplated to be amenable to preparing a wide variety of amide-substituted tetrahydroquinoline compounds having different substituents at the Y, R, and R' positions. For example, a numerous substituted tetrahydroquinolines are known in the literature and/or are commercially available, such as 2-methyl tetrahydroquinoline, 3-methyl tetrahydroquinoline, 4-methyl tetrahydroquinoline, and 6-methyl tetrahydroquinoline. Furthermore, if a functional group that is part of the Y, R, or R' group would not be amenable to a reaction condition described in Scheme 1, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, 2ⁿᵈ ed.; Wiley: New York, 1991, for further description of protecting chemistry and strategies. In certain other embodiments, a functional group in substituent Y, R, or R' in tetrahydroquinoline E can converted to another functional group using standard functional group manipulation procedures known in the art. See, for example, "Comprehensive Organic Synthesis" (B. M. Trost & I. Fleming, eds., 1991-1992).

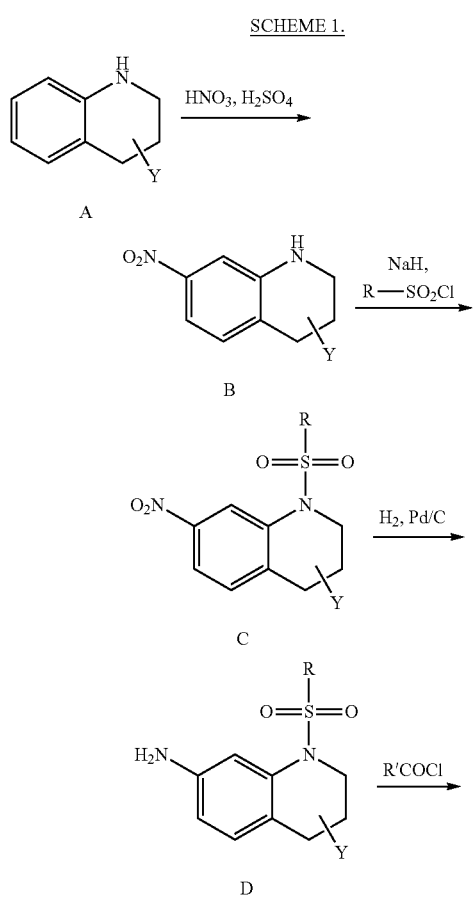

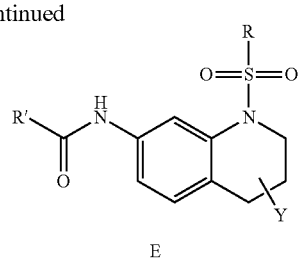

Scheme 2 illustrates a general method for preparing dihydroquinolines. Condensation of phenylene diamine A with ethyl acetoacetate under reflux (e.g., using Conrad-Limpach conditions) provides 7-amino-4-methylquinolin-2(1H)-one B. See, for example, *Med. Chem. Res.* (2010) vol. 19, pages 193-209 for additional description of synthetic procedures. The amino group on quinolinone B can be reacted with an acid chloride to acylate the exocyclic nitrogen providing amide C. Reaction of amide C with mild base and a sulfonyl chloride (R'SO₂Cl) provides sulfonamido-dihydroquinoline D.

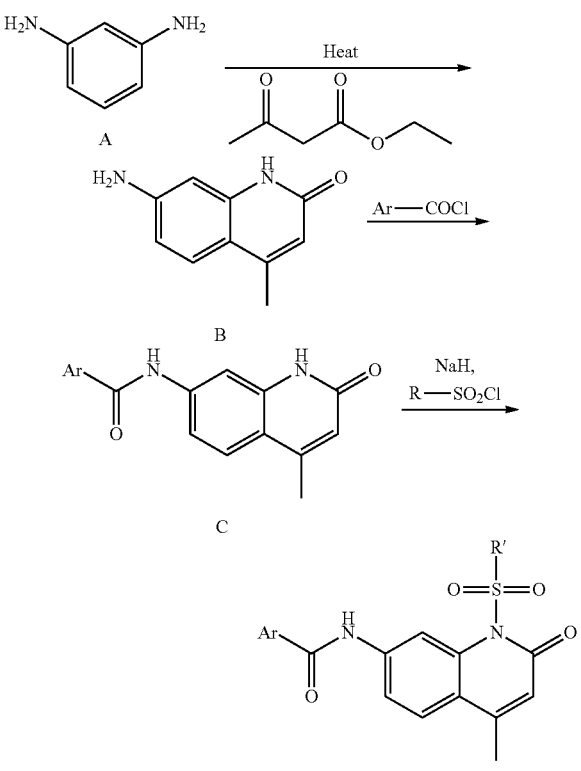

Scheme 3 illustrates a general method for preparing fluoro-substituted, hydroxyl-substituted, and alkoxy-substituted tetrahydroquinoline compounds. Oxidation of tetrahydroquinoline A using potassium permanganate provides ketone B. Ketone B can reduced to alcohol C, reacted with a fluorinating agent (such as DAST) to provide difluorotetrahydroquinoline D, or further oxidized to dihydroquinoline E. The oxidative conversion of ketone B to dihydroquinoline E can be carried using, for example, manganese dioxide, DDQ or selenium dioxide. Reaction of dihydroquinoline E with a fluorinating agent (such as DAST) provides fluorodihydroquinoline F. The identity of the oxidant and fluorinating agent can be selected to accommodate various functional groups that may be present on the synthetic intermediates shown in Scheme 3. Finally, as depicted below alkoxy-substituted tetrahydroquinoline G can be prepared by reaction of alcohol C with methanesulfonyl chloride to provide an intermediate mesylate that is reacted with an alkoxide, such as sodium methoxide, to provide alkoxy-substituted tetrahydroquinoline G.

reduction, such as sodium in liquid ammonia or an aluminum-mercury amalgam, to provide dihydroquinolin-2-one D. Sulfonylation of the amide nitrogen can be carried out by reacting dihydroquinolin-2-one D with a mild base and sulfonyl chloride (RSO$_2$Cl) to provide sulfamide E. Reduction of the nitro group in sulfonamide E can be carried out Raney nickel to provide amine F, which can be reacted with an acid chloride (or carboxylic acid under amide coupling conditions) to provide the desired bicyclopyridone G.

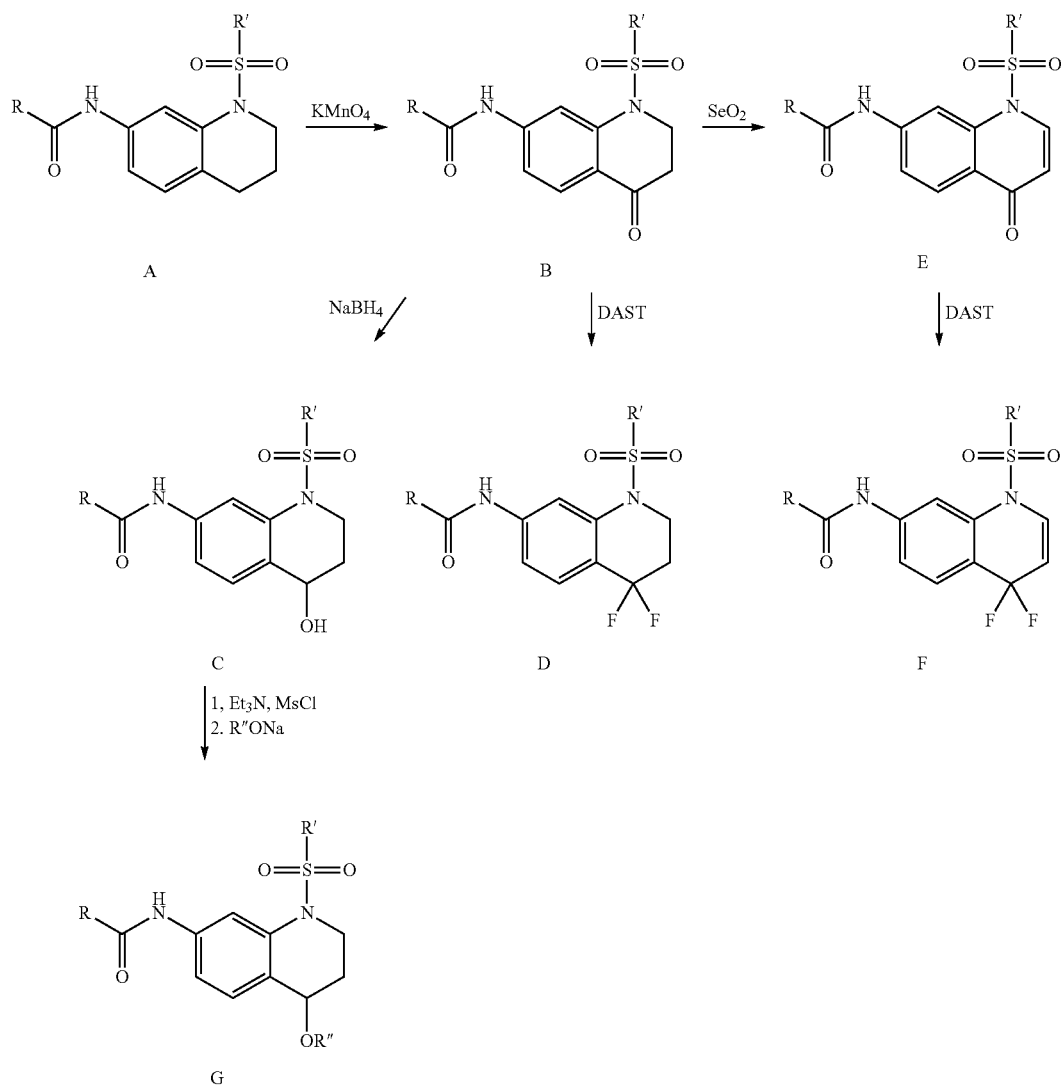

Scheme 4 illustrates a general method for preparing tetrahydroquinolines having, for example, a methyl group at the 4-position. Reaction of aniline A with an α,β-unsaturated acid chloride under Schotten-Baumen conditions (or using a solution of the acid chloride in a solvent such as pyridine, THF, or DMF with a nucleophilic catalyst and added organic base if appropriate) provides amide B. Intramolecular Heck reaction can be used to convert amide B to quinoline-2-one C. Selective reduction of the enamide double bond in compound C may be carried using a dissolving metal

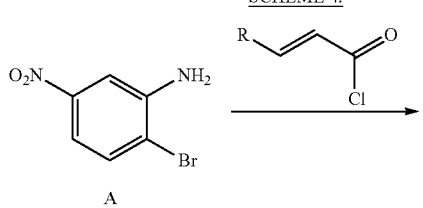

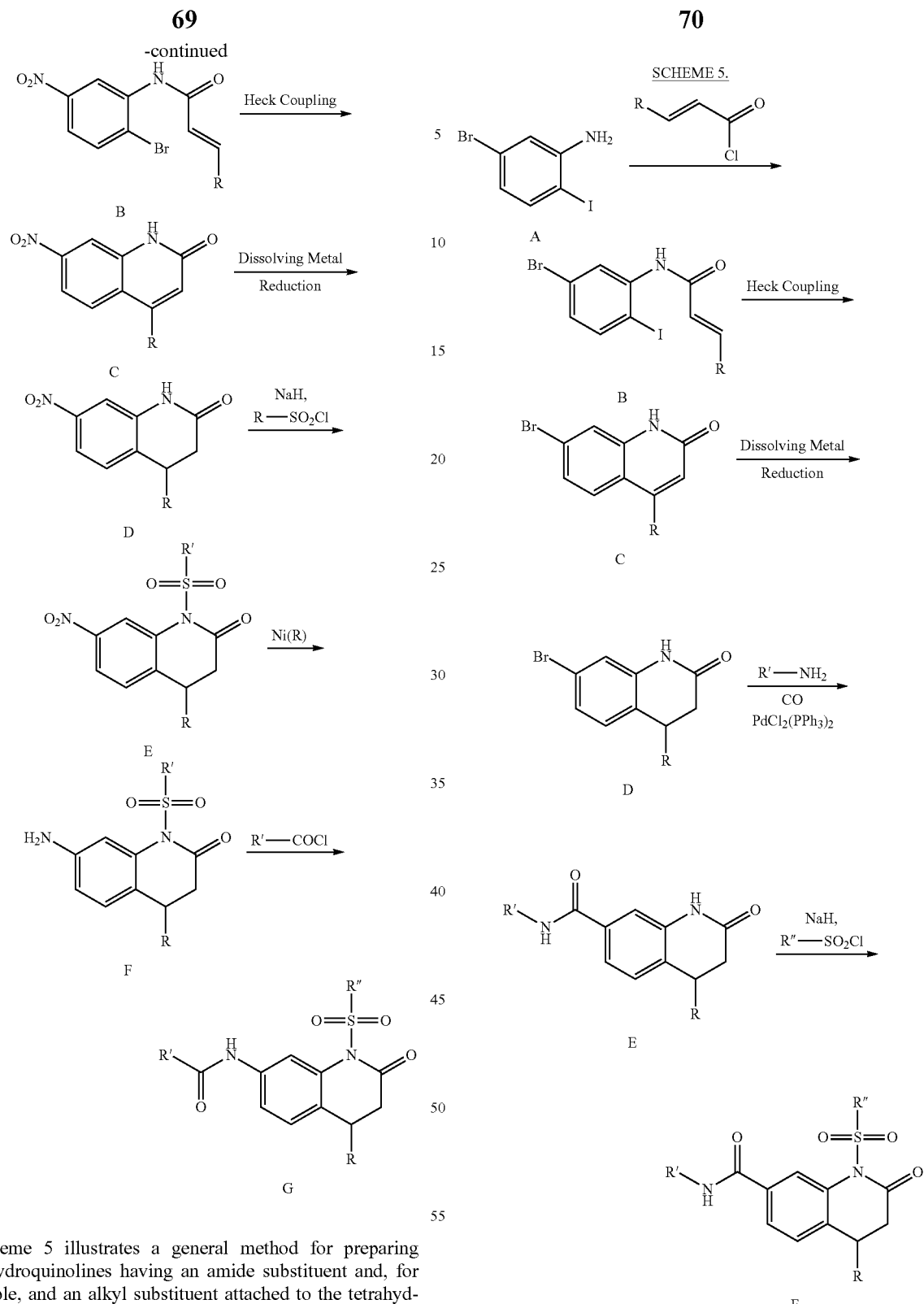

Scheme 5 illustrates a general method for preparing tetrahydroquinolines having an amide substituent and, for example, and an alkyl substituent attached to the tetrahydroquinoline core. Amide coupling of halo-aniline A with an acid chloride provides amide B. Synthetic intermediate B is subjected to Heck Coupling conditions to provide bromo-quinolin-2(1H)-one C, which can be reduced to bromo-dihydroquinolin-2(1H)-one D. Synthetic intermediate D can be converted to amide E, and subsequent reaction with the desired sulfonyl chloride provides the desired tetrahydroquinoline F.

R is, for example, alkyl.
R″ and R″″ are, for example, aryl.

Scheme 6 illustrates an alternative procedure for preparing tetrahydroquinolines having an amide substituent and, for example, and an alkyl substituent attached to the tetrahydroquinoline core.

SCHEME 6.

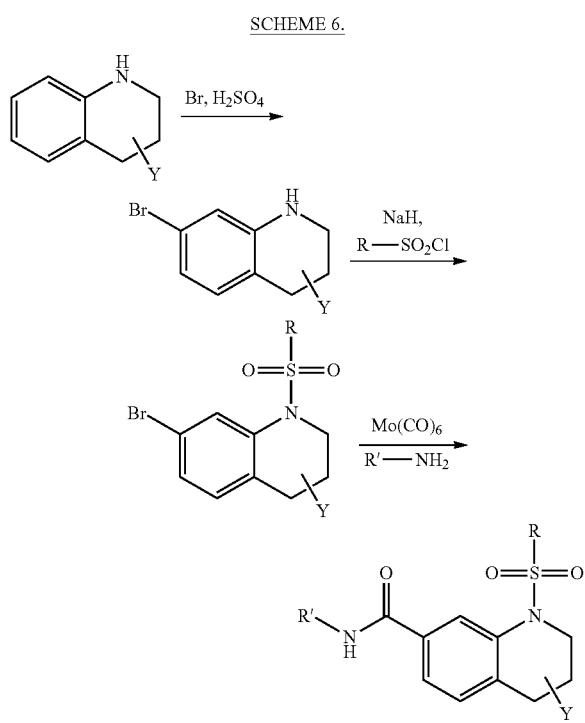

Scheme 7 illustrates a general method for preparing fluorinated tetrahydroquinoline compounds. The starting tetrahydroquinoline-7-carbaldehyde compound shown in Scheme 7 has been described in the literature. See, for example, International Patent Application Publication WO 2010/038901.

SCHEME 7.

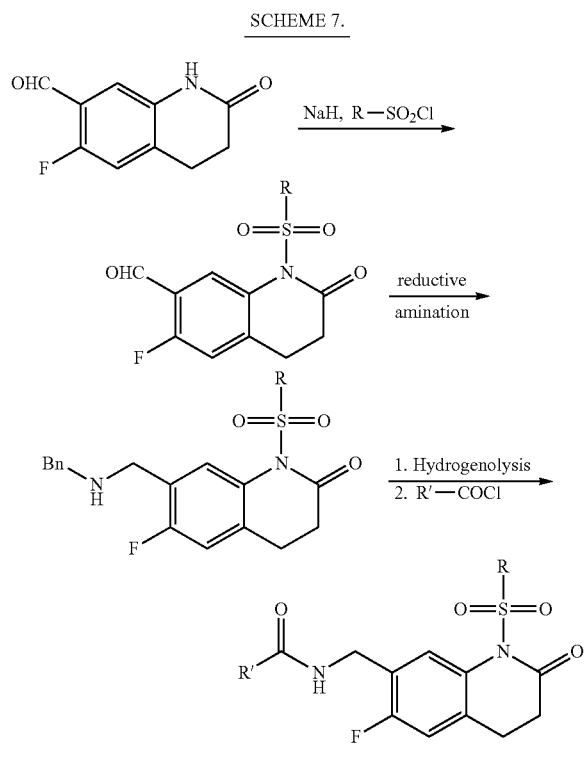

Scheme 8 illustrates a general method for preparing tetrahydroquinoline compounds having a —CH$_2$-amide substituent at the 7-position. Numerous indoles, indolinones, benzimidazoles, benzimidazolones and the like are known in the literature, and they are contemplated to be amenable for use as starting material in the synthetic scheme below to provide various functionalized 6,5-fused bicyclic ring systems.

SCHEME 8.

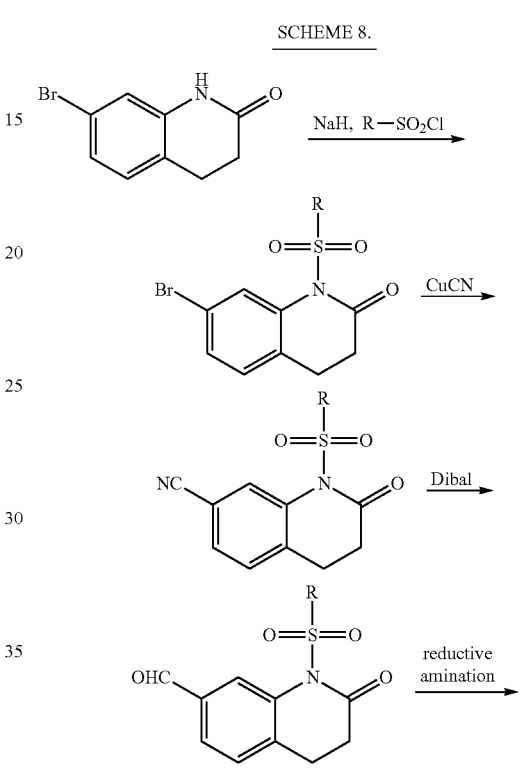

Scheme 9 illustrates multiple general procedures for preparing various indoles, indolinones and related compounds

SCHEME 9.

(A)

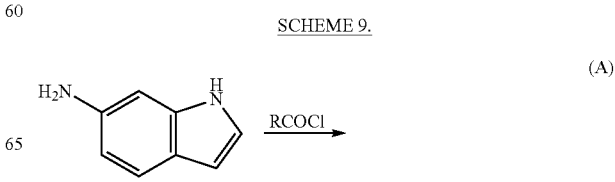

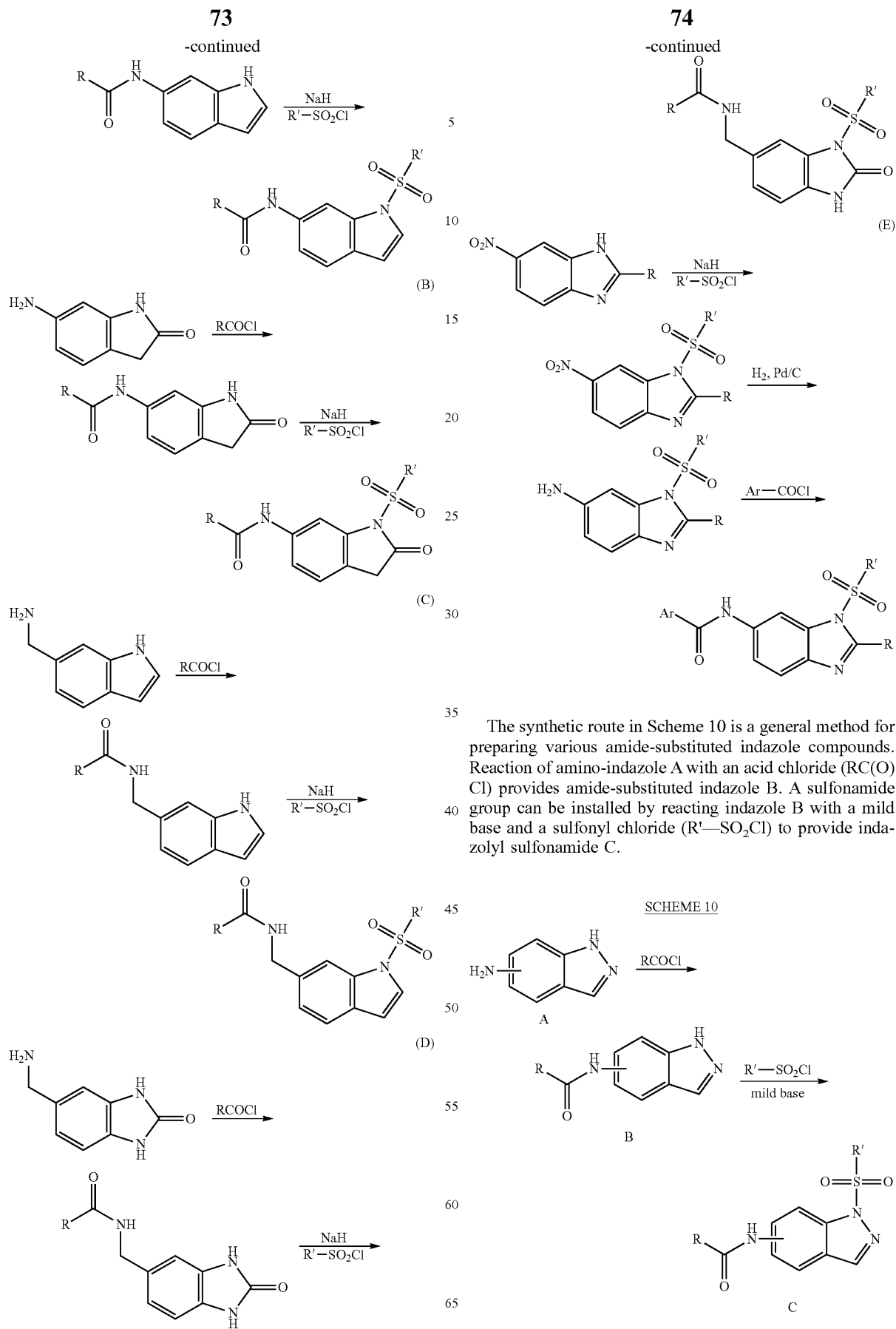
The synthetic route in Scheme 10 is a general method for preparing various amide-substituted indazole compounds. Reaction of amino-indazole A with an acid chloride (RC(O)Cl) provides amide-substituted indazole B. A sulfonamide group can be installed by reacting indazole B with a mild base and a sulfonyl chloride (R'—SO₂Cl) to provide indazolyl sulfonamide C.

The synthetic route in Scheme 11 is a general method for preparing various 3-substituted indazole compounds. Reaction of amino-indazole A with an acid chloride (RC(O)Cl) provides amide-substituted indazole B. Treatment of indazole B with iodine provides iodo-indazole C, which may be subjected to palladium coupling conditions to provide 3-vinyl-imidazole D. A sulfonamide group can be installed by reacting 3-vinyl-imidazole D with a mild base and a sulfonyl chloride (R'—SO$_2$Cl) to provide indazolyl sulfonamide E. Dihydroxylation of the vinyl group may be achieved by treating indazole E with osmium tetraoxide to provide dihydroxy-ethyl indazole F. Sodium perioidate cleavage of the dihydroxy group produces aldehyde G, which may be reduced to provide 3-hydroxylmethylindazole H.

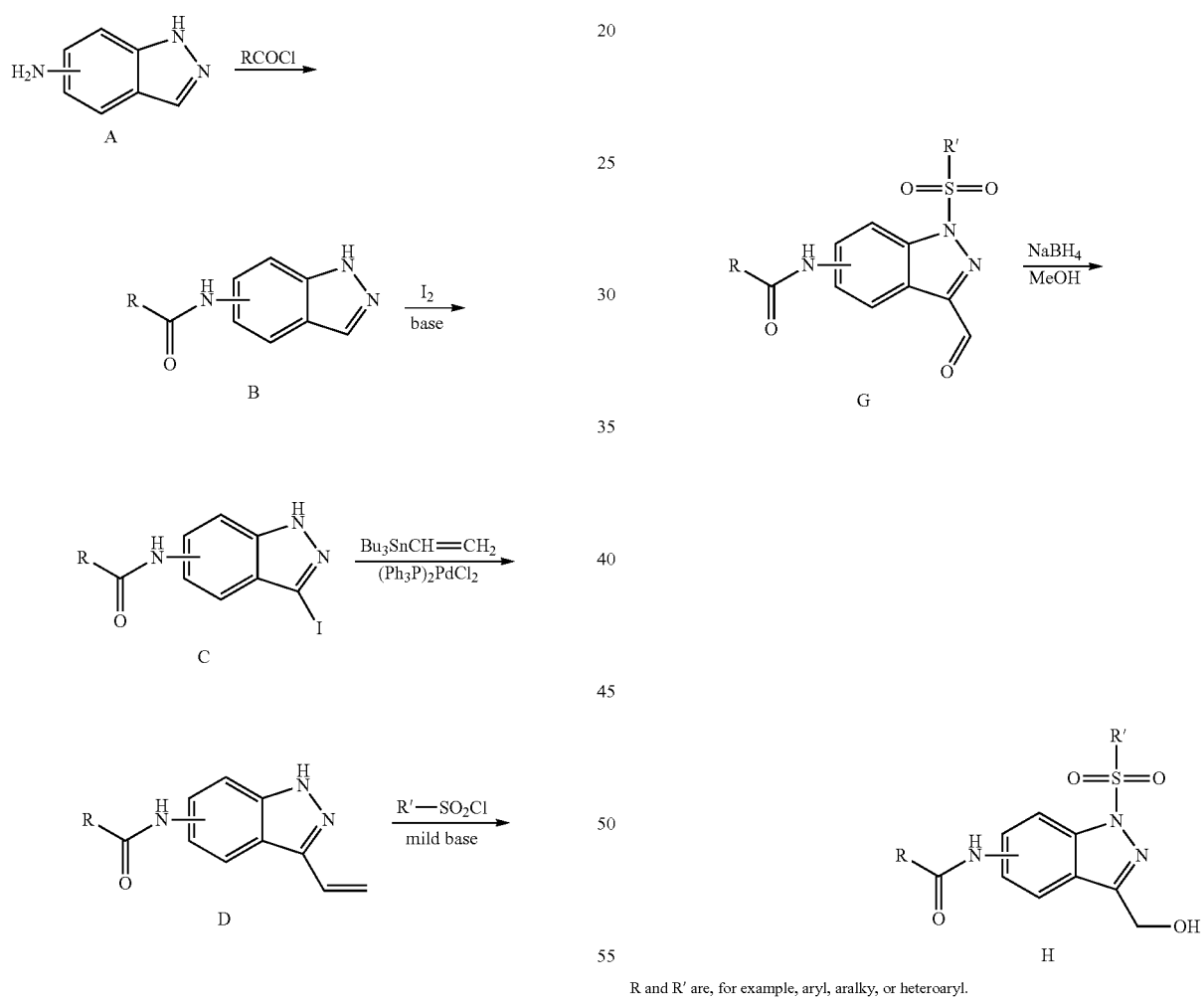
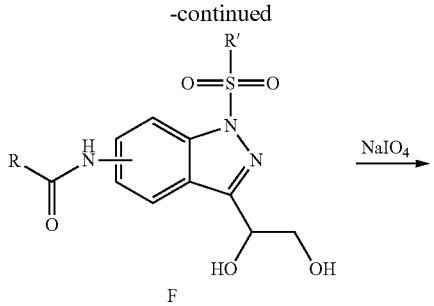

R and R' are, for example, aryl, aralky, or heteroaryl.

Scheme 12 provides an alternative general method for preparing various amide-substituted indazole compounds. Treatment of bromo-phenylsulfonyl indazole A with lithium diisopropylamide (LDA), n-butyl lithium (n-BuLi), and a ketone or aldehyde (R'C(O)R") provides indazole B. Treatment of bromo-phenylsulfonyl indazole A with lithium diisopropylamide (LDA), n-butyl lithium (n-BuLi), and the amide compound R'C(O)N(Me)(OMe) provides indazole C.

SCHEME 12.

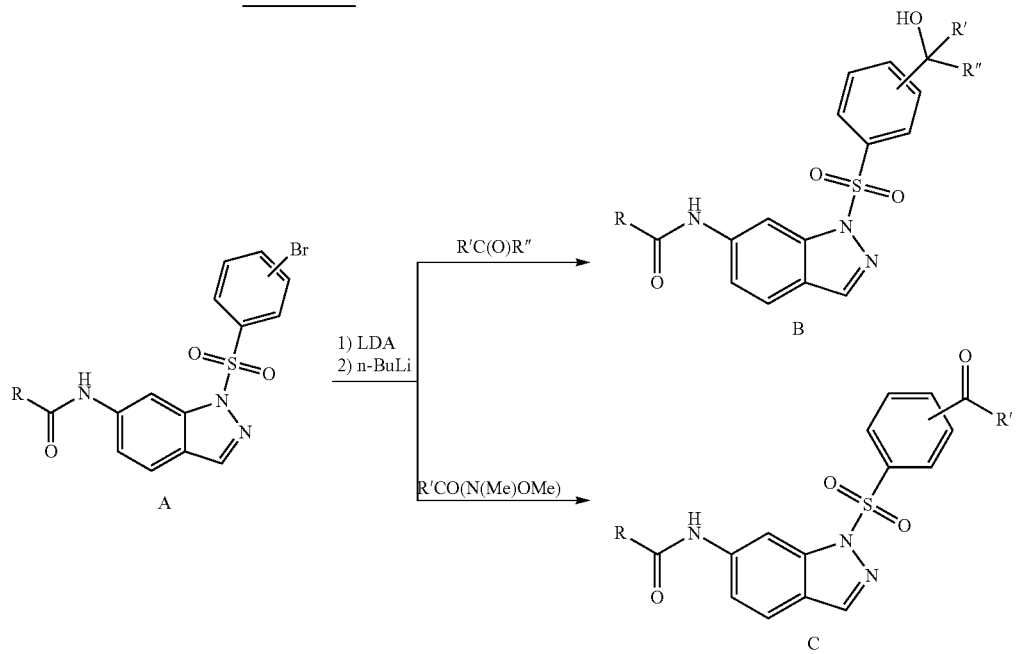

R is, for example, aryl, aralkyl, or heteroaryl;
R' is, for example, alkyl;
R" is, for example, hydrogen or alkyl.

The synthetic route in Scheme 13 is a general method for preparing various amide-substituted benzoxazine compounds. Reaction of nitro-aryl sulfonamide A with an epoxide provides benzoxazine B. The nitro group in benzoxazine B can be reduced to an amino group to provide amino-benzoxazine C. Reaction of amino-benzoxazine C with an acid chloride (R"C(O)Cl) provides amide-substituted benzoxazine D.

SCHEME 13.

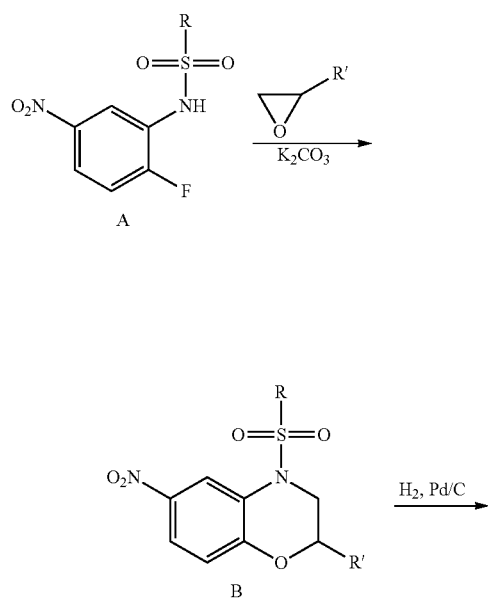

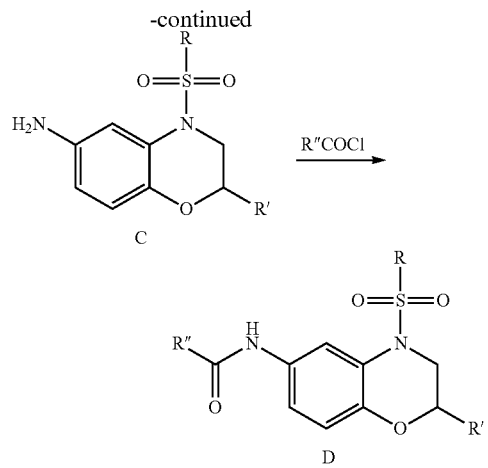

R and R" are, for example, aryl, aralky, or heteroaryl; and R' is, for example, alkyl.

Scheme 14 provides an alternative general method for preparing various amide-substituted benzoxazine compounds. Dichloro-hydroxybenzene A is reacted with a protecting group agent (e.g., tert-butyl-dimethylsilylchloride) to provide intermediate B, which can be treated with sec-butyl lithium (sec-BuLi) and dimethylformamide (DMF, an electrophilic formaldehyde source) to provide aldehyde C. Treatment of aldehyde C with an oxidizing agent (e.g., KMnO$_4$) provide substituted benzoic acid D. Amide coupling of substituted benzoic acid D and amino-benzoxazine E provides benzoxazine amide F. The protecting group (Pg) of benzoxazine amide F can be removed to provide hydroxy-benzamide G, which, if desired, can be converted to its alkyl ether (e.g., where R' is alkyl).

SCHEME 14.

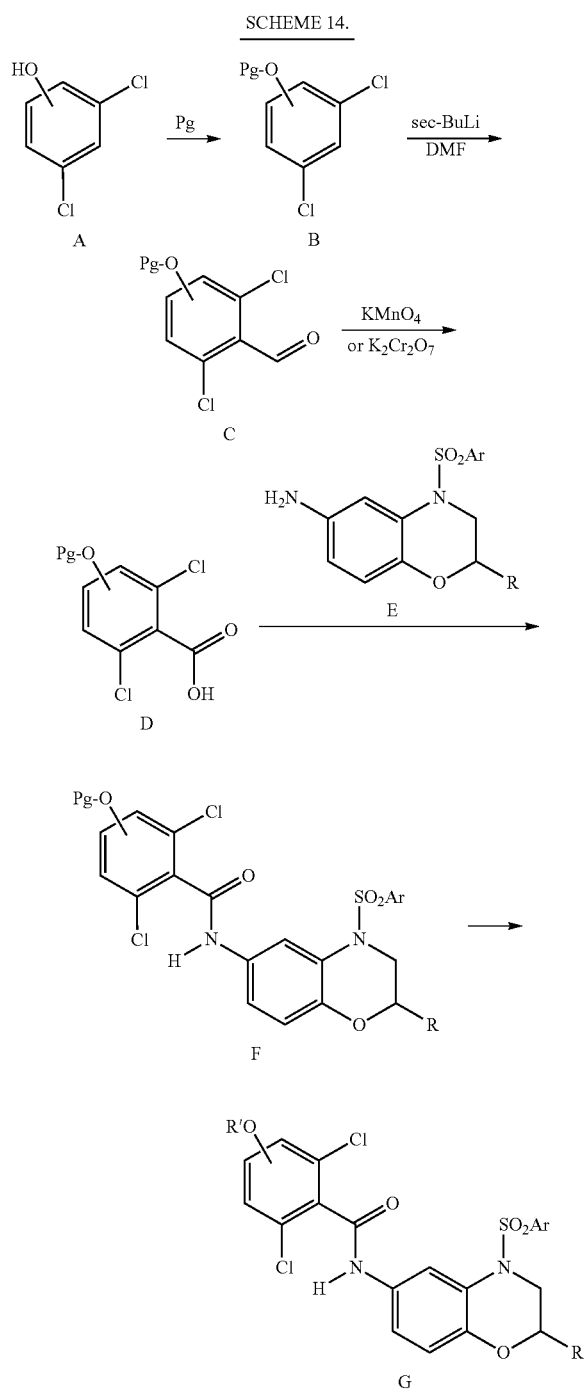

Pg is a protecting group;
R is, for example, alkyl, hydroxyalkyl, aminoalkyl, alkylene-heterocyclic, heterocyclic, or alkylene-CO₂H; and
R' is, for example, hydrogen, alkyl, or haloalkyl.

Scheme 15 provides an alternative general method for preparing various amide-substituted benzoxazine compounds. Reaction of fluoro-dinitrobenzene A with α-hydroxyester B provides benzoxazinone C. The amide group in benzoxazinone C can be reduced using, for example, lithium aluminum hydride (LiAlH₄) to provide benzoxazine D. Amide coupling of benzoxazine D with an acid chloride provides amido-benzoxazine E.

SCHEME 15.

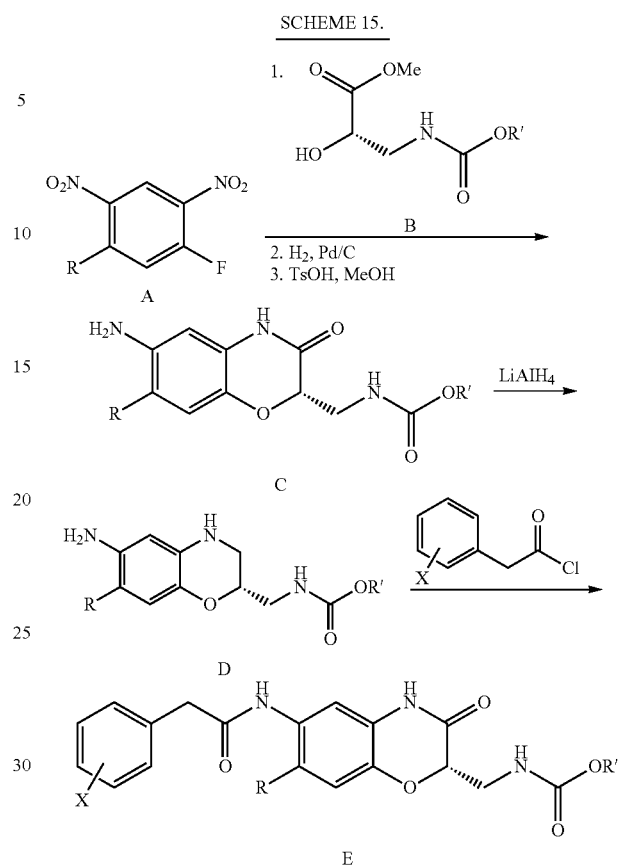

R is hydrogen or fluorine;
R' is, for example, alkyl; and
X is a substituent.

Tetrahydroquinoline and related compounds described herein can be combined with a pharmaceutically acceptable carrier to form a pharmaceutical composition. For example, one aspect of the invention provides a pharmaceutical composition comprising (i) a pharmaceutically acceptable carrier and (ii) a compound represented by Formula V or VI, wherein Formula V and VI are as defined above. In certain other embodiments, the pharmaceutical composition comprises a compound of Formula V. In certain embodiments, the compound is one of the more specific embodiments specified above for Formula V, such as where A is phenyl substituted with 1, 2, or 3 substituents independently selected from the group consisting of halogen, hydroxyl, $C_{1-6}$alkyl, $C_{1-6}$haloalkyl, $-N(R^3)(R^4)$, $-CN$, $-CO_2R^6$, $-C(O)-C_{1-6}$alkyl, $-C_{1-6}$alkylene-$N(R^3)(R^4)$, $-C_{1-6}$alkylene-$C_{1-6}$alkoxy, $-C_{1-6}$alkylene-$CO_2R^6$, $-O-C_{1-6}$alkylene-$N(R^3)(R^4)$, and $-N(R^6)C(O)-C_{1-6}$alkylene-$N(R^3)(R^4)$. In yet other embodiments, A is phenyl substituted with 1, 2, or 3 substituents independently selected from the group consisting of halogen and $C_{1-6}$haloalkyl. In certain other embodiments, X is $-[C(R^5)_2]_n-\psi$, $-C(R^5)_2C(R^6)=C(R^6)-\psi$, $-C(R^6)=C(R^6)C(R^5)_2-\psi$, or $-C(R^6)=C(R^6)-\psi$. In certain other embodiments, X is $-O-[C(R^6)_2]_m-\psi$ or $-O-[C(R^6)(R^9)C(R^6)_2]-\psi$. In certain other embodiments, X is $-C(R^6)=N-\psi$ or $-C(R^{10})=N-\psi$. In certain other embodiments, X is $(CH_2)_3-\psi$. In certain embodiments, $R^2$ is attached to the 7-position of the tetrahydroquinoline ring. In certain embodiments, $R^2$ is $-N(R^7)C(O)R^8$. In certain embodiments, $R^8$ is aryl or aralkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, and —S—$C_{1-6}$alkyl. In certain other embodiments, $R^8$ is aryl substituted with 1, 2, or 3 substituents independently selected from the group consisting of halogen, $C_{1-6}$alkyl, and $C_{1-6}$haloalkyl. In certain other embodiments, $R^8$ is phenyl substituted with 1, 2, or 3 substituents independently selected from the group consisting of halogen, $C_{1-6}$alkyl, and $C_{1-6}$haloalkyl.

In certain other embodiments, the pharmaceutical composition comprises a compound of Formula V-A. In certain embodiments, the compound is one of the more specific embodiments specified above for Formula V-A, such as where A is aryl optionally substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^1$, —$C_{1-6}$alkylene-N($R^3$)($R^4$), —$C_{1-6}$alkylene-$CO_2R^1$, —O—$C_{1-6}$alkylene-N($R^3$)($R^4$), and —N($R^1$)C(O)—$C_{1-6}$alkylene-N($R^3$)($R^4$). In certain embodiments, A is phenyl substituted with 1, 2, or 3 substituents independently selected from the group consisting of halogen and $C_{1-6}$haloalkyl. In certain embodiments, A is phenyl substituted at the 4-position with fluorine or chlorine. In certain embodiments, X is —[C($R^5$)$_2$]$_m$-ψ, —C($R^5$)$_2$C($R^6$)=C($R^8$)-ψ, —C($R^6$)=C($R^6$)C($R^5$)$_2$-ψ, or —C($R^6$)=C($R^6$)-ψ. In certain embodiments, X is —(CH$_2$)$_3$-ψ. In certain embodiments, X is —O—[C($R^6$)$_2$]$_m$-ψ, —N($R^6$)—[C($R^6$)$_2$]$_m$-ψ, —N=C($R^6$)-ψ, or —N=C($R^6$)C($R^6$)$_2$-ψ. In certain embodiments, $R^2$ is —N($R^7$)C(O)$R^8$. In certain embodiments, $R^8$ is aryl or aralkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, and —S—$C_{1-6}$alkyl.

In certain other embodiments, the pharmaceutical composition comprises a compound of Formula VI. In certain embodiments, the compound is one of the more specific embodiments specified above for Formula VI, such as where A is aryl substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^6$, —$C_{1-6}$alkylene-N($R^3$)($R^4$), —$C_{1-6}$alkylene-$CO_2R^6$, —O—$C_{1-6}$alkylene-N($R^3$)($R^4$), and —N($R^6$)C(O)—$C_{1-6}$alkylene-N($R^3$)($R^4$). In certain other embodiments, A is phenyl substituted at the 4-position with fluorine or chlorine. In certain embodiments, $R^8$ is phenyl substituted with 2 or 3 substituents independently selected from the group consisting of halogen, $C_{1-6}$alkyl, and $C_{1-6}$haloalkyl.

In certain other embodiments, the pharmaceutical composition comprises a compound of Formula VI-A. In certain embodiments, the compound is one of the more specific embodiments specified above for Formula VI-A, such as where A is aryl optionally substituted with 1, 2, or 3 substituents independently selected from the group consisting of halogen, hydroxyl, $C_{1-6}$alkyl, $C_{1-6}$haloalkyl, —N($R^3$)($R^4$), —$CO_2R^1$, —$C_{1-6}$alkylene-N($R^3$)($R^4$), —$C_{1-6}$alkylene-$CO_2R^1$, —O—$C_{1-6}$alkylene-N($R^3$)($R^4$), and —N($R^1$)C(O)—$C_{1-6}$alkylene-N($R^3$)($R^4$). In certain embodiments, A is phenyl substituted at the 4-position with fluorine or chlorine. In certain embodiments, $R^8$ is phenyl substituted with 2 or 3 substituents independently selected from the group consisting of halogen, $C_{1-6}$alkyl, $C_{1-6}$haloalkyl, and —CN.

Another aspect of the invention provides the tetrahydroquinoline (and related compounds) described herein in the form of an isolated composition having a chemical purity of at least 95% w/w. In certain embodiments, the invention provides a compound of any one of Formulae I, II, III, or IV or a specific compound described herein (such as in Tables 1-6) in the form of an isolated composition having a chemical purity of at least 95% w/w, or at least 98% w/w.

II. Therapeutic Applications of Tetrahydroquinoline and Related Compounds

It is contemplated that the tetrahydroquinoline and related compounds described herein, such as a compound of Formula I, II, III, IV, V, VI, VII, VIII, and IX provide therapeutic benefits to subjects suffering from an immune disorder or inflammatory disorder. Accordingly, one aspect of the invention provides a method of treating a disorder selected from the group consisting of an immune disorder or inflammatory disorder. The method comprises administering a therapeutically effective amount of a tetrahydroquinoline or related compound described herein, such as a compound of Formula I, II, III, IV, V, VI, VII, VIII, and IX, to a subject in need thereof to ameliorate a symptom of the disorder, wherein Formula I, II, III, IV, V, VI, VII, VIII, and IX are as described above. In certain embodiments, the particular compound of Formula I, II, III, IV, V, VI, VII, VIII, and IX is the compound defined by one of the embodiments described above. In certain other embodiments, the tetrahydroquinoline or related compound described herein is a compound of Formula IX.

For example, in certain embodiments, the method comprises administering a therapeutically effective amount of a compound of Formula IX (wherein Formula IX is as described in Section 1 above) to a subject in need thereof to ameliorate a symptom of the disorder. In certain embodiments, the compound is a compound Formula IX, wherein A is aryl substituted with 1, 2, or 3 substituents independently selected from the group consisting of halogen, hydroxyl, $C_{1-6}$alkyl, $C_{1-6}$haloalkyl, —N($R^3$)($R^4$), —CN, —$CO_2R^6$, —C(O)—$C_{1-6}$alkyl, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), and —N($R^6$)C(O)—$C_{1-6}$alkylene-N($R^3$)($R^4$). In certain other embodiments, A is phenyl substituted with 1, 2, or 3 substituents independently selected from the group consisting of halogen, hydroxyl, $C_{1-6}$alkyl, $C_{1-6}$haloalkyl, —N($R^3$)($R^4$), —CN, —$CO_2R^6$, —C(O)—$C_{1-6}$alkyl, —$C_{1-6}$alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), and —N($R^6$)C(O)—$C_{1-6}$alkylene-N($R^3$)($R^4$). In yet other embodiments, A is phenyl substituted with 1, 2, or 3 substituents independently selected from the group consisting of halogen, hydroxyl, $C_{1-6}$alkoxy, $C_{1-6}$alkyl, $C_{1-6}$haloalkyl, and —N($R^3$)($R^4$). In yet other embodiments, A is phenyl substituted with 1, 2, or 3 substituents independently selected from the group consisting of halogen, hydroxyl, $C_{1-6}$alkyl, $C_{1-6}$haloalkyl, and —CN. In yet other embodiments, A is phenyl substituted with 1, 2, or 3 substituents independently selected from the group consisting of halogen and $C_{1-6}$haloalkyl. In certain embodiments, X is —O—[C($R^6$)$_2$]$_m$-ψ or —O—[C($R^6$)($R^9$)C($R^6$)$_2$]-ψ. In certain other embodiments, X is —C($R^6$)=N-ψ or —C($R^{10}$)=N-ψ. In yet other embodiments, X is —C($R^5$)($C_{1-6}$alkyl)-[C($R^5$)$_2$]$_m$-ψ, —[C($R^5$)$_2$]$_m$—C($R^5$)($C_{1-6}$alkyl)-ψ, —C($R^5$)$_2$—C($R^5$)($C_{1-6}$alkyl)-C($R^5$)$_2$-ψ, —C($R^5$)$_2$C($R^6$)=C($R^6$)-ψ, —C($R^6$)=C($R^6$)C($R^5$)$_2$-ψ, or —C($R^6$)=C($R^6$)-ψ. In certain embodiments, X is —(CH$_2$)$_3$-ψ. In certain embodiments, $R^2$ is attached to the 7-position of the tetrahydroquinoline ring. In certain embodiments, X is —C(O)—[C($R^6$)$_2$]$_m$-ψ. In certain embodiments, $R^2$ is —N($R^7$)C(O)$R^8$. In certain embodiments, $R^8$ is aryl or aralkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, and —S—$C_{1-6}$alkyl. In certain other embodiments, $R^8$ is aryl substituted with 1, 2, or 3 substituents independently selected from the group consisting of halogen, $C_{1-6}$alkyl, and $C_{1-6}$haloalkyl. In yet other embodiments, $R^8$ is phenyl substituted with 1, 2, or 3 substituents independently selected from the group consisting of halogen, $C_{1-6}$alkyl, and $C_{1-6}$haloalkyl. In certain embodiments, $R^8$ is phenyl substituted with 2 substituents independently selected from the group consisting of halogen, $C_{1-6}$alkyl, and $C_{1-6}$haloalkyl, where the first substituent is located at the 2-position of the phenyl group, and the second substituent is located at the 6-position of the phenyl group. In certain embodiments, y is 1.

In certain other embodiments, the tetrahydroquinoline or related compound described herein used in the method is a compound of Formula IX-A. In certain embodiments, the compound is a compound of Formula IX-A where A is aryl optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —$CO_2R^1$, —$C_{1-6}$alkylene-N($R^3$)($R^4$), —$C_{1-6}$alkylene-$CO_2R^1$, —O—$C_{1-6}$alkylene-N($R^3$)($R^4$), and —N($R^1$)C(O)—$C_{1-6}$alkylene-N($R^3$)($R^4$). In certain embodiments, A is phenyl substituted with 1, 2, or 3 substituents independently selected from the group consisting of halogen, hydroxyl, $C_{1-6}$alkoxy, $C_{1-6}$alkyl, $C_{1-6}$haloalkyl, and —N($R^3$)($R^4$). In certain embodiments, A is phenyl substituted with 1, 2, or 3 substituents independently selected from the group consisting of halogen and $C_{1-6}$haloalkyl. In certain embodiments, X—[C($R^5$)$_2$]$_n$-ψ, —C($R^5$)$_2$C($R^6$)=C($R^8$)-ψ, —C($R^6$)=C($R^6$)C($R^5$)$_2$-ψ, or —C($R^6$)=C($R^6$)-ψ. In certain embodiments, X is —(CH$_2$)$_3$-ψ. In certain embodiments, X is —O—[C($R^6$)$_2$]$_m$-ψ, —N($R^6$)—[C($R^6$)$_2$]$_m$-ψ, —N=C($R^6$)-ψ, or —N=C($R^6$)C($R^6$)$_2$-ψ. In certain embodiments, $R^2$ is —N($R^7$)C(O)$R^8$. In certain embodiments, $R^2$ is —(C$_{1-2}$alkylene)-N($R^7$)C(O)$R^8$ or —C(O)N($R^7$)($R^8$). In certain embodiments, $R^2$ is a heteroaryl group optionally substituted with 1 or 2 substituents independently selected from the group consisting of halogen, hydroxyl, $C_{1-6}$alkoxy, $C_{1-6}$alkyl, $C_{1-6}$haloalkyl, and —N($R^3$)($R^4$). In certain embodiments, $R^8$ is aryl or aralkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, and —S—$C_{1-6}$alkyl. In certain embodiments, $R^8$ is aryl or aralkyl; each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, and —$CO_2$—$C_{1-6}$alkyl. In certain embodiments, $R^8$ is an aromatic heterocyclyl or —C($R^6$)$_2$-(aromatic heterocyclyl); each of which is optionally substituted with 1, 2, or 3 substituents independently selected from the group consisting of halogen, hydroxyl, $C_{1-6}$alkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, and —S—$C_{1-6}$alkyl.

In certain embodiments, the disorder an immune disorder. In certain other embodiments, the disorder is an inflammatory disorder. In certain other embodiments, the disorder is an autoimmune disorder. In certain other embodiments, the disorder is rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, or epidermal hyperplasia.

In certain other embodiments, the disorder is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myolitis, polymyolitis, dermatomyositis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, autoimmune hepatitis, psoriatic epidermal hyperplasia, plaque psoriasis, guttate psoriasis, inverse psoriasis, pustular psoriasis, erythrodermic psoriasis, or an immune disorder associated with or arising from activity of pathogenic lymphocytes. In certain embodiments, the psoriasis is plaque psoriasis, guttate psoriasis, inverse psoriasis, pustular psoriasis, or erythrodermic psoriasis.

In certain other embodiments, the disorder is rheumatoid arthritis.

In certain embodiments, the subject is a human. In certain embodiments, the compound is a compound of Formula IX-A, IX-B, or IX-C.

Another aspect of the invention provides for the use of a compound described herein (such as a compound of Formula I, II, III, IV, V, VI, VII, VIII, or IX) in the manufacture of a medicament. In certain embodiments, the medicament is for treating a disorder described herein, such as rheumatoid arthritis.

Another aspect of the invention provides for the use of a compound described herein (such as a compound of Formula I, II, III, IV, V, VI, VII, VIII, or IX) for treating a medical disorder, such a medical disorder described herein (e.g., rheumatoid arthritis).

Further, it is contemplated that tetrahydroquinoline and related compounds described herein, such as a compound of Formula I, II, III, IV, V, VI, VII, VIII, or IX, can inhibit the activity of RORγ. Accordingly, another aspect of the invention provides a method of inhibiting the activity of RORγ. The method comprises exposing a RORγ to an effective amount of a tetrahydroquinoline or related compound described herein, such as a compound of Formula I, II, III, IV, V, VI, VII, VIII, or IX, to inhibit said RORγ, wherein Formula I, II, III, IV, V, VI, VII, VIII, or IX are as described above. In certain embodiments, the particular compound of Formula I, II, III, IV, V, VI, VII, VIII, or IX is the compound defined by one of the embodiments described above. In certain embodiments, the tetrahydroquinoline or related compound is a compound of Formula I, II, III, IV, V, VI, VII, or VIII.

Further, it is contemplated that tetrahydroquinoline and related compounds described herein, such as a compound of Formula I, II, III, IV, V, VI, VII, VIII, and IX, can reduce the amount of interleukin-17 (IL-17) in a subject. IL-17 is a cytokine that affects numerous biological functions, including inducing and mediating pro-inflammatory responses. Accordingly, another aspect of the invention provides a method of reducing the amount of IL-17 in a subject. The method comprises administering to a subject an effective amount of a tetrahydroquinoline or related compound described herein, such as a compound of I, II, III, IV, V, VI, VII, VIII, or IX to reduce the amount of IL-17 in the subject, wherein Formula I, II, III, IV, V, VI, VII, VIII, or IX are as described above. In certain embodiments, the particular compound of Formula I, II, III, IV, V, VI, VII, VIII, or IX is the compound defined by one of the embodiments described above. In certain embodiments, the tetrahydroquinoline or related compound is a compound of Formula I, II, III, IV, V, VI, VII, or VIII.

In certain embodiments, the subject is a human. In certain embodiments, administering the compound reduces the amount of IL-17 produced by Th-17 cells in the subject. A change in the amount of IL-17 produced by, for example, Th-17 cells can be measured using procedures described in the literature, such as an ELISA assay or intracellular staining assay.

Further, it is contemplated that tetrahydroquinoline and related compounds described herein, such as a compound of Formula I, II, III, IV, V, VI, VII, VIII, and IX, may inhibit the synthesis of IL-17 in a subject. Accordingly, another aspect of the invention provides a method of inhibiting the synthesis IL-17 in a subject. The method comprises administering to a subject an effective amount of a compound described herein, e.g., a compound of Formula I, II, III, IV, V, VI, VII, VIII, and IX, to inhibit the synthesis IL-17 in the subject, wherein Formula I, II, III, IV, V, VI, VII, VIII, and IX are as described above. In certain embodiments, the particular compound of Formula I, II, III, IV, V, VI, VII, VIII, and IX is the compound defined by one of the embodiments described above. In certain embodiments, the tetrahydroquinoline or related compound is a compound of Formula I, II, III, IV, V, VI, VII, or VIII.

The description above describes multiple embodiments providing definitions for variables used herein. The application specifically contemplates all combinations of such variables, e.g., particular combinations of the definitions set forth for variables A and X.

III. Combination Therapy

Another aspect of the invention provides for combination therapy. Tetrahydroquinoline and related compounds (e.g., a compound of Formula I, II, III, IV, V, VI, VII, VIII, or IX) or their pharmaceutically acceptable salts may be used in combination with additional therapeutic agents to treat medical disorders, such as medical disorders associated with inappropriate IL-17 pathway activity. Exemplary additional therapeutic agents include, for example, (1) a TNF-α inhibitor; (2) a non-selective COX-1/COX-2 inhibitor; (3) a selective COX-2 inhibitor, such as celecoxib and rofecoxib; (4) other agents for treating inflammatory disease and autoimmune disease including, for example, methotrexate, leflunomide, sulfasalazine, azathioprine, penicillamine, bucillamine, actarit, mizoribine, lobenzarit, hydroxychloroquine, d-penicillamine, aurothiomalate, auranofin, parenteral gold, oral gold, cyclophosphamide, Lymphostat-B, a BAFF/APRIL inhibitor, CTLA-4-Ig, or a mimetic of CTLA-4-Ig; (5) a leukotriene biosynthesis inhibitor, such as a 5-lipoxygenase (5-LO) inhibitor, or a 5-lipoxygenase activating protein (FLAP) antagonist; (6) a LTD4 receptor antagonist; (7) a phosphodiesterase type IV (PDE-IV) inhibitor, such as cilomilast (ariflo) or roflumilast; (8) an antihistamine HI receptor antagonist; (9) an α1 and α2-adrenoceptor agonist; (10) an anticholinergic agent; (11) a β-adrenoceptor agonist; (12) an insulin-like growth factor type I (IGF-1) mimetic; (13) a glucocorticosoid; (14) a kinase inhibitor such as an inhibitor of a Janus Kinase (e.g., JAK1 and/or JAK2 and/or JAK3 and/or TYK2), p38 MAPK, Syk or IKK2; (15) a B-cell target biologic such as rituximab; (16) a selective co-stimulation modulator such as abatacept; (17) an interleukin inhibitor or interleukin receptor inhibitor, such as the IL-1 inhibitor anakinra, IL-6 inhibitor tocilizumab, and IL12/IL-23 inhibitor ustekimumab; (18) an anti-IL17 antibody, anti-IL21 antibody, or anti-IL22 antibody (19) a S1P1 agonist, such as fingolimod; (20) an interferon, such as interferon beta 1; (21) an integrin inhibitor such as natalizumab; (22) a mTOR inhibitor such as rapamycin, cyclosporin and tacrolimus; (23) a non-steroidal antiinflammatory agent (NSAID), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and pyrazolones (apazone, bezpiperylon, feprazone, mofebutazone, oxyphenbutazone, phenylbutazone); (24) a NRF2 pathway activator, such as the fumaric acid derivative, BG-12; and (25) a chemokine or chemokine receptor inhibitor, such as a CCR9 antagonist.

The amount tetrahydroquinoline or related compound (e.g., a compound of Formula I, II, III, IV, V, VI, VII, VIII, or IX) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a tetrahydroquinoline or related compound (e.g., a compound of any one of formulae I-IX) may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the tetrahydroquinoline or related compound (e.g., a compound of any one of formulae I-IX) and the additional therapeutic agent(s) are administered in doses commonly employed when such agents are used as monotherapy for treating the disorder. In other embodiments, the tetrahydroquinoline or related compound (e.g., a compound of any one of formulae I-IX) and the additional therapeutic agent(s) are administered in doses lower than the doses commonly employed when such agents are used as monotherapy for treating the disorder. In certain embodiments, the tetrahydroquinoline or related compound (e.g., a compound of any one of formulae I-IX) and the additional therapeutic agent(s) are present in the same composition, which is suitable for oral administration.

In certain embodiments, the tetrahydroquinoline or related compound (e.g., a compound of any one of formulae I-IX) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the tetrahydroquinoline or related compound (e.g., a compound of any one of formulae I-IX), a pharmaceutically acceptable carrier, vehicle or diluent, and optionally at least one additional therapeutic agent listed above.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a tetrahydroquinoline or related compound described herein (such as a compound of any one of Formulae I-IX or a specific compound described herein, such as in Tables 1-6) in a therapeutically effective amount for the treatment of an immune or inflammatory disorder, such as one of the particular immune disorders or inflammatory disorders described herein.

EXAMPLES

The invention now being generally described, will be more readily understood by reference to the following examples, which are included merely for purposes of illustration of certain aspects and embodiments of the present invention, and are not intended to limit the invention.

Example 1

Synthesis of 2-Chloro-6-fluoro-N-[1-(4-fluoro-benzenesulfonyl)-1,2,3,4-tetrahydro-quinolin-7-yl]-benzamide (4)

The title compound was prepared according to the synthetic procedures described in the following scheme and Parts I-III below.

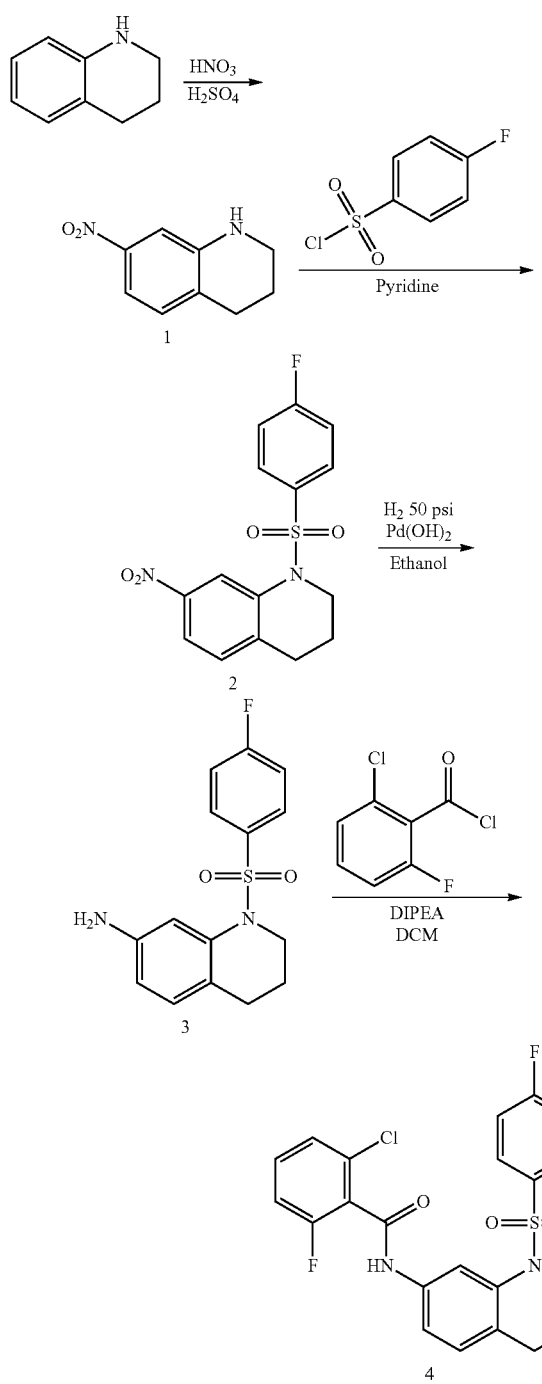

Part I—Synthesis of 1,2,3,4-Tetrahydro-7-nitroquinoline (1)

1,2,3,4-Tetrahydroquinoline (26.8 g, 0.2 mol) was dissolved in 75 mL of 96.6% sulfuric acid and cooled in a salt-ice bath to −10° C. After stirring for 30 min, 9.5 mL (0.2 mol) of 90% nitric acid in 40 mL of sulfuric acid was added at such a rate that the temperature remained at −5 to −10° C. The reaction mixture was stirred in the ice bath for 3 hr and then poured onto ice. The solution was neutralized to pH 8 with sodium carbonate and the precipitate was filtered, washed with water, and dried to provide the title compound in crude form, which was purified by column chromatography using a hexanes:ethyl acetate gradient (0-30%) to provide the title compound in pure form as an orange solid (21.4 g, 59% yield).

Part II—Synthesis of 1-(4-Fluoro-benzenesulfonyl)-7-nitro-1,2,3,4-tetrahydro-quinoline (2)

Into a 250 mL sealed reaction vessel was combined 1,2,3,4-tetrahydro-7-nitroquinoline (3 g, 0.017 mol), 4-fluorobenzene-1-sulfonyl chloride (6.61 g, 0.034 mol), and pyridine (15 mL). The mixture was heated at 80° C. for two hours, cooled, and water (100 mL) was added to provide a mixture. This mixture was extracted with dichloromethane (DCM) (3×20 mL) and the combined extracts were washed with water (3×20 mL), dried over sodium sulfate, and the solvent was removed in vacuo to yield the title compound in crude form, which was purified by column chromatography using a hexanes:ethyl acetate gradient (5-20%) to provide the title compound in pure form as a yellow solid (3.12 g, 55% yield).

Part III—Synthesis of 1-(4-Fluoro-benzenesulfonyl)-1,2,3,4-tetrahydro-quinolin-7-ylamine (3)

Into a pressure vessel was combined 1-(4-fluoro-benzenesulfonyl)-7-nitro-1,2,3,4-tetrahydro-quinoline (2.4 g, 0.007 mol), ethanol (10 mL) and dichloroethane (5 mL). A catalytic amount of palladium hydroxide (~100 mg) was added to the pressure vessel, and then the vessel was filled with hydrogen and evacuated three times. Next, the vessel was pressurized to 50 psi with hydrogen and agitated for 1.5 hours, after which the mixture was filtered over celite and concentrated to yield the title compound as an off white solid (1.97 g, 92% yield) (M+H=307.3).

Part IV—Synthesis of 2-Chloro-6-fluoro-N-[1-(4-fluoro-benzenesulfonyl)-1,2,3,4-tetrahydro-quinolin-7-yl]-benzamide (4)

Into a 20 mL reaction vessel was combined 1-(4-fluoro-benzenesulfonyl)-1,2,3,4-tetrahydro-quinolin-7-ylamine (0.1 g, 0.3 mmol), dichloromethane (1 mL) and N,N-diisopropylethylamine (0.078 g, 0.6 mmol). The compound 2-chloro-6-fluorobenzoyl chloride (0.064 g, 0.33 mmol) was added dropwise to the reaction vessel. The resultant mixture was allowed to stir for 15 minutes, after which the volatiles were removed under reduced pressure to provide the title compound in crude form. The crude compound was purified by column chromatography using a hexanes:ethyl acetate gradient (10-50%) to provide the title compound as a white solid (0.126 g, 91% yield) (M+H=463.2).

Example 2

Preparation of 2-Chloro-N-[1-(4-chlorobenzenesulfonyl)-1,2,3,4-tetrahydroquinolin-7-yl]-6-fluorobenzamide (5)

The title compound was prepared according to the procedures described below.

Part I—Synthesis of 1-(4-Chlorobenzenesulfonyl)-7-nitro-1,2,3,4-tetrahydroquinoline

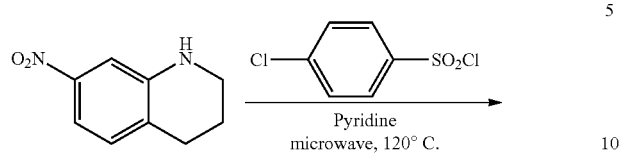

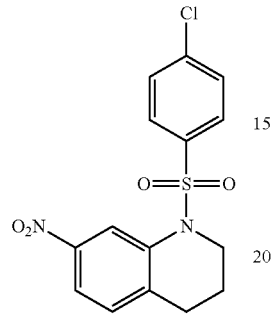

7-Nitro-1,2,3,4-tetrahydroquinoline (500 mg, 2.8 mmol), 4-chlorobenzenesulfonyl chloride (700 mg, 3.3 mmol), and pyridine (1.5 mL) were combined in a microwave vial (5 mL) and heated in a microwave reactor at 120° C. for 10 minutes. The reaction mixture was diluted with 1M HCl (aq) and extracted with $CH_2Cl_2$ (3×20 mL). The combined organic extracts were concentrated under reduced pressure and purified by column chromatography (EtOAc/hexanes) to afford 1-(4-chlorobenzene-sulfonyl)-7-nitro-1,2,3,4-tetrahydroquinoline as a solid (630 mg, 59%). LCMS (ESI): calcd. $C_{15}H_{13}ClN_2O_4S$, 352. found (M+H), 353.

Part II—Synthesis of 1-(4-Chlorobenzenesulfonyl)-1,2,3,4-tetrahydroquinolin-7-ylamine

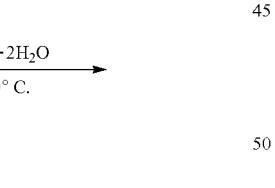

1-(4-Chlorobenzenesulfonyl)-7-nitro-1,2,3,4-tetrahydroquinoline (700 mg, 2.0 mmol) and $SnCl_2 \cdot 2H_2O$ (1.4 g, 6.2 mmol) were suspended in EtOH (10 mL) and stirred at 40° C. for 12 h. After cooling to room temperature, 2M KOH (aq) (10 mL) was added and the resulting mixture was extracted with $CH_2Cl_2$ (3×15 mL). The organic extracts were combined, dried ($Na_2SO_4$), and concentrated under reduced pressure to give 1-(4-chlorobenzenesulfonyl)-1,2,3,4-tetrahydroquinolin-7-ylamine as a crude solid (600 mg). LCMS (ESI): calcd. $C_{15}H_{15}ClN_2O_2S$, 322. found (M+H), 323.

Part III—Synthesis of 2-Chloro-N-[1-(4-chlorobenzenesulfonyl)-1,2,3,4-tetrahydroquinolin-7-yl]-6-fluorobenzamide

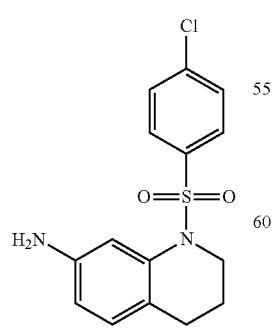

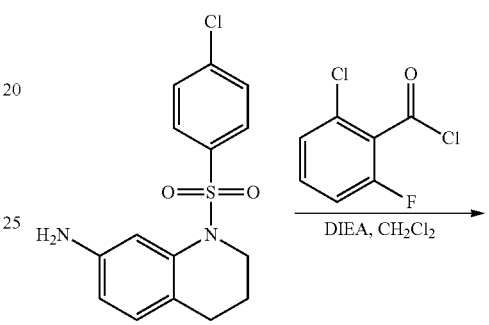

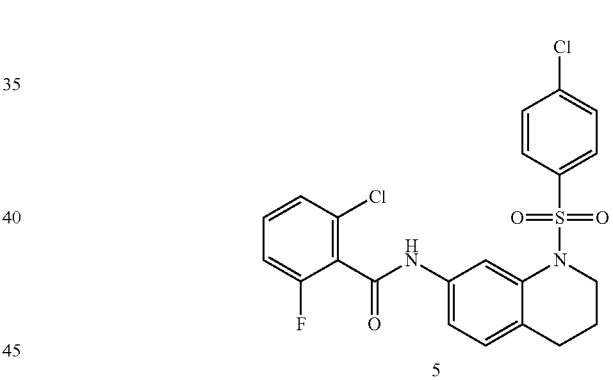

5

A solution of 1-(4-chlorobenzenesulfonyl)-1,2,3,4-tetrahydroquinolin-7-ylamine (50 mg, 0.15 mmol), 2-chloro-6-fluorobenzoyl chloride (35 mg, 0.18 mmol), and N,N-diisopropylethylamine (DIEA, 0.055 mL, 0.32 mmol) in $CH_2Cl_2$ (1 mL) was stirred at room temperature for 3 h. The resulting solution was purified by HPLC to give 2-chloro-N-[1-(4-chlorobenzenesulfonyl)-1,2,3,4-tetrahydroquinolin-7-yl]-6-fluorobenzamide (36 mg, 50%). LCMS (ESI): calcd. $C_{22}H_{17}Cl_2FN_2O_3S$, 478. found (M+H), 479.

Example 3

Preparation of 2-Chloro-6-fluoro-N-[1-(4-fluorobenzenesulfonyl)-6-methyl-1,2,3,4-tetrahydroquinolin-7-yl]benzamide (6)

The title compound was prepared according to the procedures described below.

Part I—Synthesis of 6-Methyl-7-nitro-1,2,3,4-tetrahydroquinoline

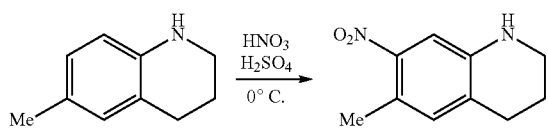 [SMILES: Cc1ccc2c(c1)CCCN2 ; Cc1cc2c(cc1[N+](=O)[O-])NCCC2]

6-Methyl-1,2,3,4-tetrahydroquinoline (2.0 g, 14 mmol) was combined with $H_2SO_4$ (5 mL) and the resulting mixture was cooled to 0° C. After a dropwise addition of a solution of $HNO_3$ (850 mg, 14 mmol) and $H_2SO_4$ (1.5 mL) (combined at 0° C. and allowed to stir for 10 minutes), the reaction was allowed to stir for 2 h. The reaction mixture was poured over ice and neutralized with aqueous $NaHCO_3$. The product was extracted with $CH_2Cl_2$ (3×30 mL). The organic extracts were combined, dried over $Na_2SO_4$, and concentrated under reduced pressure to give 6-methyl-7-nitro-1,2,3,4-tetrahydroquinoline as the major isomer in a 2:1 isomeric mixture (1.8 g). The mixture was used in the next step without purification.

Part II—Synthesis of 1-(4-Fluorobenzenesulfonyl)-6-methyl-7-nitro-1,2,3,4-tetrahydroquinoline

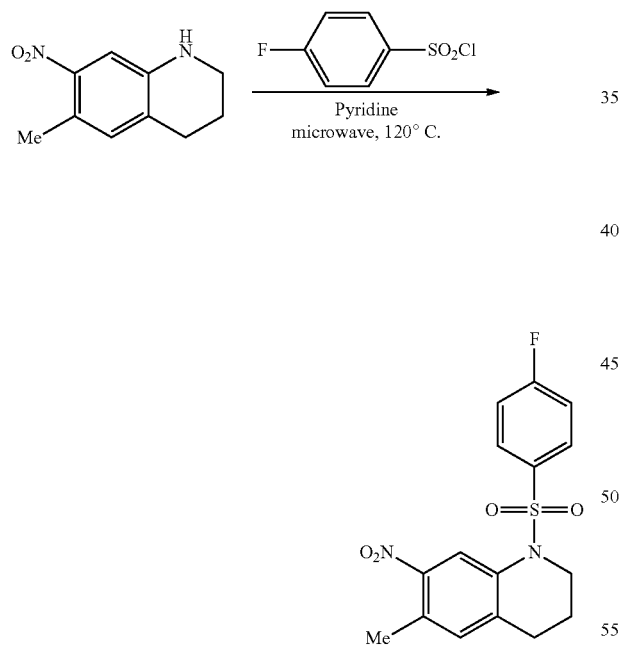

6-Methyl-7-nitro-1,2,3,4-tetrahydroquinoline (2.6 g, 14 mmol), 4-fluorobenzenesulfonyl chloride (3.2 g, 16 mmol), and pyridine (4 mL) were combined in a microwave vial (10 mL) and heated in a microwave reactor at 120° C. for 10 minutes. The reaction mixture was poured over a 1M HCl solution and extracted with $CH_2Cl_2$ (3×20 mL). The combined organic extracts were concentrated under reduced pressure and purified by column chromatography (EtOAc/hexanes) to afford 1-(4-fluorobenzenesulfonyl)-6-methyl-7-nitro-1,2,3,4-tetrahydroquinoline as a solid.

Part III—Synthesis of 1-(4-Fluorobenzenesulfonyl)-6-methyl-1,2,3,4-tetrahydroquinolin-7-ylamine

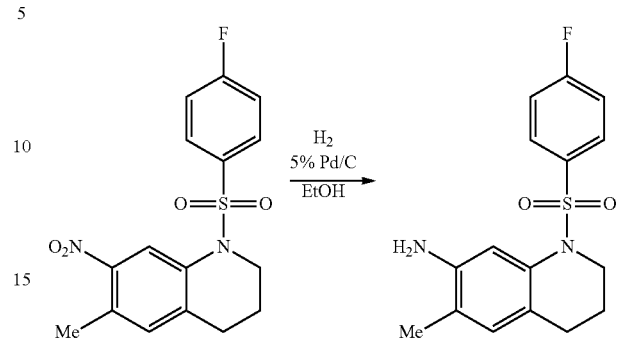

1-(4-Fluorobenzenesulfonyl)-6-methyl-7-nitro-1,2,3,4-tetrahydroquinoline (2.0 g, 5.7 mmol), 5% Pd/C (200 mg), and EtOH (30 mL) were agitated under a hydrogen atmosphere (30 p.s.i.) for 1 h using a Parr shaker. The resulting mixture was filtered through celite and concentrated under reduced pressure to give 1-(4-fluorobenzenesulfonyl)-6-methyl-1,2,3,4-tetrahydroquinolin-7-ylamine (1.7 g, 91%) as a solid. LCMS (ESI): calcd. $C_{16}H_{17}FN_2O_2S$, 320. found (M+H), 321.

Part IV—Synthesis of 2-Chloro-6-fluoro-N-[1-(4-fluorobenzenesulfonyl)-6-methyl-1,2,3,4-tetrahydroquinolin-7-yl]benzamide

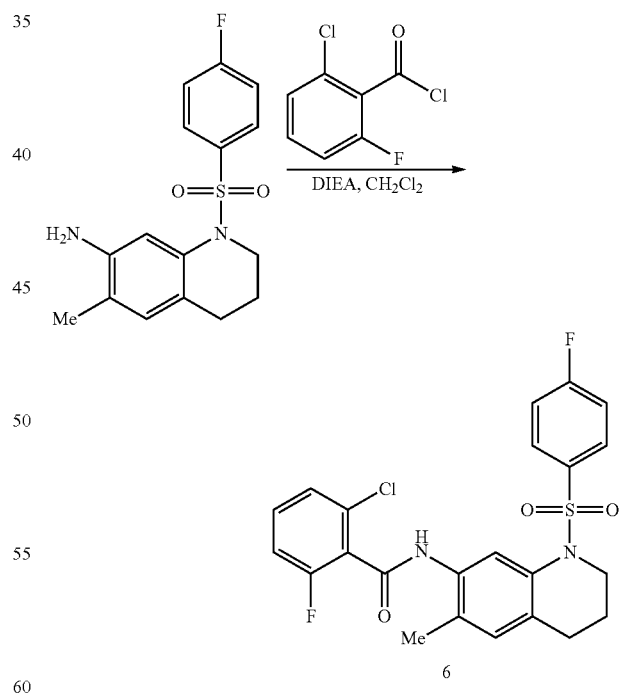

A solution of 1-(4-fluorobenzenesulfonyl)-6-methyl-1,2,3,4-tetrahydroquinolin-7-ylamine (50 mg, 0.16 mmol), 2-chloro-6-fluorobenzoyl chloride (35 mg, 0.18 mmol), and DIEA (0.055 mL, 0.32 mmol) in $CH_2Cl_2$ (1 mL) was stirred at room temperature for 3 h. The resulting solution was purified by HPLC to give 2-chloro-6-fluoro-N-[1-(4-fluorobenzenesulfonyl)-6-methyl-1,2,3,4-tetrahydroquinolin-7-yl]-benzamide (27 mg, 36%). LCMS (ESI): calcd. $C_{23}H_{19}ClF_2N_2O_3S$, 476. found (M+H), 477.

Example 4

Preparation of Additional Tetrahydroquinoline Compounds

The compounds in Table 3 below were prepared based on the experimental procedures described in Examples 1-3 and in the detailed description. Starting materials can be obtained from commercial sources or readily prepared from commercially available materials.

TABLE 3

| Compound No. | Chemical Structure |
|---|---|
| III-1 | 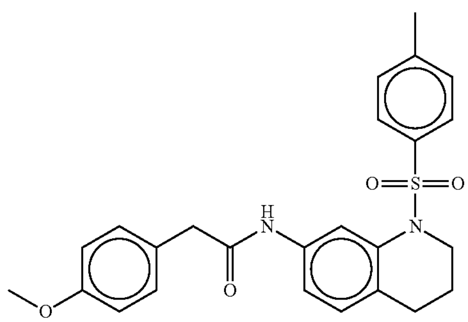 |
| III-2 | 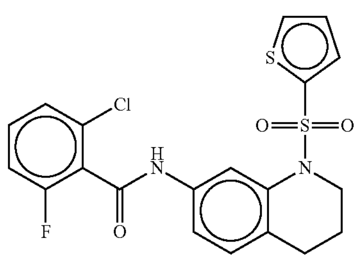 |
| III-3 | 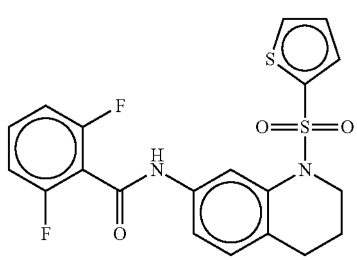 |
| III-4 | 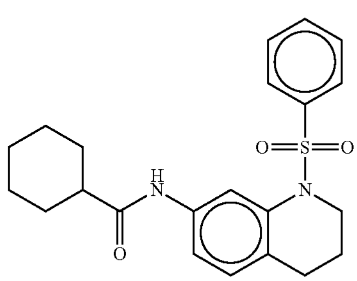 |

TABLE 3-continued

| Compound No. | Chemical Structure |
|---|---|
| III-5 | 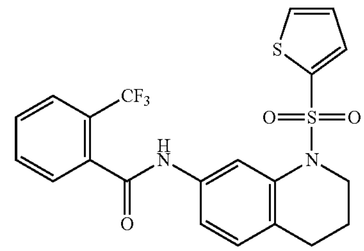 [SMILES: O=C(Nc1ccc2c(c1)N(S(=O)(=O)c1cccs1)CCC2)c1ccccc1C(F)(F)F] |
| III-6 | 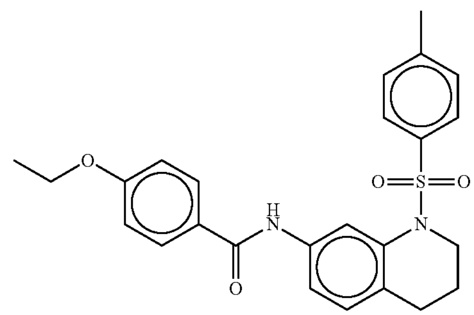 |
| III-7 | 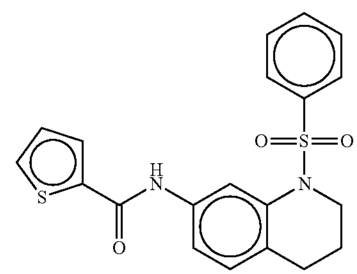 |
| III-8 | 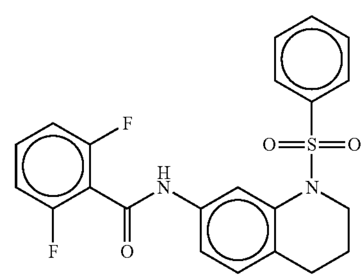 |
| III-9 | 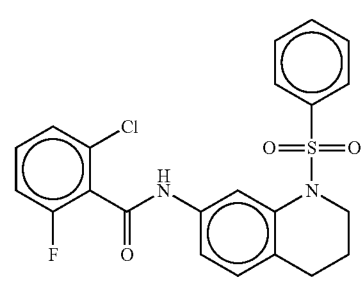 |

TABLE 3-continued

| Compound No. | Chemical Structure |
|---|---|
| III-10 | 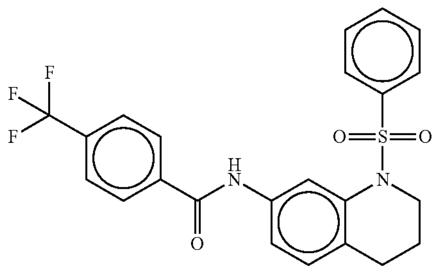 |
| III-11 | 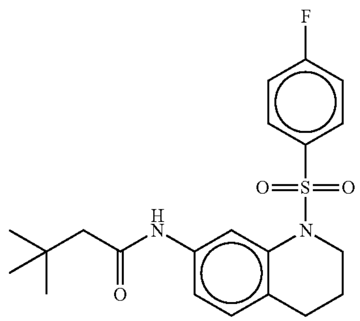 |
| III-12 | 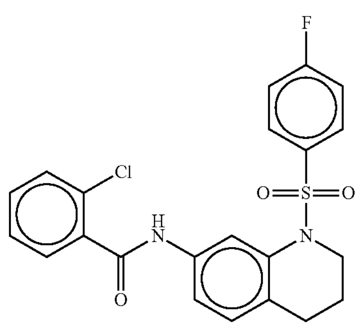 |
| III-13 | 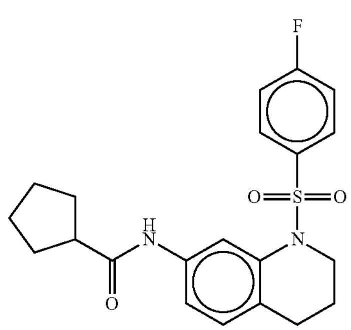 |
| III-14 | |
| III-15 | |
| III-16 | |
| III-17 | |

TABLE 3-continued

| Compound No. | Chemical Structure |
|---|---|
| III-18 | 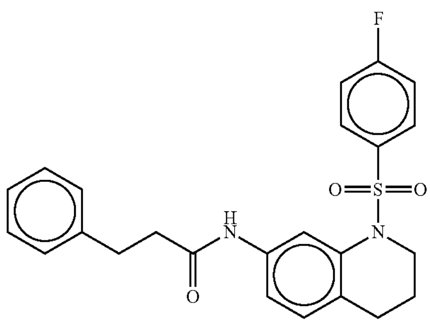 |
| III-19 | 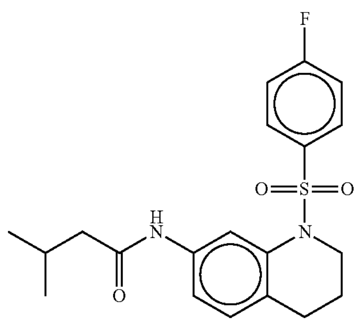 |
| III-20 | 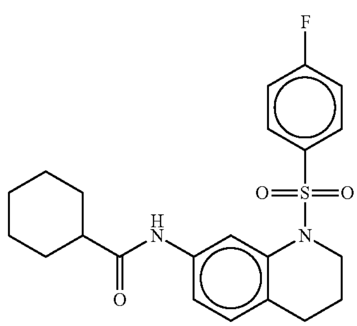 |
| III-21 | 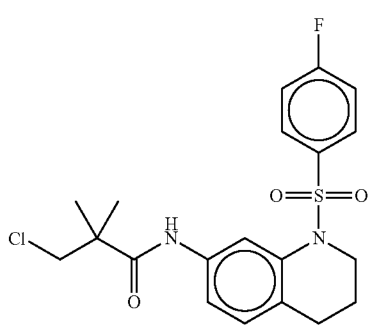 |
| III-22 | |
| III-23 | |
| III-24 | |
| III-25 | |

TABLE 3-continued

| Compound No. | Chemical Structure |
|---|---|
| III-26 | (structure) |
| III-27 | (structure) |
| III-28 | (structure) |
| III-29 | (structure) |
| III-30 | (structure) |
| III-31 | (structure) |
| III-32 | (structure) |
| III-33 | (structure) |

TABLE 3-continued

| Compound No. | Chemical Structure |
|---|---|
| III-34 | 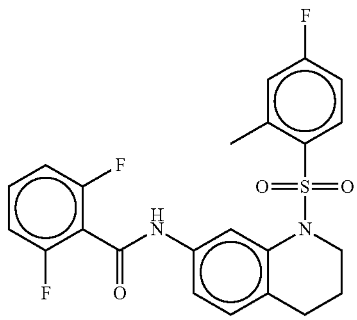 |
| III-35 | 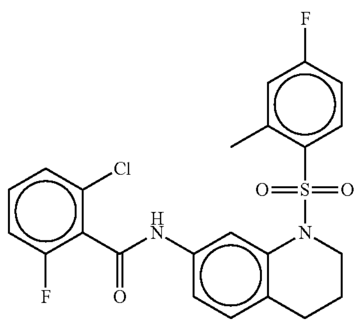 |
| III-36 | 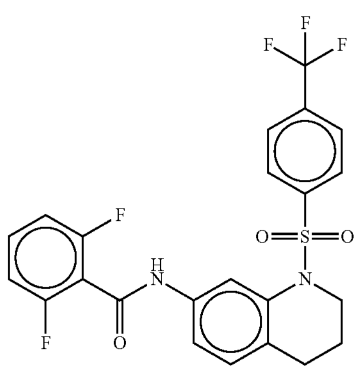 |
| III-37 | 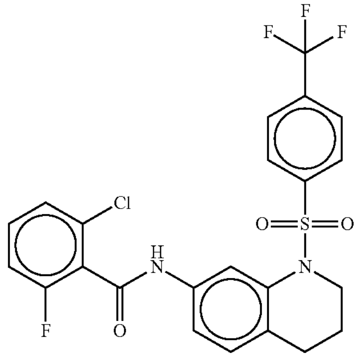 |
| III-38 | 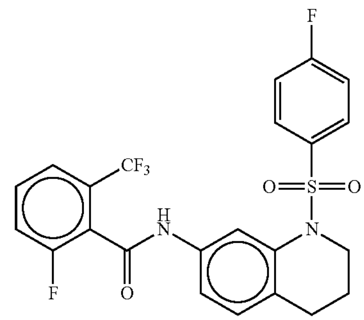 |
| III-39 | 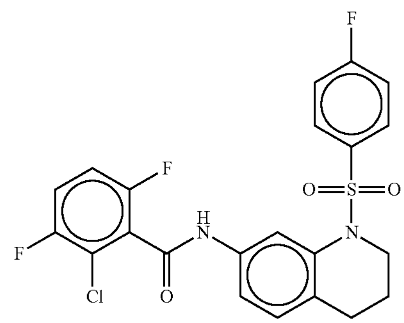 |
| III-40 | 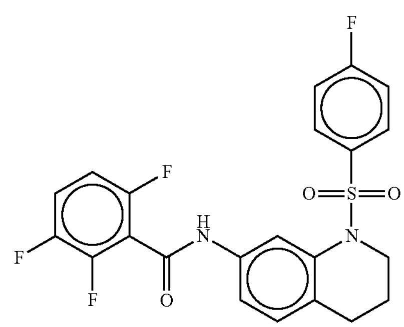 |
| III-41 | 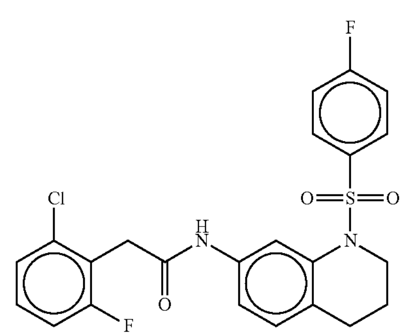 |

TABLE 3-continued

| Compound No. | Chemical Structure |
|---|---|
| III-42 | 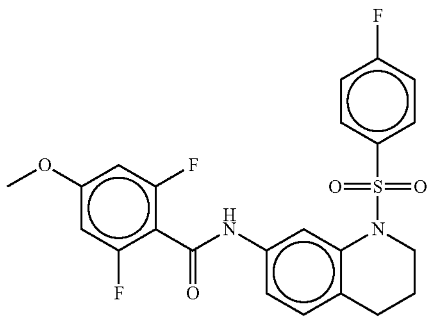 |
| III-43 | 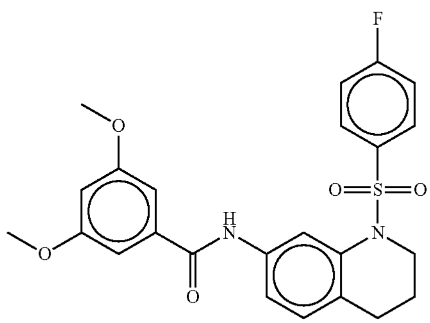 |
| III-44 | 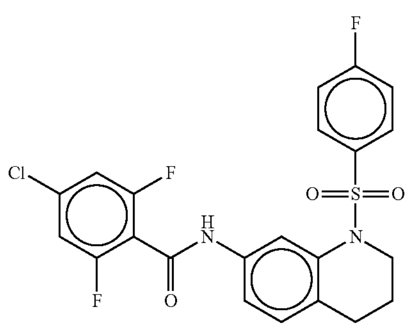 |
| III-45 | 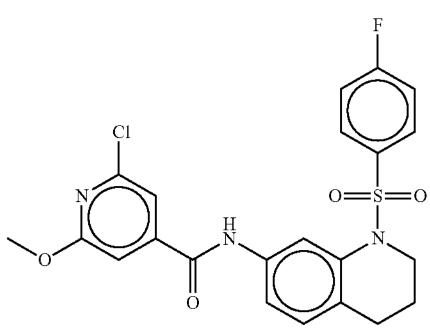 |
| III-46 | |
| III-47 | |
| III-48 | |
| III-49 | |

TABLE 3-continued

| Compound No. | Chemical Structure |
|---|---|
| III-50 | 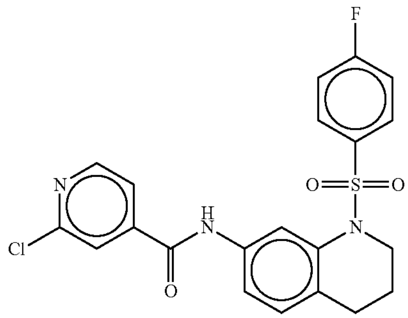 |
| III-51 | 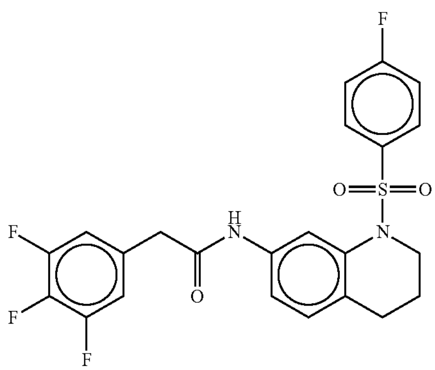 |
| III-52 | 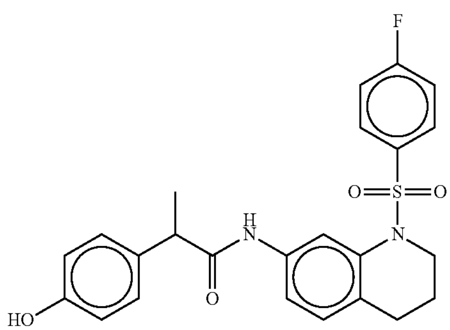 |
| III-53 | 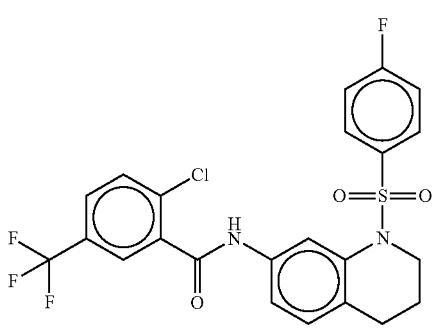 |
| III-54 | |
| III-55 | |
| III-56 | |
| III-57 | |

TABLE 3-continued

| Compound No. | Chemical Structure |
|---|---|
| III-58 | (isoxazole-5-carboxamide linked to 1-(4-fluorophenylsulfonyl)-1,2,3,4-tetrahydroquinolin-7-yl) |
| III-59 | (pyridine-4-carboxamide linked to 1-(4-fluorophenylsulfonyl)-1,2,3,4-tetrahydroquinolin-7-yl) |
| III-60 | (pyridine-3-carboxamide linked to 1-(4-fluorophenylsulfonyl)-1,2,3,4-tetrahydroquinolin-7-yl) |
| III-61 | (pyrazine-2-carboxamide linked to 1-(4-fluorophenylsulfonyl)-1,2,3,4-tetrahydroquinolin-7-yl) |
| III-62 | (5-methylisoxazole-3-carboxamide linked to 1-(4-fluorophenylsulfonyl)-1,2,3,4-tetrahydroquinolin-7-yl) |
| III-63 | (4-methyl-1,2,3-thiadiazole-5-carboxamide linked to 1-(4-fluorophenylsulfonyl)-1,2,3,4-tetrahydroquinolin-7-yl) |
| III-64 | (4-cyanobenzamide linked to 1-(4-fluorophenylsulfonyl)-1,2,3,4-tetrahydroquinolin-7-yl) |
| III-65 | (3-cyanobenzamide linked to 1-(4-fluorophenylsulfonyl)-1,2,3,4-tetrahydroquinolin-7-yl) |

TABLE 3-continued

| Compound No. | Chemical Structure |
|---|---|
| III-66 | 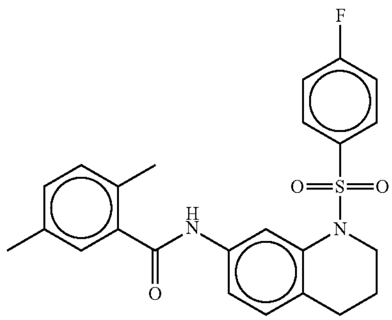 |
| III-67 | 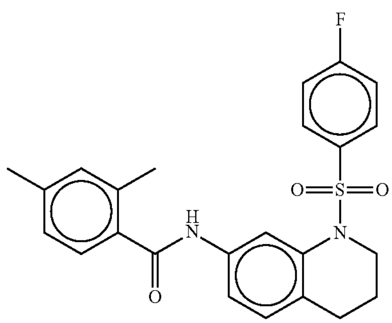 |
| III-68 | 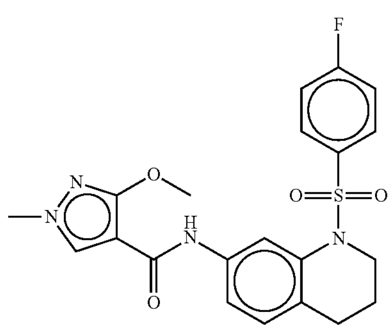 |
| III-69 | 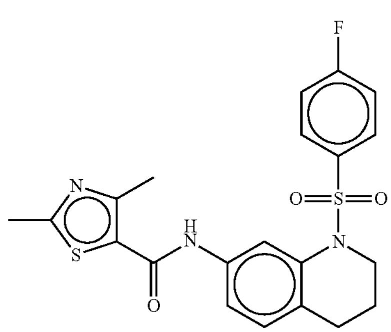 |
| III-70 | |
| III-71 | |
| III-72 | |
| III-73 | |

TABLE 3-continued

| Compound No. | Chemical Structure |
|---|---|
| III-74 | 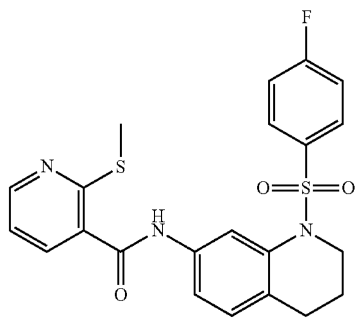 [SMILES: CSc1ncccc1C(=O)Nc1ccc2c(c1)N(S(=O)(=O)c1ccc(F)cc1)CCC2] |
| III-75 | 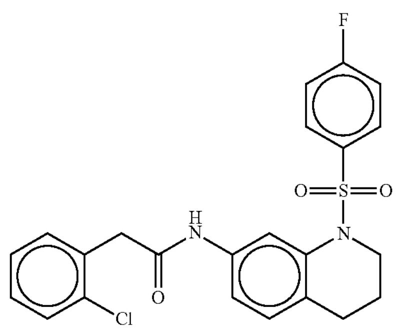 |
| III-76 | 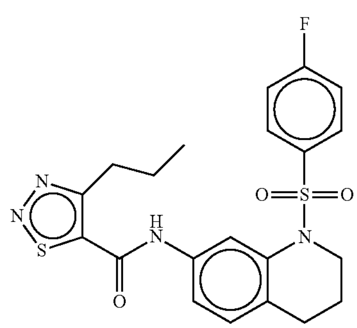 |
| III-77 | 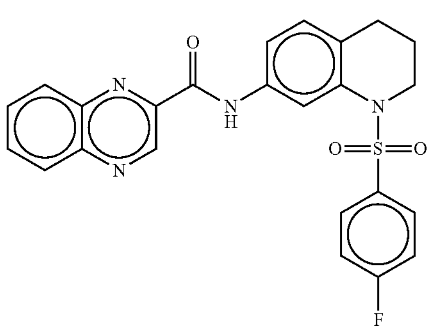 |
| III-78 | |
| III-79 | |
| III-80 | |
| III-81 | |

TABLE 3-continued
| Compound No. | Chemical Structure |
|---|---|
| III-82 | 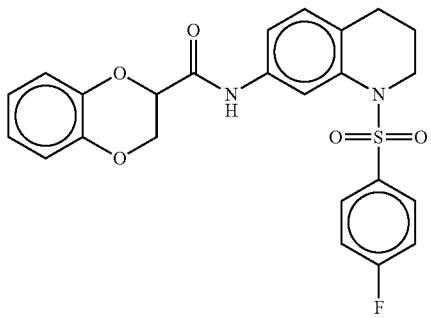 |
| III-83 | 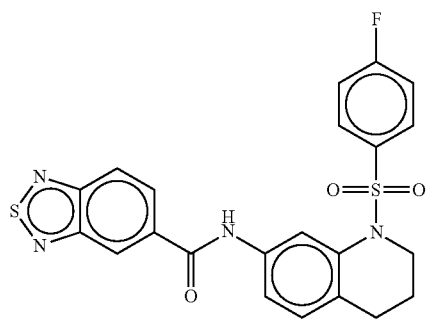 |
| III-84 | 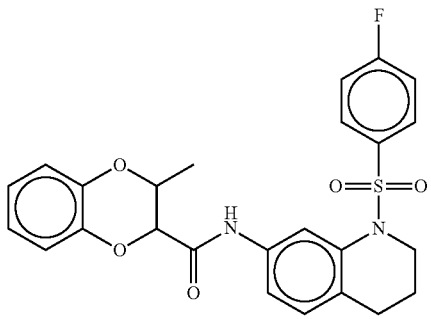 |
| III-85 | 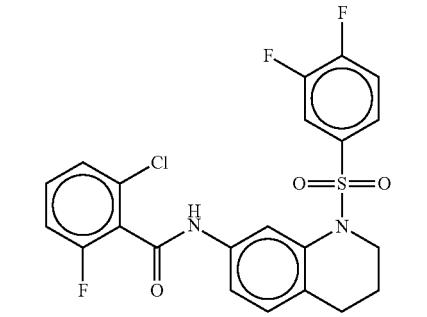 |
| III-86 | 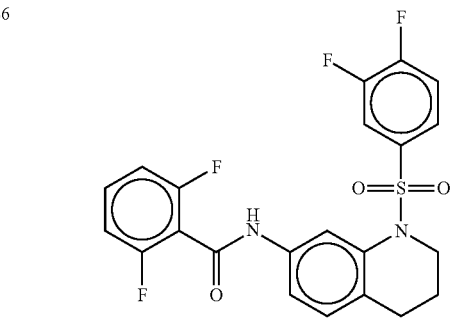 |
| III-87 | 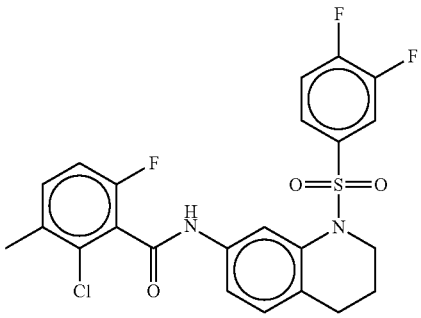 |
| III-88 | 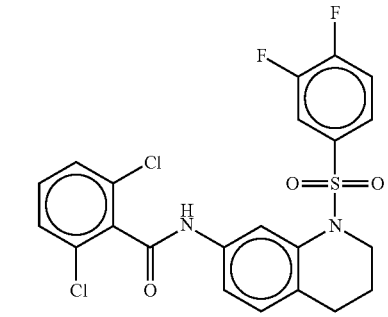 |
| III-89 | 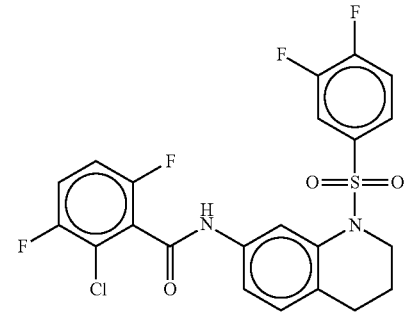 |

TABLE 3-continued

| Compound No. | Chemical Structure |
|---|---|
| III-90 | 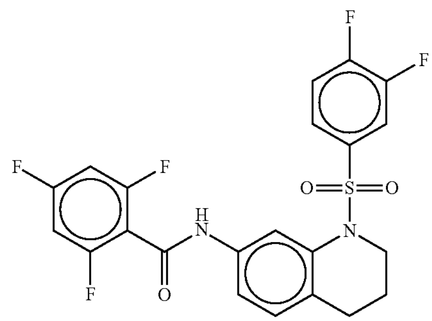 |
| III-91 | 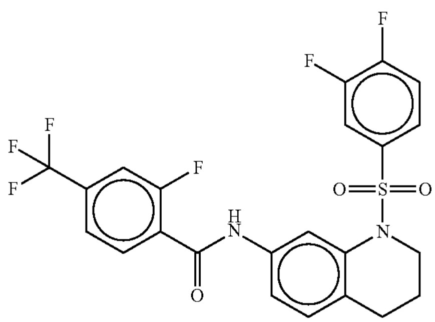 |
| III-92 | 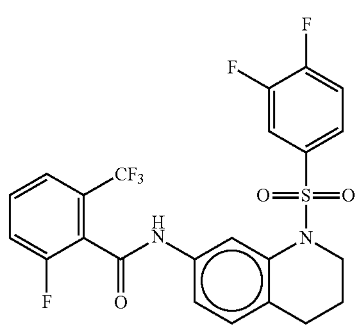 |
| III-93 | 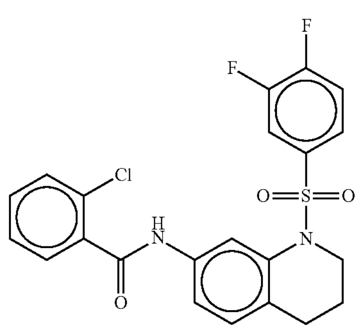 |
| III-94 | |
| III-95 | |
| III-96 | |
| III-97 | |

TABLE 3-continued

| Compound No. | Chemical Structure |
|---|---|
| III-98 | 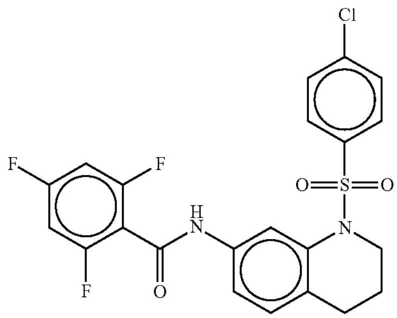 |
| III-99 | 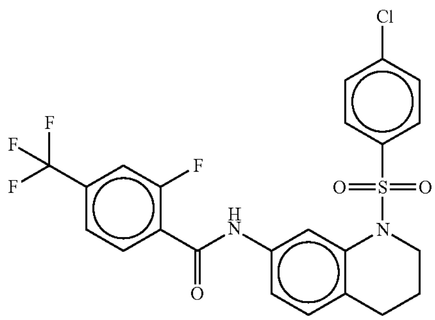 |
| III-100 | 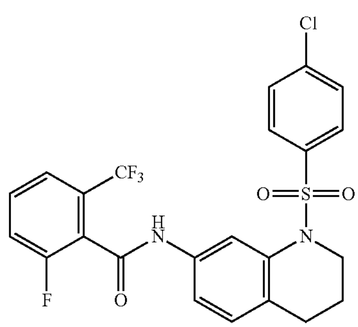 [SMILES: O=C(Nc1ccc2c(c1)N(S(=O)(=O)c1ccc(Cl)cc1)CCC2)c1c(F)cccc1C(F)(F)F] |
| III-101 | 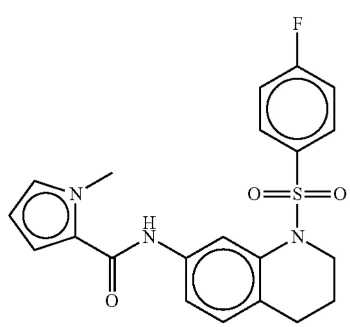 |
| III-102 | 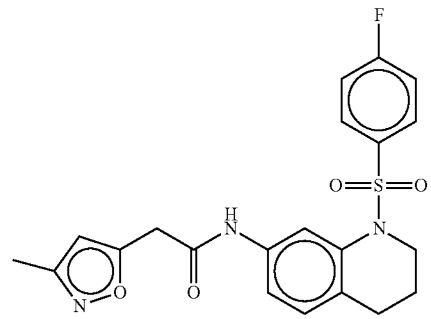 |
| III-103 | 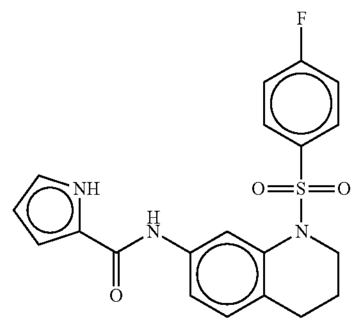 |
| III-104 | 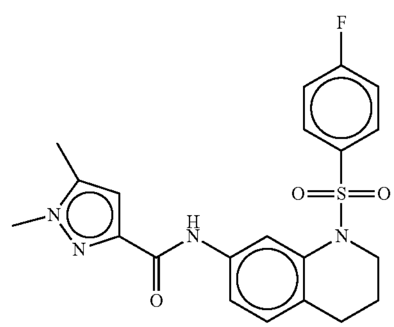 |
| III-105 | 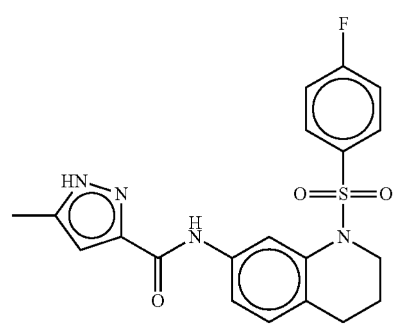 |

TABLE 3-continued

| Compound No. | Chemical Structure |
|---|---|
| III-106 | 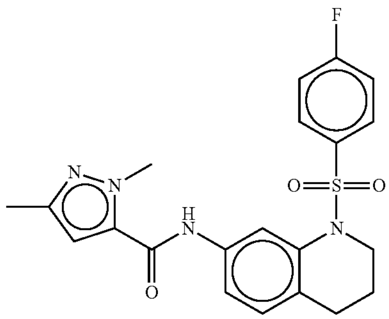 |
| III-107 | 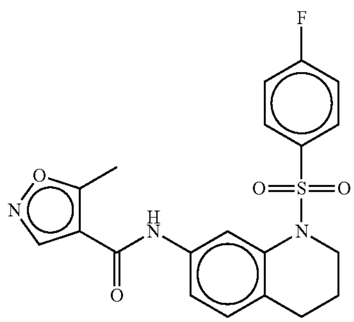 |
| III-108 | 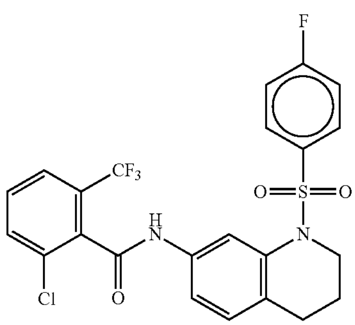 |
| III-109 | 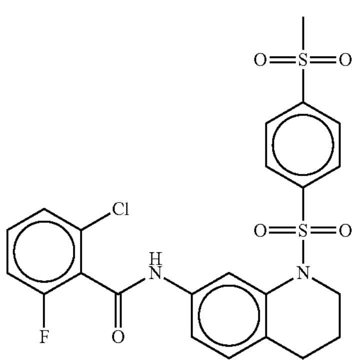 |
| III-110 | |
| III-111 | |
| III-112 | |
| III-113 | |

TABLE 3-continued

| Compound No. | Chemical Structure |
|---|---|
| III-114 | |
| III-115 | |
| III-116 | |
| III-117 | |
| III-118 | 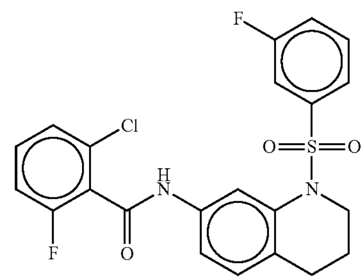 |
| III-119 | 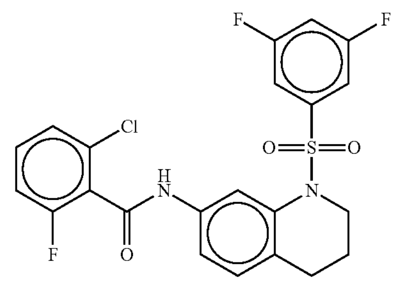 |
| III-120 | 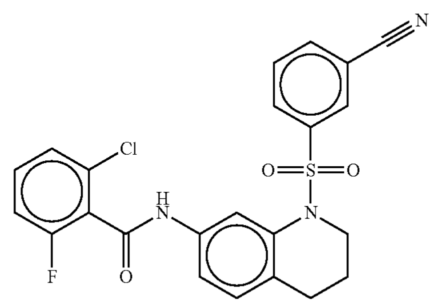 |
| III-121 | 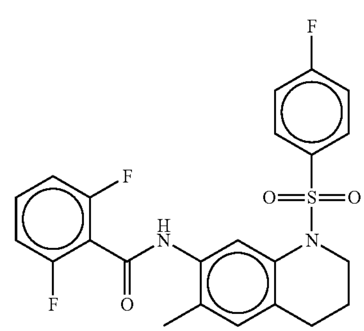 |
| III-122 | 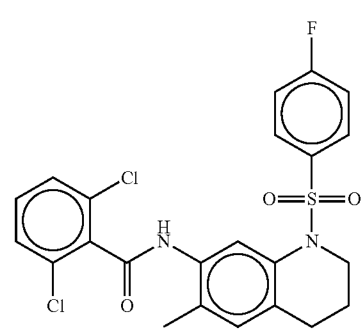 |

TABLE 3-continued

| Compound No. | Chemical Structure |
|---|---|
| III-123 | 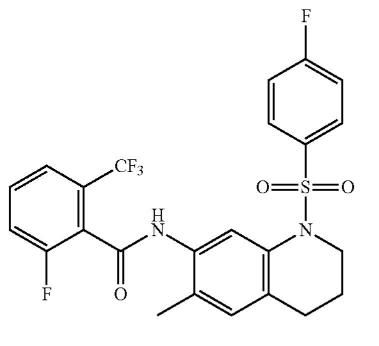 [SMILES: Cc1cc2c(cc1NC(=O)c1c(F)cccc1C(F)(F)F)N(S(=O)(=O)c1ccc(F)cc1)CCC2] |
| III-124 | 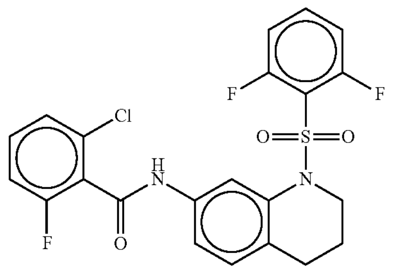 |
| III-125 | 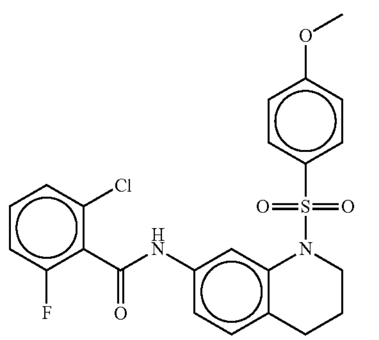 |
| III-126 | 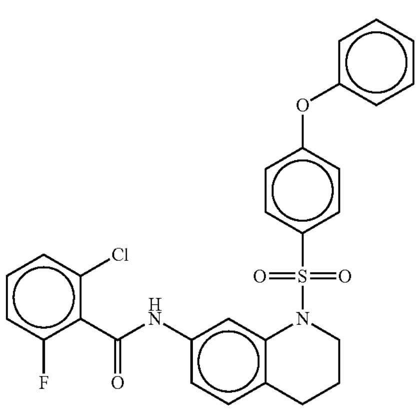 |
| III-127 | |
| III-128 | |
| III-129 | |

TABLE 3-continued
| Compound No. | Chemical Structure |
|---|---|
| III-130 | 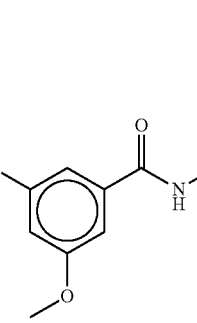 |
| III-131 | 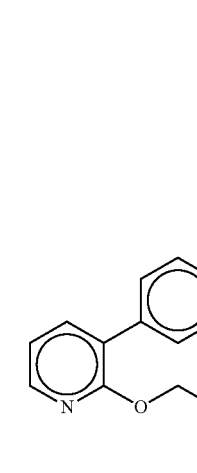 |
| III-132 | 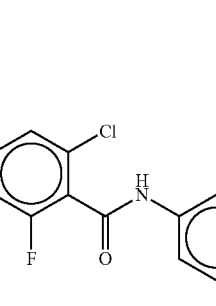 |
| III-133 | 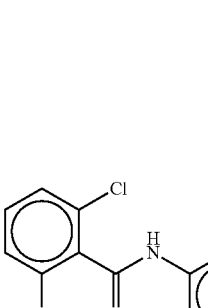 |
| III-134 | 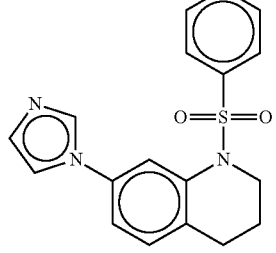 |
| III-135 | 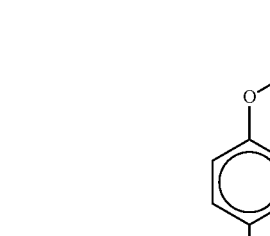 |
| III-136 | 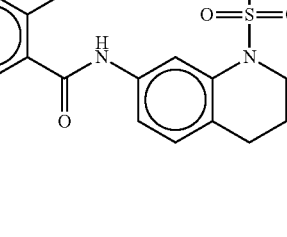 |
| III-137 | 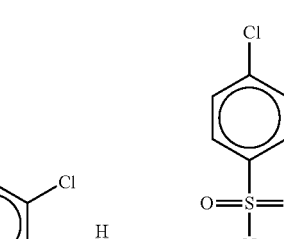 |

TABLE 3-continued

| Compound No. | Chemical Structure |
|---|---|
| III-138 | 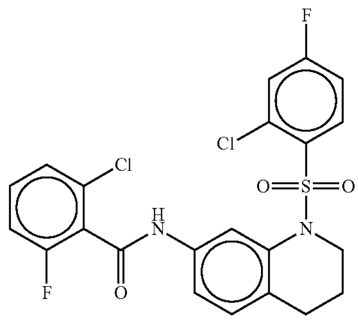 |
| III-139 | 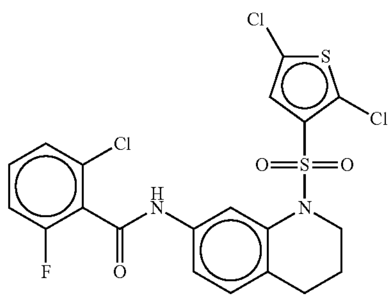 |
| III-140 | 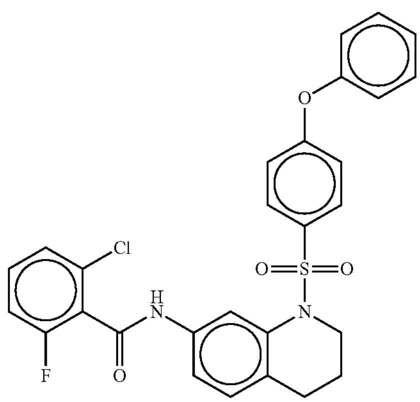 |
| III-141 | 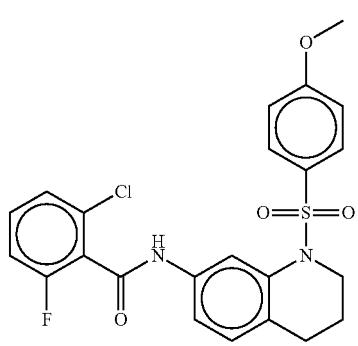 |
| III-142 | |
| III-143 | |
| III-144 | |
| III-145 | |

TABLE 3-continued

| Compound No. | Chemical Structure |
|---|---|
| III-146 | 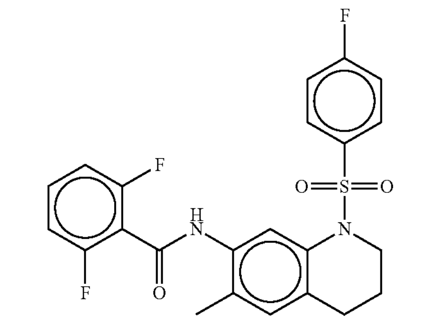 |
| III-147 | 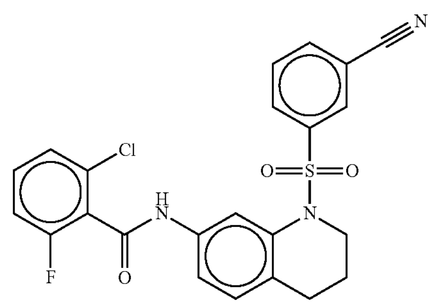 |
| III-148 | 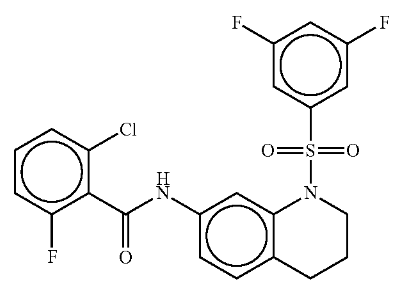 |
| III-149 | 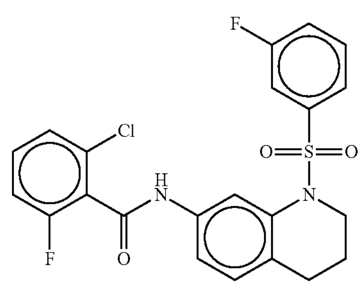 |
| III-150 | 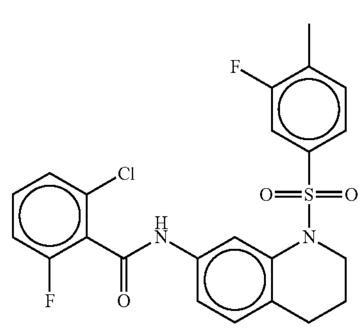 |
| III-151 | |
| III-152 | |
| III-153 | |
| III-154 | |

TABLE 3-continued

| Compound No. | Chemical Structure |
|---|---|
| III-155 | 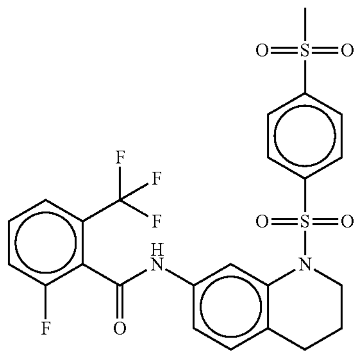 |
| III-156 | 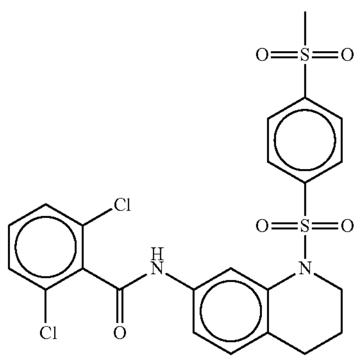 |
| III-157 | 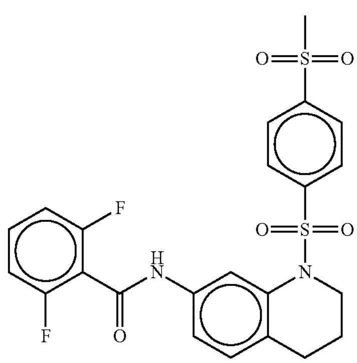 |
| III-158 | 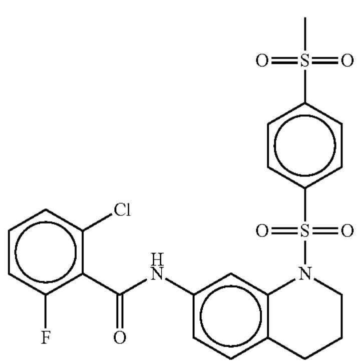 |
| III-159 | |
| III-160 | |
| III-161 | |
| III-162 | |

TABLE 3-continued

| Compound No. | Chemical Structure |
|---|---|
| III-163 | 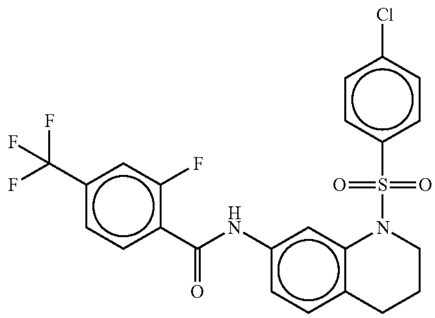 |
| III-164 | 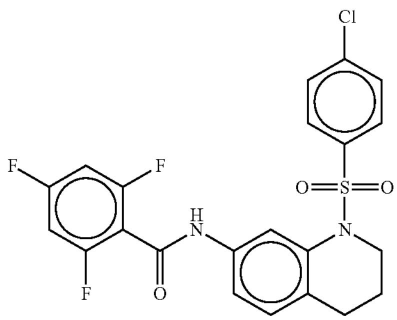 |
| III-165 | 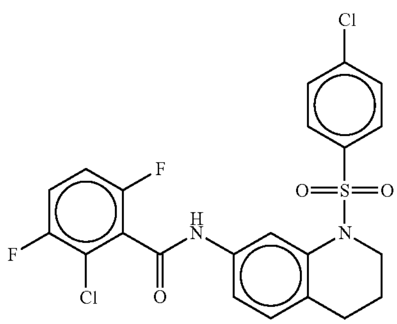 |
| III-166 | 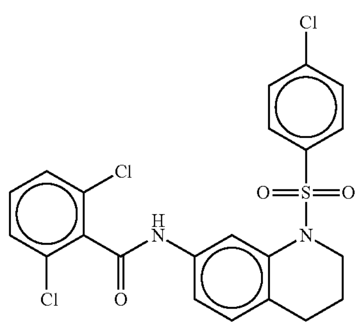 |
| III-167 | |
| III-168 | |
| III-169 | |
| III-170 | |

TABLE 3-continued

| Compound No. | Chemical Structure |
|---|---|
| III-171 | *(structure: N-methyl-N-phenyl urea linked to 1-(4-fluorobenzenesulfonyl)-1,2,3,4-tetrahydroquinolin-7-yl)* |
| III-172 | *(structure: 2,6-difluorophenyl urea linked to 1-(4-fluorobenzenesulfonyl)-1,2,3,4-tetrahydroquinolin-7-yl)* |
| III-173 | *(structure: 2,6-dichlorophenyl urea linked to 1-(4-fluorobenzenesulfonyl)-1,2,3,4-tetrahydroquinolin-7-yl)* |
| III-174 | *(structure: 2-(trifluoromethyl)phenyl urea linked to 1-(4-fluorobenzenesulfonyl)-1,2,3,4-tetrahydroquinolin-7-yl)* |

Example 5

Preparation of 2-Chloro-6-fluoro-N-[1-(4-fluorobenzenesulfonyl)-4-oxo-1,2,3,4-tetrahydroquinolin-7-yl] benzamide (7) & Related Compounds

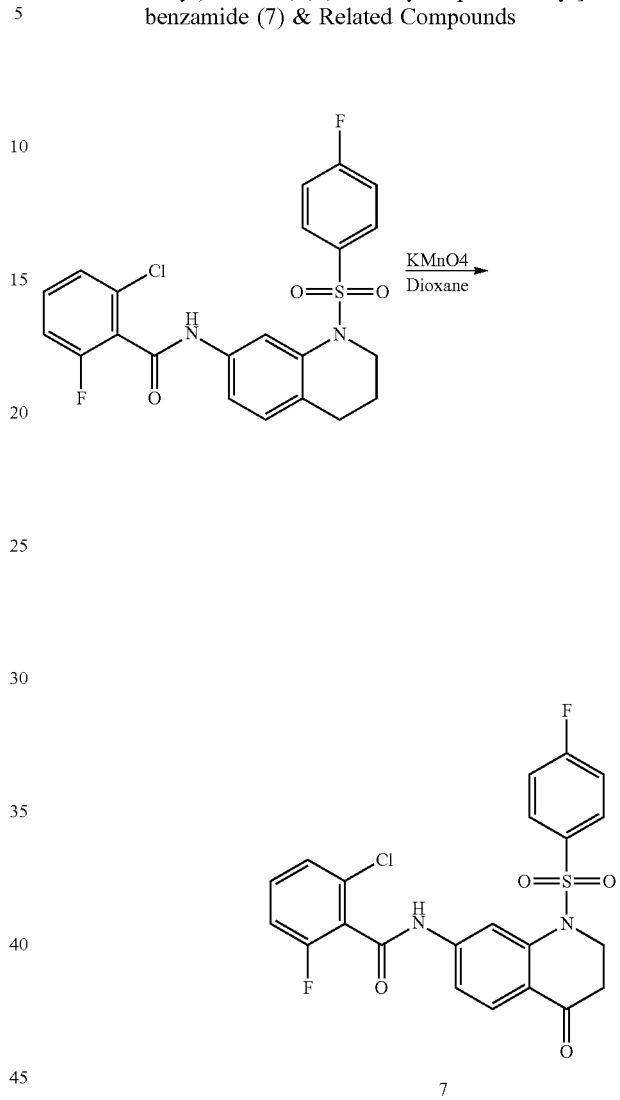

7

A solution of 2-chloro-N-[1-(4-fluorobenzenesulfonyl)-1,2,3,4-tetrahydroquinolin-7-yl]-6-fluorobenzamide (100 mg, 0.2 mmol, Example 3) and $KMnO_4$ (130 mg, 0.82 mmol) in dioxane (1 mL) was stirred for 24 h at room temperature. The reaction mixture was concentrated under reduced pressure and then suspended in a $H_2O$/acetone solution (50:1, 5 mL). The remaining purple color disappeared after 10 minutes and the aqueous layer was extracted with EtOAc (3×5 mL). The product was purified by column chromatography (EtOAc/hexanes) and followed by HPLC purification to give 2-chloro-6-fluoro-N-[1-(4-fluorobenzenesulfonyl)-4-oxo-1,2,3,4-tetrahydroquinolin-7-yl]-benzamide (23 mg, 24%). $^1$H NMR 250 MHz $CDCl_3$ δ 8.1-7.7 (m, 5H), 7.5-7.0 (m, 5H), 4.23 (t, J=6.5 Hz, 2H), 4.67 (t, J=6.5 Hz, 2H). LCMS (ESI): calcd. $C_{22}H_{15}ClF_2N_2O_4S$, 476. found (M+H), 477.

The compounds in Table 4 below were prepared based on the above procedure. Starting materials can be obtained from commercial sources or readily prepared from commercially available materials.

TABLE 4

| Compound No. | Chemical Structure |
|---|---|
| IV-1 | 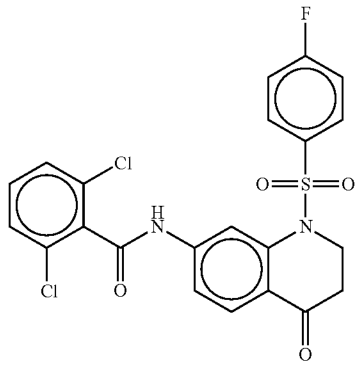 |
| IV-2 | 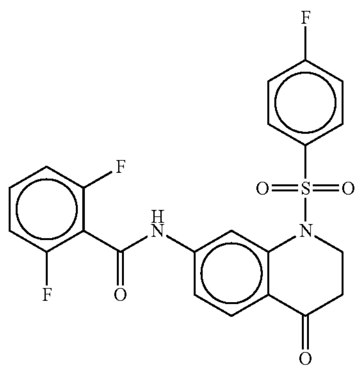 |

Example 6

Preparation of 2-Chloro-6-fluoro-N-[1-(4-fluorobenzenesulfonyl)-1H-indazol-6-yl]benzamide (8)

The title compound was prepared according to the procedures described below.

Part I—Synthesis of 2-Chloro-6-fluoro-N-(1H-indazol-6-yl)benzamide

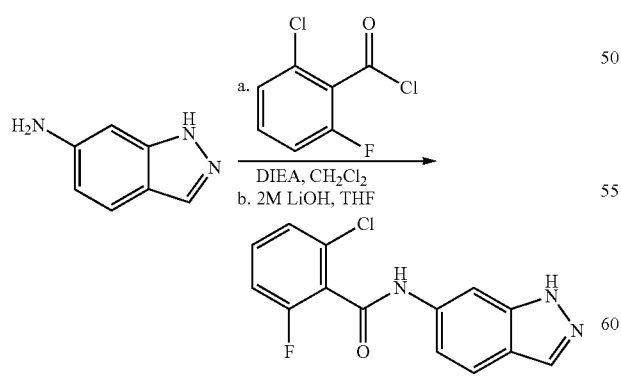

To a suspension of 6-aminoindazole (1 g, 7.5 mmol) and DIEA (4 mL) in CH$_2$Cl$_2$ (20 mL) was added 2-chloro-6-fluorobenzoyl chloride (2.9 g, 15 mmol) dropwise at −10° C. The reaction mixture was stirred for 12 h at room temperature and was diluted with EtOAc, washed with 1M HCl, aqueous NaHCO$_3$, and brine. The organic extract was dried over Na$_2$SO$_4$ and concentrated under reduced pressure to give a crude mixture of the mono-acylation and bis-acylation products. To the product mixture in THF (20 mL) was added 2M LiOH (aq) (10 mL) and the reaction was stirred for 12 h at 60° C. The organic solvent was removed under reduced pressure and the remaining aqueous mixture was acidified to pH 4 with 1M HCl (aq). The resulting solution was extracted with EtOAc (3×20 mL), and the organic extracts were dried (Na$_2$SO$_4$) and concentrated under reduced pressure to give 2-chloro-6-fluoro-N-(1H-indazol-6-yl)benzamide (1.3 g, 60%). LCMS (ESI): calcd. C$_{14}$H$_9$ClFN$_3$O, 289. found (M+H), 290.

Part II—Synthesis of 2-Chloro-6-fluoro-N-[1-(4-fluorobenzenesulfonyl)-1H-indazol-6-yl]benzamide

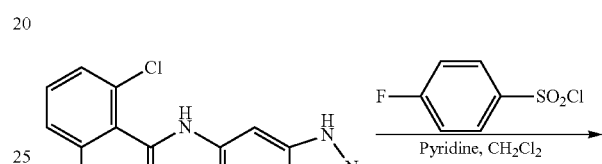

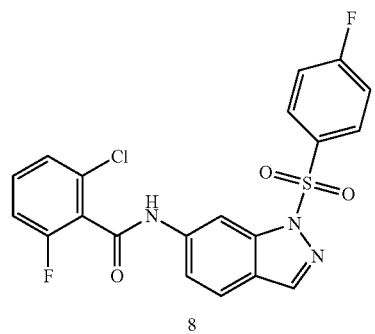

8

A solution of 2-chloro-6-fluoro-N-(1H-indazol-6-yl)benzamide (29 mg, 0.10 mmol) and 4-fluorobenzene-sulfonyl chloride (39 mg, 0.20 mmol) in CH$_2$Cl$_2$ (0.200 mL) and pyridine (0.200 mL) was stirred for 12 h at 60° C. The reaction mixture was concentrated under reduced pressure, dissolved in DMSO and purified by HPLC to afford 2-chloro-6-fluoro-N-[1-(4-fluorobenzenesulfonyl)-1H-indazol-6-yl]benzamide. LCMS (ESI): calcd. C$_{20}$H$_{12}$ClF$_2$N$_3$O$_3$S, 447. found (M+H), 448.

Example 7

Preparation of 2-Chloro-6-fluoro-N-[1-(3-trifluoromethylbenzenesulfonyl)-3-vinyl-1H-indazol-6-yl]benzamide (9)

The title compound was prepared according to the procedures described below.

Part I—Synthesis of 2-Chloro-6-fluoro-N-(3-iodo-1H-indazol-6-yl)benzamide

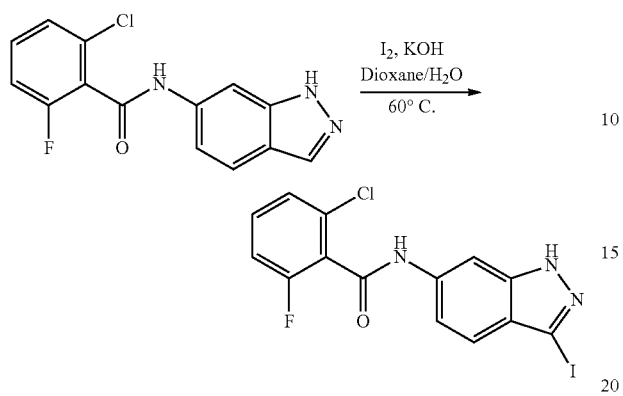

To a suspension of 2-chloro-6-fluoro-N-(1H-indazol-6-yl)benzamide (600 mg, 2.1 mmol) and KOH (210 mg, 3.8 mmol) in dioxane (6 mL) and H$_2$O (0.600 mL) was added I$_2$ (630 mg, 2.5 mmol) and the reaction was stirred at 60° C. for 1 h. The reaction was cooled to room temperature and diluted with H$_2$O (20 mL). The resulting light brown solid was filtered and dried under reduced pressure to give 2-chloro-6-fluoro-N-(3-iodo-1H-indazol-6-yl)benzamide (850 mg, 97%). LCMS (ESI): calcd. C$_{14}$H$_8$ClFIN$_3$O, 415. found (MAI), 416.

Part II—Synthesis of 2-Chloro-6-fluoro-N-(3-vinyl-1H-indazol-6-yl)benzamide

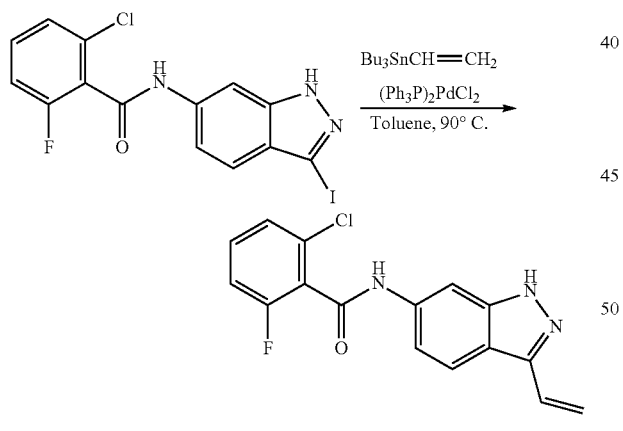

A suspension of 2-chloro-6-fluoro-N-(3-iodo-1H-indazol-6-yl)benzamide (200 mg, 0.48 mmol), tributyl(vinyl)tin (210 mg, 0.67 mmol), and bis(triphenylphosphine)palladium(II) dichloride (34 mg, 0.048 mmol) in toluene (6 mL) was heated at 90° C. for 4 h. The reaction was concentrated under reduced pressure and purified by column chromatography (EtOAc/hexanes) to give 2-chloro-6-fluoro-N-(3-vinyl-1H-indazol-6-yl)benzamide (90 mg, contaminated with organic tin byproducts). This mixture was used in the next step without further purification. LCMS (ESI): calcd. C$_{16}$H$_{11}$ClFN$_3$O, 315. found (M+H), 316.

Part III—Synthesis of 2-Chloro-6-fluoro-N-[1-(3-trifluoromethylbenzenesulfonyl)-3-vinyl-1H-indazol-6-yl]benzamide

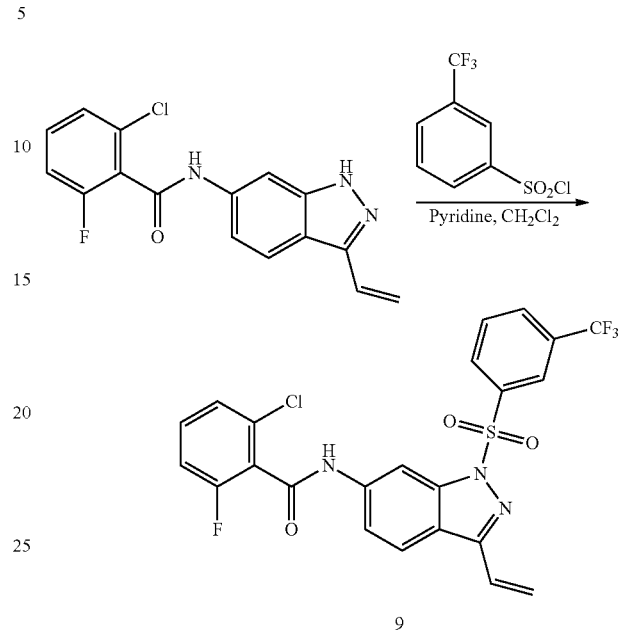

A solution of 2-chloro-6-fluoro-N-(3-vinyl-1H-indazol-6-yl)benzamide (90 mg, 0.29 mmol) and 3-(trifluoromethyl)benzenesulfonyl chloride (110 mg, 0.43 mmol) in pyridine (2 mL) and CH$_2$Cl$_2$ (2 mL) was stirred for 12 h at 65° C. The reaction mixture was cooled to room temperature and washed with 1M HCl (aq), saturated NaHCO$_3$ (aq), and brine. The organic extracts were dried (Na$_2$SO$_4$), concentrated under reduced pressure, and purified by column chromatography (EtOAc/hexanes) to give 2-chloro-6-fluoro-N-[1-(3-trifluoromethylbenzenesulfonyl)-3-vinyl-1H-indazol-6-yl]benzamide (125 mg, contaminated with organic tin byproducts). A small portion (5 mg) was successfully purified by HPLC while the rest was used in the next reaction without further purification. LCMS (ESI): calcd. C$_{23}$H$_{14}$ClF$_4$N$_3$O$_3$S, 523. found (M+H), 524.

Example 8

Preparation of 2-Chloro-N-[3-(1,2-dihydroxyethyl)-1-(3-trifluoromethylbenzenesulfonyl)-1H-indazol-6-yl]-6-fluorobenzamide (10)

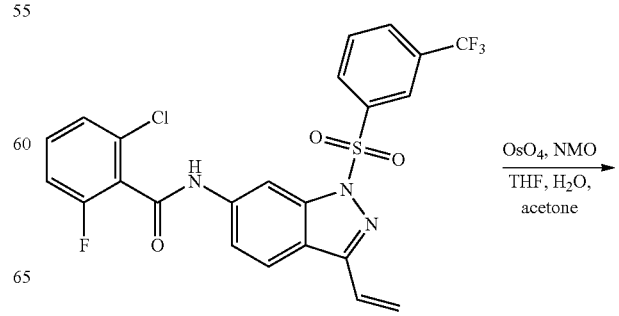

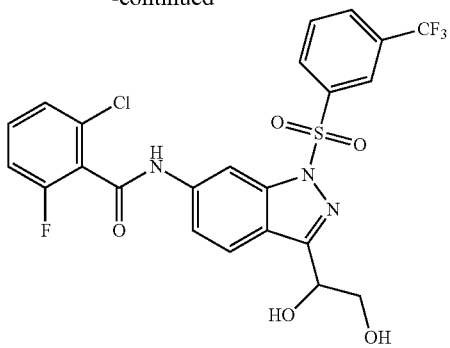

10

To a solution of 2-chloro-6-fluoro-N-[1-(3-trifluoromethylbenzenesulfonyl)-3-vinyl-1H-indazol-6-yl]benzamide (120 mg, 0.23 mmol) in THF/acetone/H₂O (1:1:1, 1.2 mL) was added N-methylmorpholine-N-oxide (NMO, 40 mg, 0.31 mmol) and OsO₄ (2.5 wt % solution in t-BuOH, 0.320 mL). The reaction was stirred for 3 h at room temperature. Sodium bisulfite (260 mg, 2.3 mmol) in H₂O (6 mL) was added and the solution was stirred for 10 minutes. The solution was diluted with brine and the product was extracted with EtOAc (3×10 mL). The organic extracts were dried (Na₂SO₄), concentrated under reduced pressure, and purified by column chromatography (EtOAc, hexanes) to give 2-chloro-N-[3-(1,2-dihydroxyethyl)-1-(3-trifluoromethylbenzenesulfonyl)-1H-indazol-6-yl]-6-fluorobenzamide (70 mg, 55%). ¹H NMR 250 MHz CDCl₃ (with 5% CD₃OD) δ 8.49 (d, J=1.6 Hz, 1H), 8.23 (s, 1H), 8.14 (d, J=8.0 Hz, 1H), 7.86 (d, J=8.8 Hz, 1H), 7.79 (d, J=8.0 Hz, 1H), 7.62 (dd, J=8.8, 1.8 Hz, 1H), 7.60 (t, 8.3 Hz, 1H), 7.34 (td, 8.0, 5.8 Hz, 1H), 7.24 (d, 8.0 Hz, 1H), 7.08 (t, J=8.3 Hz, 1H), 5.03 (t, J=5.5 Hz, 1H), 3.84 (d, J=5.5 Hz, 2H). LCMS (ESI): calcd. C₂₃H₁₆ClF₄N₃O₅S, 557. found (M+H), 558.

Example 9

Preparation of 2-Chloro-6-fluoro-N-[3-hydroxymethyl-1-(3-trifluoromethylbenzene-sulfonyl)-1H-indazol-6-yl]benzamide (11)

The title compound was prepared according to the procedures described below.

Part I—Synthesis of 2-Chloro-6-fluoro-N-[3-formyl-1-(3-trifluoromethylbenzenesulfonyl)-1H-indazol-6-yl]benzamide

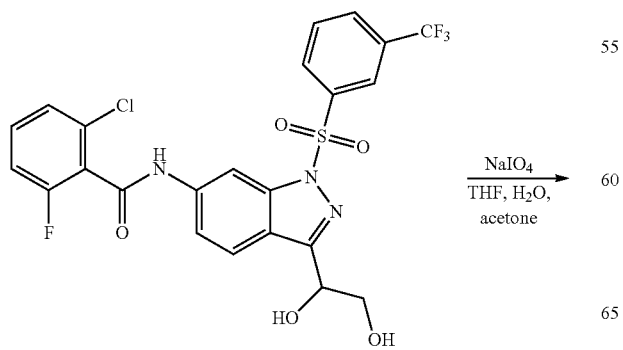

To a solution of 2-chloro-N-[3-(1,2-dihydroxyethyl)-1-(3-trifluoromethylbenzenesulfonyl)-1H-indazol-6-yl]-6-fluorobenzamide (60 mg, 0.11 mmol) in THF (0.200 mL) and THF/acetone/H₂O (1:1:1, 2 mL) was added NaIO₄ (40 mg, 0.2 mmol). The reaction was stirred at room temperature for 12 h. Brine was added and the product was extracted with EtOAc (3×10 mL). The organic extracts were dried (Na₂SO₄) and concentrated under reduced pressure to give 2-chloro-6-fluoro-N-[3-formyl-1-(3-trifluoromethylbenzenesulfonyl)-1H-indazol-6-yl]benzamide (35 mg, crude). LCMS (ESI): calcd. C₂₂H₁₂ClF₄N₃O₄S, 525. found (M+H), 526.

Part II—Synthesis of 2-Chloro-6-fluoro-N-[3-hydroxymethyl-1-(3-trifluoromethylbenzene-sulfonyl)-1H-indazol-6-yl]benzamide

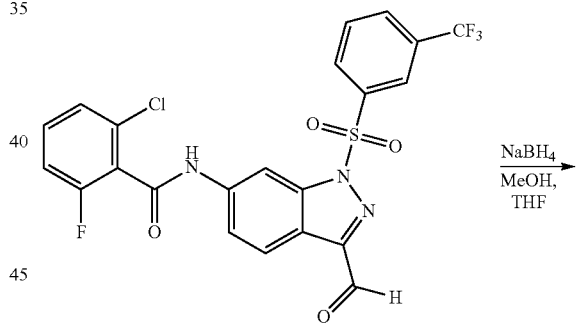

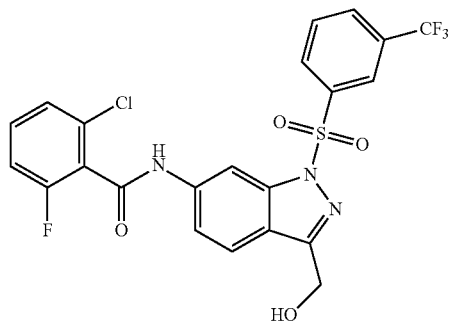

11

2-Chloro-6-fluoro-N-[3-formyl-1-(3-trifluoromethylbenzenesulfonyl)-1H-indazol-6-yl]benzamide (30 mg, 0.06 mmol) and NaBH₄ (10 mg, 0.26 mmol) were dissolved in MeOH/THF (1:2, 1 mL) and stirred for 1 h at room temperature. The organic solvents were removed and the product was purified by column chromatography (EtOAc/hexanes) to give 2-chloro-6-fluoro-N-[3-hydroxymethyl-1-(3-trifluoro-methylbenzenesulfonyl)-1H-indazol-6-yl]benzamide (20 mg, 60%). ¹H NMR 250 MHz CDCl₃ (with 5% CD₃OD) δ 8.50 (d, J=1.6 Hz, 1H), 8.22 (s, 1H), 8.14 (d, J=8.0 Hz, 1H), 7.77 (d, J=8.5 Hz, 2H), 7.63 (dd, J=8.8, 1.8 Hz, 1H), 7.59 (t, 8.0 Hz, 1H), 7.33 (td, 8.2, 6.0 Hz, 1H), 7.22 (d, 8.0 Hz, 1H), 7.06 (t, J=8.5 Hz, 1H), 4.83 (s, 2H). LCMS (ESI): calcd. $C_{22}H_{14}ClF_4N_3O_4S$, 527. found (M+H), 528.

Example 10

Preparation of Additional Indazole Compounds

The compounds in Table 5 below were prepared based on the experimental procedures described in Examples 6-9 and in the detailed description. Starting materials can be obtained from commercial sources or readily prepared from commercially available materials.

TABLE 5

| Compound No. | Chemical Structure |
|---|---|
| V-1 | 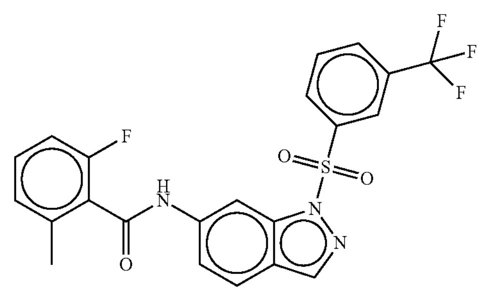 |
| V-2 | 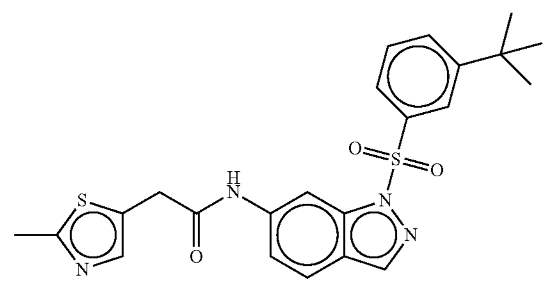 |
| V-3 | 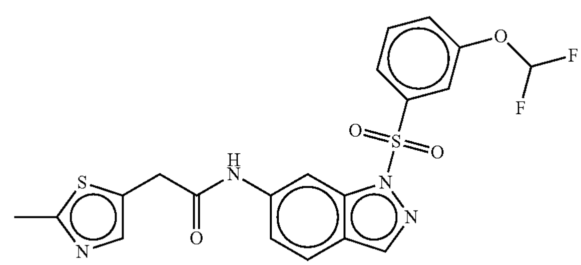 |
| V-4 | 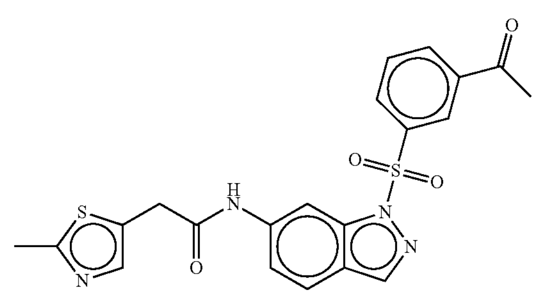 |

TABLE 5-continued
| Compound No. | Chemical Structure |
|---|---|
| V-5 | 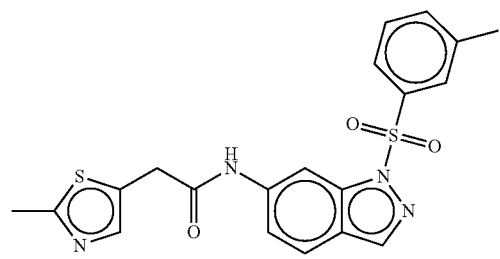 |
| V-6 | 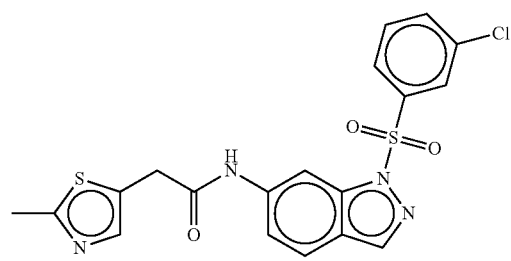 |
| V-7 | 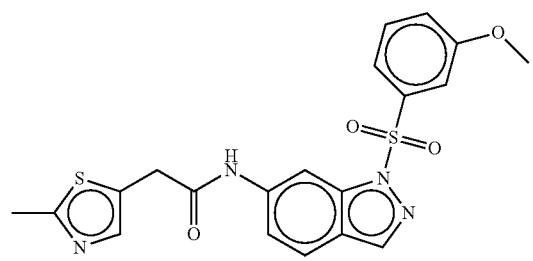 |
| V-8 | 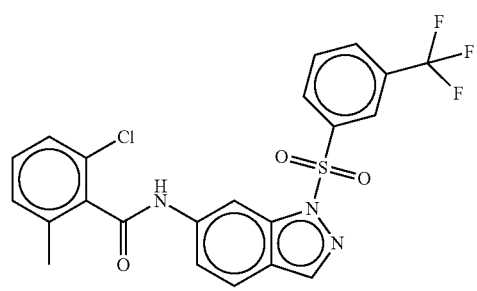 |
| V-9 | 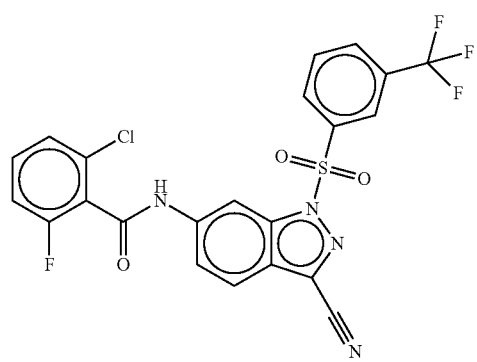 |

TABLE 5-continued

| Compound No. | Chemical Structure |
|---|---|
| V-10 | 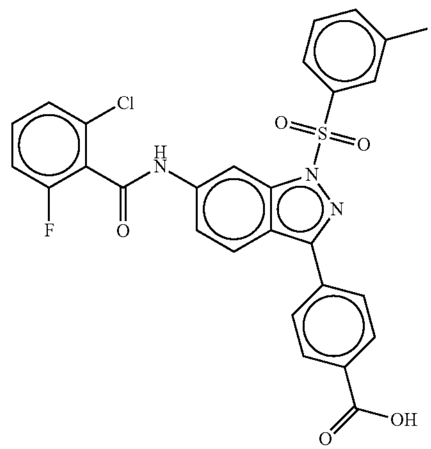 |
| V-11 | 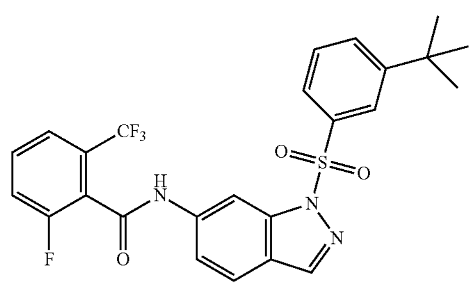 [SMILES: CC(C)(C)c1cccc(S(=O)(=O)n2ncc3ccc(NC(=O)c4c(F)cccc4C(F)(F)F)cc32)c1] |
| V-12 | 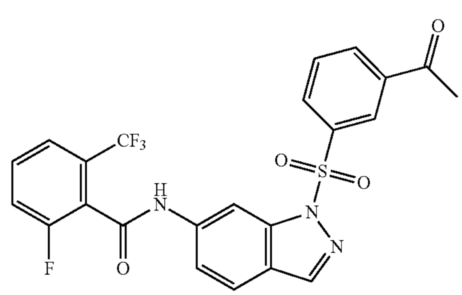 [SMILES: CC(=O)c1cccc(S(=O)(=O)n2ncc3ccc(NC(=O)c4c(F)cccc4C(F)(F)F)cc32)c1] |
| V-13 | 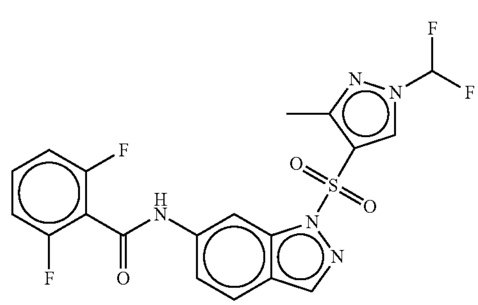 |

TABLE 5-continued
| Compound No. | Chemical Structure |
|---|---|
| V-14 | 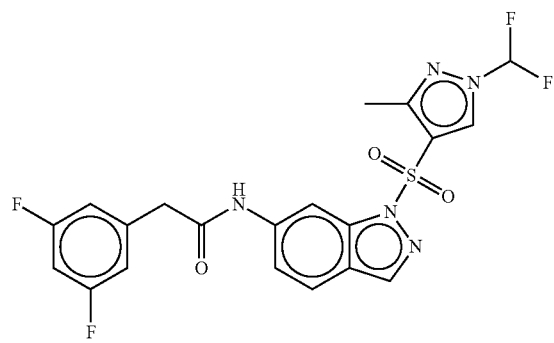 |
| V-15 | 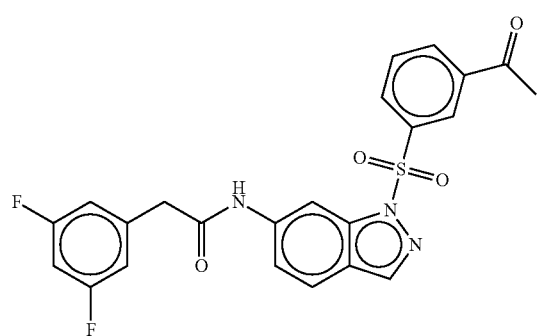 |
| V-16 | 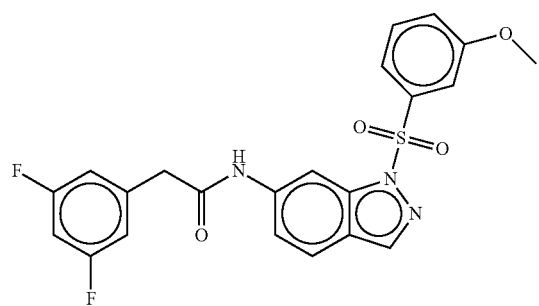 |
| V-17 | 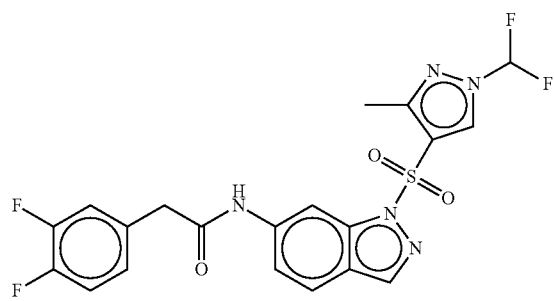 |
| V-18 | 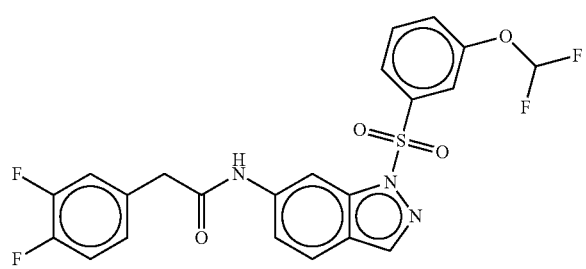 |

TABLE 5-continued
| Compound No. | Chemical Structure |
|---|---|
| V-19 | 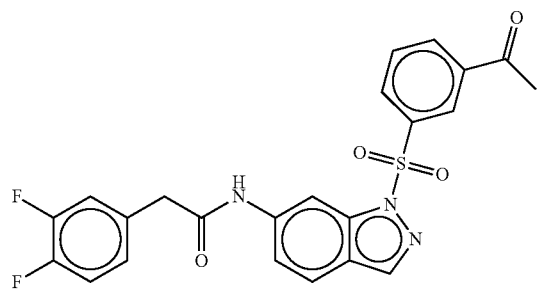 |
| V-20 | 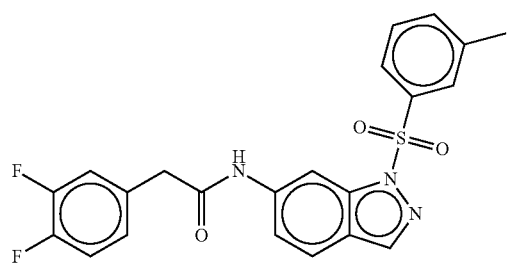 |
| V-21 | 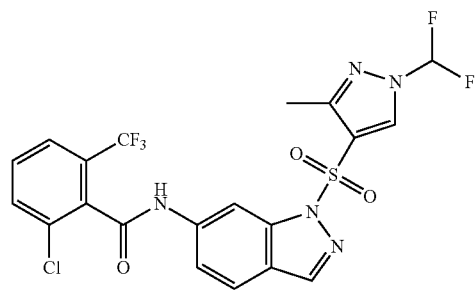 [SMILES: Cc1nn(C(F)F)cc1S(=O)(=O)n1ncc2ccc(NC(=O)c3c(Cl)cccc3C(F)(F)F)cc21] |
| V-22 | 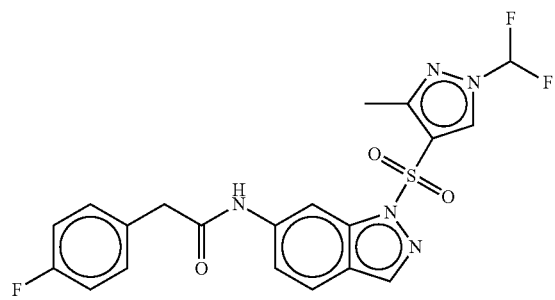 |
| V-23 | 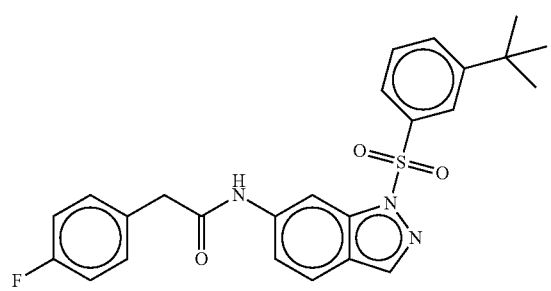 |

TABLE 5-continued
| Compound No. | Chemical Structure |
|---|---|
| V-24 | 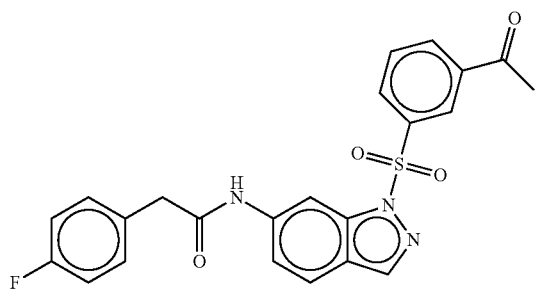 |
| V-25 | 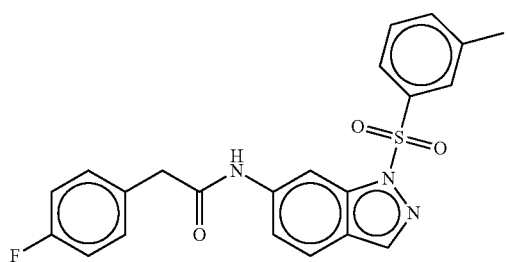 |
| V-26 | 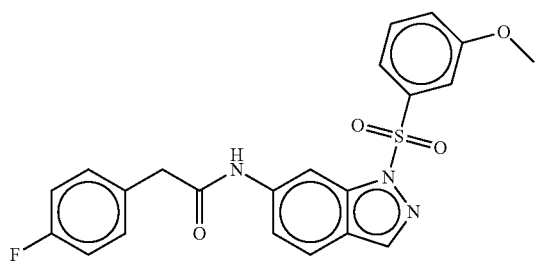 |
| V-27 | 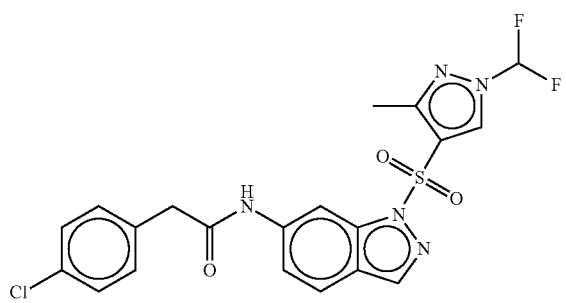 |
| V-28 | 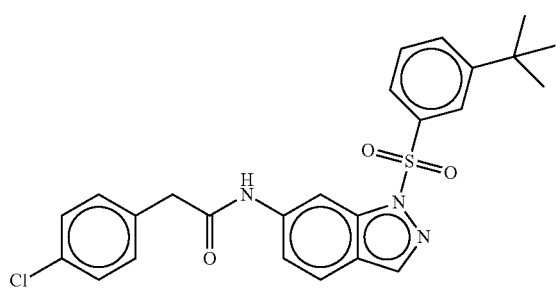 |

TABLE 5-continued
| Compound No. | Chemical Structure |
| --- | --- |
| V-29 | 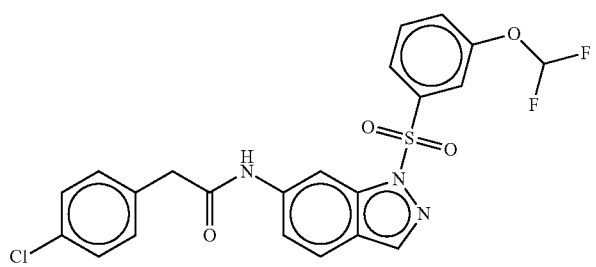 |
| V-30 | 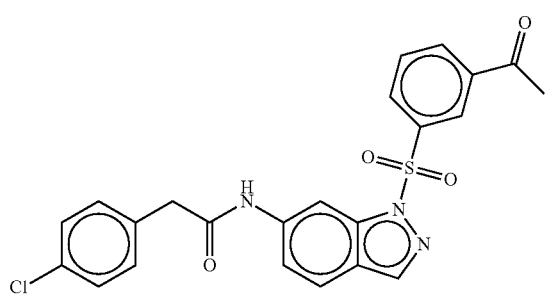 |
| V-31 | 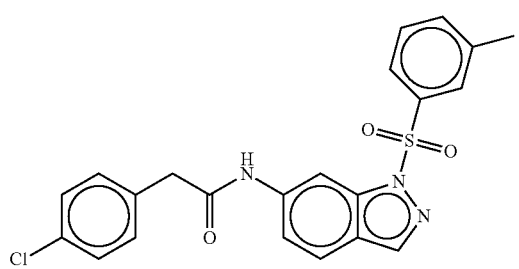 |
| V-32 | 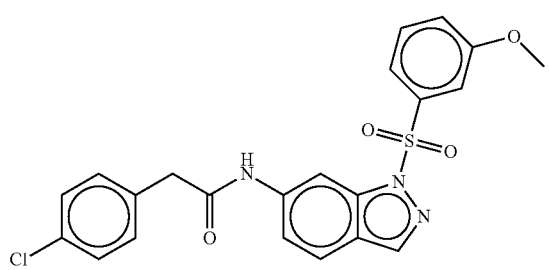 |
| V-33 | 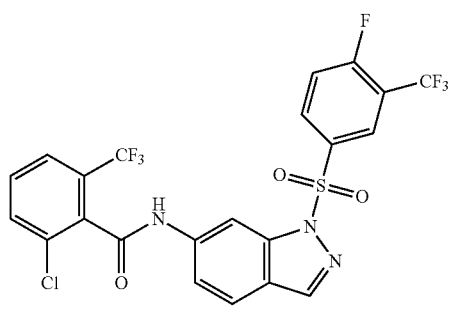 [SMILES: O=C(Nc1ccc2cnn(S(=O)(=O)c3ccc(F)c(C(F)(F)F)c3)c2c1)c1c(Cl)cccc1C(F)(F)F] |

US 9,512,111 B2
163
TABLE 5-continued
| Compound No. | Chemical Structure |
|---|---|
| V-34 | 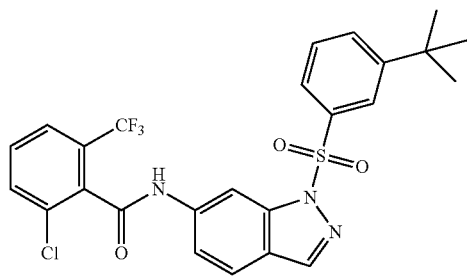 [SMILES: CC(C)(C)c1cccc(S(=O)(=O)n2ncc3ccc(NC(=O)c4c(Cl)cccc4C(F)(F)F)cc32)c1] |
| V-35 | 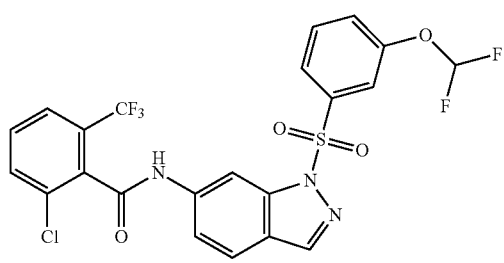 |
| V-36 | 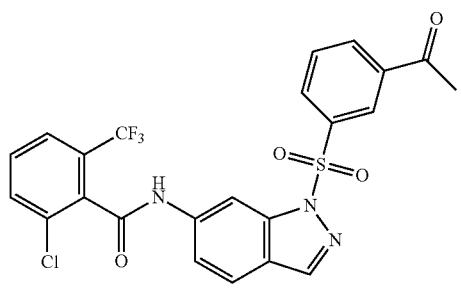 [SMILES: CC(=O)c1cccc(S(=O)(=O)n2ncc3ccc(NC(=O)c4c(Cl)cccc4C(F)(F)F)cc32)c1] |
| V-37 | 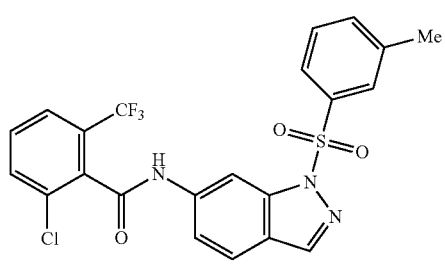 [SMILES: Cc1cccc(S(=O)(=O)n2ncc3ccc(NC(=O)c4c(Cl)cccc4C(F)(F)F)cc32)c1] |
| V-38 | 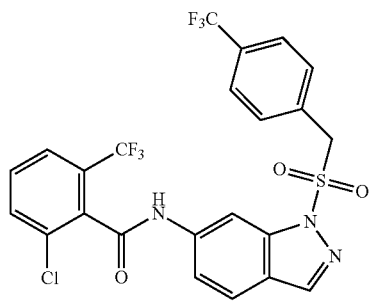 [SMILES: O=C(Nc1ccc2cnn(S(=O)(=O)Cc3ccc(C(F)(F)F)cc3)c2c1)c1c(Cl)cccc1C(F)(F)F] |

TABLE 5-continued
| Compound No. | Chemical Structure |
|---|---|
| V-39 | 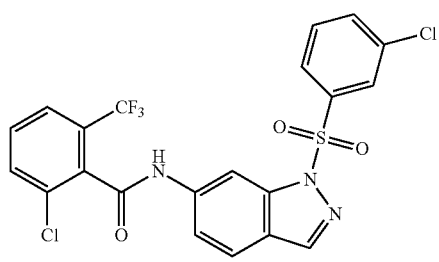 [SMILES: O=C(Nc1ccc2cnn(S(=O)(=O)c3cccc(Cl)c3)c2c1)c1c(Cl)cccc1C(F)(F)F] |
| V-40 | 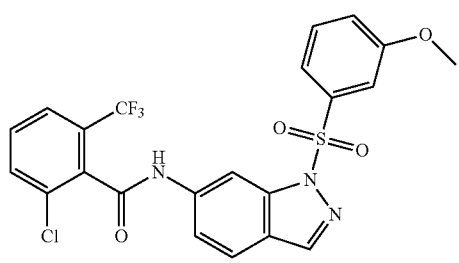 [SMILES: COc1cccc(S(=O)(=O)n2ncc3ccc(NC(=O)c4c(Cl)cccc4C(F)(F)F)cc32)c1] |
| V-41 | 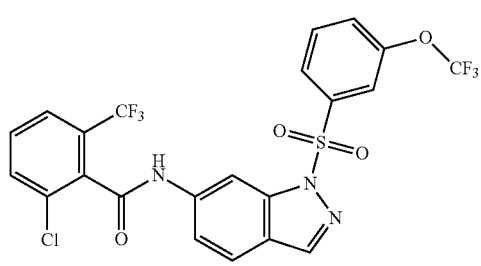 [SMILES: O=C(Nc1ccc2cnn(S(=O)(=O)c3cccc(OC(F)(F)F)c3)c2c1)c1c(Cl)cccc1C(F)(F)F] |
| V-42 | 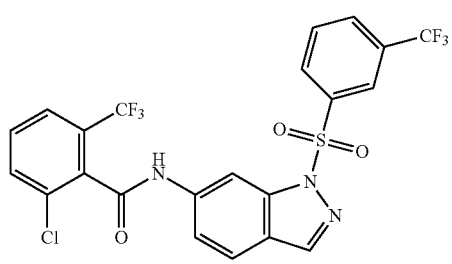 |
| V-43 | 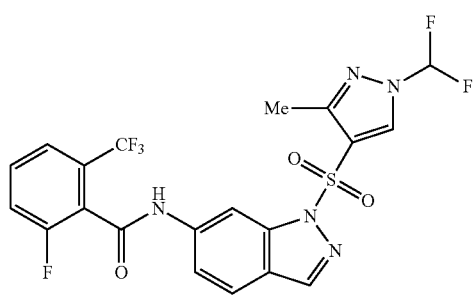 [SMILES: Cc1nn(C(F)F)cc1S(=O)(=O)n1ncc2ccc(NC(=O)c3c(F)cccc3C(F)(F)F)cc21] |

TABLE 5-continued
| Compound No. | Chemical Structure |
|---|---|
| V-44 | 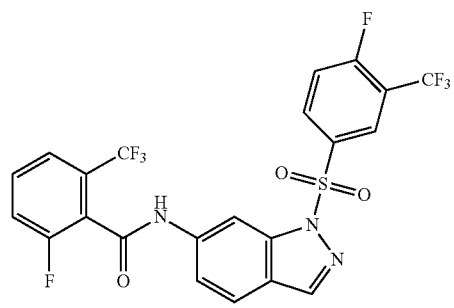 [SMILES: O=C(Nc1ccc2cnn(S(=O)(=O)c3ccc(F)c(C(F)(F)F)c3)c2c1)c1c(F)cccc1C(F)(F)F] |
| V-45 | 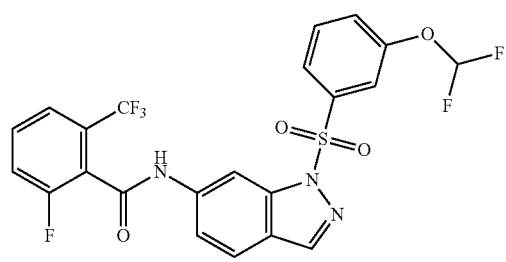 [SMILES: O=C(Nc1ccc2cnn(S(=O)(=O)c3cccc(OC(F)F)c3)c2c1)c1c(F)cccc1C(F)(F)F] |
| V-46 | 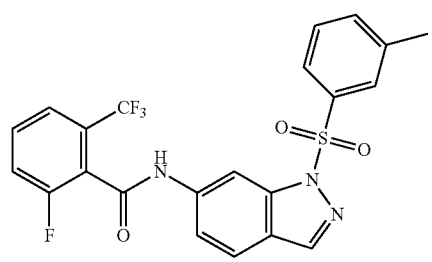 [SMILES: Cc1cccc(S(=O)(=O)n2ncc3ccc(NC(=O)c4c(F)cccc4C(F)(F)F)cc32)c1] |
| V-47 | 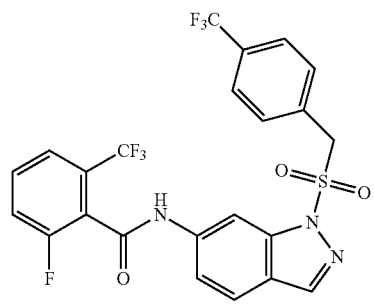 [SMILES: O=C(Nc1ccc2cnn(S(=O)(=O)Cc3ccc(C(F)(F)F)cc3)c2c1)c1c(F)cccc1C(F)(F)F] |
| V-48 | 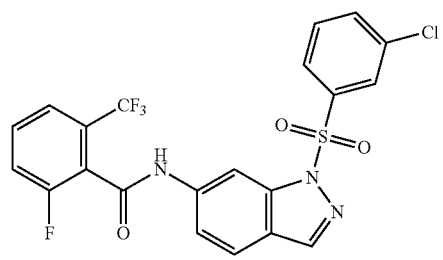 |

TABLE 5-continued
| Compound No. | Chemical Structure |
|---|---|
| V-49 | 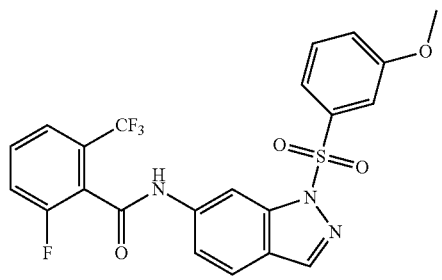 [SMILES: COc1cccc(S(=O)(=O)n2ncc3ccc(NC(=O)c4c(F)cccc4C(F)(F)F)cc32)c1] |
| V-50 | 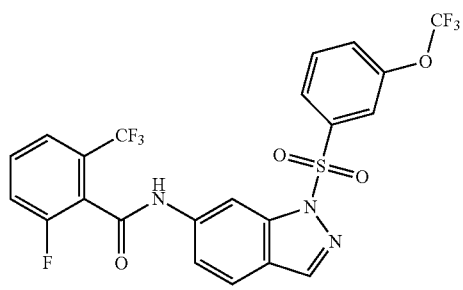 [SMILES: O=C(Nc1ccc2cnn(S(=O)(=O)c3cccc(OC(F)(F)F)c3)c2c1)c1c(F)cccc1C(F)(F)F] |
| V-51 | 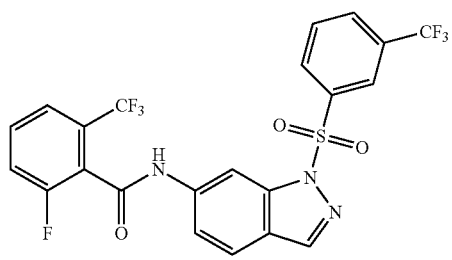 [SMILES: O=C(Nc1ccc2cnn(S(=O)(=O)c3cccc(C(F)(F)F)c3)c2c1)c1c(F)cccc1C(F)(F)F] |
| V-52 | 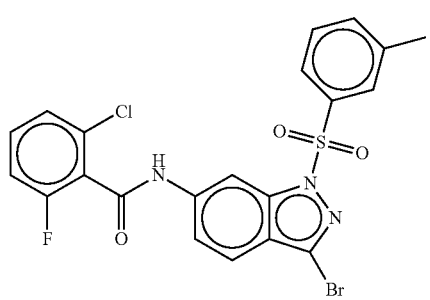 |
| V-53 | 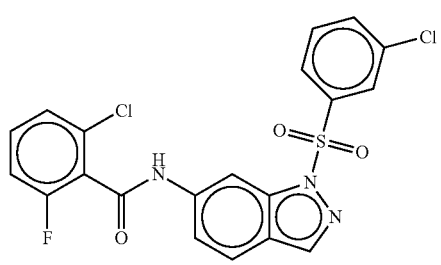 |

TABLE 5-continued
| Compound No. | Chemical Structure |
|---|---|
| V-54 | 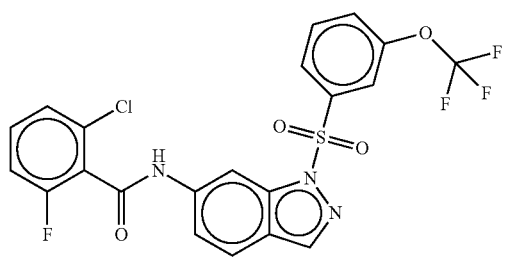 |
| V-55 | 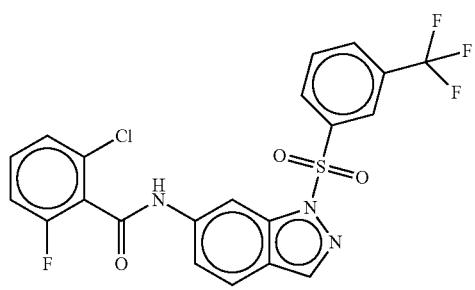 |
| V-56 | 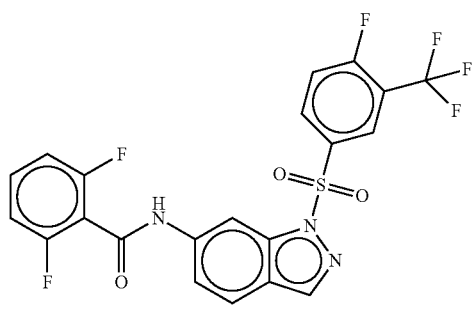 |
| V-57 | 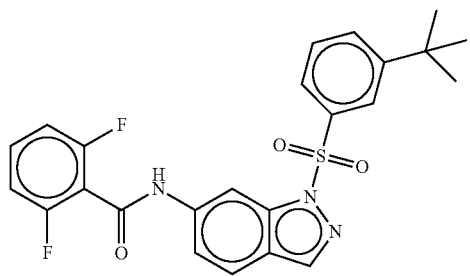 |
| V-58 | 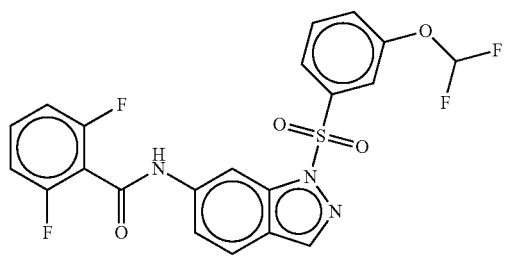 |

TABLE 5-continued
| Compound No. | Chemical Structure |
|---|---|
| V-59 | 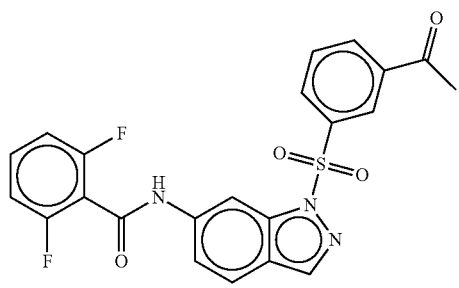 |
| V-60 | 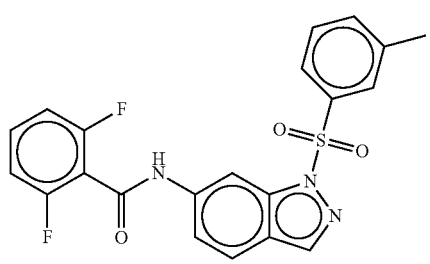 |
| V-61 | 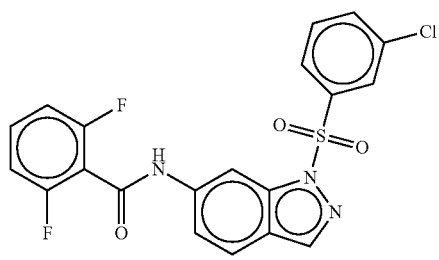 |
| V-62 | 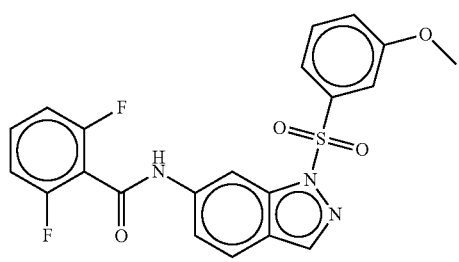 |
| V-63 | 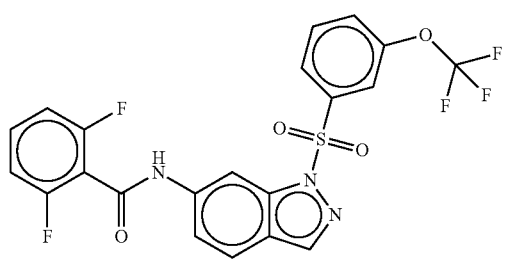 |

TABLE 5-continued
| Compound No. | Chemical Structure |
| --- | --- |
| V-64 | 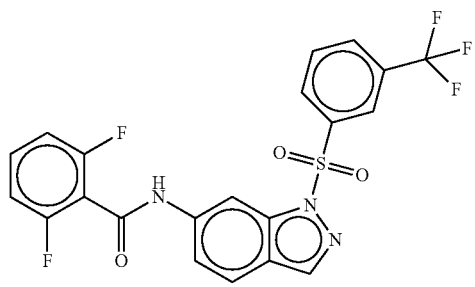 |
| V-65 | 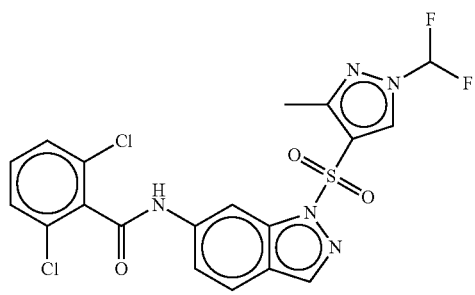 |
| V-66 | 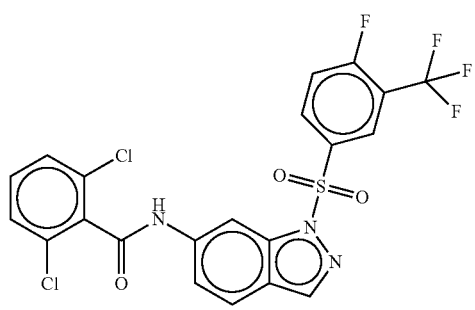 |
| V-67 | 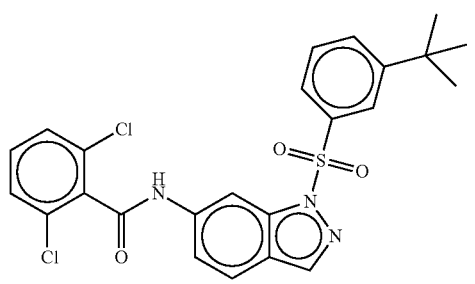 |
| V-68 | 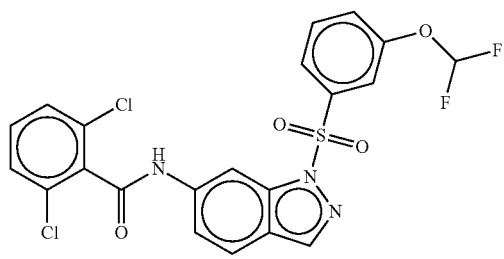 |

TABLE 5-continued
| Compound No. | Chemical Structure |
|---|---|
| V-69 | 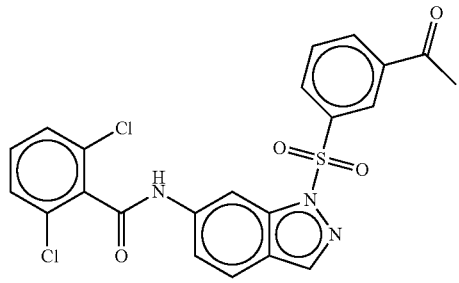 |
| V-70 | 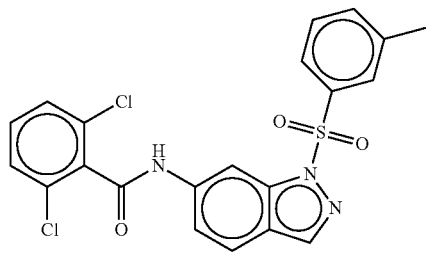 |
| V-71 | 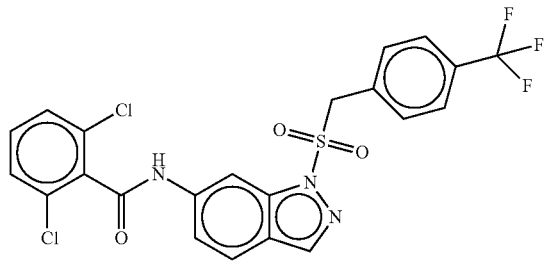 |
| V-72 | 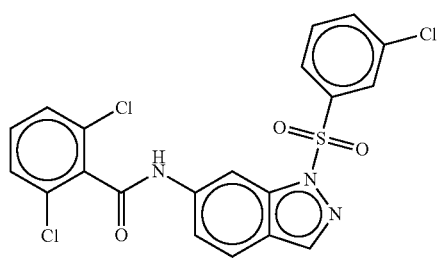 |
| V-73 | 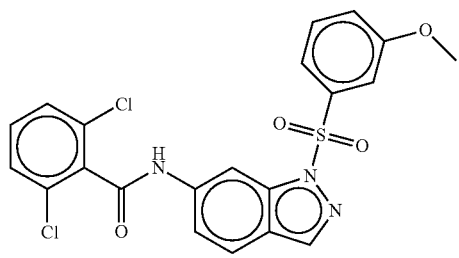 |

TABLE 5-continued
| Compound No. | Chemical Structure |
|---|---|
| V-74 | 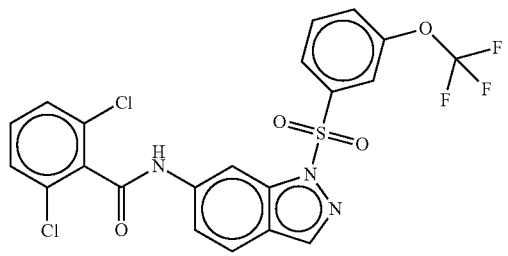 |
| V-75 | 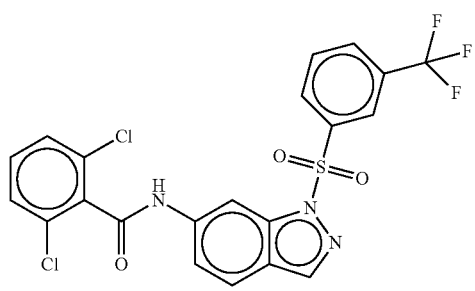 |
| V-76 | 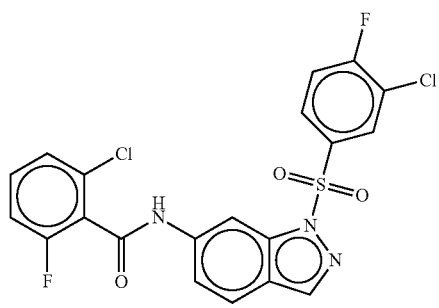 |
| V-77 | 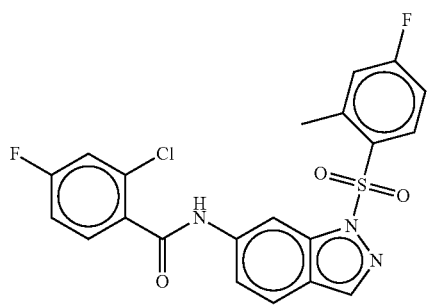 |
| V-78 | 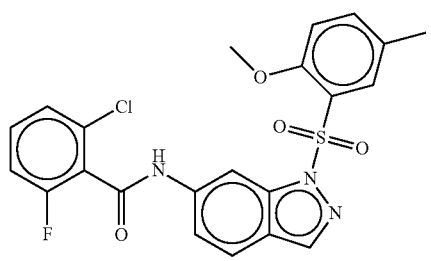 |

TABLE 5-continued
| Compound No. | Chemical Structure |
|---|---|
| V-79 | 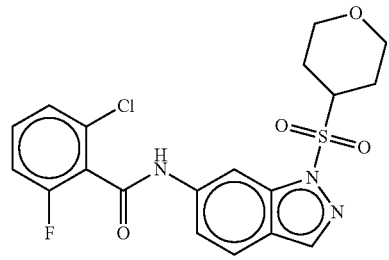 |
| V-80 | 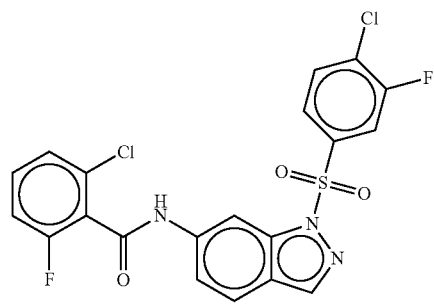 |
| V-81 | 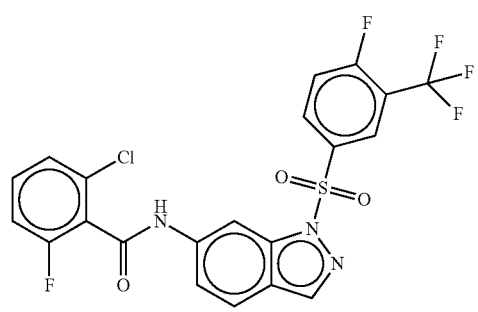 |
| V-82 | 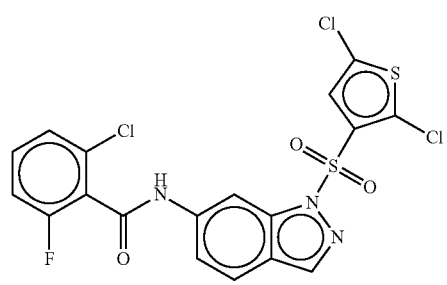 |
| V-83 | 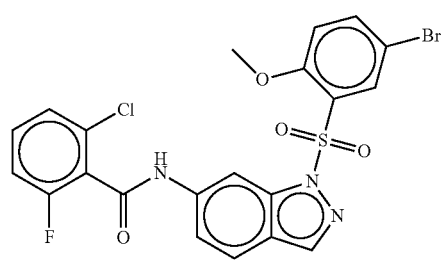 |

TABLE 5-continued
| Compound No. | Chemical Structure |
|---|---|
| V-84 | 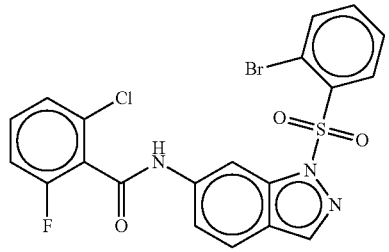 |
| V-85 | 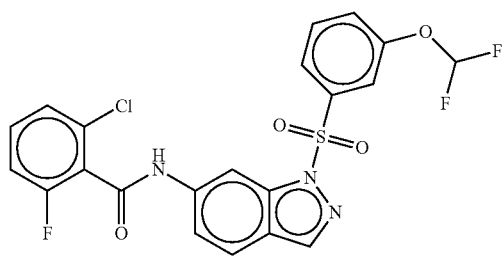 |
| V-86 | 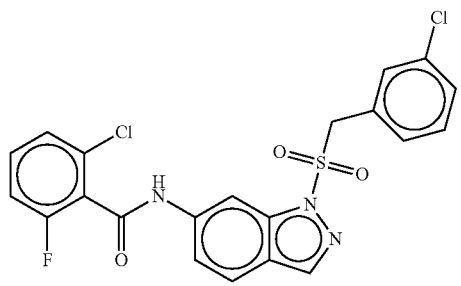 |
| V-87 | 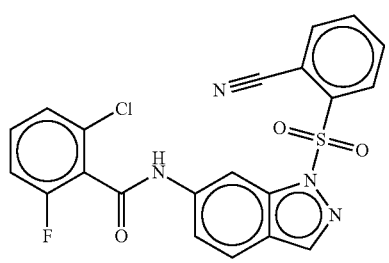 |
| V-88 | 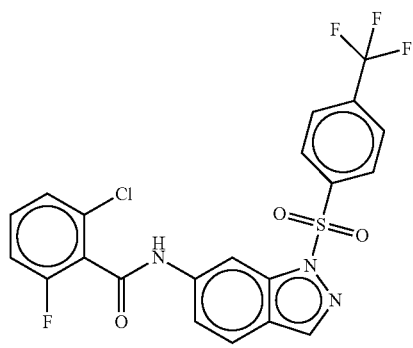 |

TABLE 5-continued
| Compound No. | Chemical Structure |
| --- | --- |
| V-89 | 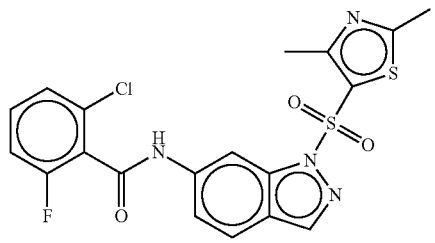 |
| V-90 | 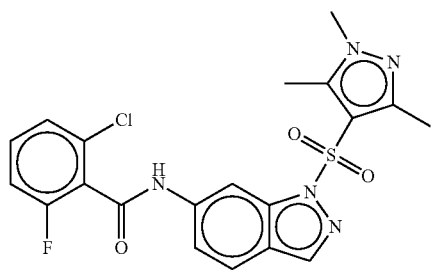 |
| V-91 | 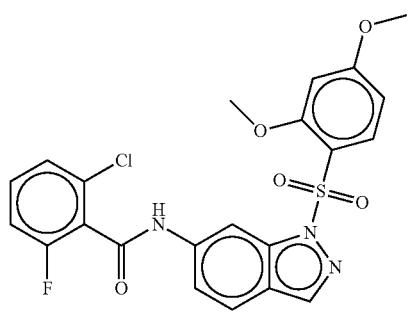 |
| V-92 | 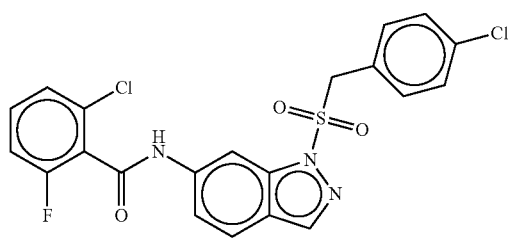 |
| V-93 | 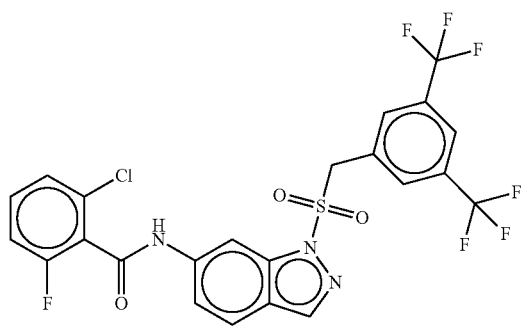 |

TABLE 5-continued
| Compound No. | Chemical Structure |
|---|---|
| V-94 | 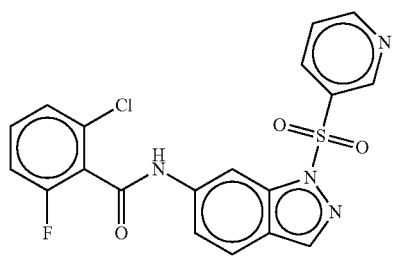 |
| V-95 | 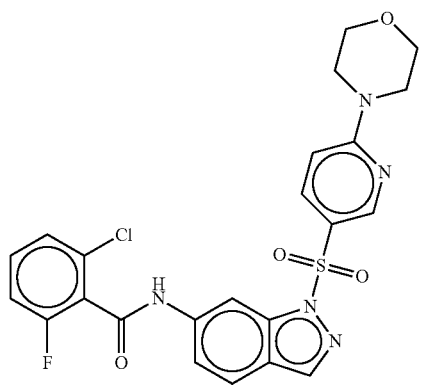 |
| V-96 | 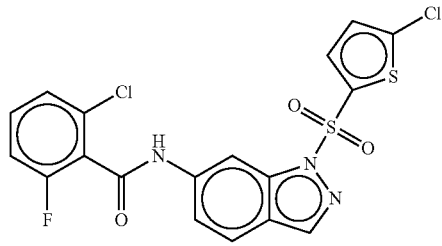 |
| V-97 | 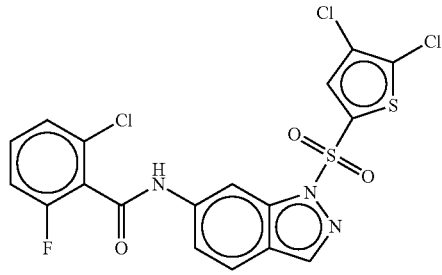 |
| V-98 | 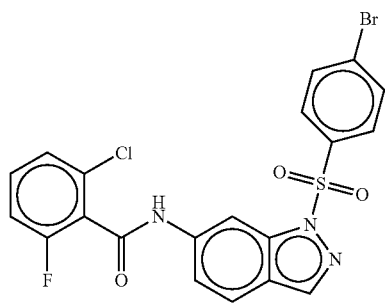 |

US 9,512,111 B2
189
190
TABLE 5-continued
| Compound No. | Chemical Structure |
|---|---|
| V-99 | 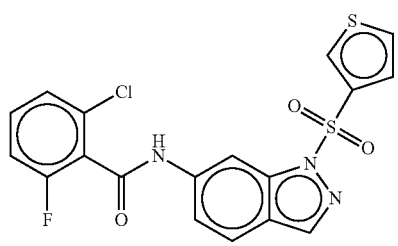 |
| V-100 | 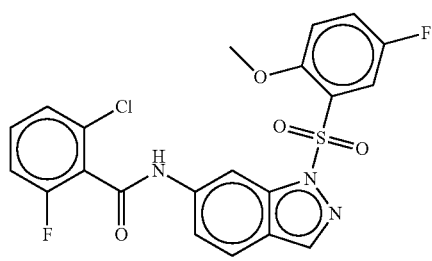 |
| V-101 | 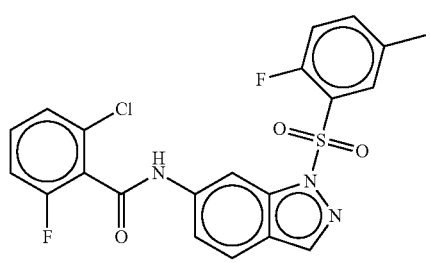 |
| V-102 | 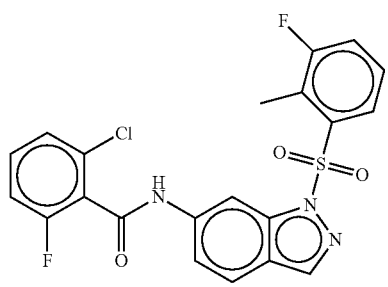 |
| V-103 | 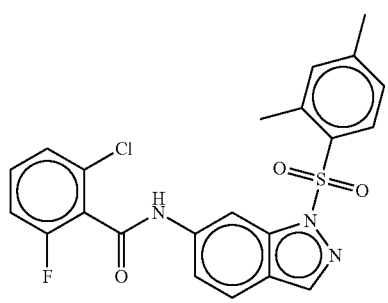 |

TABLE 5-continued
| Compound No. | Chemical Structure |
|---|---|
| V-104 | 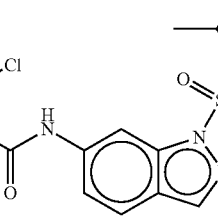 |
| V-105 | 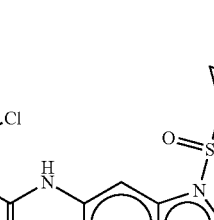 |
| V-106 | 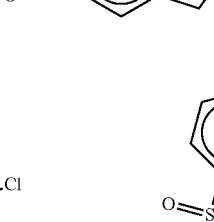 |
| V-107 | 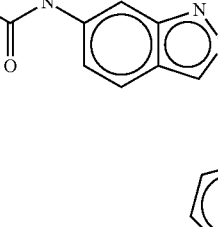 |
| V-108 | 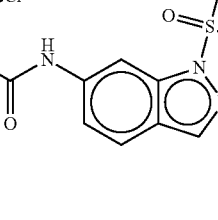 |

TABLE 5-continued
| Compound No. | Chemical Structure |
|---|---|
| V-109 | 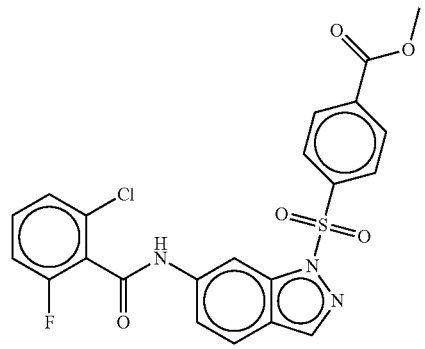 |
| V-110 | 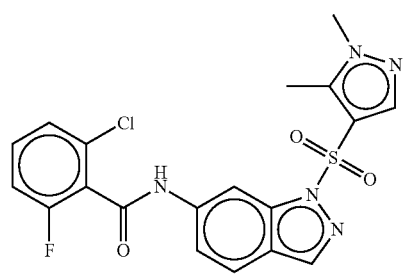 |
| V-111 | 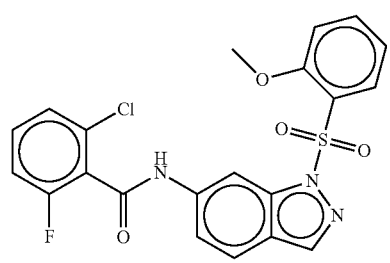 |
| V-112 | 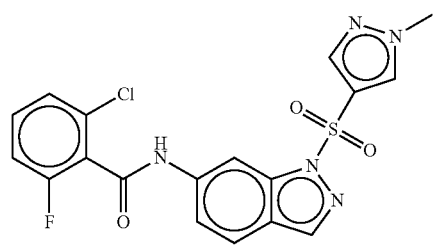 |
| V-113 | 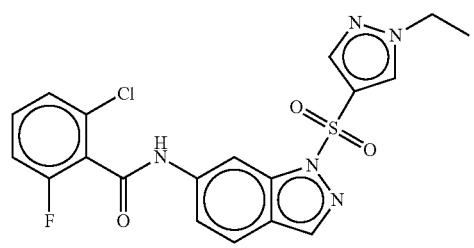 |

TABLE 5-continued
| Compound No. | Chemical Structure |
|---|---|
| V-114 | 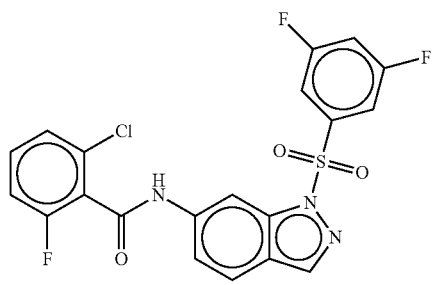 |
| V-115 | 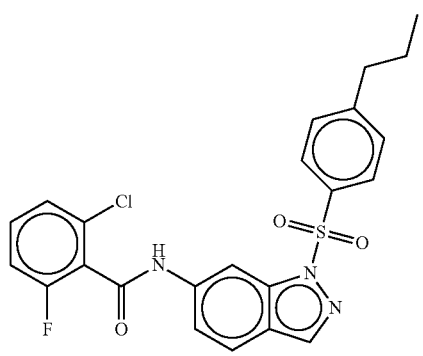 |
| V-116 | 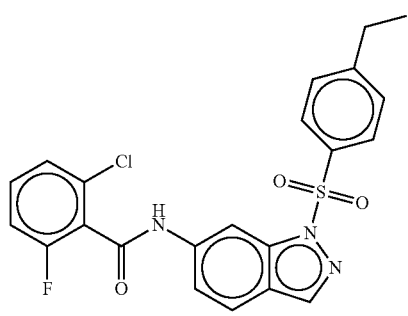 |
| V-117 | 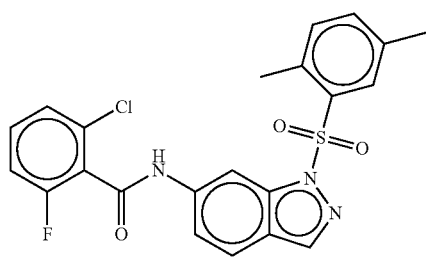 |
| V-118 | 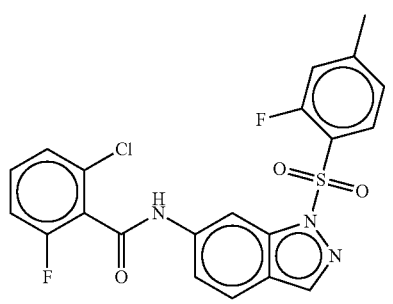 |

TABLE 5-continued
| Compound No. | Chemical Structure |
| --- | --- |
| V-119 | 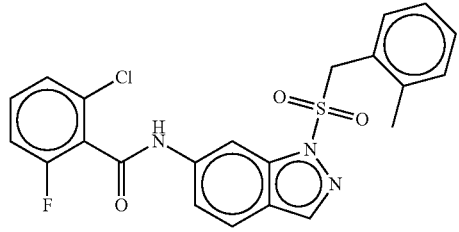 |
| V-120 | 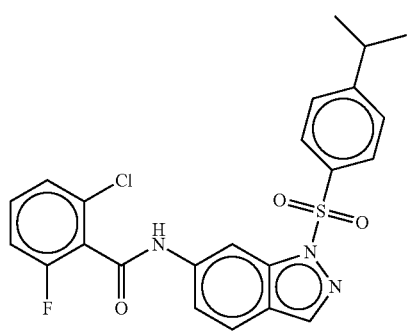 |
| V-121 | 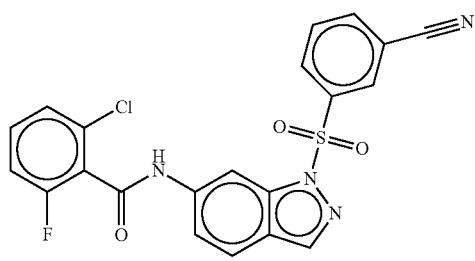 |
| V-122 | 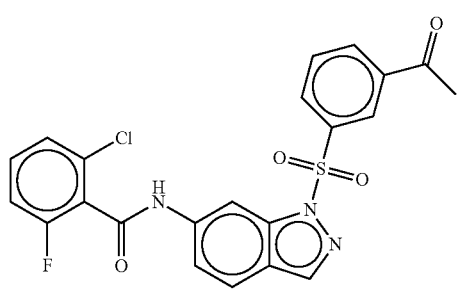 |
| V-123 | 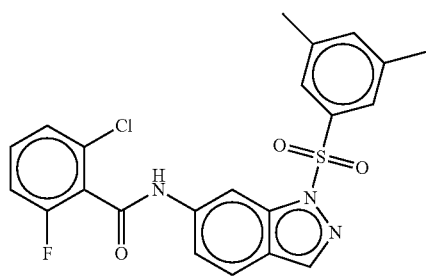 |

TABLE 5-continued
| Compound No. | Chemical Structure |
|---|---|
| V-124 | 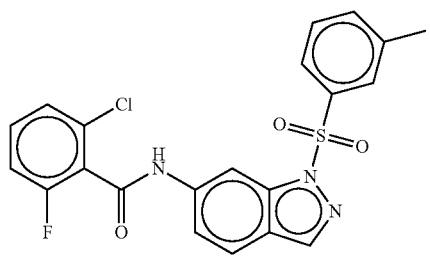 |
| V-125 | 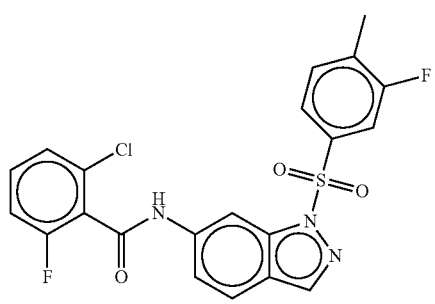 |
| V-126 | 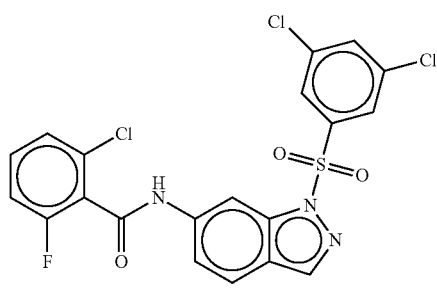 |
| V-127 | 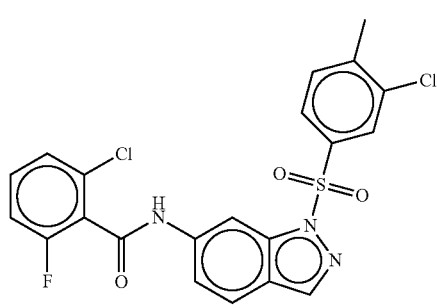 |
| V-128 | 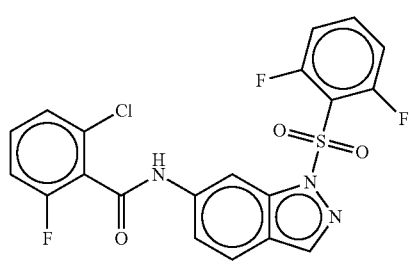 |

TABLE 5-continued
| Compound No. | Chemical Structure |
|---|---|
| V-129 | 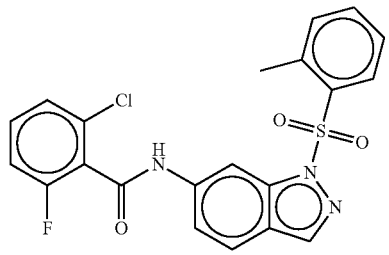 |
| V-130 | 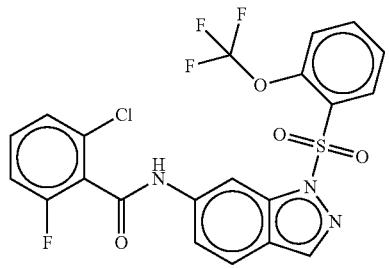 |
| V-131 | 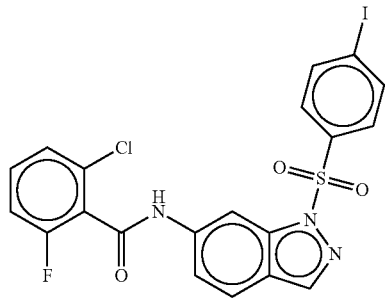 |
| V-132 | 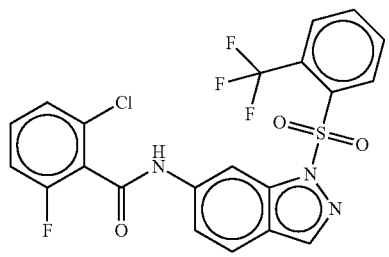 |
| V-133 | 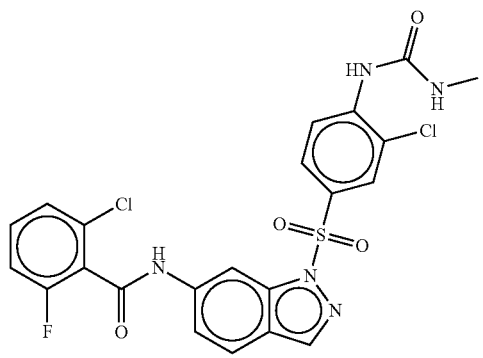 |

TABLE 5-continued

| Compound No. | Chemical Structure |
|---|---|
| V-134 | 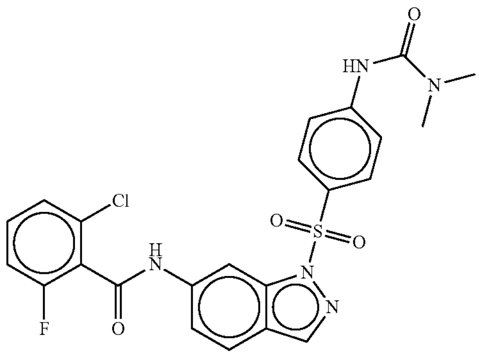 |
| V-135 | 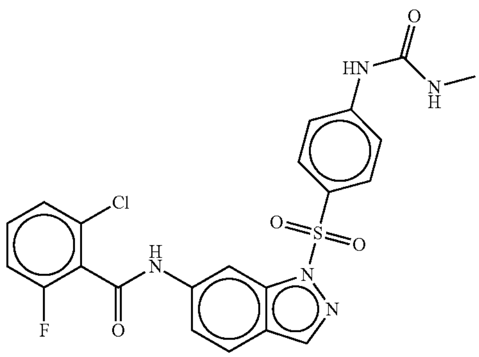 |
| V-136 | 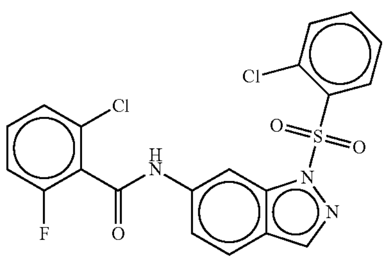 |
| V-137 | 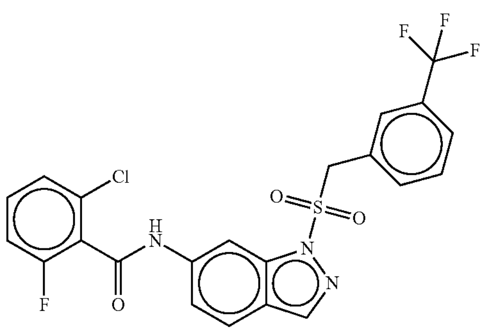 |
| V-138 | 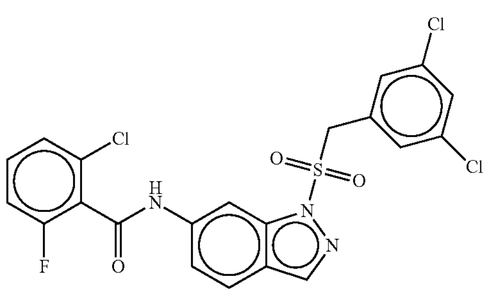 |

TABLE 5-continued
| Compound No. | Chemical Structure |
|---|---|
| V-139 | 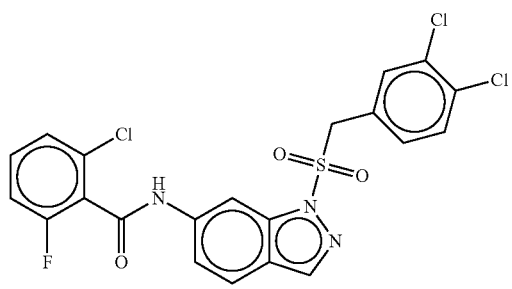 |
| V-140 | 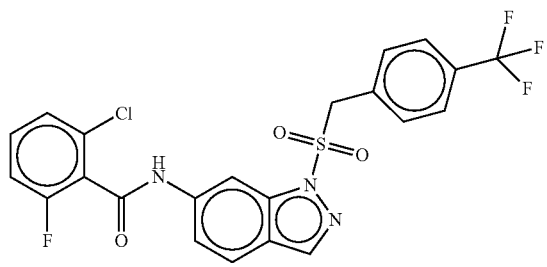 |
| V-141 | 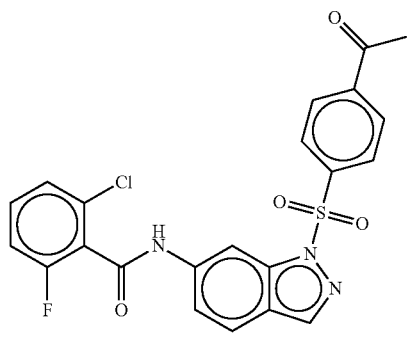 |
| V-142 | 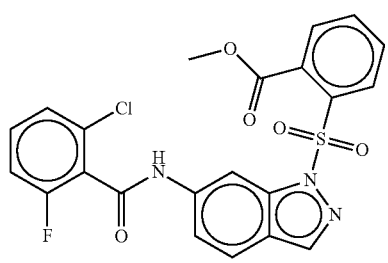 |
| V-143 | 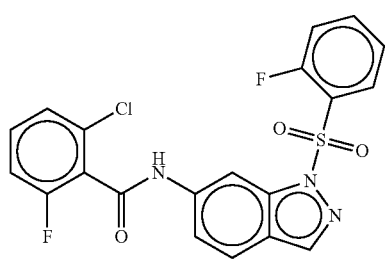 |

TABLE 5-continued
| Compound No. | Chemical Structure |
|---|---|
| V-144 | 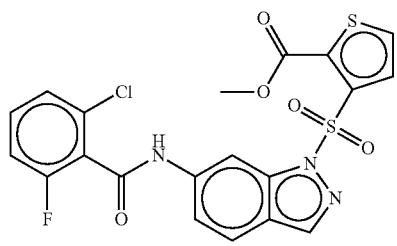 |
| V-145 | 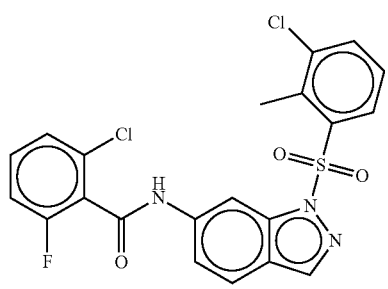 |
| V-146 | 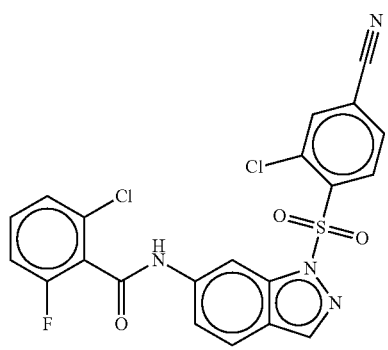 |
| V-147 | 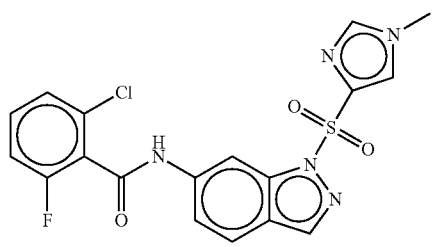 |
| V-148 | 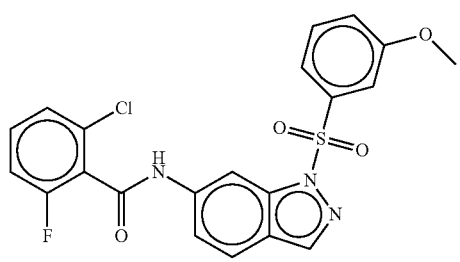 |

TABLE 5-continued
| Compound No. | Chemical Structure |
|---|---|
| V-149 | 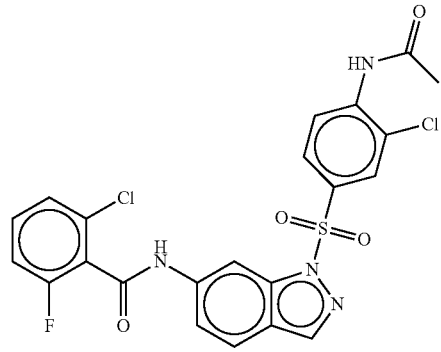 |
| V-150 | 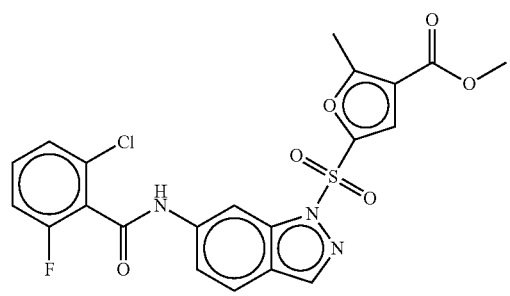 |
| V-151 | 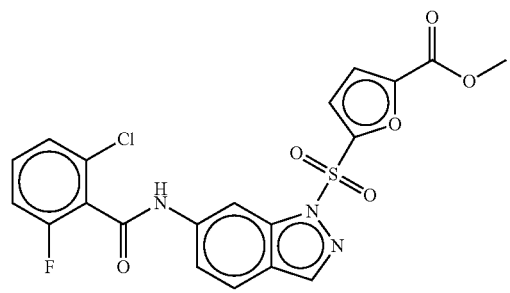 |
| V-152 | 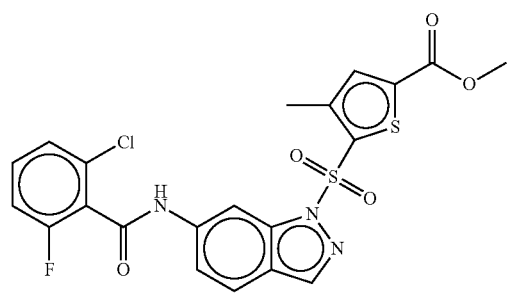 |
| V-153 | 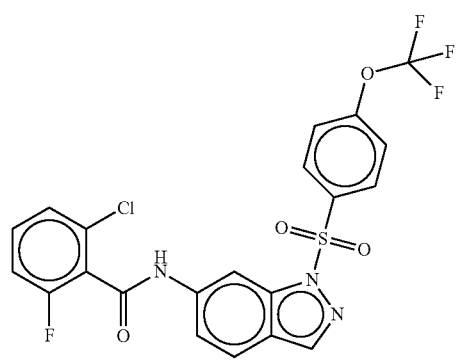 |

TABLE 5-continued
| Compound No. | Chemical Structure |
|---|---|
| V-154 | 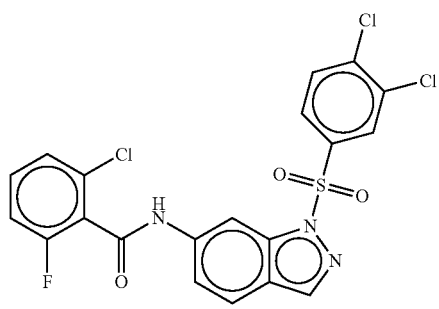 |
| V-155 | 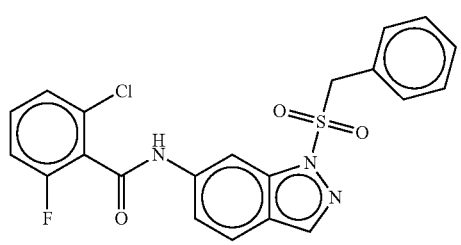 |
| V-156 | 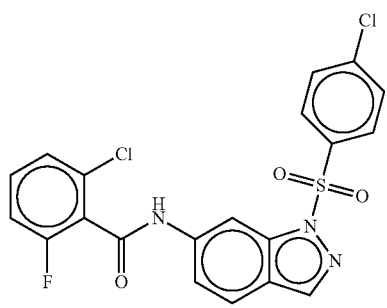 |
| V-157 | 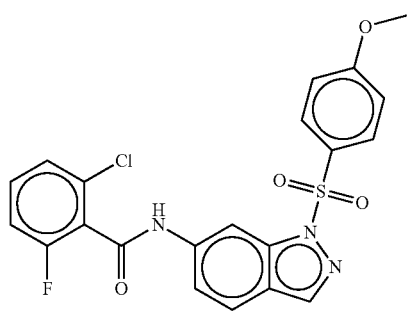 |
| V-158 | 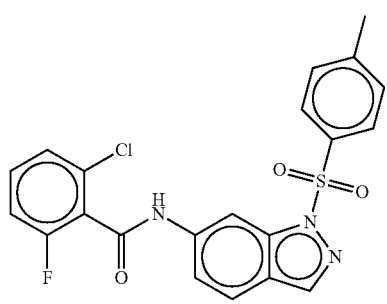 |

TABLE 5-continued
| Compound No. | Chemical Structure |
|---|---|
| V-159 | 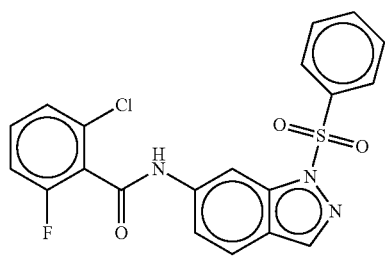 |
| V-160 | 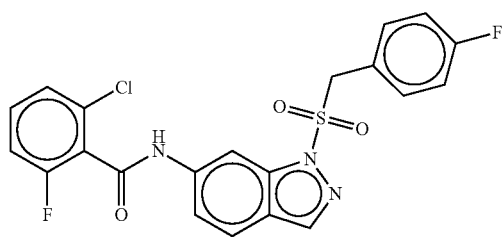 |
| V-161 | 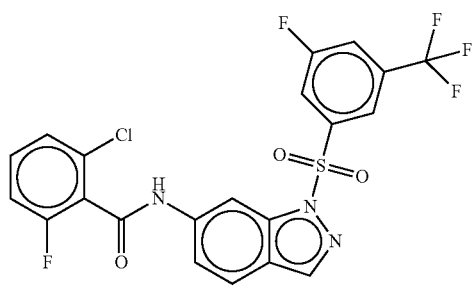 |
| V-162 | 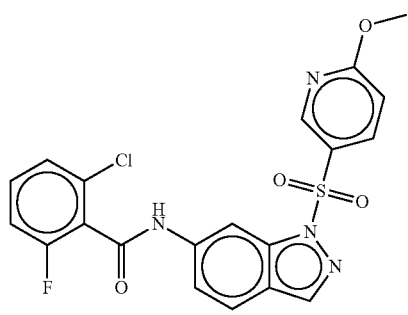 |
| V-163 | 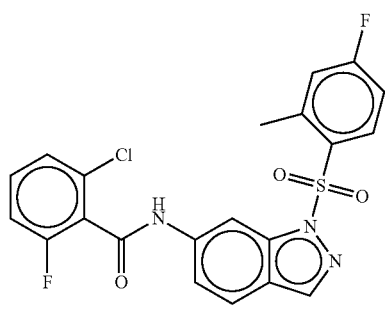 |

TABLE 5-continued
| Compound No. | Chemical Structure |
|---|---|
| V-164 | 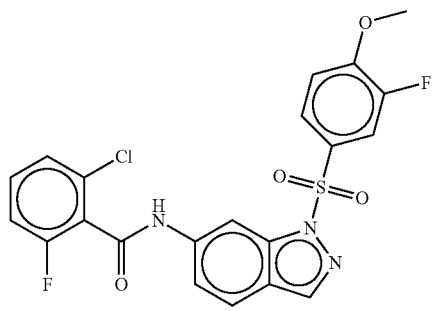 |
| V-165 | 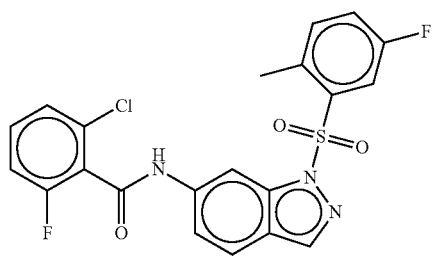 |
| V-166 | 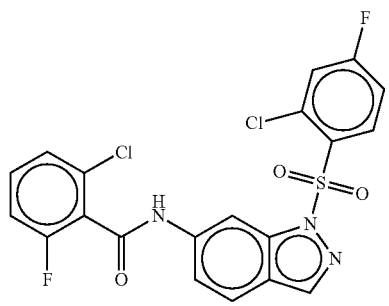 |
| V-167 | 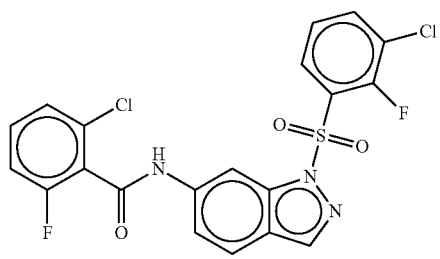 |
| V-168 | 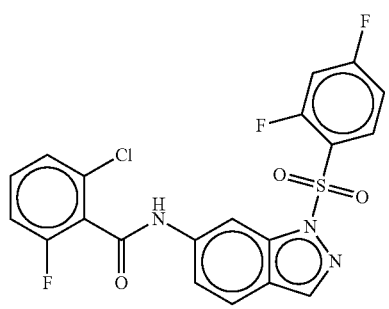 |

TABLE 5-continued

| Compound No. | Chemical Structure |
|---|---|
| V-169 | (structure) |
| V-170 | (structure) |
| V-171 | (structure) |

Example 11

Preparation of 2-Chloro-6-fluoro-N-[7-fluoro-4-(4-fluorobenzenesulfonyl)-2-methoxymethyl-3,4-dihydro-2H-benzo[1,4]oxazin-6-yl]benzamide (12)

The title compound was prepared according to the procedures described below.

Part I—Synthesis of N-(2,4-Difluoro-5-nitrophenyl)-4-fluorobenzenesulfonamide

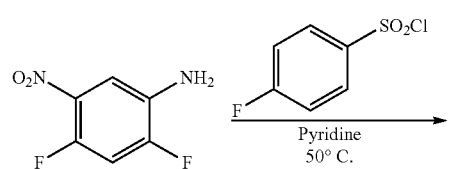

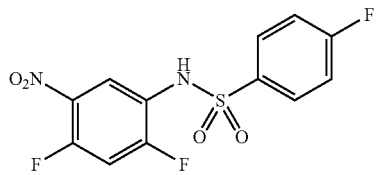

p-Fluorobenzenesulfonyl chloride (0.52 g, 2.7 mmol) was added to a solution of 2,4-difluoro-5-nitrophenylamine (0.31 g, 1.77 mmol) in pyridine (2 mL). The reaction mixture was stirred at 50° C. for 1 h. The reaction mixture was diluted with EtOAc (50 mL) and washed with 1M HCl and then brine (1×10 mL) to provide an organic extract. The organic extract was dried (MgSO$_4$), concentrated under reduce pressure, and purified by column chromatography (EtOAc/hexanes) to afford N-(2,4-difluoro-5-nitrophenyl)-4-fluorobenzenesulfonamide (0.30 g, 52%). $^1$H NMR 250 MHz CDCl$_3$ δ 8.35 (t, J=7.75 Hz, 1H), 7.83-7.89 (m, 2H), 7.16-7.23 (m, 2H), 6.97-7.05 (m, 1H).

Part II—Synthesis of 7-Fluoro-4-(4-fluorobenzenesulfonyl)-2-methoxymethyl-6-nitro-3,4-dihydro-2H-benzo[1,4]oxazine

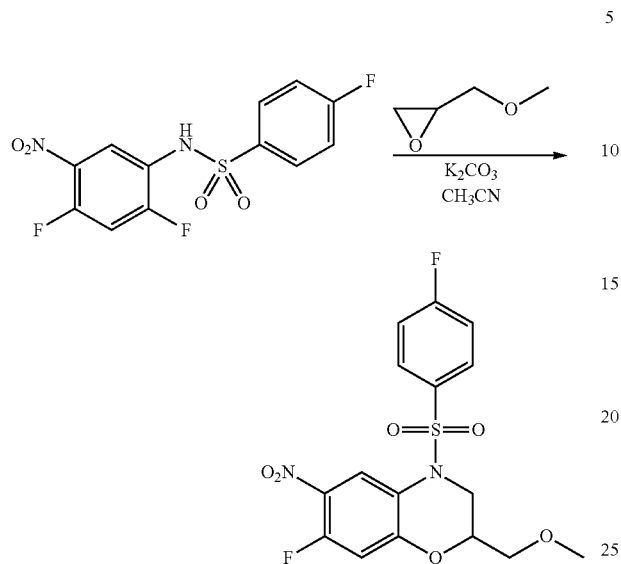

Glycidyl methyl ether (64 mg, 0.72 mmol) was added to a solution of potassium carbonate (66 mg, 0.48 mmol) and N-(2,4-difluoro-5-nitrophenyl)-4-fluorobenzenesulfonamide (40 mg, 0.12 mmol) in CH$_3$CN (0.7 mL). The reaction mixture was heated in a microwave reactor at 140° C. for 1 h. The reaction mixture was diluted with EtOAc (50 mL) and washed with H$_2$O (1×10 mL) and brine (1×10 mL) to provide an organic extract. The organic extract was dried (MgSO$_4$) and concentrated under reduced pressure to provide the crude product, which was purified by chromatography (EtOAc/hexanes) to afford 7-fluoro-4-(4-fluorobenzenesulfonyl)-2-methoxymethyl-6-nitro-3,4-dihydro-2H-benzo[1,4]oxazine (20 mg, 42%). $^1$H NMR 250 MHz CDCl$_3$ δ 8.62 (d, J=7.75 Hz, 1H), 7.73-7.78 (m, 2H), 7.18-7.25 (m, 2H), 6.75 (d, J=11.5 Hz, 1H), 4.35 (dd, J=2.5, 14.75 Hz, 1H), 3.66-3.72 (m, 1H), 3.51 (dd, J=2.5, 7.75 Hz, 1H), 3.37 (s, 3H).

Part III—Synthesis of 7-Fluoro-4-(4-fluorobenzenesulfonyl)-2-methoxymethyl-3,4-dihydro-2H-benzo[1,4]oxazine-6-ylamine

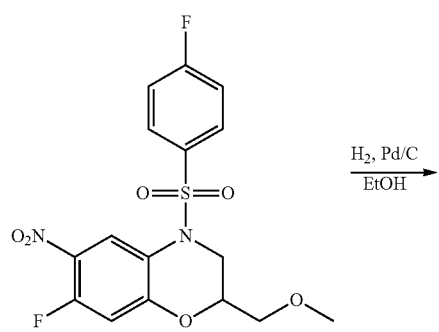

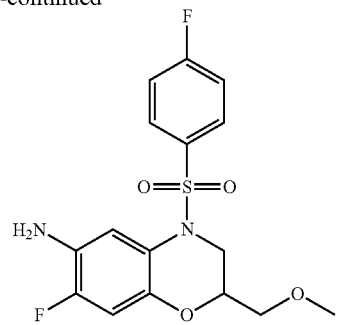

7-Fluoro-4-(4-fluorobenzenesulfonyl)-2-methoxymethyl-6-nitro-3,4-dihydro-2H-benzo[1,4]oxazine (20 mg, 0.05 mmol) and 10% Pd/C (5 mg) were suspended in ethanol (25 mL) and agitated under a hydrogen atmosphere (60 p.s.i.) for 2 h. The reaction mixture was filtered and concentrated under reduced pressure to yield 7-fluoro-4-(4-fluorobenzenesulfonyl)-2-methoxymethyl-3,4-dihydro-2H-benzo[1,4]oxazine-6-ylamine (15 mg, 80%), which was used in the next step without purification. LCMS (ESI): calcd. C$_{16}$H$_{16}$F$_2$N$_2$O$_4$S, 370.38. found (M+H), 371.

Part IV—Synthesis of 2-Chloro-6-fluoro-N-[7-fluoro-4-(4-fluorobenzenesulfonyl)-2-methoxymethyl-3,4-dihydro-2H-benzo[1,4]oxazin-6-yl]benzamide

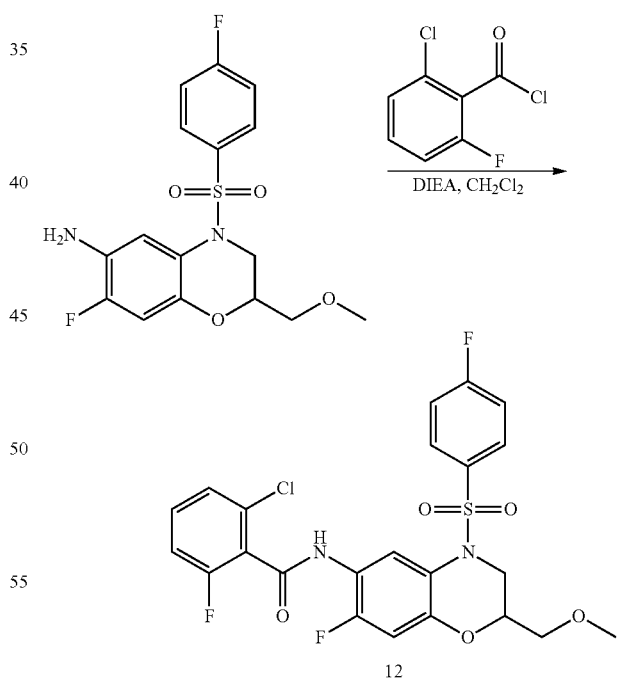

12

2-Chloro-6-fluorobenzoyl chloride (0.02 mL, 0.15 mmol) and diisopropylethylamine (0.05 mL, 0.17 mmol) were added to 7-fluoro-4-(4-fluorobenzenesulfonyl)-2-methoxymethyl-3,4-dihydro-2H-benzo[1,4]oxazine-6-ylamine (15 mg, 0.040 mmol) in CH$_2$Cl$_2$ (1 mL). The reaction was stirred at room temperature 1 h and concentrated under reduced pressure. The crude product was purified by HPLC to afford 2-chloro-6-fluoro-N-[7-fluoro-4-(4-fluorobenzenesulfonyl)-2-methoxymethyl-3,4-dihydro-2H-benzo[1,4]oxazin-6-yl]benzamide. LCMS (ESI): calcd. $C_{23}H_{18}ClF_3N_2O_5S$, 526.92. found (M+H), 527.

Example 12

Preparation of 2-Chloro-6-fluoro-N—[(S)-4-(4-fluorobenzesulfonyl)-2-methyl-3,4-dihydro-2Hbenzo[1,4]oxazine-6-yl]-benzamide (13)

The title compound was prepared according to the procedures described below.

Part I—Synthesis of (S)-4-(4-Fluorobenzenesulfonyl)-2-methyl-6-nitro-3,4-dihydro-2Hbenzo[1,4]oxazine

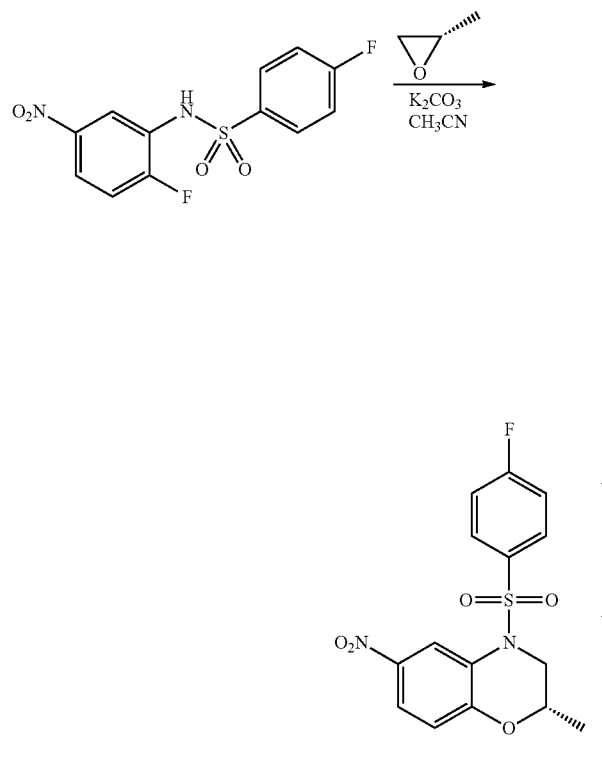

(S)-Propylene oxide (0.37 mL, 5.3 mmol) was added to a mixture of 4-fluoro-N-(2-fluoro-5-nitrophenyl)-benzenesulfonamide (0.559 g, 1.78 mmol) and potassium carbonate (0.98 g, 7.1 mmol) in $CH_3CN$ (5 mL). The reaction mixture was heated in a microwave reactor at 140° C. for 2 h. The reaction mixture was diluted with EtOAc (50 mL) and washed with $H_2O$ (1×10 mL) and brine (1×10 mL), dried ($MgSO_4$), and concentrated under reduced pressure to provide the crude product, which was purified by chromatography (EtOAc/hexanes) to yield (S)-4-(4-fluorobenzenesulfonyl)-2-methyl-6-nitro-3,4-dihydro-2Hbenzo[1,4]oxazine (0.32 g, 51%). $^1$H NMR 250 MHz $CDCl_3$ δ 8.73 (d, J=2.75 Hz, 1H), 7.96 (dd, J=2.5, 9.0 Hz, 1H), 7.74-7.79 (m, 2H), 7.15-7.23 (m, 2H), 6.90 (d, J=9.0 Hz, 1H), 4.30 (dd, J=2.25, 14.25 Hz, 1H), 3.72-380 (m, 1H), 3.13 (dd, J=9.75, 14.25 Hz, 1H), 1.33 (d, J=6.35 Hz, 3H).

Part II—Synthesis (S)-4-(4-Fluorobenzenesulfonyl)-2-methyl-3,4-dihydro-2H-benzo[1,4]oxazin-6-ylamine

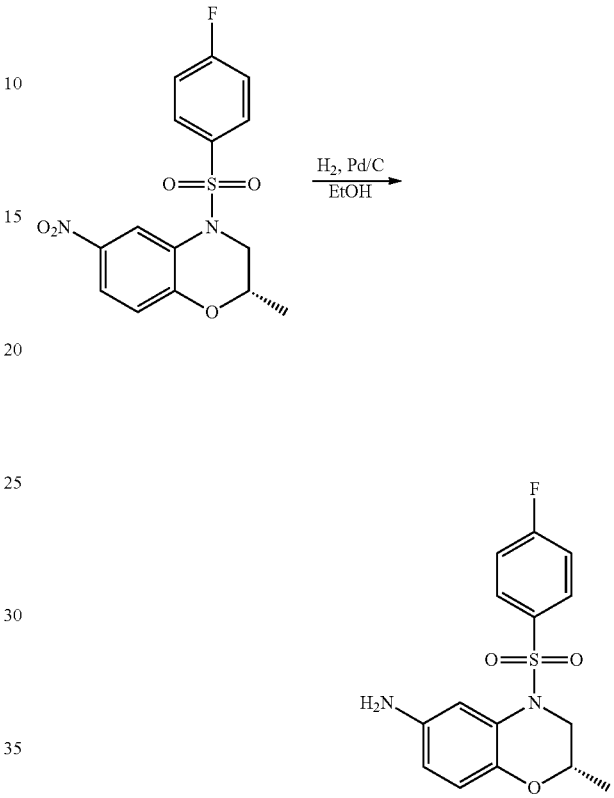

(S)-4-(4-Fluorobenzenesulfonyl)-2-methyl-6-nitro-3,4-dihydro-2Hbenzo[1,4]oxazine (0.32 g, 0.91 mmol) was hydrogenated over 10% Pd/C (30 mg) at 60 psi in ethanol (50 mL) for 1 h. The reaction mixture was filtered and concentrated under reduced pressure to yield the crude product (0.29 g, 99%). LCMS (ESI): calcd. $C_{15}H_{15}FN_2O_3S$, 322.36. found (M+H), 323.

Part III—Synthesis 2-Chloro-6-fluoro-N—[(S)-4-(4-fluorobenzesulfonyl)-2-methyl-3,4-dihydro-2Hbenzo[1,4]oxazine-6-yl]-benzamide

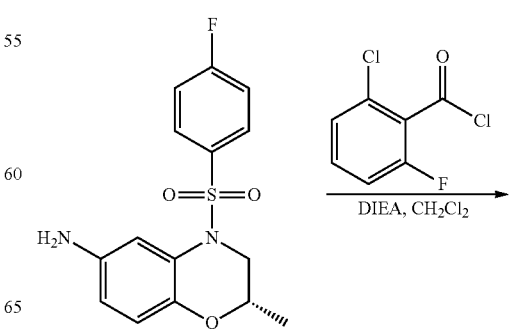

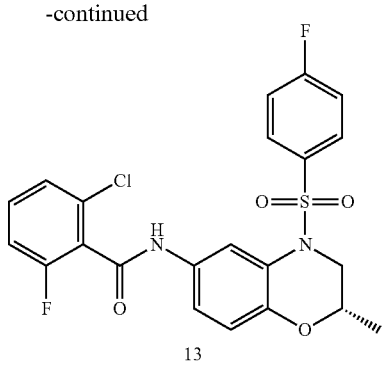

2-Chloro-6-fluorobenzoyl chloride was added to a solution of diisopropylethylamine (0.020 mL, 0.15 mmol) and (S)-4-(4-fluorobenzenesulfonyl)-2-methyl-3,4-dihydro-2H-benzo[1,4]oxazin-6-ylamine (20 mg, 0.062 mmol) in CH$_2$Cl$_2$ (1 mL). The reaction mixture was stirred at room temperature for 3 h, and the crude product was purified by HPLC to afford 2-chloro-6-fluoro-N—[(S)-4-(4-fluorobenzesulfonyl)-2-methyl-3,4-dihydro-2Hbenzo[1,4]oxazine-6-yl]-benzamide. LCMS (ESI): calcd. C$_{22}$H$_{17}$ClF$_2$N$_2$O$_4$S, 478.91. found (M+H), 479.

Example 13

Preparation of 2-Chloro-6-fluoro-N-[4-(4-fluorobenzenesulfonyl-2-methylaminomethyl-3,4-dihydro-2H-benzo[1,4]oxazin-6-yl]benzamide (14)

The title compound was prepared according to the procedures described below.

Part I—Synthesis of 2-[4-(4-Fluorobenzenesulfonyl)-6-nitro-3,4-dihydro-2H-benzo[1,4]oxazine-2-ylmethyl]isoindole-1,3-dione

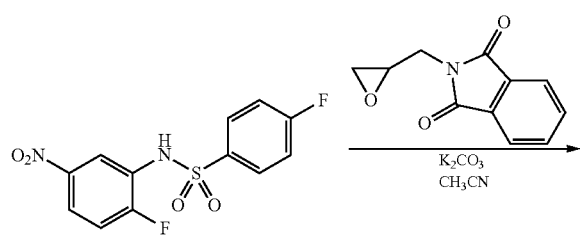

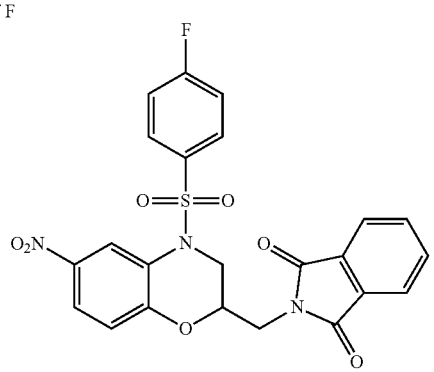

N-(2,3-Epoxypropyl)phthalimide (3.9 g, 19 mmol) was added to a solution of 4-fluoro-N-(2-fluoro-5-nitrophenyl)-benzenesulfonamide (1.99 g, 6.3 mmol) and potassium carbonate (3.5 g, 25 mmol) in CH$_3$CN (12 mL). The reaction mixture was heated in a microwave reactor at 140° C. for 3 h. Then, the reaction mixture was diluted with EtOAc (150 mL) and washed with H$_2$O (1×20 mL) and brine (1×10 mL), dried (MgSO$_4$), and concentrated under reduced pressure to provide the crude product, which was purified by column chromatography (EtOAc/hexanes) to yield 2-[4-(4-fluorobenzenesulfonyl)-6-nitro-3,4-dihydro-2H-benzo[1,4]oxazine-2-ylmethyl]isoindole-1,3-dione (1.30 g, 41%). LCMS (ESI): calcd. C$_{23}$H$_{26}$FN$_3$O$_7$S, 497.46. found (M+H+ DMSO), 577.

Part II—Synthesis of [4-(4-Fluorobenzenesulfonyl)-6-nitro-3,4-dihydro-2H-benzo[1,4]oxazine-2-ylmethyl]-carbamic acid tert-butyl ester

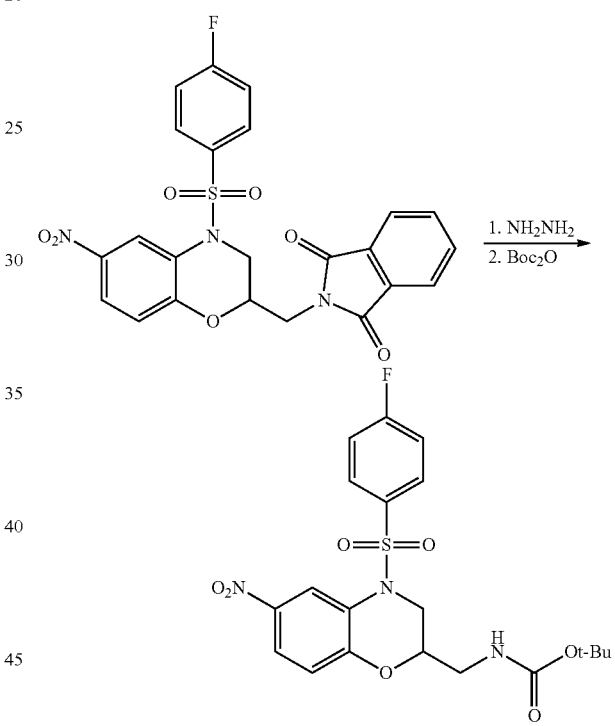

Hydrazine hydrate (0.38 mL, 7.7 mmol) was added to a solution of 2-[4-(4-fluorobenzene-sulfonyl)-6-nitro-3,4-dihydro-2H-benzo[1,4]oxazine-2-ylmethyl]isoindole-1,3-dione (0.775 g, 1.55 mmol) in methanol (20 mL). The reaction mixture was heated at 80° C. for 30 minutes. Then, the reaction mixture was diluted with EtOAc (100 mL) and washed with H$_2$O (1×20 mL) and brine (1×10 mL), dried (MgSO$_4$), and concentrated under reduced pressure to yield the crude amine.

Di-tert-butyl dicarbonate (1.0 g, 4.6 mmol) was added to a solution of the crude amine in CH$_2$Cl$_2$ (50 mL) and the reaction mixture was stirred at room temperature for 1 h. The crude product was purified by column chromatography (EtOAc/hexanes) to give [4-(4-fluorobenzenesulfonyl)-6-nitro-3,4-dihydro-2H-benzo[1,4]oxazine-2-ylmethyl]-carbamic acid tert-butyl ester (0.481 g, 66%). LCMS (ESI): calcd. C$_{20}$H$_{22}$FN$_3$O$_7$S, 467.48. found (M+H), 468.

Part III—Synthesis of [4-(4-Fluorobenzenesulfo-nyl)-6-nitro-3,4-dihydro-2H-benzo[1,4]oxazine-2-ylmethyl]methylcarbamic acid tert-butyl ester

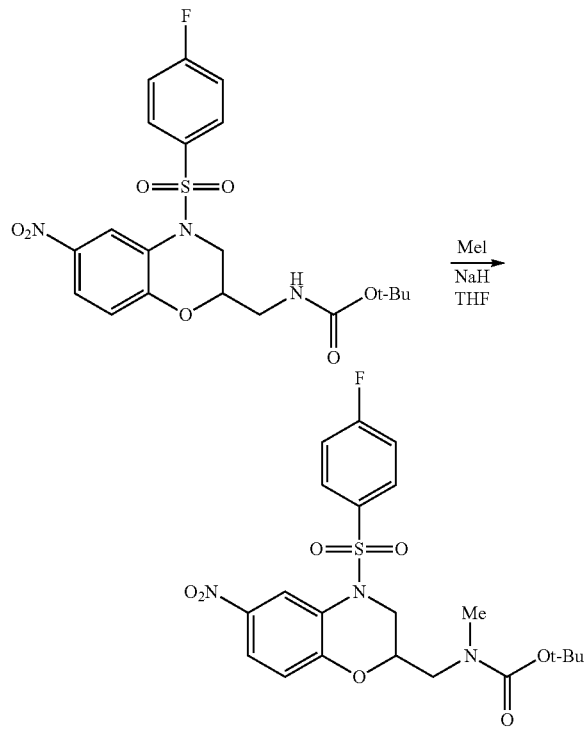

To a solution of [4-(4-fluorobenzenesulfonyl)-6-nitro-3,4-dihydro-2H-benzo[1,4]oxazine-2-ylmethyl]-carbamic acid tert-butyl ester (75 mg, 0.16 mmol) in THF (2 mL) was added methyl iodide (0.05 mL, 0.80 mmol) and sodium hydride (15 mg, 0.38 mmol) in a successive manner. The reaction mixture was stirred at room temperature 1 h. Then, the reaction mixture was diluted with EtOAc (30 mL) and washed with 1M HCl (1×5 mL) and brine (1×5 mL), dried (MgSO$_4$), and concentrated under reduced pressure provide the crude product, which was purified by chromatography (EtOAc/hexanes) to yield [4-4-fluorobenzenesulfonyl)-6-nitro-3,4-dihydro-2H-benzo[1,4]oxazine-2-ylmethyl]methylcarbamic acid tert-butyl ester (52 mg, 66%). LCMS (ESI): calcd. $C_{21}H_{24}FN_3O_7S$, 481.50. found (M+H), 482.

Part IV—Synthesis of 2-Chloro-6-fluoro-N-[4-(4-fluorobenzenesulfonyl)-2-methylaminomethyl-3,4-dihydro-2H-benzo[1,4]oxazin-6-yl]benzamide

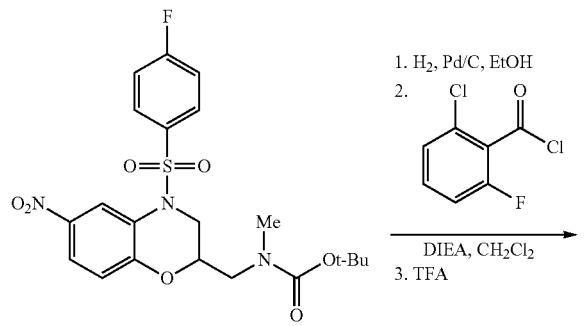

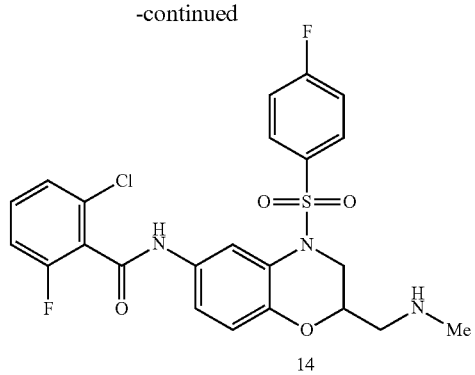

[4-(4-Fluorobenzenesulfonyl)-6-nitro-3,4-dihydro-2H-benzo[1,4]oxazine-2-ylmethyl]methyl-carbamic acid tert-butyl ester (52 mg, 0.11 mmol) was hydrogenated at 60 psi over 10% Pd/C (5 mg) in ethanol (40 mL). The catalyst was removed by filtration and the reaction mixture was concentrated under reduced pressure to yield the crude amine.

To a solution of the crude amine in CH$_2$Cl$_2$ (1 mL) was added 2-chloro-6-fluorobenzoyl chloride (0.02 mL, 0.15 mmol) and DIEA (0.05 mL, 0.17 mmol) and the reaction mixture was stirred at room temperature for 1 h. Then, the reaction mixture was concentrated under reduced pressure to yield the crude amide.

The crude amide was subjected to trifluoroacetic acid (TFA, 2 mL) at room temperature for 1 h and then the crude product was purified by HPLC to afford 2-chloro-6-fluoro-N-[4-(4-fluorobenzenesulfonyl)-2-methylaminomethyl-3,4-dihydro-2H-benzo[1,4]oxazin-6-yl]benzamide. LCMS (ESI): calcd. $C_{23}H_{20}ClF_2N_3O_4S$, 507.95. found (M+H), 509.

Example 14

Preparation of 2-Chloro-N-[2-ethoxymethyl-4-(4-fluoro-benzenesulfonyl)-3,4-dihydro-2H-benzo[1,4]oxazin-6-yl]-6-trifluoromethyl-benzamide (15)

The title compound was prepared according to the procedures described below.

Part I—Synthesis of 2-Ethoxymethyl-4-(4-fluoro-benzenesulfonyl)-6-nitro-3,4-dihydro-2H-benzo[1,4]oxazine

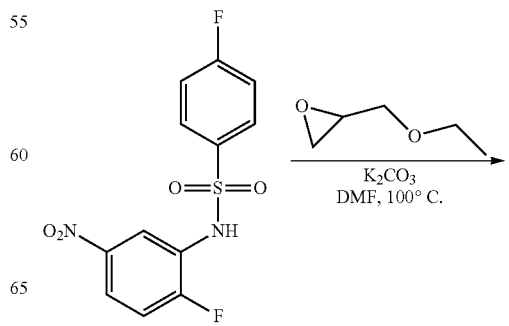

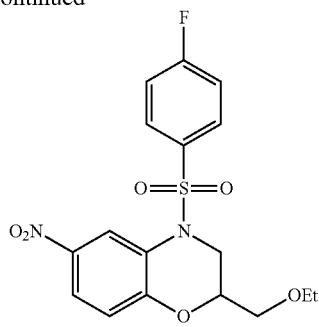

4-Fluoro-N-(2-fluoro-5-nitro-phenyl)-benzenesulfonamide (300 mg, 0.95 mmol), $K_2CO_3$ (265 mg, 1.92 mmol), and ethyl glycidyl ether (105 mg, 1.43 mmol) were suspended in DMF (2 mL) and heated at 100° C. for 16 h. Upon reaction completion, the solution was diluted with EtOAc (10 mL) and $H_2O$ (20 mL). The organic layer was washed with 1M $K_2CO_3$ (10 mL) and brine (5 mL), dried ($MgSO_4$), and concentrated under reduced pressure to yield 2-ethoxymethyl-4-(4-fluoro-benzenesulfonyl)-6-nitro-3,4-dihydro-2H-benzo[1,4]-oxazine (420 mg, 98.9%). LCMS (ESI): calcd. $C_{17}H_{17}FN_2O_6S$, 396. found (M+DMSO+H), 475.

Part II—Synthesis of 2-Ethoxymethyl-4-(4-fluoro-benzenesulfonyl)-3,4-dihydro-2H-benzo[1,4]oxazin-6-ylamine

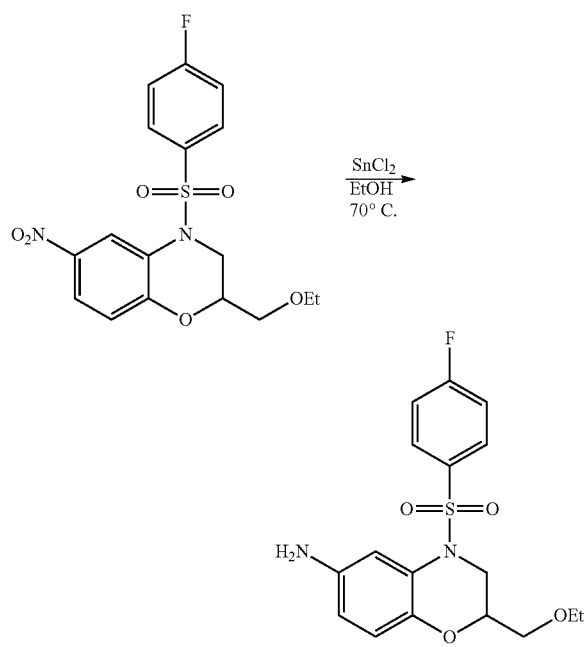

2-Ethoxymethyl-4-(4-fluoro-benzenesulfonyl)-6-nitro-3,4-dihydro-2H-benzo[1,4]oxazine (420 mg, 0.94 mmol) and $SnCl_2 \cdot 2H_2O$ (842 mg, 3.76 mmol) were dissolved in EtOH (10 mL) and heated to 70° C. for 16 h. The reaction mixture was cooled to room temperature and 2 g of celite was added. The resulting suspension was stirred, and saturated $NaHCO_3$ (aq) was added to the vigorously stirring suspension until the pH was basic. Next, the mixture was filtered through celite followed by EtOAc washes. The resulting solution was concentrated under reduced pressure to give 2-ethoxymethyl-4-(4-fluoro-benzenesulfonyl)-3,4-dihydro-2H-benzo[1,4]oxazin-6-ylamine (246 mg, 71.5%). LCMS (ESI): calcd. $C_{17}H_{19}FN_2O_4S$, 366. found (M+H), 367.

Part III—Synthesis of 2-Chloro-N-[2-ethoxymethyl-4-(4-fluoro-benzenesulfonyl)-3,4-dihydro-2H-benzo[1,4]oxazin-6-yl]-6-trifluoromethyl-benzamide

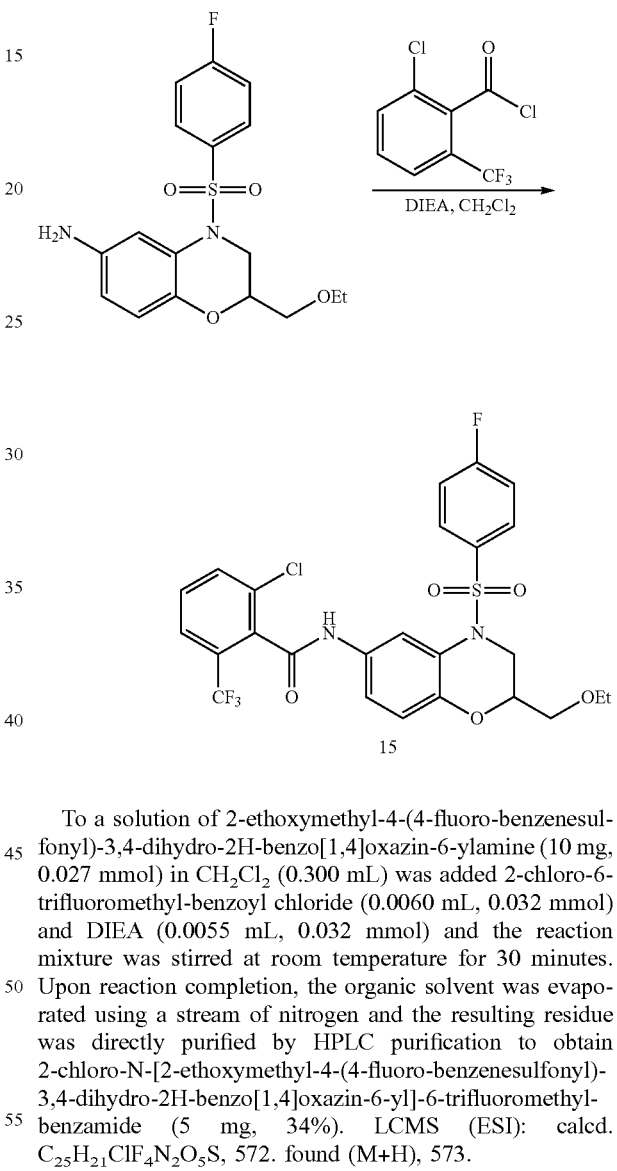

To a solution of 2-ethoxymethyl-4-(4-fluoro-benzenesulfonyl)-3,4-dihydro-2H-benzo[1,4]oxazin-6-ylamine (10 mg, 0.027 mmol) in $CH_2Cl_2$ (0.300 mL) was added 2-chloro-6-trifluoromethyl-benzoyl chloride (0.0060 mL, 0.032 mmol) and DIEA (0.0055 mL, 0.032 mmol) and the reaction mixture was stirred at room temperature for 30 minutes. Upon reaction completion, the organic solvent was evaporated using a stream of nitrogen and the resulting residue was directly purified by HPLC purification to obtain 2-chloro-N-[2-ethoxymethyl-4-(4-fluoro-benzenesulfonyl)-3,4-dihydro-2H-benzo[1,4]oxazin-6-yl]-6-trifluoromethyl-benzamide (5 mg, 34%). LCMS (ESI): calcd. $C_{25}H_{21}ClF_4N_2O_5S$, 572. found (M+H), 573.

Example 15

Preparation of 2-Chloro-6-fluoro-N-(4-((4-fluorophenyl)sulfonyl)-2,2-dimethyl-3,4-dihydro-2H-benzo[b][1,4]oxazin-6-yl)benzamide (16)

The title compound was prepared according to the procedures described below.

Part I—Synthesis of Ethyl 2-(4-bromo-2-nitrophenoxy)-2-methylpropanoate

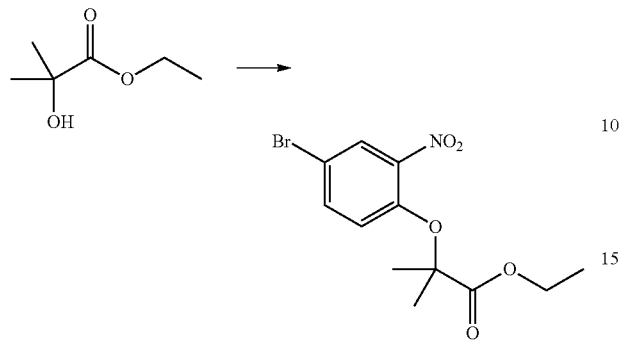

To ethyl 2-hydroxyisobutyrate (2.74 mL, 20.5 mmol) in anhydrous tetrahydrofuran (40 mL) at 0° C. was added 15-crown-5 (54 µL, 0.27 mmol) followed by the portionwise addition of 60% sodium hydride in mineral oil (0.82 g, 20.5 mmol). The reaction mixture was stirred at 0° C. for 10 minutes then a solution of 1-bromo-4-fluoro-3-nitrobenzene (3.0 g, 13.6 mmol) in anhydrous tetrahydrofuran (10 mL) was added. Next, the reaction mixture was stirred at 0° C. for 2 hours, then allowed to warm to ambient temperature. After 1 hour the reaction was quenched with water (100 mL), acidified with 1M hydrogen chloride (25 mL), and extracted with ethyl acetate to provide an organic extract. The organic extract was washed with brine, dried with sodium sulfate, filtered and concentrated in vacuo to provide the crude product, which was purified by column chromatography (eluting with a gradient of 0-20% ethyl acetate in hexanes) to yield the title compound (4.15 g, 92% yield).

Part II—Synthesis of 6-Bromo-2,2-dimethyl-2H-benzo[b][1,4]oxazin-3(4H)-one

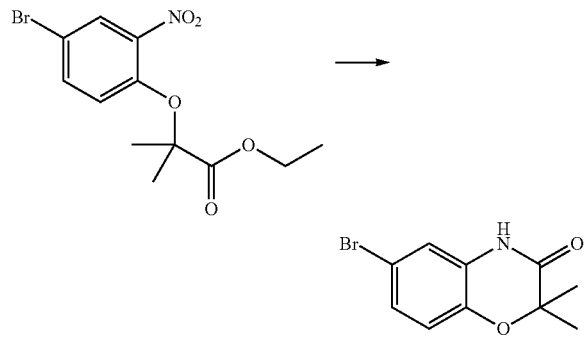

To a solution of ethyl 2-(4-bromo-2-nitrophenoxy)-2-methylpropanoate (4.15 g, 12.5 mmol) in acetic acid (40 mL) was added powdered iron (3.5 g, 62.5 mmol) and the resulting mixture was stirred at 70° C. for 5 hours. Next, the suspension was cooled, and then filtered through celite washing with ethyl acetate. The filtrates were washed with water, saturated sodium bicarbonate, brine, dried with sodium sulfate, and filtered and concentrated in the presence of silica to provide the crude product, which was purified by column chromatography (eluting with a gradient of 2-30% ethyl acetate in hexanes) to provide the title compound. (2.46 g, 77% yield).

Part III—Synthesis of 6-Bromo-2,2-dimethyl-3,4-dihydro-2H-benzo[b][1,4]oxazine

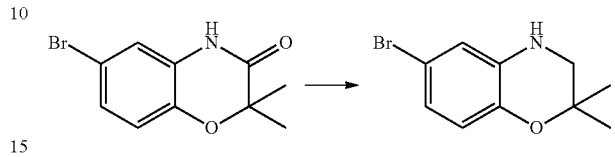

To a solution of 6-bromo-2,2-dimethyl-2H-benzo[b][1,4]oxazin-3(4H)-one (2.46 g, 9.6 mmol) in anhydrous tetrahydrofuran (40 mL) under a nitrogen atmosphere was added a 10M solution of borane dimethyl sulfide complex in tetrahydrofuran (3.8 mL, 38.4 mmol) slowly. The resulting solution was refluxed for 2 hours. Next, the reaction mixture was cooled to ambient temperature and carefully quenched with the addition of methanol (10 mL). The resulting mixture was heated to reflux for 10 minutes, and then the mixture was cooled and concentrated in vacuo to provide the crude product. The crude product was redissolved in ethyl acetate, washed with water, brine, dried with sodium sulfate, filtered and concentrated in vacuo to yield title compound (2.29 g, 98% yield).

Part IV—Synthesis of 6-Bromo-4-((4-fluorophenyl)sulfonyl)-2,2-dimethyl-3,4-dihydro-2H-benzo[b][1,4]oxazine

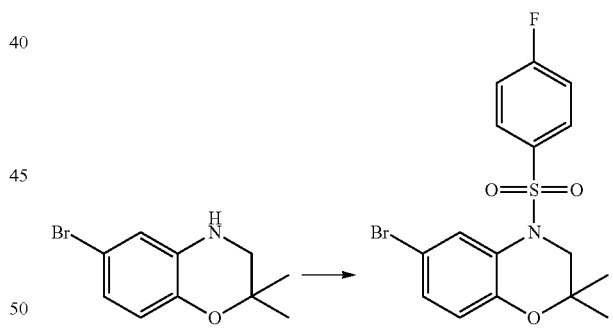

To a solution of 6-bromo-2,2-dimethyl-3,4-dihydro-2H-benzo[b][1,4]oxazine (1.7 g, 7.0 mmol) in dichloromethane (15 mL) was added pyridine (1.14 mL, 14.0 mmol) followed by 4-fluorobenzenesulfonyl chloride (1.64 g, 8.4 mmol). Next, a catalytic amount of 4-(dimethylamino)pyridine (~10 mg) was added to the reaction mixture, and the reaction mixture was stirred at ambient temperature overnight. Then, the reaction mixture was concentrated in vacuo to provide a residue, which was redissolved in ethyl acetate, washed with 1M hydrogen chloride, brine, dried with sodium sulfate, filtered and concentrated in vacuo to provide the crude product. The crude product was purified by column chromatography (eluting with a gradient of 0-30% ethyl acetate in hexanes) to provide the title compound (2.05 g, 73% yield).

Part V—Synthesis of 4-((4-Fluorophenyl)sulfonyl)-2,2-dimethyl-3,4-dihydro-2H-benzo[b][1,4]oxazin-6-amine

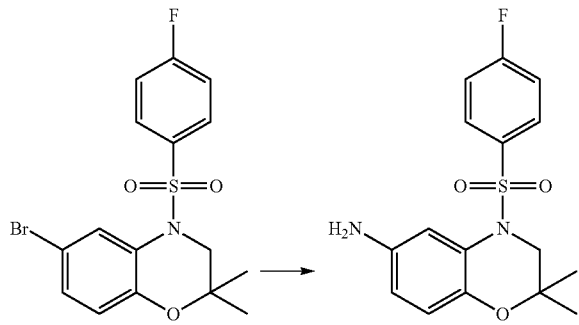 [SMILES: CC1(C)CN(S(=O)(=O)c2ccc(F)cc2)c2cc(Br)ccc2O1 ; CC1(C)CN(S(=O)(=O)c2ccc(F)cc2)c2cc(N)ccc2O1]

A suspension of 6-bromo-4-((4-fluorophenyl)sulfonyl)-2,2-dimethyl-3,4-dihydro-2H-benzo[b][1,4]oxazine (2.05 g, 5.1 mmol), benzophenone imine (1.1 g, 6.2 mmol), cesium carbonate (2.5 g, 7.7 mmol), and 2-dicyclohexylphosphino-2',4',6'-triisopropylbiphenyl (0.12 g, 0.26 mmol) in anhydrous 1,4-dioxane (24 mL) was evacuated under vacuum and refilled with nitrogen three times. To the reaction flask was added tris(dibenzylideneacetone)dipalladium(0) (0.23 g, 0.26 mmol), then the reaction vessel was purged again. Next, the reaction mixture was heated to 110° C. for 4 hours. The reaction mixture was cooled, diluted with ethyl acetate, washed with water, brine, dried with sodium sulfate, filtered and concentrated in vacuo. The resulting mixture was dissolved in tetrahydrofuran (30 mL), 6M hydrogen chloride (15 mL) was added to produce a mixture that was stirred at ambient temperature for 1 hour, then at 50° C. for 1 hour. Next, the mixture mixture was cooled, diluted with ethyl acetate, washed carefully with sat. sodium bicarbonate, brine, dried with sodium sulfate, filtered and concentrated in vacuo to provide the crude product, which was purified by column chromatography (eluting with a gradient of 10-70% ethyl acetate in hexanes) to provide the title compound (0.97 g, 56% yield).

Part VI—Synthesis of 2-Chloro-6-fluoro-N-(4-((4-fluorophenyl)sulfonyl)-2,2-dimethyl-3,4-dihydro-2H-benzo[b][1,4]oxazin-6-yl)benzamide

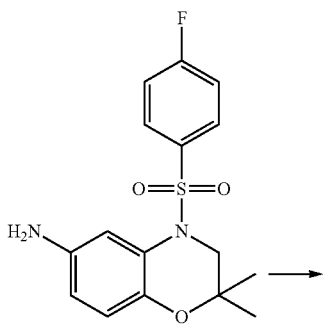

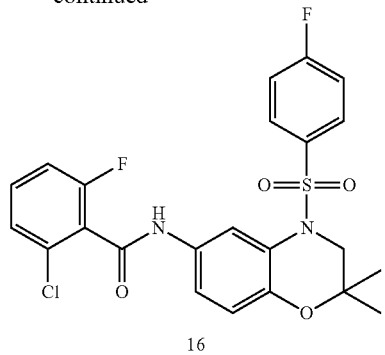

To a solution of 4-((4-fluorophenyl)sulfonyl)-2,2-dimethyl-3,4-dihydro-2H-benzo[b][1,4]oxazin-6-amine (215 mg, 0.64 mmol) in tetrahydrofuran (1 mL) was added N,N-diisopropylethylamine (0.22 mL, 1.3 mmol) followed by the addition of 2-fluoro-6-chlorobenzoyl chloride (0.1 mL, 0.77 mmol). The reaction mixture was shaken at ambient temperature for 1 hour. Then, the reaction mixture was diluted with ethyl acetate, washed with 1M hydrogen chloride, brine, dried with sodium sulfate, filtered and concentrated in vacuo to provide the crude product, which was purified by column chromatography (eluting with a gradient of ethyl acetate in hexanes) to provide the title compound (167 mg, 53% yield). ESI m/z 514.97, 516.94 (M+Na+H). $^1$H NMR (400 MHz, DMSO-$d_6$) δ 10.65 (s, 1H), 8.09 (m, 3H), 7.52 (m, 1H), 7.45 (m, 3H), 7.36 (m, 1H), 7.22 (m, 1H), 6.79 (d, 1H), 3.75 (s, 2H), 1.27 (s, 6H).

Example 16

Preparation of 2-Chloro-6-fluoro-N-(4-((4-fluorophenyl)sulfonyl)-3,4-dihydro-2H-benzo[b][1,4]oxazin-6-yl)benzamide (17)

The title compound was prepared according to the procedures described below.

Part I—Synthesis of Methyl 2-(4-bromo-2-nitrophenoxy)acetate

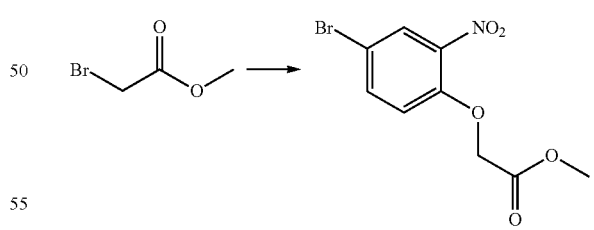

To a flask containing acetone (20 mL) was sequentially added 4-bromo-2-nitrophenol (1 g, 4.6 mmol), potassium carbonate (0.76 g, 5.5 mmol), and methyl bromoacetate (0.47 mL, 5.1 mmol). The resulting mixture was refluxed overnight, and then the mixture was cooled, partitioned between ethyl acetate and water, separated, washed with saturated sodium bicarbonate, brine, dried with sodium sulfate, filtered and concentrated in vacuo to yield title compound. The compound was used in Part II below further without purification. (1.3 g, 100% yield).

Part II—Synthesis of 6-Bromo-2H-benzo[b][1,4]oxazin-3(4H)-one

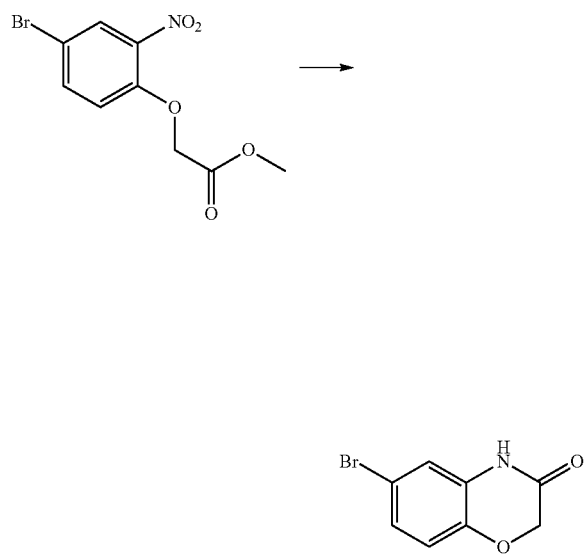

To a solution of methyl 2-(4-bromo-2-nitrophenoxy)acetate (1.3 g, 4.5 mmol) in acetic acid (15 mL) was added powdered iron (1.25 g, 22.4 mmol). The resulting mixture was stirred at 60° C. for 4 hours, then the mixture was cooled. Next, the mixture was filtered through celite, washing with ethyl acetate. The filtrates were washed with water, saturated sodium bicarbonate, brine, dried with sodium sulfate, filtered and concentrated in vacuo to provide the crude product, which was purified by column chromatography (eluting with a gradient of 20-100% ethyl acetate in hexane) to provide the title compound (0.79 g, 77% yield).

Part III—Synthesis of 6-Bromo-3,4-dihydro-2H-benzo[b][1,4]oxazine

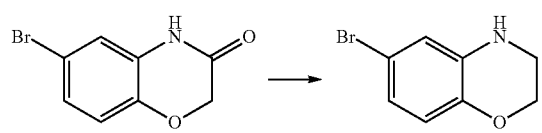 [SMILES: O=C1COc2ccc(Br)cc2N1 ; Brc1ccc2c(c1)NCCO2]

To a solution of 6-bromo-2H-benzo[b][1,4]oxazin-3(4H)-one (400 mg, 1.75 mmol) in anhydrous tetrahydrofuran (3 mL) under a nitrogen atmosphere was added a 1M solution of borane dimethyl sulfide complex in tetrahydrofuran (7.0 mL, 7.0 mmol) slowly. The resulting solution was refluxed for 3 hours. Then, the reaction mixture was cooled to ambient temperature and carefully quenched with the addition of methanol (10 mL). Next, the reaction mixture was heated to reflux for 10 minutes, and then the reaction mixture was cooled and concentrated in vacuo to provide a residue. The residue was redissolved in ethyl acetate, washed with water, brine, dried with sodium sulfate, filtered and concentrated in vacuo to yield title compound. The title compound was used in Part IV below without purification. (350 mg, 93% yield) ESI m/z 214.03, 216.0 (M+H).

Part IV—Synthesis of 6-Bromo-4-((4-fluorophenyl)sulfonyl)-3,4-dihydro-2H-benzo[b][1,4]oxazine

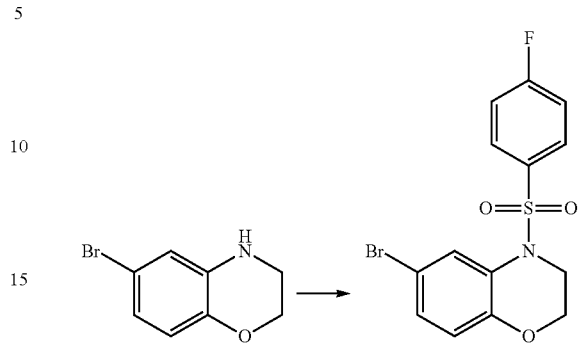

To a solution of 6-bromo-3,4-dihydro-2H-benzo[b][1,4] oxazine (350 mg, 1.6 mmol) in dichloromethane (5 mL) was added pyridine (0.53 mL, 6.5 mmol) followed by 4-fluorobenzenesulfonyl chloride (0.38 g, 2.0 mmol). The reaction mixture was stirred at ambient temperature for 4 hours. Then, the reaction mixture was concentrated in vacuo to provide a residue, which was redissolved in ethyl acetate, washed with 1M hydrogen chloride, brine, dried with sodium sulfate, filtered and concentrated in vacuo to provide the crude product. The crude product was purified by column chromatography (eluting with a gradient of 0-30% ethyl acetate in hexanes) to provide the title compound (0.49 g, 81% yield).

Part V—Synthesis of 4-((4-Fluorophenyl)sulfonyl)-3,4-dihydro-2H-benzo[b][1,4]oxazin-6-amine

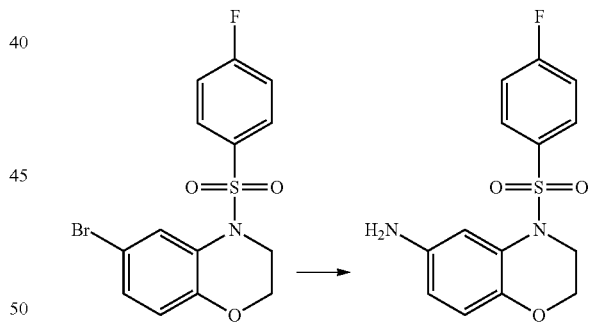

To anhydrous 1,4-dioxane (2 mL) under nitrogen was added 6-bromo-4-((4-fluorophenyl)sulfonyl)-3,4-dihydro-2H-benzo[b][1,4]oxazine (100 mg, 0.27 mmol), benzophenone imine (58 mg, 0.32 mmol), cesium carbonate (131 mg, 0.40 mmol), and 2-dicyclohexylphosphino-2',4',6'-triisopropylbiphenyl (6 mg, 0.01 mmol), followed by tris(dibenzylideneacetone)dipalladium(0) (12 mg, 0.01 mmol). The reaction mixture was heated to 100° C. for 4 hours. Then, the reaction mixture was cooled, diluted with ethyl acetate, washed with water, brine, dried with sodium sulfate, filtered and concentrated in vacuo to provide the crude imine intermediate compound, which was purified by column chromatography (eluting with a gradient of 10-70% ethyl acetate in hexanes) to provide the imine intermediate compound (80 mg) in purified form.

Next, the imine intermediate compound was dissolved in tetrahydrofuran (2 mL), 6M hydrogen chloride (0.14 mL) as added to the mixture of imine intermediate compound and THF. The reaction mixture was stirred at ambient temperature for 1 hour. Then, the reaction mixture was cooled, diluted with ethyl acetate, washed with sat. sodium bicarbonate, brine, dried with sodium sulfate, filtered and concentrated in vacuo to yield title compound (52 mg, 63% yield) ESI m/z 309.00 (M+H).

Part VI—Synthesis of 2-Chloro-6-fluoro-N-(4-((4-fluorophenyl)sulfonyl)-3,4-dihydro-2H-benzo[b][1,4]oxazin-6-yl)benzamide

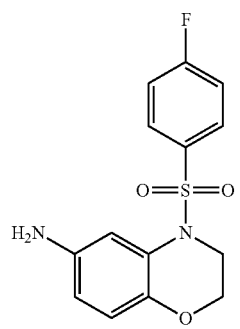

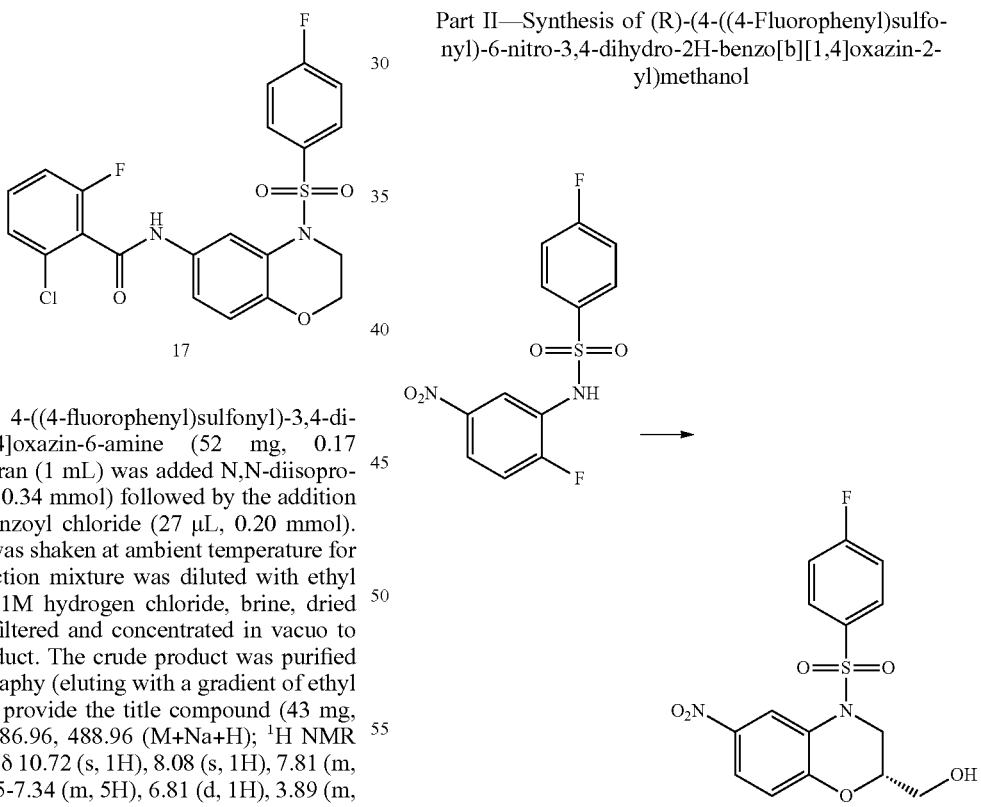

17

To a solution of 4-((4-fluorophenyl)sulfonyl)-3,4-dihydro-2H-benzo[b][1,4]oxazin-6-amine (52 mg, 0.17 mmol) in tetrahydrofuran (1 mL) was added N,N-diisopropylethylamine (59 µL, 0.34 mmol) followed by the addition of 2-fluoro-6-chlorobenzoyl chloride (27 µL, 0.20 mmol). The reaction mixture was shaken at ambient temperature for 1 hour. Then, the reaction mixture was diluted with ethyl acetate, washed with 1M hydrogen chloride, brine, dried with sodium sulfate, filtered and concentrated in vacuo to provide the crude product. The crude product was purified by column chromatography (eluting with a gradient of ethyl acetate in hexanes) to provide the title compound (43 mg, 54% yield) ESI m/z 486.96, 488.96 (M+Na+H); $^1$H NMR (400 MHz, DMSO-d$_6$) δ 10.72 (s, 1H), 8.08 (s, 1H), 7.81 (m, 2H), 7.52 (m, 1H), 7.45-7.34 (m, 5H), 6.81 (d, 1H), 3.89 (m, 2H), 3.77 (m, 2H).

Example 17

Preparation of (R)-2-Chloro-6-fluoro-N-(4-((4-fluorophenyl)sulfonyl)-2-(hydroxymethyl)-3,4-dihydro-2H-benzo[b][1,4]oxazin-6-yl)benzamide (18)

The title compound was prepared according to the procedures described below.

Part I—Synthesis of 4-Fluoro-N-(2-fluoro-5-nitrophenyl)benzenesulfonamide

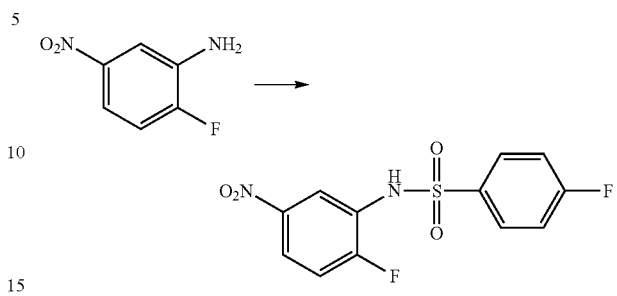

To a solution of 2-fluoro-5-nitroaniline (10 g, 64 mmol) in anhydrous pyridine (50 mL) under a nitrogen atmosphere was added 4-fluorobenzenesulfonyl chloride (13 g, 67 mmol) and the reaction mixture was heated to 60° C. for 4 hours. Next, solvent was mostly removed in vacuo from the reaction mixture, and the resulting solution was diluted with ethyl acetate, washed with water, 1M hydrogen chloride, brine, dried with sodium sulfate, filtered and concentrated in vacuo to yield title compound which was used further without purification (20.1 g, 99% yield).

Part II—Synthesis of (R)-(4-((4-Fluorophenyl)sulfonyl)-6-nitro-3,4-dihydro-2H-benzo[b][1,4]oxazin-2-yl)methanol In three separate microwave tubes was combined 4-fluoro-N-(2-fluoro-5-nitrophenyl)benzenesulfonamide (2 g, 6.3 mmol), potassium carbonate (1.3 g, 9.5 mmol) and (S)-glycidol (3 mL, 15 mmol) in tetrahydrofuran (15 mL). The resulting mixture was heated in a microwave at 140° C. for 2 hours. Next, the three separate, cooled reactions were combined, diluted with ethyl acetate, washed with water, brine, dried with sodium sulfate, filtered and concentrated in

237 vacuo to provide the crude product. The crude product was purified by column chromatograph (eluting with a gradient of 20-80% ethyl acetate in hexanes) to provide the title compound (4.6 g, 65% yield).

Part III—Synthesis of (R)-(6-Amino-4-((4-fluorophenyl)sulfonyl)-3,4-dihydro-2H-benzo[b][1,4]oxazin-2-yl)methanol

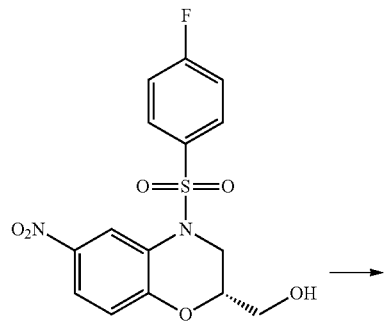

In a three necked flask equipped with a condenser, a suspension of (R)-(4-((4-fluorophenyl)sulfonyl)-6-nitro-3,4-dihydro-2H-benzo[b][1,4]oxazin-2-yl)methanol (4.6 g, 12.5 mmol) and ammonium formate (3.9 g, 62.4 mmol) in methanol (40 mL) and tetrahydrofuran (10 mL) under a nitrogen atmosphere was evacuated under vacuum and refilled with nitrogen three times before adding 10% palladium on carbon (700 mg). The resulting suspension was refluxed for 1 hour then cooled to ambient temperature. Next, the suspension was filtered through celite, and concentrated in vacuo to provide a concentrate. The concentrate was then partitioned between ethyl acetate and brine, dried with sodium sulfate, filtered and concentrated in vacuo to yield the title compound which was used further without purification (4.1 g, 97% yield).

238

Part IV—Synthesis of (R)-2-Chloro-6-fluoro-N-(4-((4-fluorophenyl)sulfonyl)-2-(hydroxymethyl)-3,4-dihydro-2H-benzo[b][1,4]oxazin-6-yl)benzamide

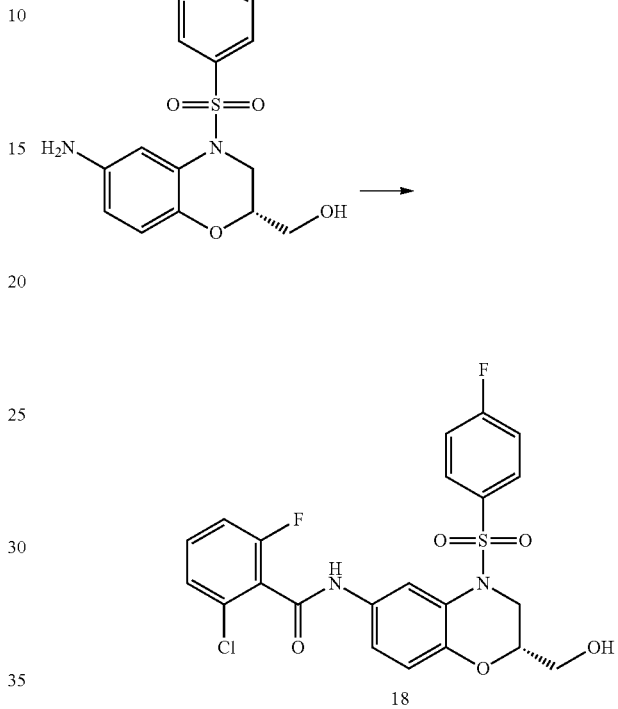

To a solution of (R)-(6-amino-4-((4-fluorophenyl)sulfonyl)-3,4-dihydro-2H-benzo[b][1,4]oxazin-2-yl)methanol (3.9 g, 11.5 mmol) in dichloromethane (40 mL) was added pyridine (0.98 mL, 12.1 mmol), cooled to 0° C., then added 2-chloro-6-fluorobenzoyl chloride (1.5 mL, 11.5 mmol) dropwise. Next, the cooling bath was remove and the reaction mixture was stirred at ambient temperature for 30 minutes. Then, the reaction mixture was concentrated in vacuo to provide a concentrate, which was diluted with ethyl acetate, washed with 1M hydrogen chloride, brine, dried with sodium sulfate, filtered, and concentrated in vacuo to provide the crude product. The crude product was purified by column chromatography (eluting with a gradient of 0.5-3% methanol in dichloromethane) to provide the title compound (5.2 g, 91% yield). ESI m/z 516.97, 518.92 (M+Na+H). $^1$H NMR (400 MHz, DMSO-$d_6$) δ 10.74 (s, 1H), 8.09 (s, 1H), 7.80 (m, 2H), 7.53 (m, 1H), 7.45-7.34 (m, 5H), 6.83 (d, 1H), 5.04 (br m, 1H), 4.3 (m, 1H), 3.55-3.3 (m, 4H).

Example 18

Preparation of (S)-2-Chloro-N-(2-(cyanomethyl)-4-((4-fluorophenyl)sulfonyl)-3,4-dihydro-2H-benzo[b][1,4]oxazin-6-yl)-6-fluorobenzamide (19)

The title compound was prepared according to the procedures described below.

Part I—Synthesis of (R)-(6-(2-Chloro-6-fluorobenzamido)-4-((4-fluorophenyl)sulfonyl)-3,4-dihydro-2H-benzo[b][1,4]oxazin-2-yl)methyl methanesulfonate

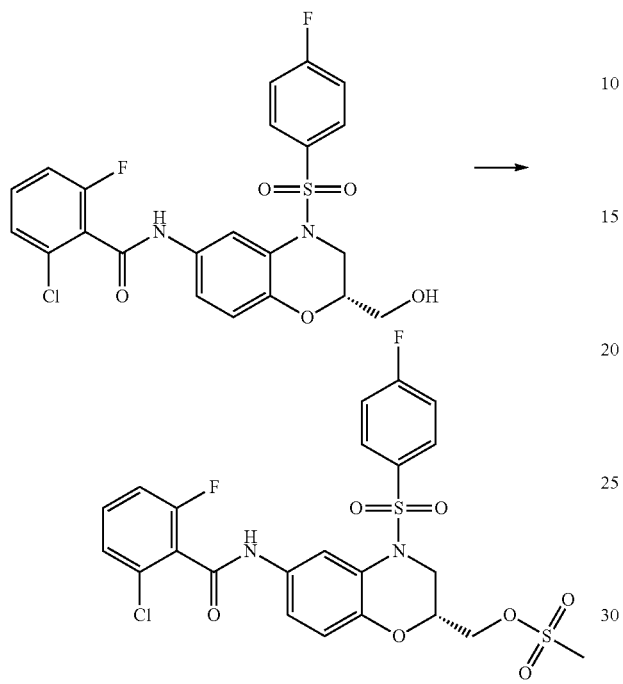

To (R)-2-chloro-6-fluoro-N-(4-((4-fluorophenyl)sulfonyl)-2-(hydroxymethyl)-3,4-dihydro-2H-benzo[b][1,4]oxazin-6-yl)benzamide (300 mg, 0.61 mmol) in dichloromethane (5 mL) at 0° C. was added N,N-diisopropylethylamine (0.21 mL, 1.2 mmol) followed by methanesulfonic anhydride (158 mg, 0.91 mmol). Next, the cooling bath was removed and the reaction mixture was stirred at ambient temperature overnight. Then, the reaction mixture was diluted with ethyl acetate, washed with 1M hydrogen chloride, brine, dried with sodium sulfate, filtered and concentrated in vacuo to yield title compound, which was used in the next reaction without further purification (360 mg, quant. yield).

Part II—Synthesis of (S)-2-Chloro-N-(2-(cyanomethyl)-4-((4-fluorophenyl)sulfonyl)-3,4-dihydro-2H-benzo[b][1,4]oxazin-6-yl)-6-fluorobenzamide

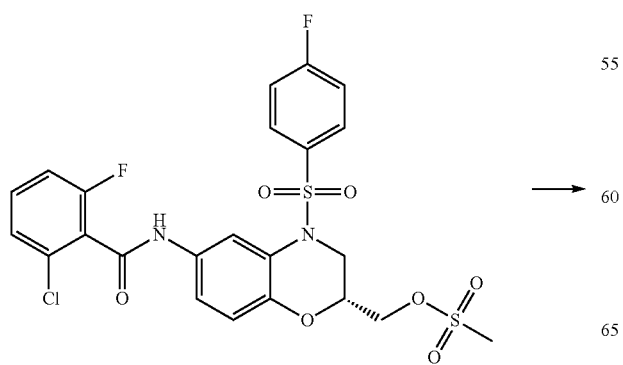

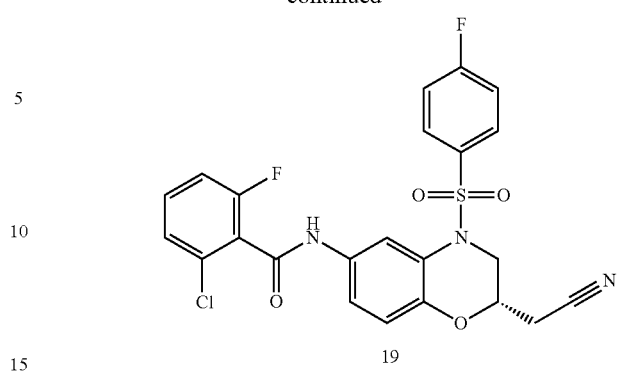

To (R)-(6-(2-chloro-6-fluorobenzamido)-4-((4-fluorophenyl)sulfonyl)-3,4-dihydro-2H-benzo[b][1,4]oxazin-2-yl) methyl methanesulfonate (50 mg, 0.09 mmol) in N,N-dimethylformamide (0.5 mL) was added potassium cyanide (11 mg, 0.17 mmol). The resulting mixture was shaken at 50° C. overnight. Then, the reaction mixture was purified by preparatory HPLC to yield the title compound (10 mg, 23% yield).

Example 19

Preparation of (R)-2-Chloro-N-(4-((3-cyanophenyl)sulfonyl)-2-(hydroxymethyl)-3,4-dihydro-2H-benzo[b][1,4]oxazin-6-yl)-6-fluorobenzamide (20)

The title compound was prepared according to the procedures described below.

Part I—Synthesis of 3-Cyano-N-(2-fluoro-5-nitrophenyl)benzenesulfonamide

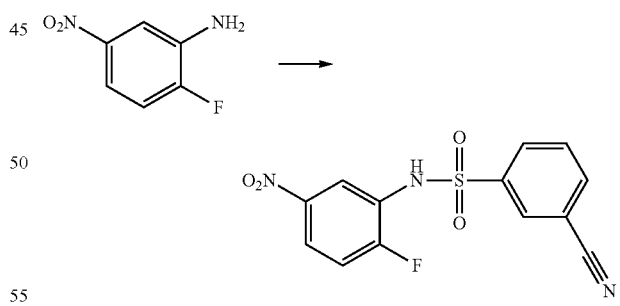

To a solution of 2-fluoro-5-nitroaniline (4 g, 25.6 mmol) in anhydrous pyridine (25 mL) under a nitrogen atmosphere was added 3-cyanobenzenesulfonyl chloride (5.7 g, 28.2 mmol). The resulting mixture was heated to 60° C. for 4 hours. Then, the solvent was mostly removed in vacuo, the resulting oil was diluted with ethyl acetate, washed with water, 1M hydrogen chloride, brine, dried with sodium sulfate, filtered and concentrated in vacuo to yield title compound which was used further without purification (7.16 g, 87% yield).

Part II—Synthesis of (R)-3-((2-(Hydroxymethyl)-6-nitro-2H-benzo[b][1,4]oxazin-4(3H)-yl)sulfonyl)benzonitrile

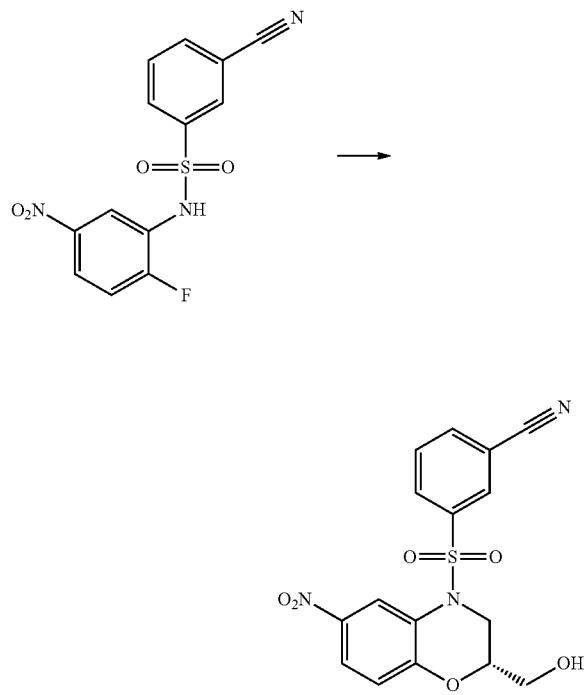 [SMILES: N#Cc1cccc(S(=O)(=O)Nc2cc([N+](=O)[O-])ccc2F)c1 ; N#Cc1cccc(S(=O)(=O)N2C[C@H](CO)Oc3ccc([N+](=O)[O-])cc32)c1]

In two separate microwave tubes was combined 3-cyano-N-(2-fluoro-5-nitrophenyl)benzenesulfonamide (2 g, 6.2 mmol), potassium carbonate (1.7 g, 12.5 mmol) and (S)-glycidol (1.24 mL, 18.5 mmol) in acetonitrile (8 mL). The reaction mixture was heated in a microwave at 140° C. for 40 minutes. Then, the two separate, cooled reactions were combined, diluted with ethyl acetate, washed with water, brine, dried with sodium sulfate, filtered and concentrated in vacuo to provide the crude product. The crude product was purified by column chromatography (eluting with a gradient of 30-100% ethyl acetate in hexanes) to provide title compound (1.2 g, 26% yield).

Part III—Synthesis of (R)-3-((6-Amino-2-(hydroxymethyl)-2H-benzo[b][1,4]oxazin-4(3H)-yl)sulfonyl)benzonitrile

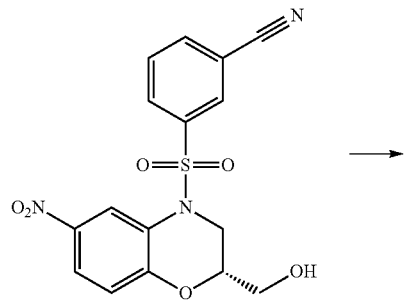

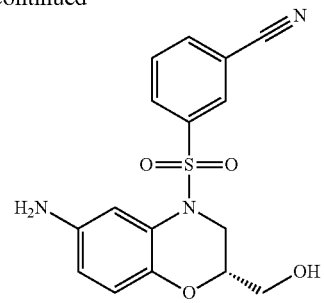

In a three-necked flask equipped with a condenser, a suspension of (R)-3-((2-(hydroxymethyl)-6-nitro-2H-benzo[b][1,4]oxazin-4(3H)-yl)sulfonyl)benzonitrile (440 mg, 1.2 mmol) and ammonium formate (370 mg, 5.9 mmol) in methanol (15 mL) under a nitrogen atmosphere was evacuated under vacuum and refilled with nitrogen three times before adding 10% palladium on carbon (120 mg). The resulting suspension was heated to reflux for 3 hours, and then cooled to ambient temperature. Next, the suspension was filtered through celite, then concentrated in vacuo to provide a concentrate. The concentrate was partitioned between ethyl acetate and brine, dried with sodium sulfate, filtered and concentrated in vacuo to yield title compound which was used further without purification (320 mg, 79% yield).

Part IV—Synthesis of (R)-2-Chloro-N-(4-((3-cyanophenyl)sulfonyl)-2-(hydroxymethyl)-3,4-dihydro-2H-benzo[b][1,4]oxazin-6-yl)-6-fluorobenzamide

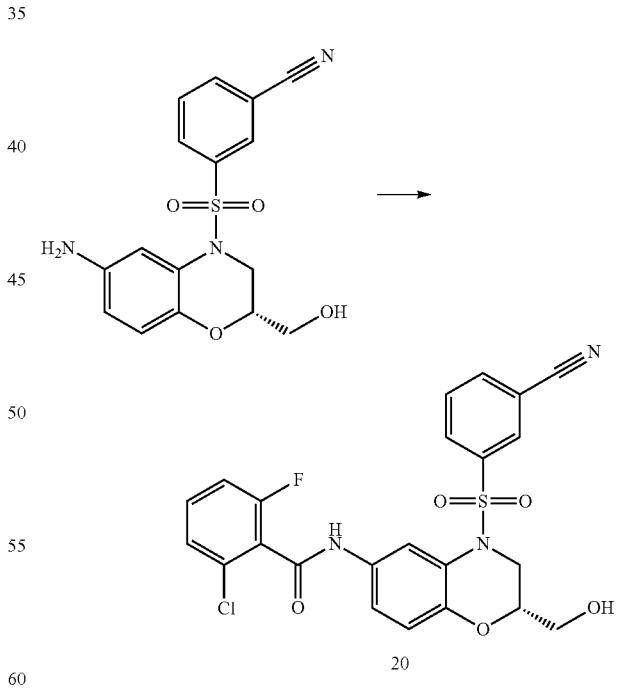

To (R)-3-((6-amino-2-(hydroxymethyl)-2H-benzo[b][1,4]oxazin-4(3H)-yl)sulfonyl)benzonitrile (550 mg, 1.6 mmol) in tetrahydrofuran (10 mL) was added N,N-diisopropylethylamine (0.28 mL, 1.6 mmol) followed by 2-chloro-6-fluorobenzoyl chloride (0.21 mL, 1.6 mmol). The reaction mixture was stirred at ambient temperature for 1 hour. Then, the reaction mixture was diluted with ethyl acetate, washed with 1M hydrogen chloride, brine, dried with sodium sulfate, filtered and concentrated in vacuo to provide the crude product. The crude product was purified twice by column chromatography (eluting with a gradient of ethyl acetate in hexanes) to provide the title compound (305 mg, 38% yield). ESI m/z 523.81, 525.81 (M+Na+H). $^1$H NMR (400 MHz, DMSO-$d_6$) δ 10.73 (s, 1H), 8.30 (s, 1H), 8.16 (m, 1H), 8.11 (s, 1H), 8.04 (m, 1H), 7.78 (m, 1H), 7.52 (m, 1H), 7.43 (m, 1H), 7.36 (m, 2H), 6.84 (d, 1H), 5.05 (m, 1H), 4.34 (m, 1H), 3.6-3.4 (m, 4H).

Example 20

Preparation of (S)-2-Chloro-N-(4-((3-cyanophenyl)sulfonyl)-2-(pyrrolidin-1-ylmethyl)-3,4-dihydro-2H-benzo[b][1,4]oxazin-6-yl)-6-fluorobenzamide (21)

The title compound was prepared according to the procedures described below.

Part 1—Synthesis of (R)-(6-(2-Chloro-6-fluorobenzamido)-4-((3-cyanophenyl)sulfonyl)-3,4-dihydro-2H-benzo[b][1,4]oxazin-2-yl)methyl methanesulfonate

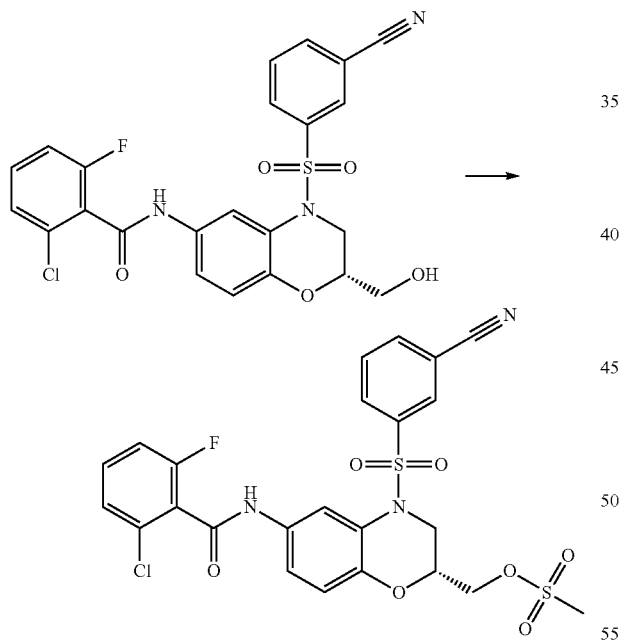

To (R)-2-chloro-N-(4-((3-cyanophenyl)sulfonyl)-2-(hydroxymethyl)-3,4-dihydro-2H-benzo[b][1,4]oxazin-6-yl)-6-fluorobenzamide (100 mg, 0.2 mmol) in dichloromethane (2 mL) was added N,N-diisopropylethylamine (52 μL, 0.3 mmol) followed by methanesulfonic anhydride (52 mg, 0.3 mmol). The reaction mixture was stirred reaction at ambient temperature for 2 hours, then diluted with ethyl acetate, washed with 1M hydrogen chloride, brine, dried with sodium sulfate, filtered and concentrated in vacuo to yield title compound as a crude mixture. (115 mg, 99% yield).

Part II—Synthesis of (S)-2-Chloro-N-(4-((3-cyanophenyl)sulfonyl)-2-(pyrrolidin-1-ylmethyl)-3,4-dihydro-2H-benzo[b][1,4]oxazin-6-yl)-6-fluorobenzamide

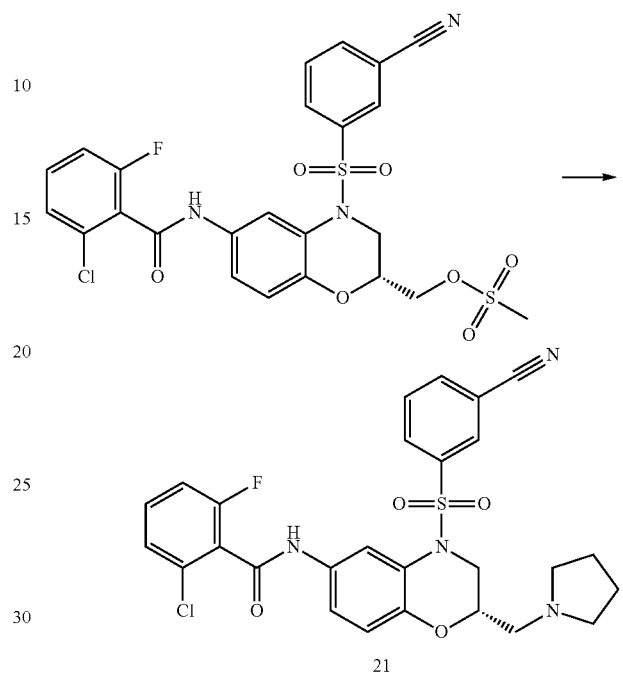

21

To (R)-(6-(2-chloro-6-fluorobenzamido)-4-((3-cyanophenyl)sulfonyl)-3,4-dihydro-2H-benzo[b][1,4]oxazin-2-yl) methyl methanesulfonate (58 mg, 0.1 mmol) in N,N-dimethylformamide (1 mL) was added pyrrolidine (30 μL, 0.36 mmol). The reaction mixture was stirred at ambient temperature for 1 hour, then the reaction mixture was stirred at 60° C. for 1 hour. Analytical analysis indicated that a majority of the starting material remained Therefore, the reaction mixture was stirred at 100° C. for 18 hours. Next, the reaction mixture was concentrated in vacuo to provide the crude product, which was purified by preparatory HPLC to yield the title compound (10 mg, 18% yield). ESI m/z 554.93, 556.9 (M+H).

Example 21

Preparation of (R)-2-Chloro-6-fluoro-N-(2-(fluoromethyl)-4-((4-fluorophenyl)sulfonyl)-3,4-dihydro-2H-benzo[b][1,4]oxazin-6-yl)benzamide (22)

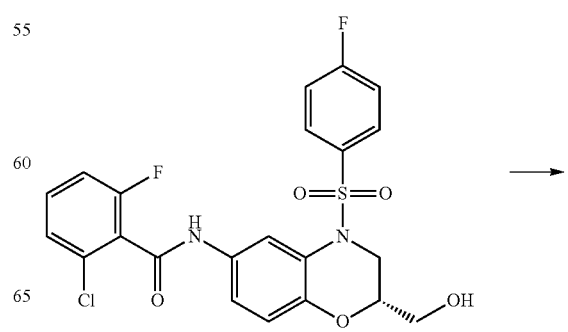

-continued

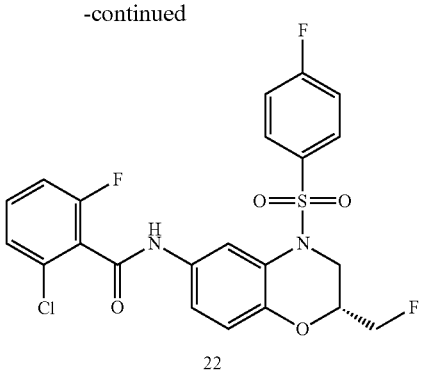

22

To (R)-2-chloro-6-fluoro-N-(4-((4-fluorophenyl)sulfonyl)-2-(hydroxymethyl)-3,4-dihydro-2H-benzo[b][1,4]oxazin-6-yl)benzamide (60 mg, 0.12 mmol) in anhydrous dichloromethane (2 mL) under a nitrogen atmosphere at 0° C. was added bis-(2-methoxyethyl)aminosulfur trifluoride (0.02 mL, 0.12 mmol). Then, the cooling bath was removed and the reaction mixture was stirred at ambient temperature for 1 hour. Next, the reaction mixture was diluted with dichloromethane, washed with brine, dried with sodium sulfate, filtered and concentrated in vacuo to provide the crude product. The crude product was purified by column chromatography (eluting with a gradient of ethyl acetate in hexanes) to provide the title compound (16 mg, 27% yield). ESI m/z 518.79, 520.80 (M+Na+H). $^1$H NMR (400 MHz, DMSO-$d_6$) δ 10.76 (s, 1H), 8.11 (s, 1H), 7.85 (m, 2H), 7.53 (m, 1H), 7.46-7.35 (m, 5H), 6.88 (d, 1H), 4.68 (m, 1H), 4.57 (m, 1H), 4.4 (m, 1H), 3.38 (m, 2H).

Example 22

Preparation of 2-Chloro-6-fluoro-N-[4-(4-fluorobenzenesulfonyl)-3-hydroxymethyl-3,4-dihydro-2H-benzo[1,5]oxazin-6-yl]benzamide (23)

The title compound was prepared according to the procedures described below.

Part I—Synthesis of N-2-(Allyloxy-5-nitrophenyl)-4-fluorobenzensulfonamide

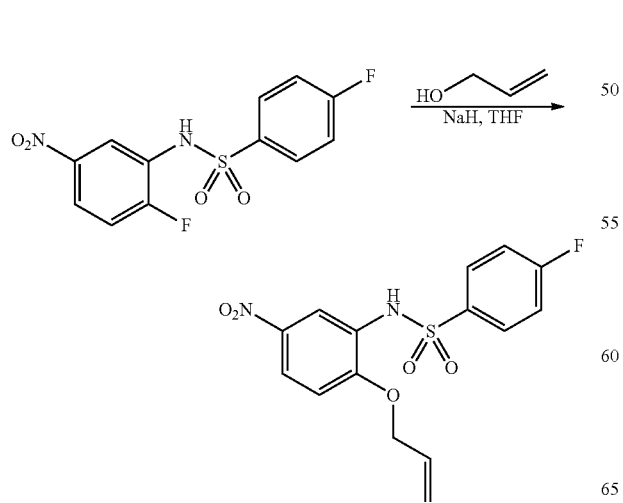

Sodium hydride (0.26 g, 6.6 mmol) was added to allyl alcohol (0.45 mL, 6.6 mmol) in THF (5 mL) and stirred for 3 minutes. 4-Fluoro-N-(2-fluoro-5-nitrophenyl)-benzenesulfonamide (0.42 g, 1.3 mmol) was added and the reaction mixture was stirred for 3 hours. The reaction was quenched by adding 1M HCl (10 mL), and then the resulting mixture was extracted with EtOAc (2×50 mL). The organic extracts were washed with brine (1×10 mL), dried (MgSO$_4$), and concentrated to provide the crude product, which was purified by chromatography (SiO$_2$, eluent EtOAc/hexanes) to provide the title compound. Yield=76 mg (16%). $^1$H NMR 250 MHz CDCl$_3$ δ 8.39 (d, 1H, J=3.0 Hz), 7.93 (dd, 1H, J=2.75, 9.0 Hz), 7.0-7.86 (m, 2H), 7.07-7.14 (m, 2H), 6.82 (d, 1H, J=9.0 Hz), 5.80-5.92 (m, 1H), 5.22-5.34 (m, 2H), 4.52-4.55 (m, 2H).

Part II—Synthesis of 4-Fluoro-N-(5-nitro-2-oxiranylmethoxyphenyl)-benzenesulfonamide

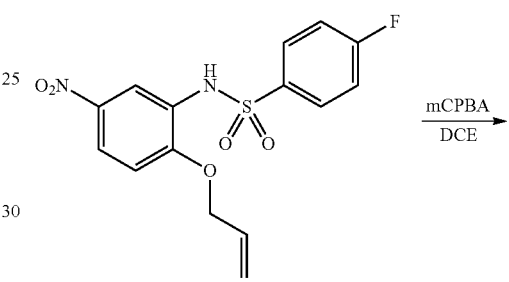

meta-Chloroperoxybenzoic acid (mCPBA; 83 mg, 0.34 mmol) was added to a solution of N-2-(allyloxy-5-nitrophenyl)-4-fluorobenzensulfonamide (76 mg, 0.22 mmol) in dichloroethane (DCE; 2 mL) and heated at reflux for 30 min. Then, the reaction mixture was diluted with diethyl ether (40 mL) and washed with Na$_2$S$_2$O$_4$ (10 mL), Na$_2$CO$_3$ (3×10 mL), and brine (10 mL) and concentrated to provide the title compound. Yield=78 mg (97%). LCMS (ESI): calc. C$_{15}$H$_{13}$FN$_2$O$_6$S=368.34; obs. M+H=369.

Part III—Synthesis of [4-(4-Fluorobenzenesulfonyl)-6-nitro-3,4-dihydro-2H-benzo[1,4]oxazin-3-yl]methanol

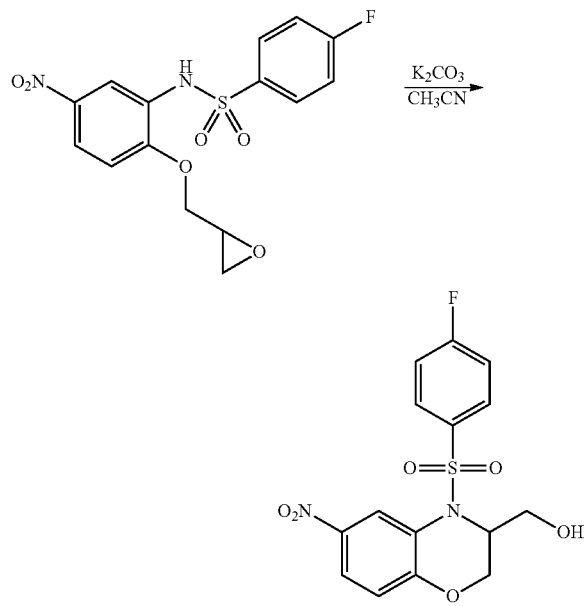

K₂CO₃ (100 mg, 0.74 mmol) was added to 4-fluoro-N-(5-nitro-2-oxiranylmethoxyphenyl)-benzenesulfonamide (70 mg, 0.19 mmol) in CH₃CN (1.5 mL). The reaction mixture was heated at 140° C. by microwave irradiation for 40 min. Then, the reaction mixture was diluted with EtOAc (50 mL) and washed with water (1×10 mL) and brine (1×10 mL), dried (MgSO₄), and concentrated to provide the title compound. Yield=47 mg (70%). ¹H NMR 250 MHz CDCl₃ δ 8.81 (d, 1H, J=2.75 Hz), 7.98 (dd, 1H, J=2.5, 9.0 Hz), 7.70-7.76 (m, 1H), 7.16-7.22 (m, 2H), 6.94 (d, 1H, J=9.0 Hz), 4.35-4.50 (m, 1H), 4.39 (dd, 1H, J=1.5, 11.5 Hz), 3.65-3.73 (m, 1H), 3.53 (dd, 1H, J=7.75 Hz, 11.25 Hz), 3.36 (dd, 1H, J=3.0, 11.25 Hz).

Part IV—Synthesis of [6-Amino-4-(4-fluorobenzenesulfonyl)-3,4-dihydro-2H-benzo[1,4]oxazin-3-yl]methanol

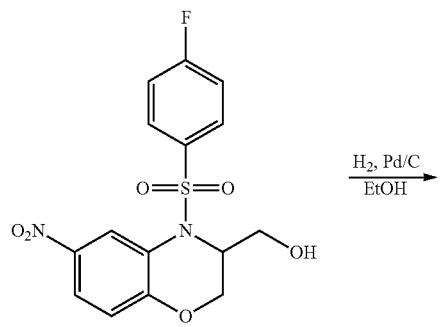

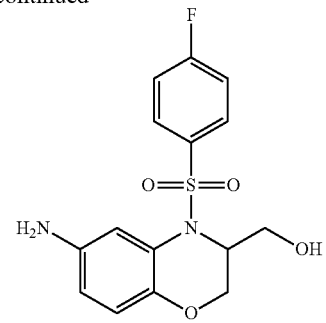

[4-(4-Fluorobenzenesulfonyl)-6-nitro-3,4-dihydro-2H-benzo[1,4]oxazin-3-yl]methanol (47 mg, 0.13 mmol) was hydrogenated at 60 psi over 10% Pd/C (5 mg) in ethanol (30 mL) for 45 min. Then, the reaction mixture was filtered and concentrated to provide the title compound. Yield=24 mg (55%). ¹H NMR 250 MHz CDCl₃ 7.63-7.18 (m, 2H), 7.30 (d, 1H, J=2.75 Hz), 7.09-7.16 (m, 2H), 6.62 (d, 1H, J=8.75), 6.67 (dd, 1H, J=2.75, 8.75 Hz), 4.30-4.37 (m, 1H), 4.01-4.16 (m, 1H), 3.46-3.73 (m, 2H), 3.12 (dd, 1H, J=3.25, 11.5 Hz).

Part V—Synthesis of 2-Chloro-6-fluoro-N-[4-(4-fluorobenzenesulfonyl)-3-hydroxymethyl-3,4-dihydro-2H-benzo[1,5]oxazin-6-yl]benzamide

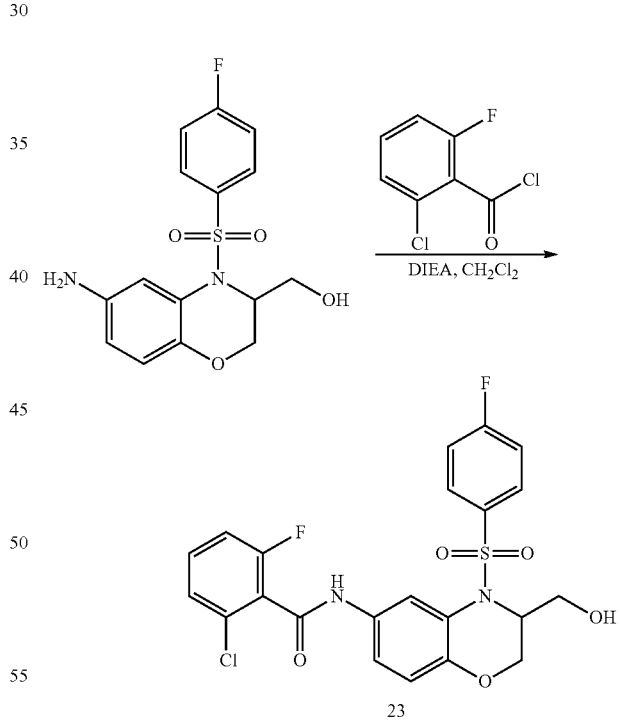

2-Chloro-6-fluorobenzenesulfonyl chloride (0.02 mL, 0.15 mmol) and diisopropylethylamine (DIEA; 0.05 mL, 0.17 mmol) were added to [6-amino-4-(4-fluorobenzenesulfonyl)-3,4-dihydro-2H-benzo[1,4]oxazin-3-yl]methanol (24 mg, 0.071 mmol) in CH₂Cl₂ (1 mL). Then, the reaction mixture was stirred at room temperature for 1 hr and then concentrated to provide the crude product, which was purified by HPLC to provide the title compound. LCMS (ESI): calc. C₂₂H₁₇ClF₂N₂O₅S=494.90; obs. M+H=495.

Example 23

Preparation of Additional Benzoxazine Compounds

The compounds in Table 6 below were prepared based on the experimental procedures described in Examples 11-22 and in the detailed description. Starting materials can be obtained from commercial sources or readily prepared from commercially available materials.

TABLE 6

| Compound No. | Chemical Structure |
|---|---|
| VI-1 | (structure) |
| VI-2 | (structure) |
| VI-3 | (structure) |
| VI-4 | (structure) |
| VI-5 | (structure) |
| VI-6 | (structure) |
| VI-7 | (structure) |
| VI-8 | (structure) |

TABLE 6-continued
| Compound No. | Chemical Structure |
|---|---|
| VI-9 | 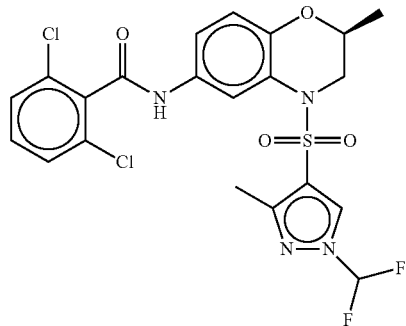 |
| VI-10 | 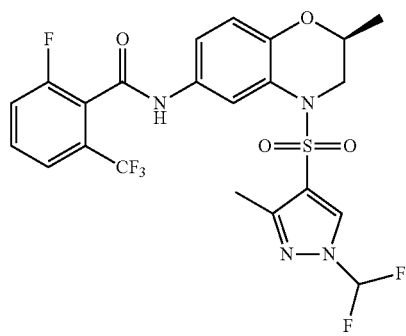 [SMILES: Cc1nn(C(F)F)cc1S(=O)(=O)N1C[C@H](C)Oc2ccc(NC(=O)c3c(F)cccc3C(F)(F)F)cc21] |
| VI-11 | 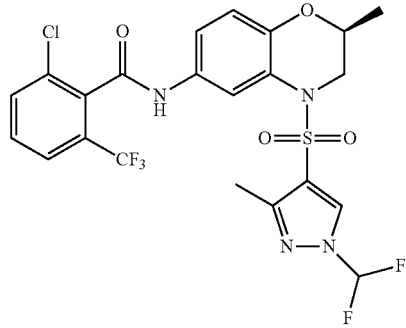 [SMILES: Cc1nn(C(F)F)cc1S(=O)(=O)N1C[C@H](C)Oc2ccc(NC(=O)c3c(Cl)cccc3C(F)(F)F)cc21] |
| VI-12 | 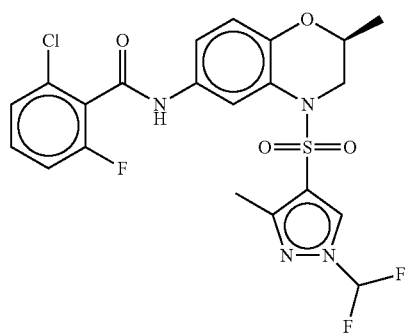 |
| VI-13 | 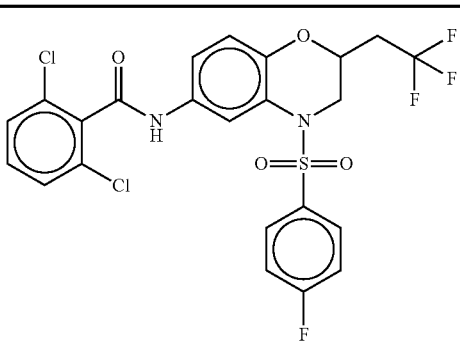 |
| VI-14 | 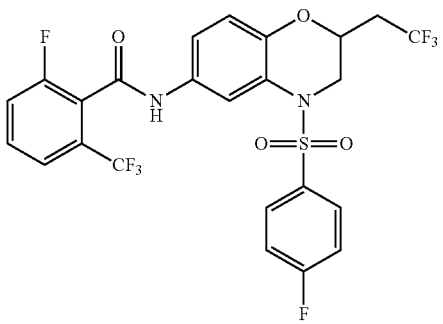 [SMILES: O=C(Nc1ccc2c(c1)N(S(=O)(=O)c1ccc(F)cc1)CC(CC(F)(F)F)O2)c1c(F)cccc1C(F)(F)F] |
| VI-15 | 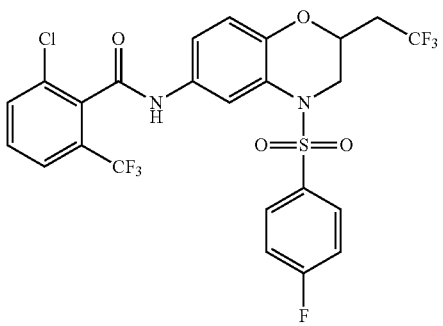 [SMILES: O=C(Nc1ccc2c(c1)N(S(=O)(=O)c1ccc(F)cc1)CC(CC(F)(F)F)O2)c1c(Cl)cccc1C(F)(F)F] |
| VI-16 | 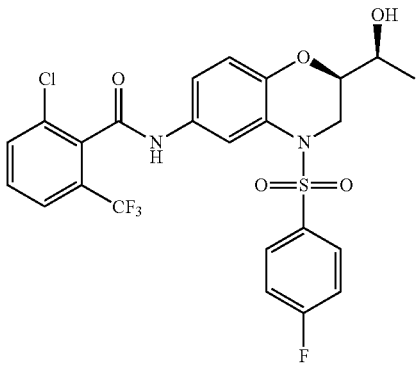 [SMILES: C[C@H](O)[C@H]1CN(S(=O)(=O)c2ccc(F)cc2)c2cc(NC(=O)c3c(Cl)cccc3C(F)(F)F)ccc2O1] |

TABLE 6-continued
| Compound No. | Chemical Structure |
|---|---|
| VI-17 | 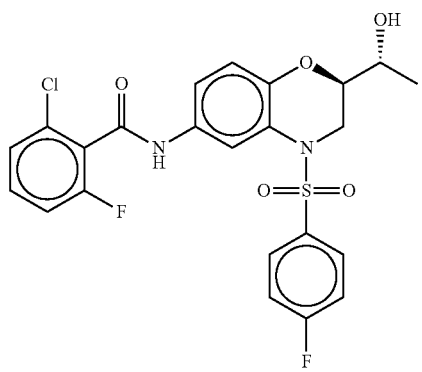 |
| VI-18 | 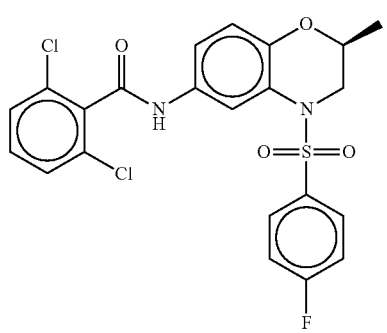 |
| VI-19 | 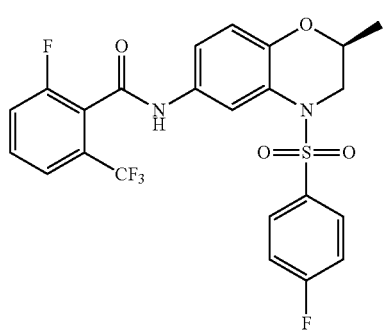 [SMILES: C[C@H]1CN(S(=O)(=O)c2ccc(F)cc2)c2cc(NC(=O)c3c(F)cccc3C(F)(F)F)ccc2O1] |
| VI-20 | 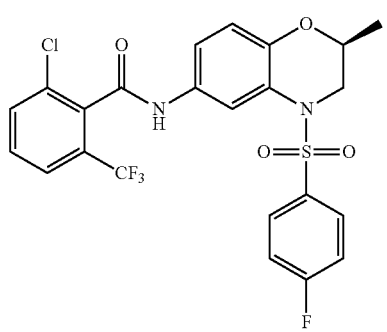 [SMILES: C[C@H]1CN(S(=O)(=O)c2ccc(F)cc2)c2cc(NC(=O)c3c(Cl)cccc3C(F)(F)F)ccc2O1] |
| VI-21 | 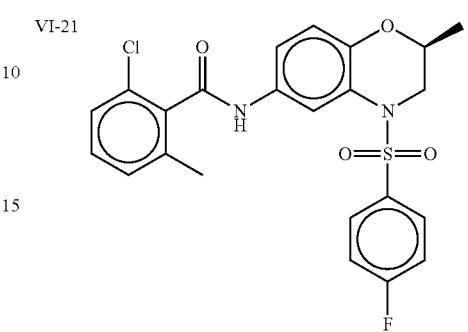 |
| VI-22 | 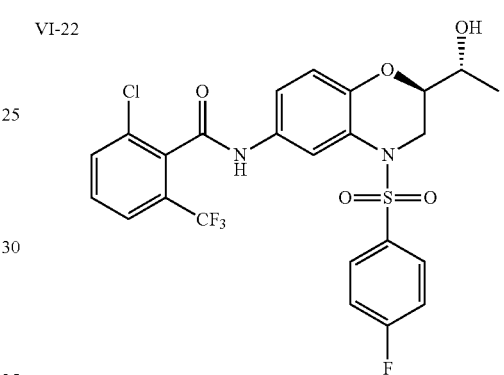 |
| VI-23 | 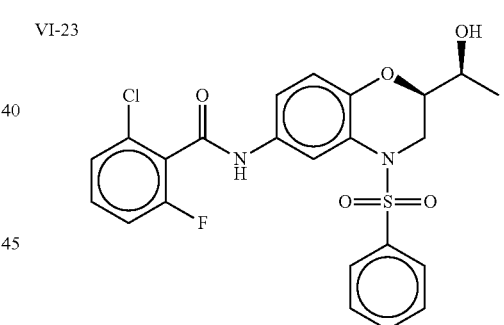 |
| VI-24 | 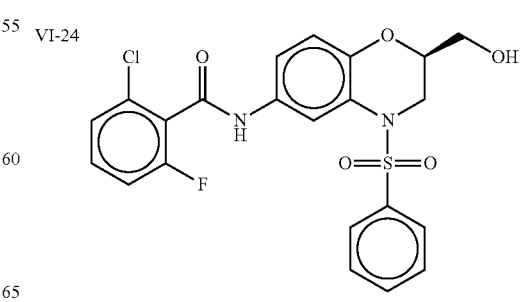 |

TABLE 6-continued
| Compound No. | Chemical Structure |
|---|---|
| VI-25 | 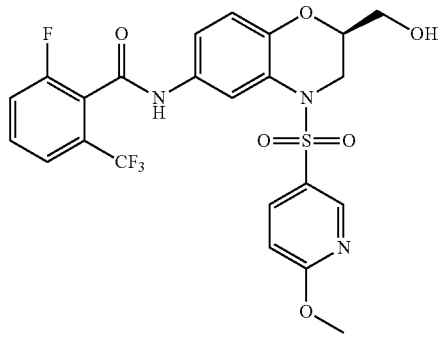 [SMILES: COc1ccc(S(=O)(=O)N2C[C@H](CO)Oc3ccc(NC(=O)c4c(F)cccc4C(F)(F)F)cc32)cn1] |
| VI-26 | 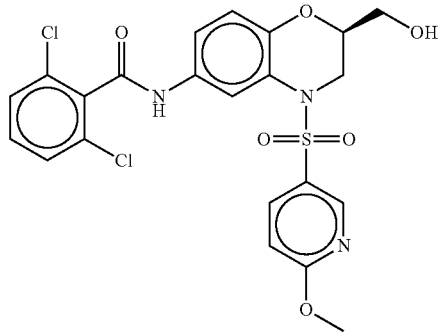 |
| VI-27 | 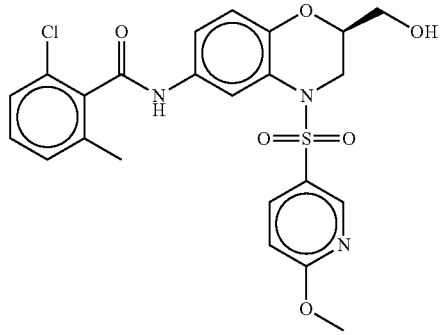 |
| VI-28 | 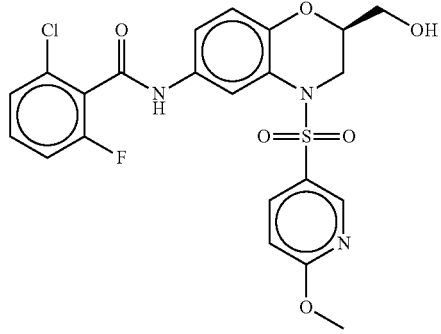 |
| VI-29 | 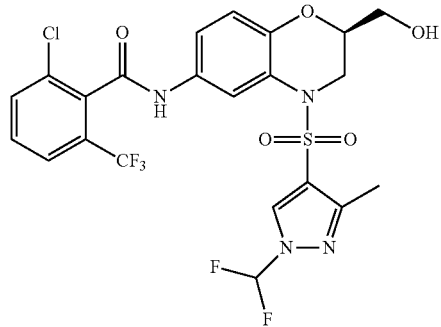 [SMILES: Cc1nn(C(F)F)cc1S(=O)(=O)N1C[C@H](CO)Oc2ccc(NC(=O)c3c(Cl)cccc3C(F)(F)F)cc21] |
| VI-30 | 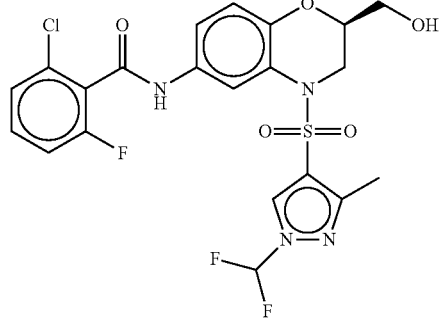 |
| VI-31 | 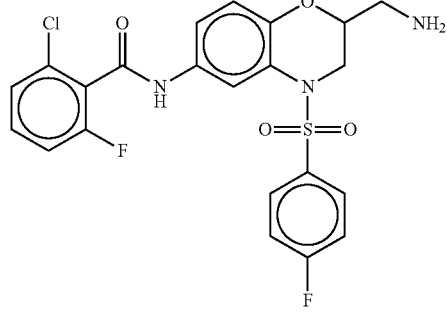 |
| VI-32 | 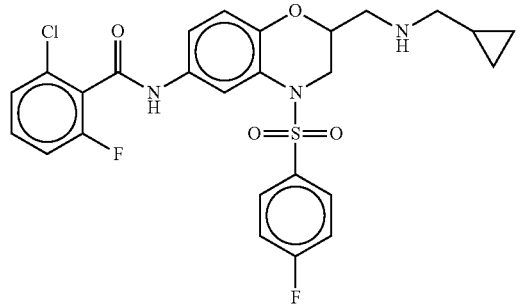 |

TABLE 6-continued
| Compound No. | Chemical Structure |
|---|---|
| VI-33 | 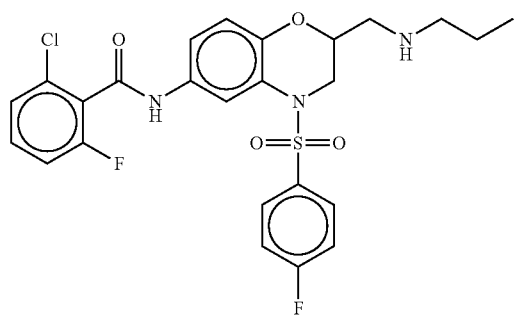 |
| VI-34 | 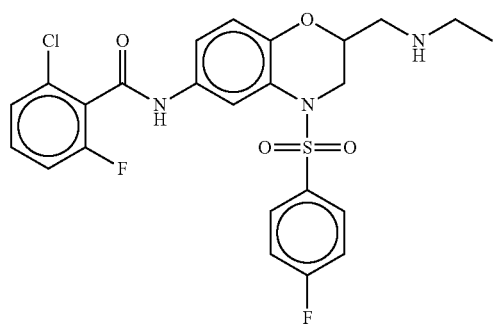 |
| VI-35 | 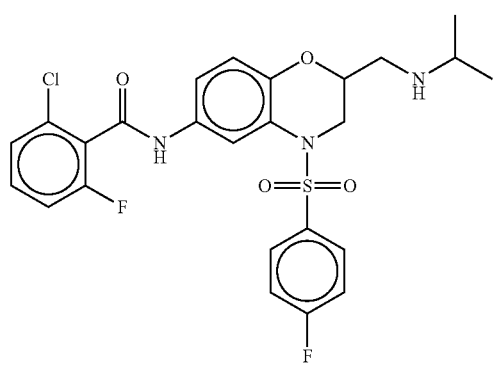 |
| VI-36 | 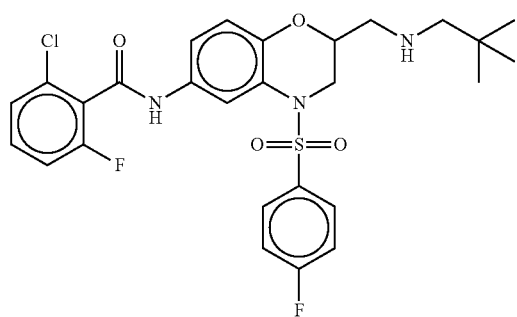 |
| VI-37 | 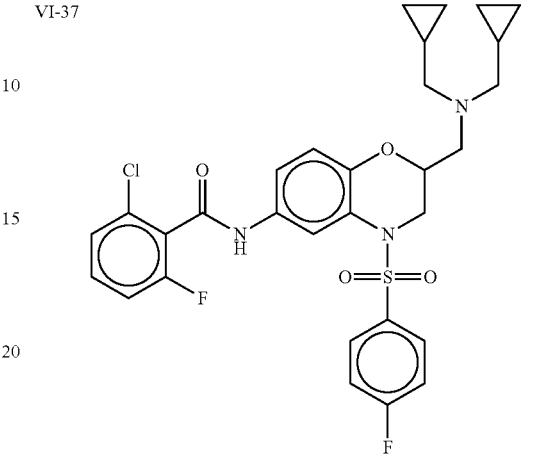 |
| VI-38 | 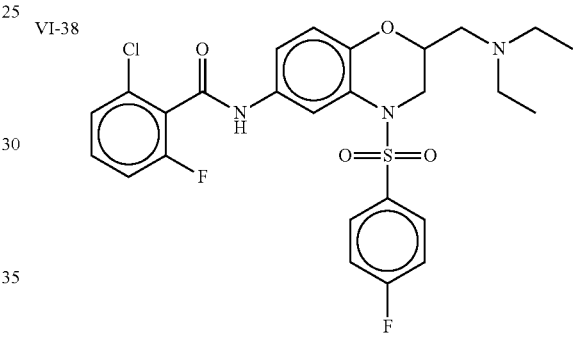 |
| VI-39 | 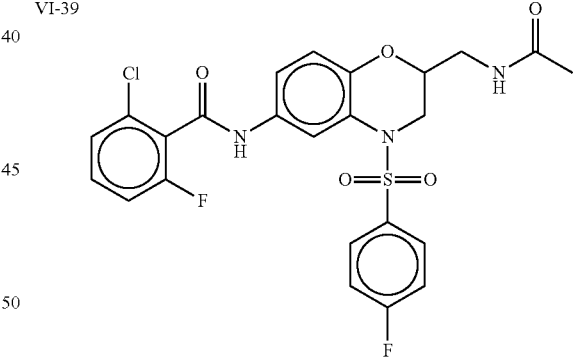 |
| VI-40 | 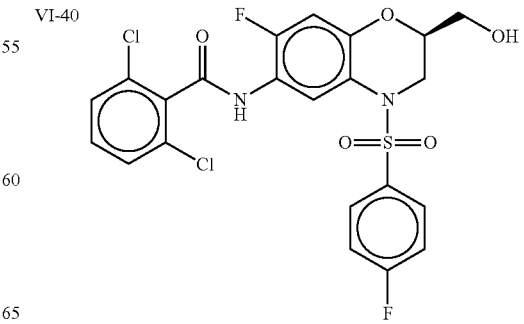 |

TABLE 6-continued
| Compound No. | Chemical Structure |
|---|---|
| VI-41 | 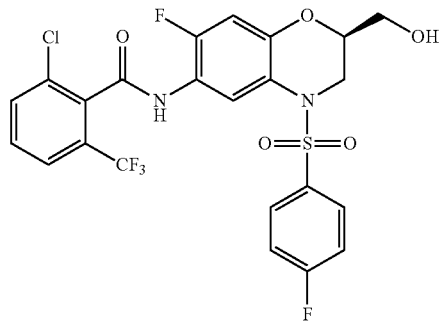 [SMILES: O=C(Nc1cc2c(cc1F)O[C@@H](CO)CN2S(=O)(=O)c1ccc(F)cc1)c1c(Cl)cccc1C(F)(F)F] |
| VI-42 | 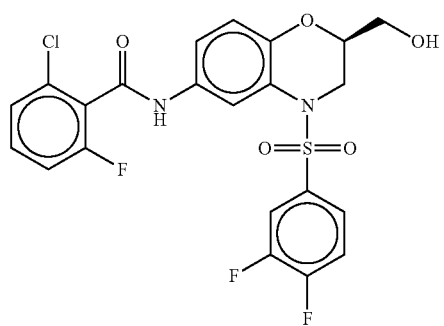 |
| VI-43 | 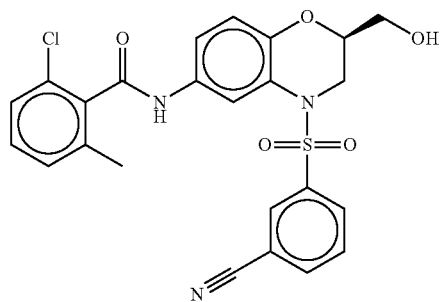 |
| VI-44 | 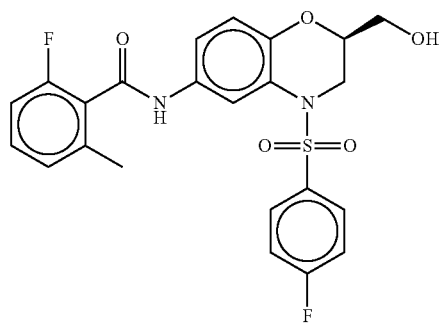 |
| VI-45 | 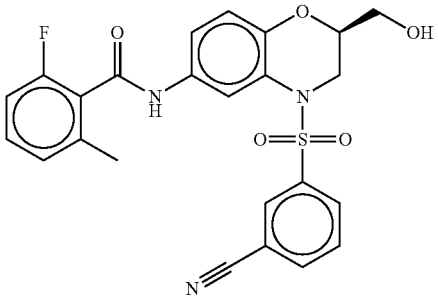 |
| VI-46 | 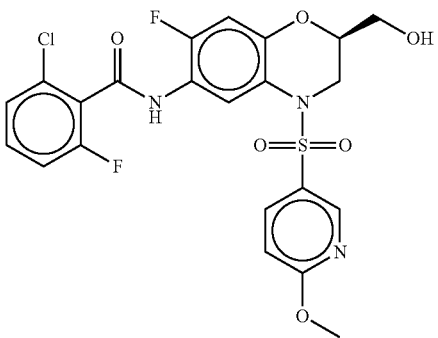 |
| VI-47 | 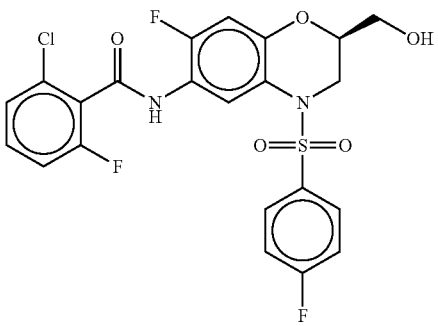 |
| VI-48 | 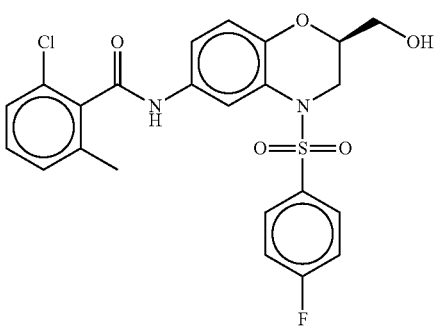 |

TABLE 6-continued

| Compound No. | Chemical Structure |
|---|---|
| VI-49 | 2,6-dimethylbenzamide-N-(benzoxazine-2-methanol)-4-sulfonyl-(4-fluorophenyl) |
| VI-50 | 2-(4-chlorophenyl)acetamide-N-(benzoxazine-2-methanol)-4-sulfonyl-(4-chlorophenyl) |
| VI-51 | 2-fluoro-6-(trifluoromethyl)benzamide-N-(benzoxazine-2-methanol)-4-sulfonyl-(4-chlorophenyl) |
| VI-52 | 2,6-dichlorobenzamide-N-(benzoxazine-2-methanol)-4-sulfonyl-(4-chlorophenyl) |
| VI-53 | 2-(4-fluorophenyl)acetamide-N-(benzoxazine-2-methanol)-4-sulfonyl-(4-chlorophenyl) |
| VI-54 | 2-chloro-6-fluorobenzamide-N-(benzoxazine-2-methanol)-4-sulfonyl-(4-chlorophenyl) |
| VI-55 | 2,6-difluorobenzamide-N-(benzoxazine-2-methanol)-4-sulfonyl-(4-chlorophenyl) |
| VI-56 | 2-(4-chlorophenyl)acetamide-N-(benzoxazine-2-methanol)-4-sulfonyl-(3-cyanophenyl) |
| VI-57 | 2-fluoro-6-(trifluoromethyl)benzamide-N-(benzoxazine-2-methanol)-4-sulfonyl-(3-cyanophenyl) |

TABLE 6-continued

| Compound No. | Chemical Structure |
|---|---|
| VI-58 | 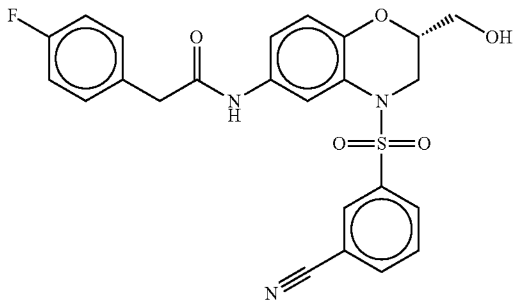 |
| VI-59 | 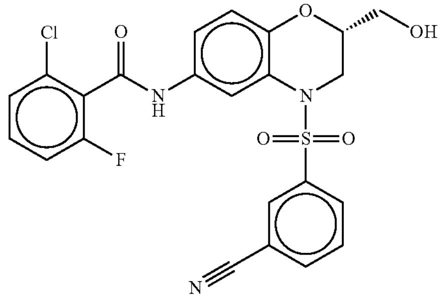 |
| VI-60 | 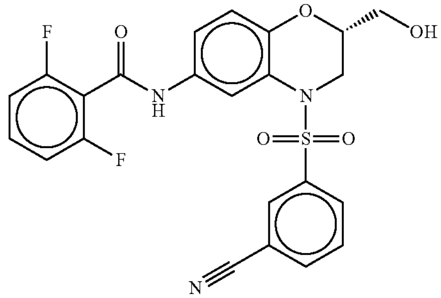 |
| VI-61 | 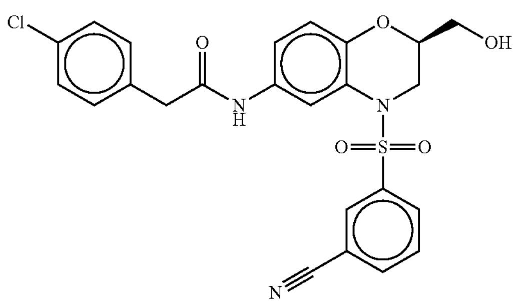 |
| VI-62 | 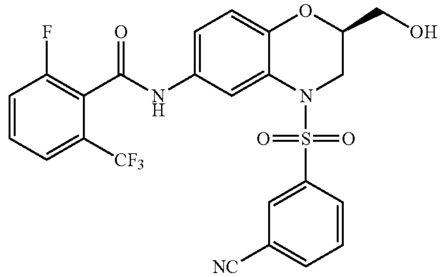 [SMILES: N#Cc1cccc(S(=O)(=O)N2C[C@H](CO)Oc3ccc(NC(=O)c4c(F)cccc4C(F)(F)F)cc32)c1] |
| VI-63 | |
| VI-64 | |
| VI-65 | |
| VI-66 | |
| VI-67 | |

TABLE 6-continued

| Compound No. | Chemical Structure |
|---|---|
| VI-68 | (structure) |
| VI-69 | (structure) |
| VI-70 | (structure) |
| VI-71 | (structure) |
| VI-72 | (structure) |
| VI-73 | (structure) |
| VI-74 | (structure) |
| VI-75 | (structure) |

TABLE 6-continued
| Compound No. | Chemical Structure |
|---|---|
| VI-76 | 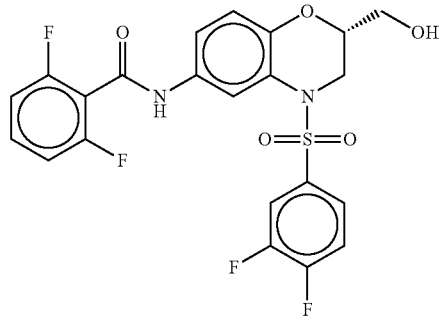 |
| VI-77 | 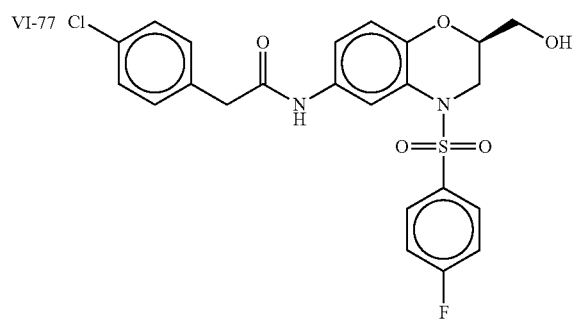 |
| VI-78 | 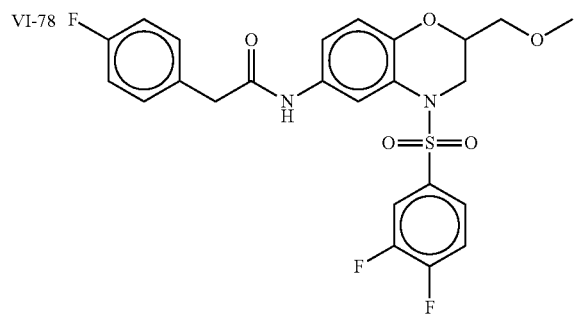 |
| VI-79 | 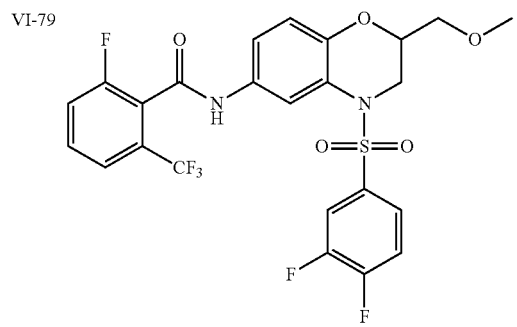 |
| VI-80 | 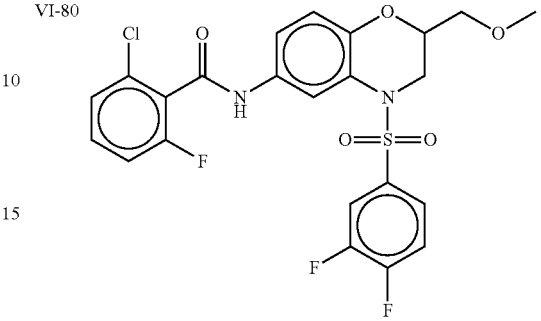 |
| VI-81 | 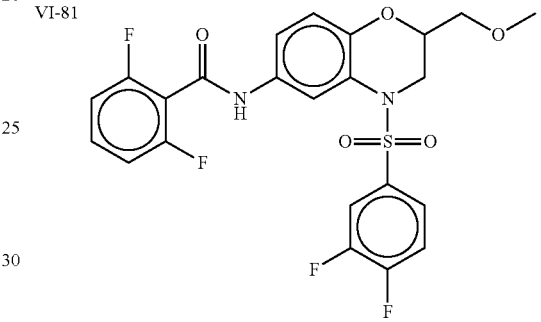 |
| VI-82 | 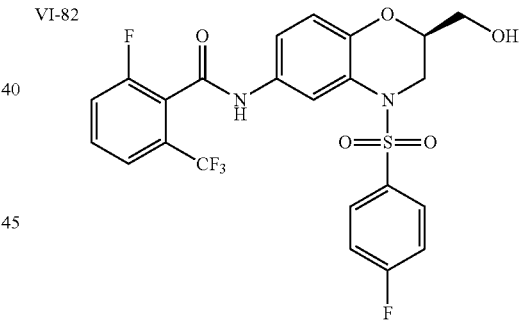 |
| VI-83 | 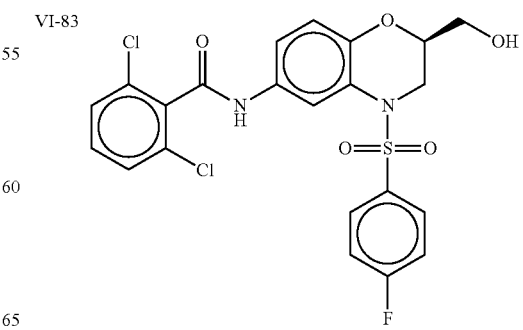 |

TABLE 6-continued
| Compound No. | Chemical Structure |
|---|---|
| VI-84 | 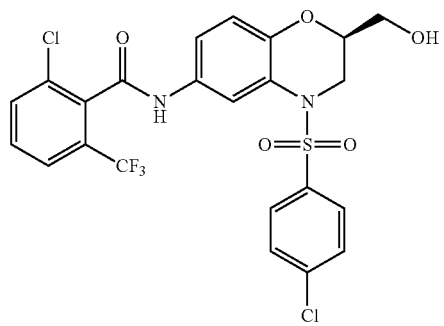 [SMILES: O=C(Nc1ccc2c(c1)N(S(=O)(=O)c1ccc(Cl)cc1)C[C@H](CO)O2)c1c(F)cccc1C(F)(F)F] |
| VI-85 | 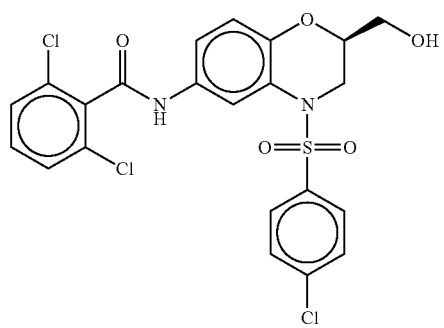 |
| VI-86 | 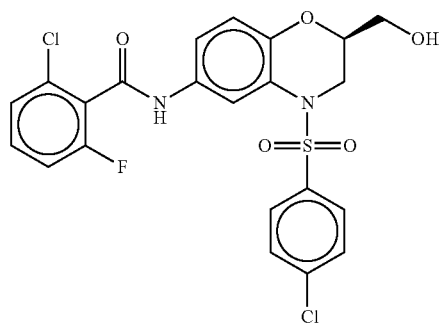 |
| VI-87 | 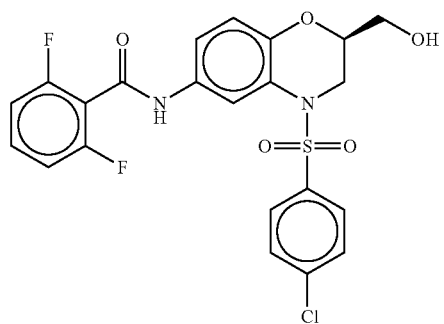 |
| VI-88 | 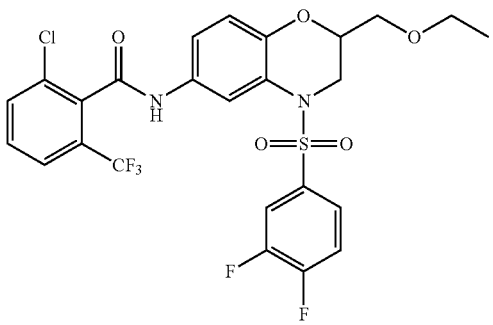 [SMILES: CCOCC1CN(S(=O)(=O)c2ccc(F)c(F)c2)c2cc(NC(=O)c3c(Cl)cccc3C(F)(F)F)ccc2O1] |
| VI-89 | 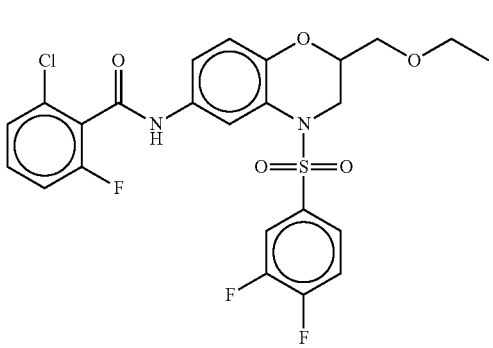 |
| VI-90 | 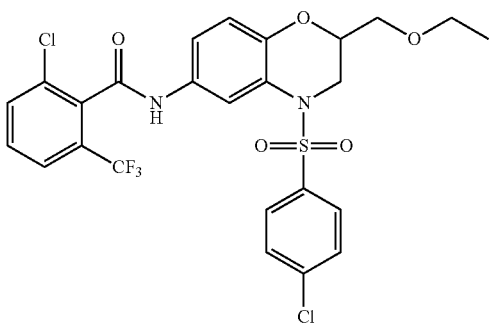 [SMILES: CCOCC1CN(S(=O)(=O)c2ccc(Cl)cc2)c2cc(NC(=O)c3c(Cl)cccc3C(F)(F)F)ccc2O1] |
| VI-91 | 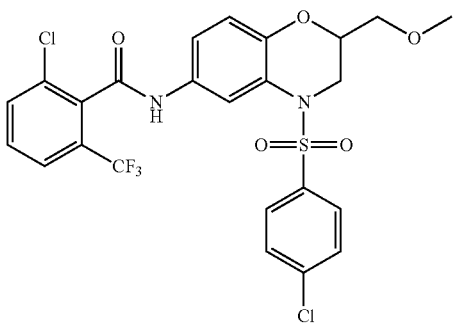 |

TABLE 6-continued

| Compound No. | Chemical Structure |
|---|---|
| VI-92 | 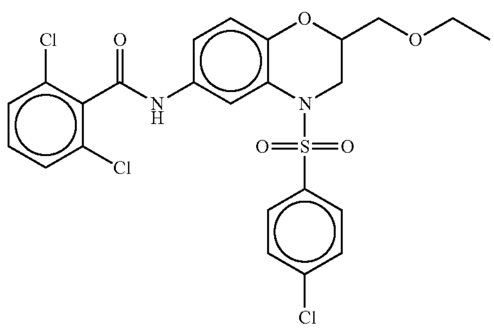 |
| VI-93 | 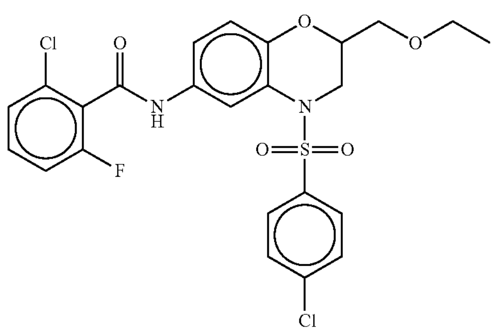 |
| VI-94 | 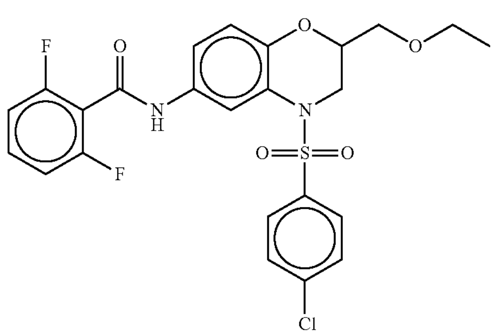 |
| VI-95 | 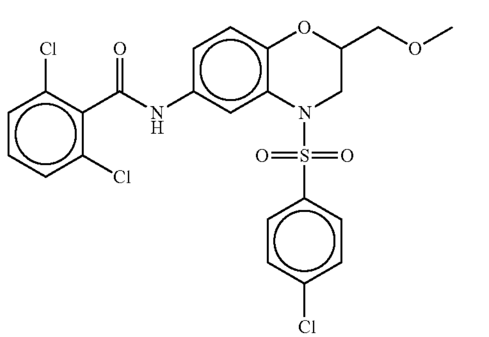 |
| VI-96 | |
| VI-97 | |
| VI-98 | |
| VI-99 | |

TABLE 6-continued
| Compound No. | Chemical Structure |
|---|---|
| VI-100 | 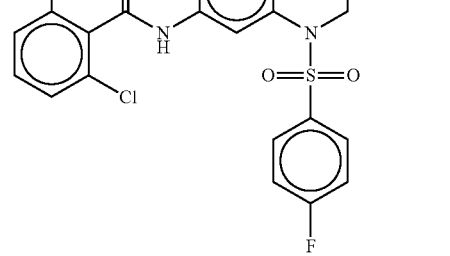 |
| VI-101 | 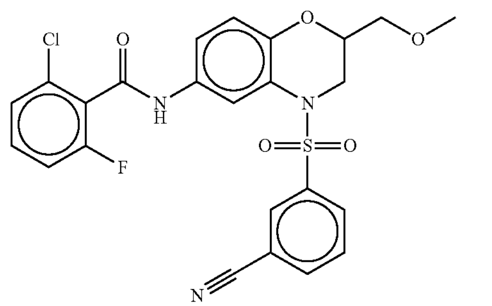 |
| VI-102 | 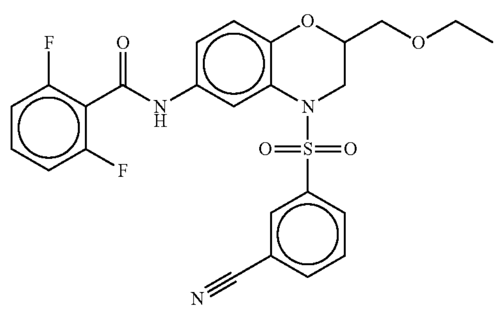 |
| VI-103 | 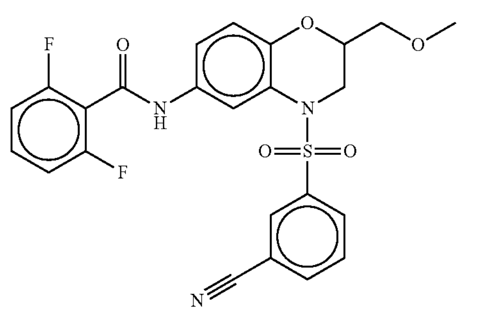 |
| VI-104 | 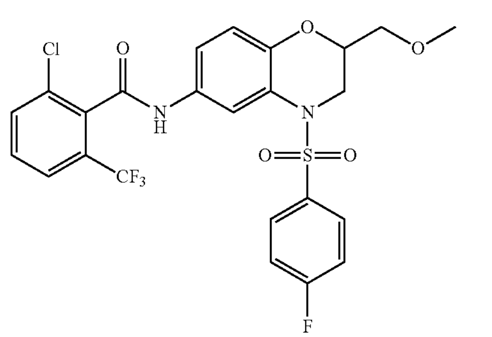 [SMILES: COCC1CN(S(=O)(=O)c2ccc(F)cc2)c2cc(NC(=O)c3c(Cl)cccc3C(F)(F)F)ccc2O1] |
| VI-105 | 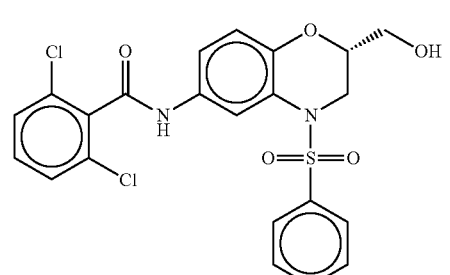 |
| VI-106 | |
| VI-107 | |
| VI-108 | |

TABLE 6-continued
| Compound No. | Chemical Structure |
|---|---|
| VI-109 | 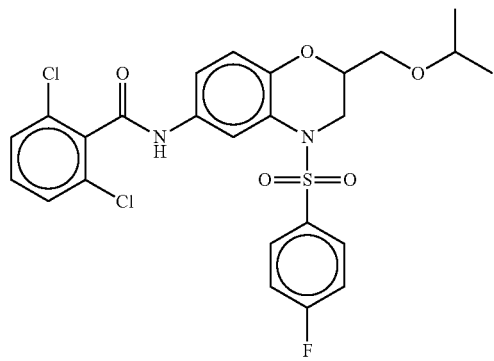 |
| VI-110 | 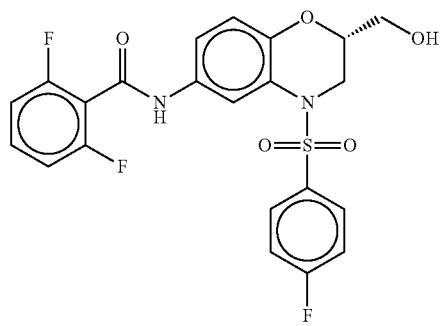 |
| VI-111 | 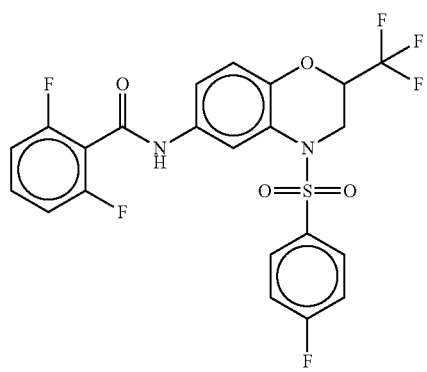 |
| VI-112 | 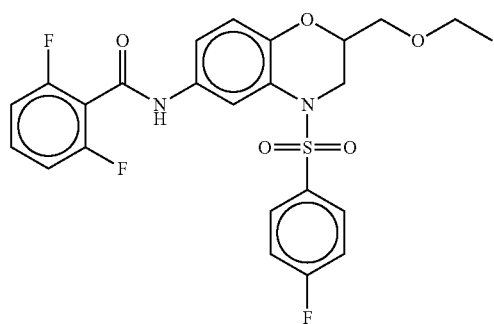 |
| VI-113 | 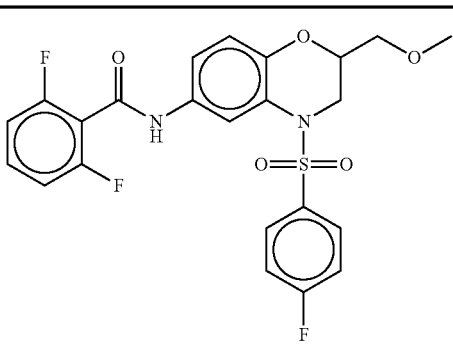 |
| VI-114 | 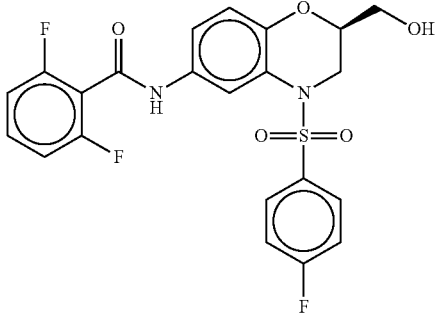 |
| VI-115 | 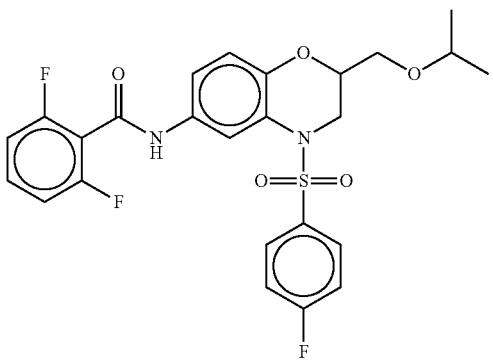 |
| VI-116 | 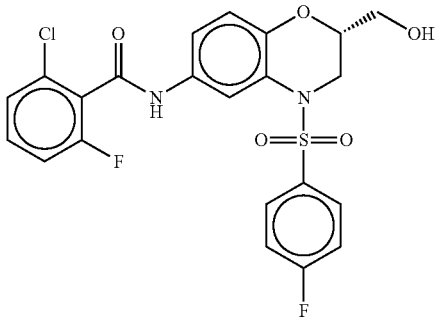 |

TABLE 6-continued
| Compound No. | Chemical Structure |
|---|---|
| VI-117 | 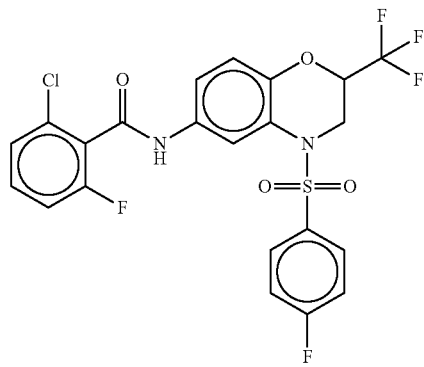 |
| VI-118 | 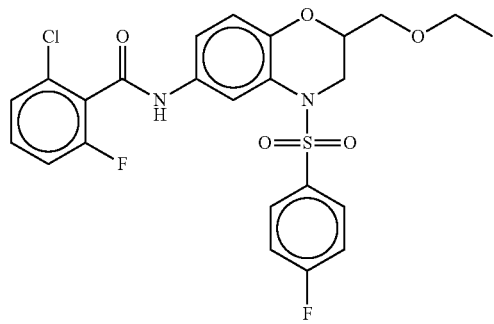 |
| VI-119 | 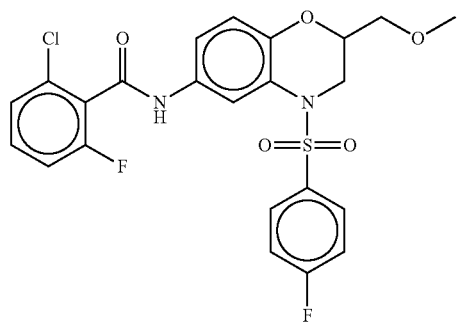 |
| VI-120 | 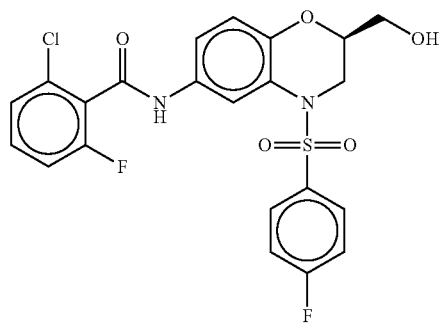 |
| VI-121 | 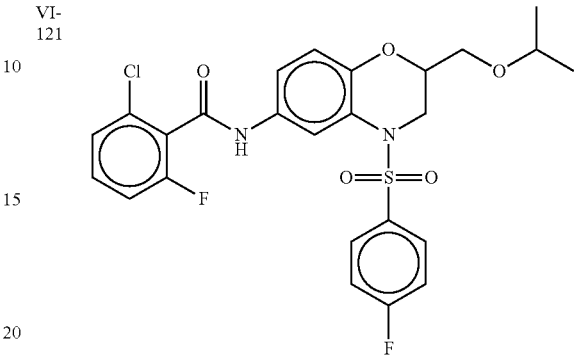 |
| VI-122 | 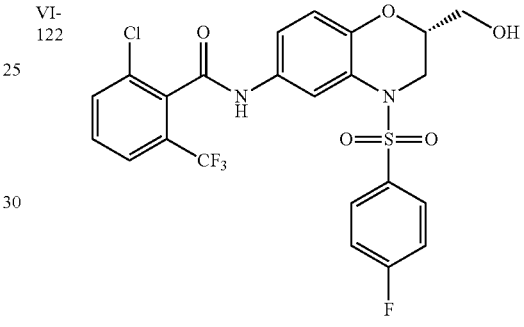 |
| VI-123 | 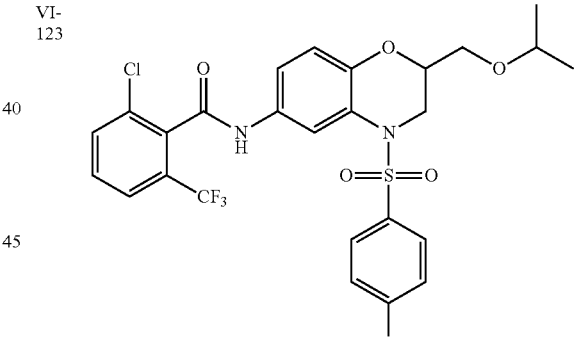 |
| VI-124 | 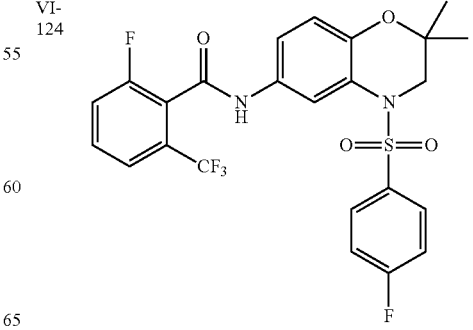 |

TABLE 6-continued
| Compound No. | Chemical Structure |
|---|---|
| VI-125 | 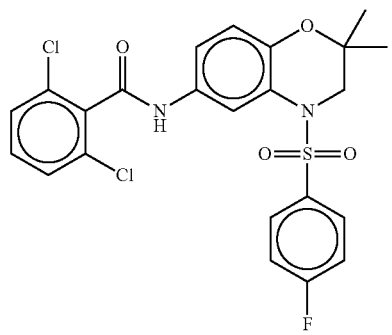 |
| VI-126 | 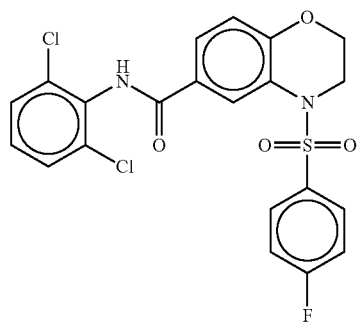 |
| VI-127 | 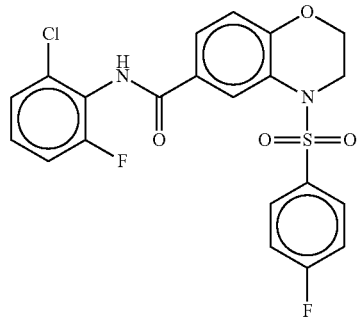 |
| VI-128 | 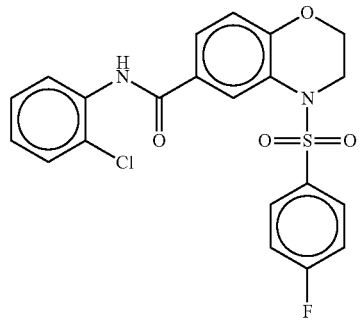 |
| VI-129 | 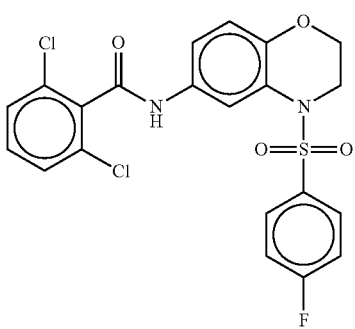 |
| VI-130 | 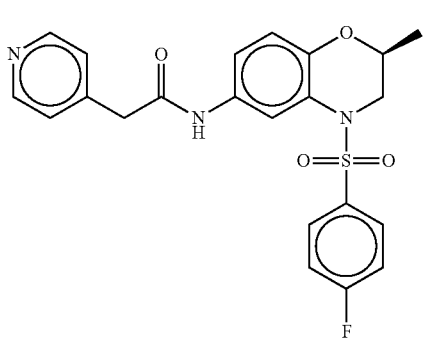 |
| VI-131 | 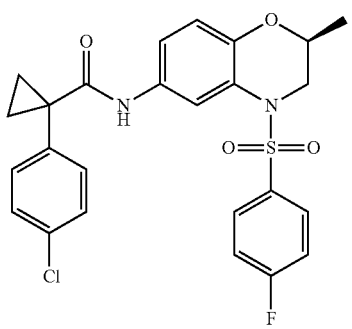 [SMILES: C[C@H]1CN(S(=O)(=O)c2ccc(F)cc2)c2cc(NC(=O)C3(c4ccc(Cl)cc4)CC3)ccc2O1] |
| VI-132 | 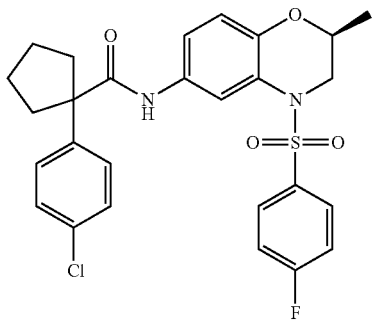 [SMILES: C[C@H]1CN(S(=O)(=O)c2ccc(F)cc2)c2cc(NC(=O)C3(c4ccc(Cl)cc4)CCCC3)ccc2O1] |

TABLE 6-continued

| Compound No. | Chemical Structure |
|---|---|
| VI-133 | (structure) |
| VI-134 | (structure) |
| VI-135 | (structure) |
| VI-136 | (structure) |

Example 24

Biological Assays for Inhibition of RORγ

Exemplary compounds from Examples 1-23 were tested for ability to inhibit RORγ activity using a RORγ Reporter Assay and a RORγ-Ligand Binding Domain TR-FRET Assay. Assay procedures and results are described below.

Part 1—Procedures for RORγ Reporter Assay

General Description

Inhibition of RORγt in cells was determined using a GAL4-UAS reporter system in HEK293 cells employing a luciferase readout. The RORγt DNA binding domain (DBD) was replaced with the heterologous yeast GAL4 DBD using standard recombinant DNA methods. The resulting GAL4-RORγt-LBD fusion construct was placed under the control of a constitutive cytomegalovirus (CMV) promoter by cloning it into the CMV-driven mammalian expression vector pcDNA3.1+– (Promega Corporation, Madison, Wis.).

A transcriptional reporter expression construct was used to monitor GAL4-RORγ activity, which contained five copies of the GAL4 binding site enhancer (UAS) controlling expression of a firefly luciferase reporter. This construct, pGL4.31, is commercially available from Promega Corporation, Madison Wis. Both expression constructs were transfected in bulk into HEK-293 cells using standard lipid-based transfection techniques, which allowed the GAL4 RORγ-LBD fusion protein to drive expression of the luciferase reporter. Control transfections were performed with an empty pCDN3.1+ vector.

The next day, cells were plated into 384 well plates, test compound was added, and the plates were incubated overnight. Test compounds capable of blocking the GAL4-RORg fusion protein from initiating expression of the luciferase signal were identified. Promega firefly assays kits were used to stabilize the luciferase signal, and the intensity of the luciferase signal was measured using an EnVision Multilabel Plate Reader (Perkin Elmer, Waltham, Mass.).

Detailed Description of the HEK293 Gal4 Rporter Assay

HEK 293 cells are transfected with GAL4-NR construct (CMV:NR-LBD in pcDNA3.1neo) and the pGL4.31 GAL4-luciferase reporter construct (Promega). For a background control, use empty pcDNA3.1neo and pGL4.31. Transfection protocol is for a single T75 flask performed with Minis Trans-It 293 reagent. A 60 µL aliquot of Trans-IT reagent at room temperature is added drop wise to 1.5 mL of Optimem (Invitrogen). The resulting solution is mixed by inversion and incubated for 5-20 minutes at room temperature. This reagent mixture is added to 10 µg of DNA (5 µg of each expression vector used at a concentration of 1 mg/mL). The solution is mixed by inversion and incubated at room temperature for 20 minutes.

While the Trans-IT reagent and DNA are incubating, harvest HEK-293 cells. Remove media from flasks via aspiration and add enough TrypLE Express (stable Trypsin-like reagent, Invitrogen) to cover the bottom of the flask. The mixture is incubated at room temperature until the cells are visibly loose in the flask (approximately 2-5 minutes). Add an equal volume of complete growth media, and then pipette to achieve a single cell suspension. Spin down $1 \times 10^7$ cells and re-suspend the cells in 10 mL of complete growth media (DMEM high glucose/10% dialyzed FBS/pen/strep; Invitrogen). The cells and transfection mixture are added to one T75 flask. The contents of the T75 flax are mixed and incubated overnight at 37° C. and 5% $CO_2$.

After 16-24 hours, cells are harvested and plated for test compound screening. Cells may be harvested as described above. Next, cells are counted and an appropriate number of cells are spun down. Then, cells are aspirated and re-suspended in complete growth media at a concentration of $0.5 \times 10^6$ cells/mL to provide a cell suspension. Plate 20 µL of the cell suspension into a white, tissue-culture treated 384 well plate. (10,000 cells/well).

A 10 mM stock solution of test compound in dimethylsulfoxide (DMSO) was diluted to 500× the final test concentration in DMSO, then diluted to 5× the final test concentration with complete growth medium to provide the Test Compound Solution. The concentration of DMSO in the Test Compound Solution was 0.2%. A 5 μL aliquot of Test Compound Solution was added to each test well in the 384 well plate previously plated with the cell suspension. Next, plates are spun briefly and incubated overnight at 37° C. and 5% $CO_2$.

After 16-24 hours, the luciferase assay is performed. Plates and luciferase reagent (e.g. One-Glo® or Dual Glo®; Promega, Madison, Wis.) are brought to room temperature. Next, a 25 μL aliquot of luciferase reagent is added to each well. Plates are spun down briefly and incubated at room temperature for 10 minutes. The luciferase signal is measured on an Envision plate reader (Perkin Elmer) set to the ultra sensitive luminescence setting. $IC_{50}$ values for test compounds were calculated from the luciferase signal data using GraphPad Prism software.

Part II—Procedures for RORγ-Ligand Binding Domain TR-FRET Assay

HIS-tagged RORγ-LBD was recombinantly expressed in SF9 cells using a baculovirus expression system. The protein was not purified. Cells were lysed and the lysate was used as a source for RORγ-LBD for the assay. A 1:80 dilution of RORγ-LBD lysate in assay buffer (25 mM HEPES pH 7.0, 100 mM NaCl, 0.01% Tween, 0.1% BSA) was prepared and 5 μL was added to each well (RORγ-LBD final concentration ~10 nM). Control wells received lysate from SF9 cells not expressing RORγ-LBD.

Compounds to be tested were diluted to 100× final test concentration in DMSO and further diluted to 4× final test concentration using assay buffer to provide the test compound mixture. An aliquot (5 μL) of the test compound mixture was added to each well.

A 4× stock of biotinylated-LXXLL peptide from SRC1-2 (Biotin-CPSSHSSLTERHKILHRLLQEGSPS) was prepared in assay buffer and a 5 μL aliquot added to each well (450 nM final concentration). A 4× solution of europium tagged anti-HIS antibody (2 nM final concentration) and APC conjugated streptavidin (60 nM final concentration) were prepared and a 5 μL aliquot added to each well.

The final assay mixture was incubated for 4 hours to overnight, and the fluorescence signal was measured on an Envision plate reader: (Excitation filter=340 nm; APC emission=665 nm; Europium emission=615 nm; dichroic mirror=D400/D630; delay time=100 μs, integration time=200 μs).

$IC_{50}$ values for test compounds were calculated from the quotient of the fluorescence signal at 665 nm divided by the fluorescence signal at 615 nm using GraphPad Prism software.

Part III—Results

RORγ inhibition data for exemplary compounds is provided in Tables 7-9 below. The term "NA" indicates that no data was available.

TABLE 7

RORγ INHIBITION DATA FOR EXEMPLARY TETRAHYDROQUINOLINES

| Compound No. | RORγ FRET $IC_{50}$ (μM) | RORγ HEK $IC_{50}$ (μM) |
|---|---|---|
| 4 | NA | <15 |
| 5 | NA | <15 |
| 6 | NA | <15 |
| III-175 | NA | <15 |
| III-176 | NA | <15 |
| III-177 | NA | <15 |
| III-178 | NA | <15 |
| III-179 | NA | <15 |
| III-180 | NA | <15 |
| III-181 | NA | <15 |
| III-182 | NA | <15 |
| III-183 | NA | <15 |
| III-184 | NA | <15 |
| III-185 | NA | <15 |
| III-186 | NA | <15 |
| III-187 | NA | <15 |
| III-188 | NA | <15 |
| III-189 | NA | <15 |
| III-190 | NA | <15 |
| III-191 | NA | <15 |
| III-192 | NA | <15 |
| III-193 | NA | <15 |
| III-194 | NA | <15 |
| III-195 | NA | <15 |
| III-196 | NA | <15 |
| III-197 | NA | <15 |
| III-198 | NA | 15 |
| III-199 | NA | <15 |
| III-200 | NA | <15 |
| III-201 | NA | <15 |
| III-202 | NA | <15 |
| III-203 | NA | <15 |
| III-204 | NA | <15 |
| III-205 | NA | <15 |
| III-206 | NA | <15 |
| III-207 | NA | <15 |
| III-208 | NA | <15 |
| III-209 | NA | <15 |
| III-210 | NA | <15 |
| III-211 | NA | <15 |
| III-212 | NA | <15 |
| III-213 | NA | <15 |
| III-214 | NA | <15 |
| III-215 | NA | <15 |
| III-216 | NA | <15 |
| III-217 | NA | <15 |
| III-218 | NA | <15 |
| III-219 | NA | <15 |
| III-220 | NA | >15 |
| III-221 | NA | >15 |
| III-222 | NA | <15 |
| III-223 | NA | <15 |
| III-224 | NA | <15 |
| III-225 | NA | <15 |
| III-226 | NA | <15 |
| III-227 | NA | <15 |
| III-228 | NA | <15 |
| III-229 | NA | <15 |
| III-230 | NA | <15 |
| III-231 | NA | <15 |
| III-232 | NA | >15 |
| III-233 | NA | <15 |
| III-234 | NA | >15 |
| III-235 | NA | >15 |
| III-236 | NA | <15 |
| III-237 | NA | <15 |
| III-238 | NA | <15 |
| III-239 | NA | <15 |
| III-240 | NA | <15 |
| III-241 | NA | <15 |
| III-242 | NA | >15 |
| III-243 | NA | <15 |
| III-244 | NA | <15 |
| III-245 | NA | <15 |

TABLE 7-continued

RORγ INHIBITION DATA FOR EXEMPLARY TETRAHYDROQUINOLINES

| Compound No. | RORγ FRET IC$_{50}$ (μM) | RORγ HEK IC$_{50}$ (μM) |
|---|---|---|
| III-246 | NA | <15 |
| III-247 | NA | <15 |
| III-248 | NA | <15 |
| III-249 | NA | <15 |
| III-250 | NA | <15 |
| III-251 | NA | >15 |
| III-252 | NA | <15 |
| III-253 | NA | <15 |
| III-254 | NA | <15 |
| III-255 | NA | <15 |
| III-256 | NA | <15 |
| III-257 | NA | <15 |
| III-258 | NA | NA |
| III-259 | NA | <15 |
| III-260 | NA | <15 |
| III-261 | NA | <15 |
| III-262 | NA | <15 |
| III-263 | NA | <15 |
| III-264 | NA | <15 |
| III-265 | NA | <15 |
| III-266 | NA | <15 |
| III-267 | NA | <15 |
| III-268 | NA | <15 |
| III-269 | NA | <15 |
| III-270 | NA | <15 |
| III-271 | NA | <15 |
| III-272 | NA | <15 |
| III-273 | NA | <15 |
| III-274 | NA | <15 |
| III-275 | NA | <15 |
| III-276 | NA | <15 |
| III-277 | NA | >15 |
| III-278 | NA | >15 |
| III-279 | NA | >15 |
| III-280 | NA | >15 |
| III-281 | NA | >15 |
| III-282 | NA | <15 |
| III-283 | NA | <15 |
| III-284 | NA | <15 |
| III-285 | NA | <15 |
| III-286 | NA | <15 |
| III-287 | NA | <15 |
| III-288 | NA | <15 |
| III-289 | NA | <15 |
| III-290 | NA | <15 |
| III-291 | NA | <15 |
| III-292 | NA | <15 |
| III-293 | NA | <15 |
| III-294 | NA | <15 |
| III-295 | NA | <15 |
| III-296 | NA | <15 |
| III-297 | NA | <15 |
| III-298 | NA | <15 |
| III-299 | NA | <15 |
| III-300 | NA | <15 |
| III-301 | NA | <15 |
| III-302 | NA | <15 |
| III-303 | NA | <15 |
| III-304 | NA | <15 |
| III-305 | NA | <15 |
| III-306 | <15 | <15 |
| III-307 | <15 | <15 |
| III-308 | >15 | >15 |
| III-309 | NA | <15 |
| III-310 | NA | <15 |
| III-311 | NA | <15 |
| III-312 | NA | <15 |
| III-313 | <15 | <15 |
| III-314 | NA | <15 |
| III-315 | NA | <15 |
| III-316 | NA | <15 |
| III-317 | NA | <15 |
| III-318 | NA | <15 |
| III-319 | NA | <15 |
| III-320 | NA | <15 |
| III-321 | NA | <15 |
| III-322 | NA | <15 |
| III-323 | NA | <15 |
| III-324 | NA | <15 |
| III-325 | NA | <15 |
| III-326 | NA | <15 |
| III-327 | NA | <15 |
| III-328 | NA | <15 |
| III-329 | NA | <15 |
| III-330 | NA | <15 |
| III-331 | NA | <15 |
| III-332 | NA | <15 |
| III-333 | <15 | <15 |
| III-334 | NA | <15 |
| III-335 | NA | <15 |
| III-336 | NA | <15 |
| III-337 | NA | <15 |
| III-338 | NA | <15 |
| III-339 | NA | <15 |
| III-340 | NA | <15 |
| III-341 | NA | <15 |
| III-342 | NA | <15 |
| III-343 | NA | <15 |
| III-344 | NA | <15 |
| III-345 | NA | <15 |
| III-346 | NA | <15 |
| III-347 | NA | <15 |
| III-348 | NA | <15 |

TABLE 8

RORγ INHIBITION DATA FOR EXEMPLARY INDAZOLES

| Compound No. | RORγ FRET IC$_{50}$ (μM) | RORγ HEK IC$_{50}$ (μM) |
|---|---|---|
| 9 | <15 | NA |
| 11 | <15 | NA |
| 10 | <15 | NA |
| V-1 | <15 | NA |
| V-2 | <15 | NA |
| V-3 | <15 | NA |
| V-4 | <15 | NA |
| V-5 | <15 | NA |
| V-6 | <15 | NA |
| V-7 | <15 | NA |
| V-8 | <15 | NA |
| V-9 | <15 | NA |
| V-10 | <15 | NA |
| V-11 | <15 | NA |
| V-12 | <15 | NA |
| V-13 | <15 | NA |
| V-14 | <15 | NA |
| V-15 | <15 | NA |
| V-16 | <15 | NA |
| V-17 | <15 | NA |
| V-18 | <15 | NA |
| V-19 | <15 | NA |
| V-20 | <15 | NA |
| V-21 | <15 | NA |
| V-22 | <15 | NA |
| V-23 | <15 | NA |
| V-24 | <15 | NA |
| V-25 | <15 | NA |
| V-26 | <15 | NA |
| V-27 | <15 | NA |
| V-28 | <15 | NA |
| V-29 | <15 | NA |
| V-30 | <15 | NA |
| V-31 | <15 | NA |

TABLE 8-continued

RORγ INHIBITION DATA FOR EXEMPLARY INDAZOLES

| Compound No. | RORγ FRET IC$_{50}$ (µM) | RORγ HEK IC$_{50}$ (µM) |
|---|---|---|
| V-32 | <15 | NA |
| V-33 | <15 | NA |
| V-34 | <15 | NA |
| V-35 | <15 | NA |
| V-36 | <15 | NA |
| V-37 | <15 | NA |
| V-38 | <15 | NA |
| V-39 | <15 | NA |
| V-40 | <15 | NA |
| V-41 | <15 | NA |
| V-42 | <15 | NA |
| V-43 | <15 | NA |
| V-44 | <15 | NA |
| V-45 | <15 | NA |
| V-46 | <15 | NA |
| V-47 | <15 | NA |
| V-48 | <15 | NA |
| V-49 | <15 | NA |
| V-50 | <15 | NA |
| V-51 | <15 | NA |
| V-52 | <15 | NA |
| V-53 | <15 | NA |
| V-54 | <15 | NA |
| V-55 | <15 | NA |
| V-56 | <15 | NA |
| V-57 | <15 | NA |
| V-58 | <15 | NA |
| V-59 | <15 | NA |
| V-60 | <15 | NA |
| V-61 | <15 | NA |
| V-62 | <15 | NA |
| V-63 | <15 | NA |
| V-64 | <15 | NA |
| V-65 | <15 | NA |
| V-66 | <15 | NA |
| V-67 | <15 | NA |
| V-68 | <15 | NA |
| V-69 | <15 | NA |
| V-70 | <15 | NA |
| V-71 | <15 | NA |
| V-72 | <15 | NA |
| V-73 | <15 | NA |
| V-74 | <15 | NA |
| V-75 | <15 | NA |
| V-76 | <15 | NA |
| V-77 | <15 | NA |
| V-78 | <15 | NA |
| V-79 | <15 | NA |
| V-80 | <15 | NA |
| V-81 | <15 | NA |
| V-82 | <15 | NA |
| V-83 | <15 | NA |
| V-84 | <15 | NA |
| V-85 | <15 | NA |
| V-86 | <15 | NA |
| V-87 | <15 | NA |
| V-88 | <15 | NA |
| V-89 | <15 | NA |
| V-90 | <15 | NA |
| V-91 | <15 | NA |
| V-92 | <15 | NA |
| V-93 | <15 | NA |
| V-94 | <15 | NA |
| V-95 | <15 | NA |
| V-96 | <15 | NA |
| V-97 | <15 | NA |
| V-98 | <15 | NA |
| V-99 | <15 | NA |
| V-100 | <15 | NA |
| V-101 | <15 | NA |
| V-102 | <15 | NA |
| V-103 | <15 | NA |
| V-104 | <15 | NA |
| V-105 | <15 | NA |
| V-106 | <15 | NA |
| V-107 | <15 | NA |
| V-108 | <15 | NA |
| V-109 | <15 | NA |
| V-110 | <15 | NA |
| V-111 | <15 | NA |
| V-112 | <15 | NA |
| V-113 | <15 | NA |
| V-114 | <15 | NA |
| V-115 | <15 | NA |
| V-116 | <15 | NA |
| V-117 | <15 | NA |
| V-118 | <15 | NA |
| V-119 | <15 | NA |
| V-120 | <15 | NA |
| V-121 | <15 | NA |
| V-122 | <15 | NA |
| V-123 | <15 | NA |
| V-124 | <15 | NA |
| V-125 | <15 | NA |
| V-126 | <15 | NA |
| V-127 | <15 | NA |
| V-128 | <15 | NA |
| V-129 | <15 | NA |
| V-130 | <15 | NA |
| V-131 | <15 | NA |
| V-132 | <15 | NA |
| V-133 | <15 | NA |
| V-134 | <15 | NA |
| V-135 | <15 | NA |
| V-136 | <15 | NA |
| V-137 | <15 | NA |
| V-138 | <15 | NA |
| V-139 | <15 | NA |
| V-140 | <15 | NA |
| V-141 | <15 | NA |
| V-142 | <15 | NA |
| V-143 | <15 | NA |
| V-144 | <15 | NA |
| V-145 | <15 | NA |
| V-146 | <15 | NA |
| V-147 | <15 | NA |
| V-148 | <15 | NA |
| V-149 | <15 | NA |
| V-150 | <15 | NA |
| V-151 | <15 | NA |
| V-152 | <15 | NA |
| V-153 | <15 | NA |
| V-154 | <15 | NA |
| V-155 | <15 | NA |
| V-156 | <15 | NA |
| V-157 | <15 | NA |
| V-158 | <15 | NA |
| V-159 | <15 | NA |
| V-160 | <15 | NA |
| V-161 | <15 | NA |
| V-162 | <15 | NA |
| V-163 | <15 | NA |
| V-164 | <15 | NA |
| V-165 | <15 | NA |
| V-166 | <15 | NA |
| V-167 | <15 | NA |
| V-168 | <15 | NA |
| V-169 | <15 | NA |
| V-170 | <15 | NA |
| V-171 | <15 | NA |

TABLE 9

RORγ INHIBITION DATA FOR EXEMPLARY BENZOXAZINES

| Compound No. | RORγ FRET IC$_{50}$ (μM) | RORγ HEK IC$_{50}$ (μM) |
| --- | --- | --- |
| 12 | <15 | <15 |
| 13 | <15 | <15 |
| 14 | <15 | NA |
| 15 | <15 | <15 |
| 16 | <15 | <15 |
| 17 | >15 | NA |
| 18 | >15 | NA |
| 19 | <15 | NA |
| 20 | <15 | <15 |
| 21 | <15 | <15 |
| 22 | <15 | <15 |
| 23 | <15 | NA |
| VI-1 | <15 | <15 |
| VI-2 | <15 | NA |
| VI-3 | <15 | NA |
| VI-4 | <15 | NA |
| VI-5 | <15 | NA |
| VI-6 | <15 | NA |
| VI-7 | <15 | NA |
| VI-8 | <15 | <15 |
| VI-9 | <15 | <15 |
| VI-10 | <15 | <15 |
| VI-11 | <15 | <15 |
| VI-12 | <15 | <15 |
| VI-13 | <15 | <15 |
| VI-14 | <15 | <15 |
| VI-15 | <15 | <15 |
| VI-16 | <15 | NA |
| VI-17 | <15 | NA |
| VI-18 | <15 | NA |
| VI-19 | <15 | NA |
| VI-20 | <15 | NA |
| VI-21 | <15 | NA |
| VI-22 | <15 | NA |
| VI-23 | <15 | NA |
| VI-24 | <15 | <15 |
| VI-25 | <15 | <15 |
| VI-26 | <15 | <15 |
| VI-27 | <15 | <15 |
| VI-28 | <15 | <15 |
| VI-29 | <15 | <15 |
| VI-30 | <15 | <15 |
| VI-31 | <15 | NA |
| VI-32 | <15 | <15 |
| VI-33 | <15 | NA |
| VI-34 | <15 | NA |
| VI-35 | <15 | <15 |
| VI-36 | <15 | <15 |
| VI-37 | <15 | <15 |
| VI-38 | <15 | <15 |
| VI-39 | <15 | <15 |
| VI-40 | <15 | <15 |
| VI-41 | <15 | <15 |
| VI-42 | <15 | <15 |
| VI-43 | <15 | <15 |
| VI-44 | <15 | <15 |
| VI-45 | <15 | <15 |
| VI-46 | <15 | <15 |
| VI-47 | <15 | <15 |
| VI-48 | <15 | <15 |
| VI-49 | <15 | <15 |
| VI-50 | <15 | NA |
| VI-51 | <15 | <15 |
| VI-52 | <15 | <15 |
| VI-53 | <15 | NA |
| VI-54 | <15 | NA |
| VI-55 | <15 | NA |
| VI-56 | <15 | NA |
| VI-57 | <15 | NA |
| VI-58 | <15 | NA |
| VI-59 | <15 | NA |
| VI-60 | <15 | NA |
| VI-61 | <15 | NA |
| VI-62 | <15 | <15 |
| VI-63 | <15 | <15 |
| VI-64 | <15 | NA |
| VI-65 | <15 | NA |
| VI-66 | <15 | NA |
| VI-67 | <15 | <15 |
| VI-68 | <15 | NA |
| VI-69 | >15 | NA |
| VI-70 | <15 | <15 |
| VI-71 | <15 | NA |
| VI-72 | <15 | <15 |
| VI-73 | <15 | <15 |
| VI-74 | <15 | NA |
| VI-75 | <15 | <15 |
| VI-76 | <15 | <15 |
| VI-77 | <15 | NA |
| VI-78 | <15 | <15 |
| VI-79 | <15 | <15 |
| VI-80 | <15 | <15 |
| VI-81 | <15 | <15 |
| VI-82 | <15 | <15 |
| VI-83 | <15 | <15 |
| VI-84 | <15 | <15 |
| VI-85 | <15 | <15 |
| VI-86 | <15 | <15 |
| VI-87 | <15 | <15 |
| VI-88 | <15 | <15 |
| VI-89 | <15 | <15 |
| VI-90 | <15 | <15 |
| VI-91 | <15 | <15 |
| VI-92 | <15 | <15 |
| VI-93 | <15 | <15 |
| VI-94 | <15 | <15 |
| VI-95 | <15 | <15 |
| VI-96 | <15 | <15 |
| VI-97 | <15 | <15 |
| VI-98 | <15 | <15 |
| VI-99 | <15 | <15 |
| VI-100 | <15 | <15 |
| VI-101 | <15 | <15 |
| VI-102 | <15 | <15 |
| VI-103 | <15 | <15 |
| VI-104 | <15 | <15 |
| VI-105 | <15 | <15 |
| VI-106 | <15 | <15 |
| VI-107 | <15 | <15 |
| VI-108 | <15 | <15 |
| VI-109 | <15 | <15 |
| VI-110 | <15 | <15 |
| VI-111 | <15 | NA |
| VI-112 | <15 | <15 |
| VI-113 | <15 | <15 |
| VI-114 | <15 | <15 |
| VI-115 | <15 | <15 |
| VI-116 | <15 | <15 |
| VI-117 | <15 | NA |
| VI-118 | <15 | <15 |
| VI-119 | <15 | <15 |
| VI-120 | <15 | <15 |
| VI-121 | <15 | <15 |
| VI-122 | <15 | <15 |
| VI-123 | <15 | <15 |
| VI-124 | <15 | <15 |
| VI-125 | <15 | <15 |
| VI-126 | NA | <15 |
| VI-127 | NA | <15 |
| VI-128 | NA | <15 |
| VI-129 | <15 | <15 |
| VI-130 | <15 | NA |
| VI-131 | <15 | NA |
| VI-132 | <15 | NA |
| VI-133 | <15 | NA |
| VI-134 | <15 | NA |
| VI-135 | <15 | NA |
| VI-136 | <15 | NA |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:
1. A compound represented by Formula III:

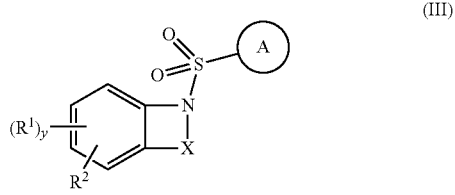

(III)

or a pharmaceutically acceptable salt or solvate thereof; wherein:
A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, —N($R^3$)($R^4$), —$CO_2R^6$, —$C_{1-6}$alkylene-N($R^3$)($R^4$), —$C_{1-6}$alkylene-$C_{1-6}$alkoxy, —$C_{1-6}$alkylene-$CO_2R^6$, —O-aryl, —O—$C_{1-6}$alkylene-N($R^3$)($R^4$), —N($R^6$)C(O)—$C_{1-6}$alkylene-N($R^3$)($R^4$), —CN, —S(O)$_p$$C_{1-6}$alkyl, —$SO_2$N($R^3$)($R^4$), —N($R^3$)$SO_2$($C_{1-6}$alkyl), heterocyclyl, C(O)$R^{11}$, —C($R^{11}$)($R^{12}$)OH, —C(O)N($R^3$)($R^4$), and —N($R^3$)C(O)N($R^3$)($R^4$);
X is —O—[C($R^6$)$_2$]$_m$-ψ, —O—[C($R^6$)($R^9$)C($R^6$)$_2$]-ψ, —O—[C($R^6$)($R^9$)]-ψ, —O—[C($R^6$)$_2$—C(hydroxyC$_{1-6}$alkyl)($R^6$)]-ψ, —N($R^6$)—[C($R^6$)$_2$]$_m$-ψ, —N=C($R^6$)-ψ, —N=C($R^6$)C($R^6$)$_2$-ψ, —C($R^6$)$_2$C(O)C($R^6$)$_2$-ψ, —[C($R^6$)$_2$]$_m$—C(O)-ψ, —C($R^6$)=C($R^6$)C(O)-ψ, —C(O)C($R^6$)=C($R^6$)-ψ, or —N($R^6$)—C(O)-ψ; wherein ψ is a bond to the sulfonamide ring nitrogen atom in Formula III;
$R^1$ represents independently for each occurrence hydrogen, halogen, or $C_{1-6}$alkyl;
$R^2$ is —N($R^7$)C(O)$R^8$, —($C_{1-2}$alkylene)-N($R^7$)C(O)$R^8$, —N($R^7$)C(O)N($R^7$)($R^8$), or heteroaryl, wherein said heteroaryl group is optionally substituted with 1 or 2 substituents independently selected from the group consisting of halogen, hydroxyl, $C_{1-6}$alkoxy, $C_{1-6}$alkyl, $C_{1-6}$haloalkyl, aryl, and heteroaryl;
$R^3$ and $R^4$ each represent independently hydrogen or $C_{1-6}$alkyl; or $R^3$ and $R^4$ taken together with the nitrogen atom to which they are attached form a 3-7 membered heterocyclic ring;
$R^5$ represents independently for each occurrence hydrogen, halogen, or $C_{1-6}$alkyl;
$R^6$ and $R^7$ each represent independently for each occurrence hydrogen or $C_{1-6}$alkyl;
$R^8$ is aryl, aralkyl, cycloalkyl, cycloalkenyl, heterocyclyl, —C($R^6$)$_2$-cycloalkyl, —C($R^6$)$_2$-cycloalkenyl, —C($R^6$)$_2$-heterocyclyl, or $C_{1-6}$alkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^3$)($R^4$), —CN, —$CO_2$—$C_{1-6}$alkyl, —C(O)—$C_{1-6}$alkyl, —C(O)N($R^3$)($R^4$), —S(O)$_p$$C_{1-6}$alkyl, —$SO_2$N($R^3$)($R^4$), and —N($R^3$)$SO_2$($C_{1-6}$alkyl);
$R^9$ is $C_{1-6}$haloalkyl, $C_{1-6}$hydroxyalkyl, —$C_{1-6}$ alkylene-N($R^3$)($R^4$), —$C_{1-6}$alkylene-N($R^3$)C(O)—$C_{1-6}$ alkyl, —$C_{1-6}$ alkylene-$CO_2R^3$, —$C_{1-6}$alkylene-CN, —$C_{1-6}$ alkylene-$C_{1-6}$alkoxy, —$C_{1-6}$alkylene-C(O)N($R^3$)($R^4$), —C(O)N($R^3$)($R^4$), —$C_{1-6}$alkylene-N($R^3$)C(O)N($R^3$)($R^4$), —$C_{1-6}$alkylene-N($R^3$)C(O)—[C(OH)($R^3$)($R^4$)], —$C_{1-6}$alkylene-O—C(O)N($R^3$)($R^4$), —$C_{1-6}$alkylene-$SO_2$N($R^3$)($R^4$), —$C_{1-6}$alkylene-N($R^3$)$SO_2$N($R^3$)($R^4$), $C_{2-4}$alkenyl, -arylene-$CO_2R^6$, or —CN;
$R^{11}$ is $C_{1-6}$alkyl, $C_{1-6}$haloalkyl, aryl, aralkyl, heteroaryl, or heterocycloalkyl; each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —$CO_2R^3$, and, —N($R^3$)($R^4$);
$R^{12}$ is hydrogen, $C_{1-6}$alkyl, $C_{1-6}$haloalkyl, aryl, aralkyl, heteroaryl, or heterocycloalkyl;
each of which is optionally substituted with 1 or 2 substituents independently selected from the group consisting of halogen, $C_{1-6}$alkyl, $C_{1-6}$haloalkyl, hydroxyl, $C_{1-6}$alkoxy, $C_{1-6}$haloalkoxy, —$CO_2R^3$, and, —N($R^3$)($R^4$);
m is 1 or 2;
p represents independently for each occurrence 0, 1, or 2;
y is 1 or 2; and
wherein the stereochemical configuration at a stereocenter in a compound represented by Formula III is R, S, or a mixture thereof.

2. The compound of claim 1, wherein A is phenyl substituted with 1, 2, or 3 substituents independently selected from the group consisting of halogen, hydroxyl, $C_{1-6}$alkyl, $C_{1-6}$haloalkyl, —N($R^3$)($R^4$), —CN, —$CO_2R^6$, —C(O)—$C_{1-6}$ alkyl, —$C_{1-6}$ alkylene-N($R^3$)($R^4$), —$C_{1-6}$alkylene-$C_{1-6}$alkoxy, —$C_{1-6}$alkylene-$CO_2R^6$, —O—$C_{1-6}$alkylene-N($R^3$)($R^4$), and —N($R^6$)C(O)—$C_{1-6}$ alkylene-N($R^3$)($R^4$).

3. The compound of claim 1, wherein A is phenyl substituted with 1, 2, or 3 substituents independently selected from the group consisting of halogen, $C_{1-6}$alkyl, $C_{1-6}$haloalkyl, and —CN.

4. The compound of claim 1, wherein X is —O—[C($R^6$)$_2$]$_m$-ψ or —O—[C($R^6$)($R^9$)C($R^6$)$_2$]-ψ.

5. The compound of claim 1, wherein $R^2$ is —N($R^7$)C(O)$R^8$.

6. The compound of claim 1, wherein $R^8$ is aryl or aralkyl, each of which is substituted with 1, 2, or 3 substituents independently selected from the group consisting of halogen, $C_{1-6}$alkyl, and $C_{1-6}$haloalkyl.

7. The compound of claim 6, wherein $R^8$ is phenyl substituted with 1, 2, or 3 substituents independently selected from the group consisting of halogen, $C_{1-6}$alkyl, and $C_{1-6}$haloalkyl.

8. The compound of claim 1, wherein said compound is represented by Formula III-C:

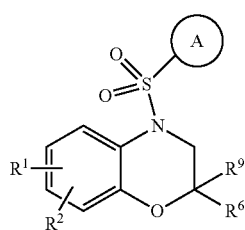

(III-C)

or a pharmaceutically acceptable salt or solvate thereof; wherein:

A is aryl or heteroaryl; each of which is substituted with 1, 2, or 3 substituents independently selected from the group consisting of halogen, hydroxyl, $C_{1-6}$alkyl, $C_{1-6}$haloalkyl, —CN, and —C(O)—$C_{1-6}$alkyl;

$R^1$ represents independently for each occurrence hydrogen, halogen, or $C_{1-6}$alkyl;

$R^2$ is —N($R^7$)C(O)$R^8$;

$R^3$ and $R^4$ each represent independently hydrogen or $C_{1-6}$alkyl; or $R^3$ and $R^4$ taken together with the nitrogen atom to which they are attached form a 3-7 membered heterocyclic ring;

$R^6$ and $R^7$ each represent independently for each occurrence hydrogen or $C_{1-6}$alkyl;

$R^8$ is aryl substituted with 1, 2, or 3 substituents independently selected from the group consisting of halogen, $C_{1-6}$alkyl, and $C_{1-6}$haloalkyl;

$R^9$ is $C_{1-6}$haloalkyl, $C_{1-6}$hydroxyalkyl, —$C_{1-6}$alkylene-N($R^3$)($R^4$), —$C_{1-6}$alkylene-N($R^3$)C(O)—$C_{1-6}$alkyl, —$C_{1-6}$alkylene-CN, or —$C_{1-6}$alkylene-$C_{1-6}$alkoxy; and wherein the stereochemical configuration at a stereocenter in a compound represented by Formula III-C is R, S, or a mixture thereof.

9. The compound of claim 8, wherein A is phenyl substituted with 1, 2, or 3 substituents independently selected from the group consisting of halogen, hydroxyl, $C_{1-6}$alkyl, $C_{1-6}$haloalkyl, and —CN.

10. The compound of claim 8, wherein $R^8$ is phenyl substituted with 1, 2, or 3 substituents independently selected from the group consisting of halogen, $C_{1-6}$alkyl, and $C_{1-6}$haloalkyl.

11. The compound of claim 8, wherein $R^9$ is $C_{1-6}$haloalkyl, $C_1$-6hydroxyalkyl, —$C_{1-6}$alkylene-N($R^3$)C(O)—$C_{1-6}$alkyl, or —$C_{1-6}$alkylene-$C_{1-6}$alkoxy.

12. The compound of claim 8, wherein $R^2$ is attached to the 6-position of the benzoxazine ring.

13. A pharmaceutical composition comprising the compound of claim 1 and a pharmaceutically acceptable carrier.

14. A pharmaceutical composition comprising the compound of claim 4 and a pharmaceutically acceptable carrier.

15. A pharmaceutical composition comprising the compound of claim 8 and a pharmaceutically acceptable carrier.

\* \* \* \* \*